United States Patent [19]
Inoue et al.

[11] Patent Number: 6,136,170
[45] Date of Patent: Oct. 24, 2000

[54] EXHAUST GAS SENSOR AND SYSTEM THEREOF

[75] Inventors: Ryuji Inoue, Tajimi; Tomohiro Fuma, Ichinomiya; Shoji Kitanoya, Kasugai; Yumi Mizutani, Yokohama; Masahito Kida; Takafumi Oshima, both of Nagoya; Takashi Hibino, Seto, all of Japan

[73] Assignee: NGK Spark Plug Co., Ltd., Aichi, Japan

[21] Appl. No.: 08/997,738

[22] Filed: Dec. 24, 1997

[30] Foreign Application Priority Data

| Dec. 29, 1996 | [JP] | Japan | 8-358789 |
|---|---|---|---|
| Mar. 19, 1997 | [JP] | Japan | 9-085792 |
| Apr. 25, 1997 | [JP] | Japan | 9-123064 |
| Aug. 26, 1997 | [JP] | Japan | 9-246092 |
| Nov. 12, 1997 | [JP] | Japan | 9-327080 |

[51] Int. Cl.$^7$ .................... G01N 27/26; G01N 27/407; G01N 27/417
[52] U.S. Cl. ................... 204/424; 204/425; 204/426; 204/408
[58] Field of Search .................. 204/424–429, 204/408

[56] References Cited

U.S. PATENT DOCUMENTS

| 4,722,779 | 2/1988 | Yamada et al. . |
| 5,250,169 | 10/1993 | Logothetis et al. . |
| 5,281,313 | 1/1994 | Visser et al. . |
| 5,527,446 | 6/1996 | Kosek et al. . |

FOREIGN PATENT DOCUMENTS

| 0 731 351 A2 | 9/1996 | European Pat. Off. . |
| 0 731 351 A3 | 9/1996 | European Pat. Off. . |
| 61-083956 | 4/1986 | Japan . |
| 61-095243 | 5/1986 | Japan . |
| 62-276453 | 12/1987 | Japan . |
| 5-180794 | 7/1993 | Japan . |
| WO 95/25277 | 9/1995 | WIPO . |

Primary Examiner—Robert J. Warden, Sr.
Assistant Examiner—Jennifer McNeil
Attorney, Agent, or Firm—Snider & Associates; Ronald R. Snider

[57] ABSTRACT

The present invention provides an apparatus for measuring the concentration of a constituent to be detected in exhaust gas, which apparatus is capable of detecting with a high accuracy the concentration of the constituent to be detected in exhaust gas even though oxygen concentration in the exhaust gas varies. In an exhaust gas sensor 1 for use in the measuring apparatus, exhaust gas is introduced into spaces 15, 16 on both sides of an oxygen concentration cell element 4, and the oxidation catalyst activities of first to third electrodes 11 to 13 are adjusted so that there occurs a difference between the space 15 and the space 16 in consumption of the constituent to be detected, which consumption is caused by the oxidation of the constituent. Thus a concentration cell electromotive force is generated in the oxygen concentration cell element 4, and an oxygen pump element 3 pumps oxygen into or out of the space 15 so that the electromotive force is held at an target value EC not more than 10 mV. The pump current at this time is taken as the detection output on the constituent to be detected. The strengths of the oxygen concentration cell element 4 and of the oxygen pump element 3 can be increased by the provision of an integrated sintered body in which the elements 4 and 3 are laminated together with the space 15 formed between the first electrode 11 and the second electrode 12. Besides, the accuracy of detecting the constituent to be detected can be improved by the control over the temperature of the oxygen concentration cell element 4 and by the temperature compensation to the pump current.

54 Claims, 75 Drawing Sheets

Fig. 3A
Fig. 3B
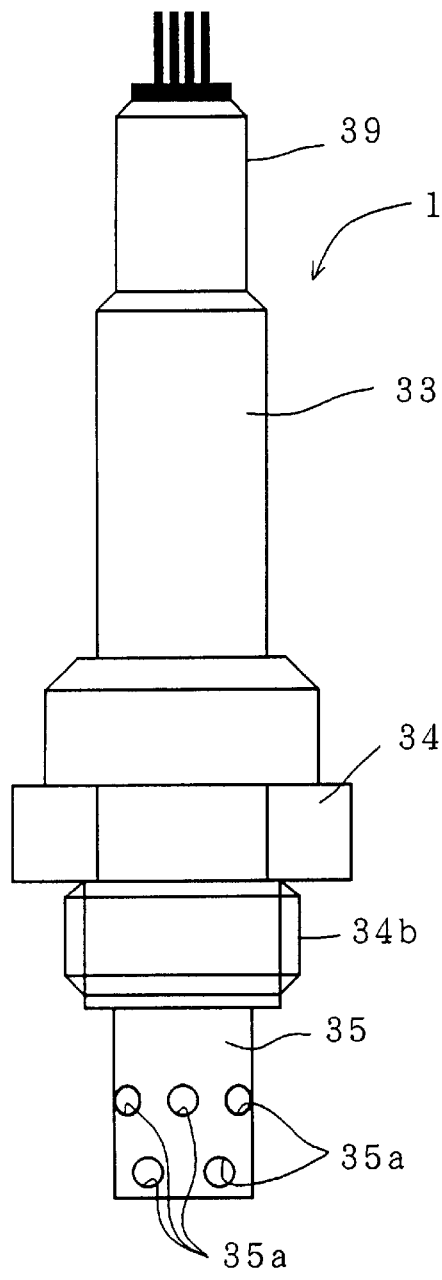
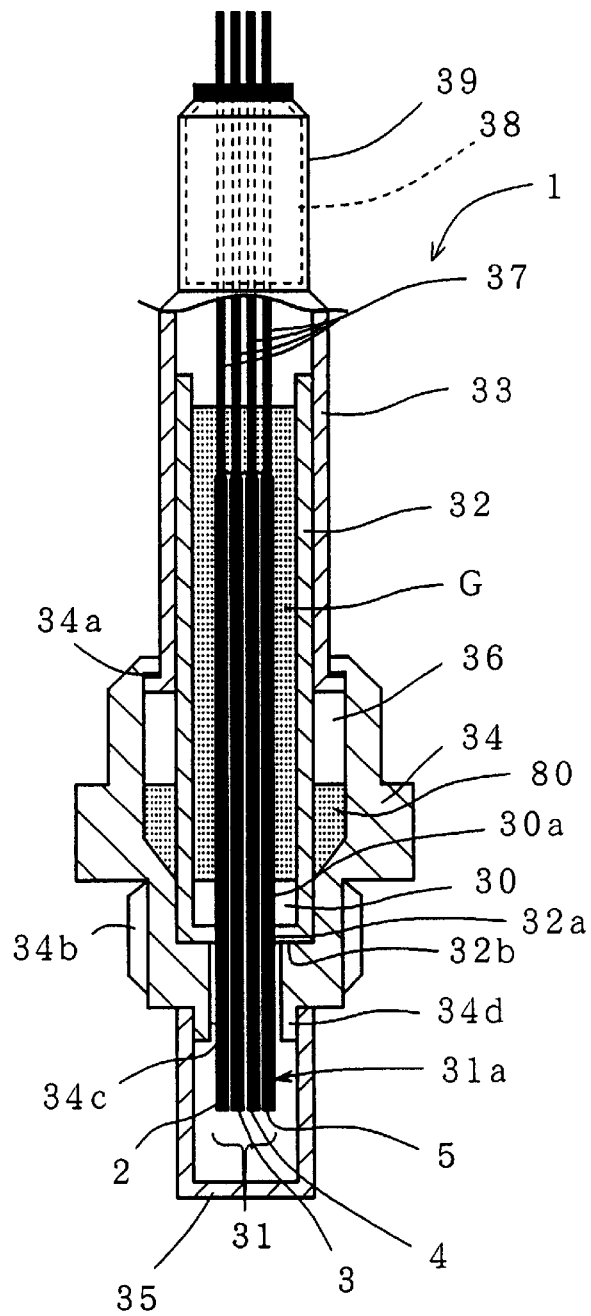

Fig. 19A
Fig. 19B
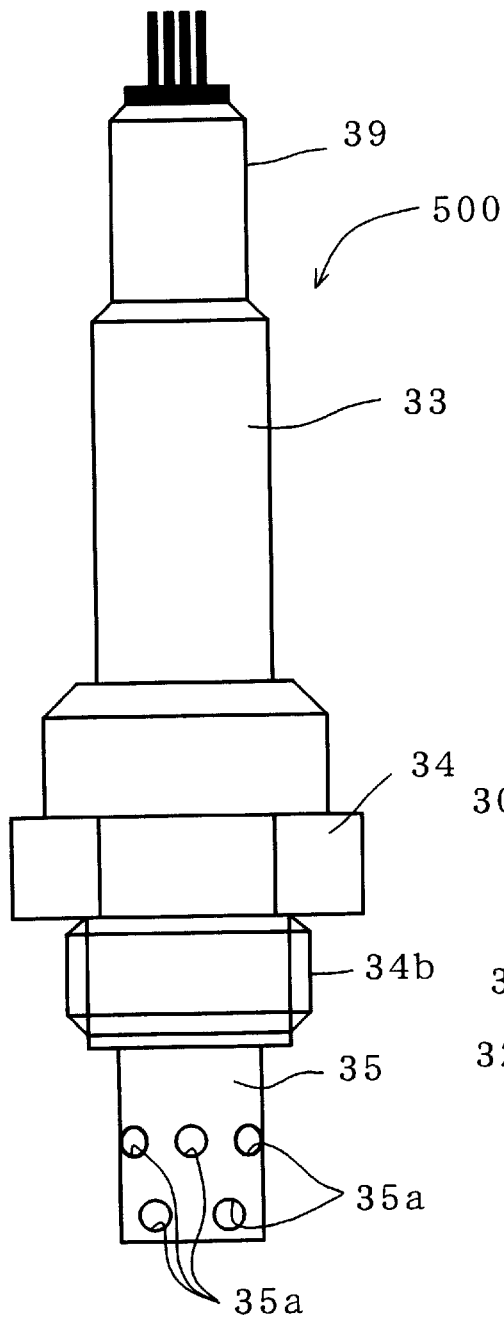
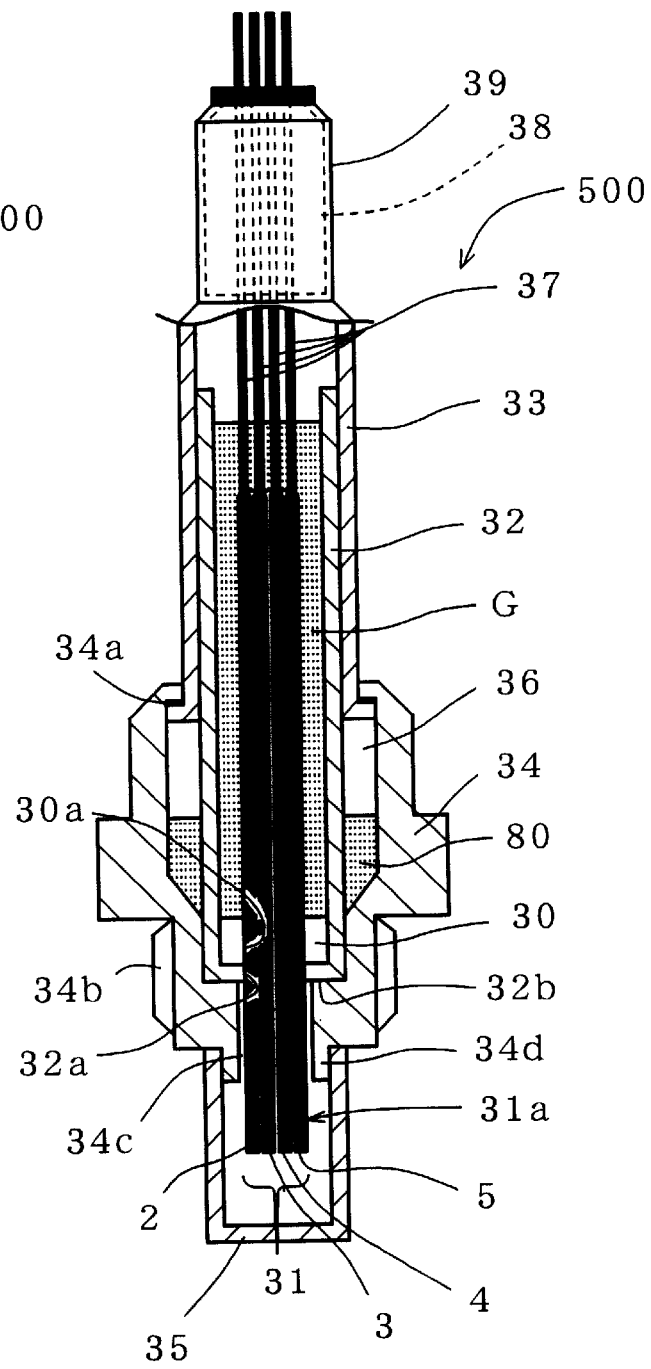

Fig. 20

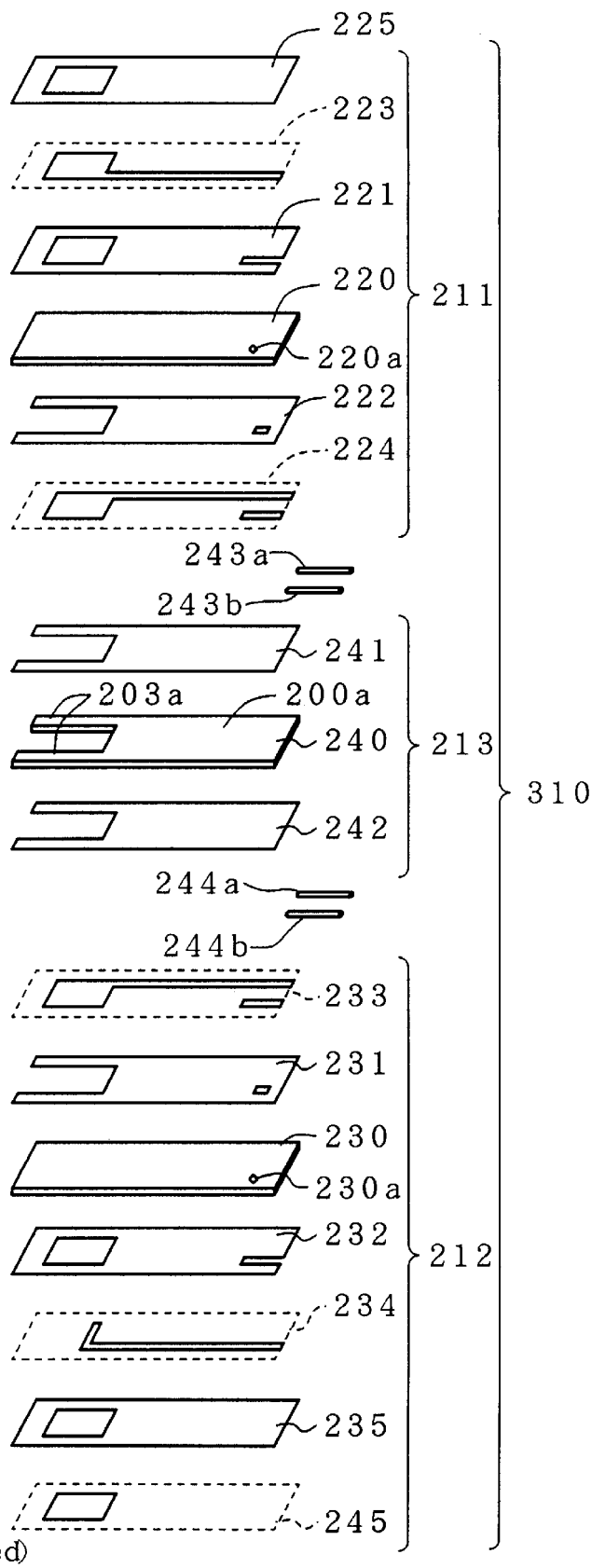

- Over coat (Alumina paste) — 225
- Pt paste pattern for outside electrode — 223
- Insulating coat (Alumina paste) — 221
- $ZrO_2$ green sheet (for oxygen pump element) — 220, 220a
- Insulating coat (Alumina paste) — 222
- Pt paste pattern for first electrode — 224

} 211

- Terminals — 243a, 243b
- Cementing coat (Alumina paste) — 241
- $ZrO_2$ green sheet (for spacer) — 203a, 200a, 240
- Cementing coat (Alumina paste) — 242

} 213

- Terminals — 244a, 244b
- Pt paste pattern for second electrode — 233
- Insulating coat (Alumina paste) — 231
- $ZrO_2$ green sheet (for concentration cell element) — 230, 230a
- Insulating coat (Alumina paste) — 232
- Pt paste pattern for third electrode lead portion — 234
- Over coat (Alumina paste) — 235
- Au paste pattern for third electrode (secondarily metallized) — 245

| | | |
|---|---|---|
| Over coat (Alumina paste) |  250 | |
| ZrO₂ green sheet (for heater body) | 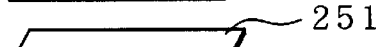 251 | |
| Insulating coat (Alumina paste) | 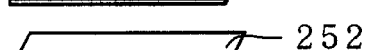 252 | 214 |
| Heater pattern (Pt paste) | 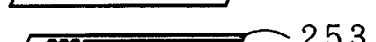 253 | |
| Over coat (Alumina paste) | 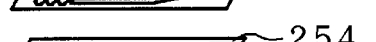 254 | |
| Additional supporting pattern for forming space (Carbon paste) | 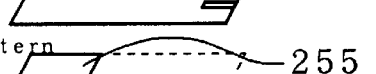 255 | |
| Cementing coat (Alumina paste) | 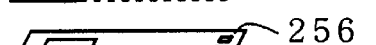 256 | |
| | 257a 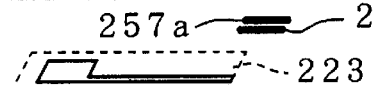 257b | |
| Pt paste pattern for outside electrode | 223 | |
| Insulating coat (Alumina paste) |  221 | |
| ZrO₂ green sheet (for oxygen pump element) | 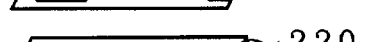 220 / 220a | 211 |
| Insulating coat (Alumina paste) | 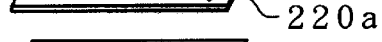 222 | |
| Pt paste pattern for first electrode | 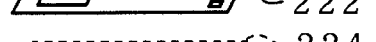 224 | |
| | 243a 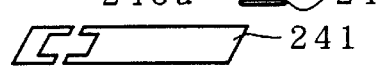 243b | |
| Cementing coat (Alumina paste) |  241 | |
| ZrO₂ green sheet (for spacer) | 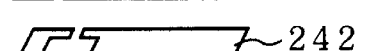 240 | 213 |
| Cementing coat (Alumina paste) |  242 | |
| | 244a 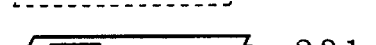 244b | |
| Pt paste pattern for second electrode |  233 | |
| Insulating coat (Alumina paste) | 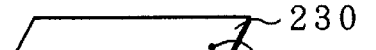 231 | |
| ZrO₂ green sheet (for oxygen concentration cell element) |  230 / 230a | |
| Insulating coat (Alumina paste) | 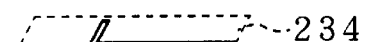 232 | 212 |
| Pt paste pattern for third electrode |  234 | |
| Over coat (Alumina paste) |  235 | |
| Au pattern for inactivating third electrode (secondarily metallized) | 245 | |

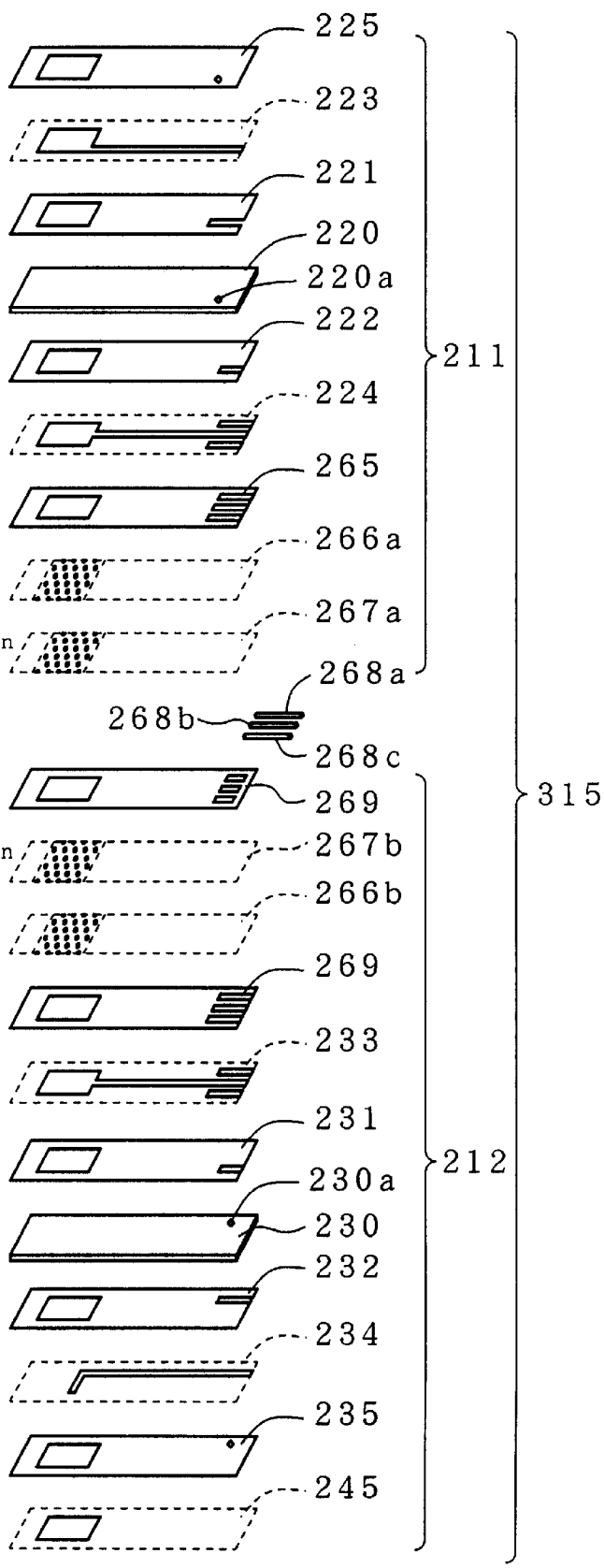

Over coat
(Alumina paste)

Pt paste pattern for
outside electrode

Insulating coat
(Alumina paste)

$ZrO_2$ green sheet
(for oxygen pump element)

Insulating coat
(Alumina paste)

Pt paste pattern for
first electrode

Insulating coat
(Alumina paste)

Prop pattern
(Porous alumina paste)

Additional supporting pattern
(Carbon paste)

Terminals

Cementing coat
(Alumina paste)

Additional supporting pattern
(Carbon paste)

Prop pattern
(Porous alumina paste)

Insulating coat
(Alumina paste)

Pt paste pattern for
second electrode

Insulating coat
(Alumina paste)

$ZrO_2$ green sheet
(for oxygen concentration
cell element)

Insulating coat
(Alumina paste)

Pt paste pattern for
third electrode

Over coat
(Alumina paste)

Au pattern for inactivating
third electrode
(secondarily metallized)

$$d = a/b = \frac{Vi}{Vmax}\lambda$$

$$Duty\ ratio = a/b = \frac{Vi + Vmax}{2Vmax}\lambda$$

Fig. 40A
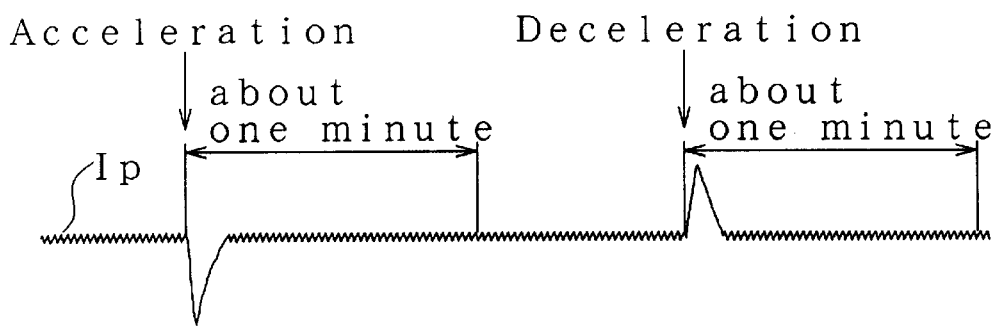
Fig. 40B
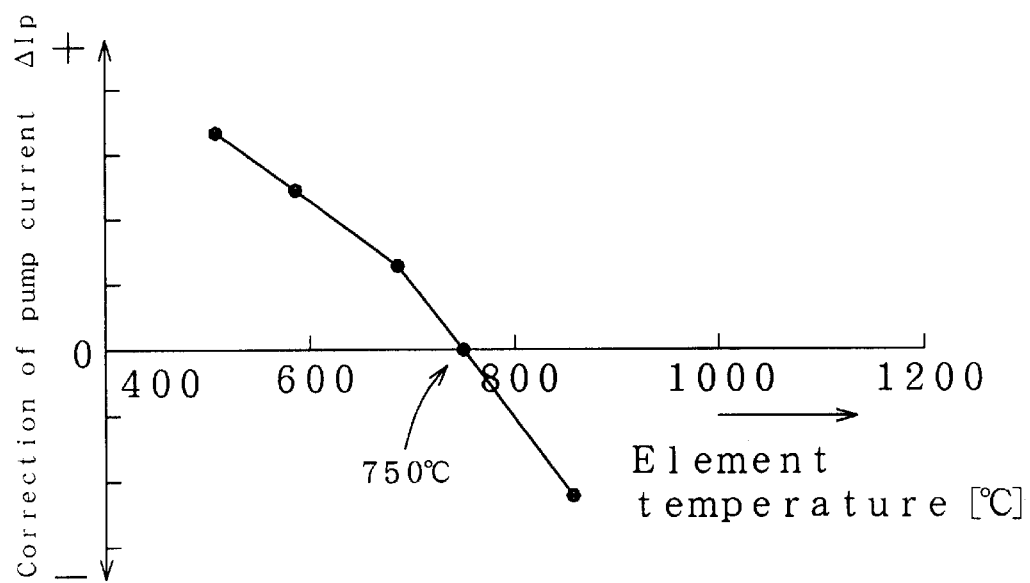
Fig. 40C
| Element temperature | T1 | T2 | T3 | T4 | ··· |
|---|---|---|---|---|---|
| ΔIp | ΔIp1 | ΔIp2 | ΔIp3 | ΔIp4 | ··· |
302

| Internal resistance | Ri1 | Ri2 | Ri3 | Ri4 | ... |
|---|---|---|---|---|---|
| $\Delta IP$ | $\Delta IP1$ | $\Delta IP2$ | $\Delta IP3$ | $\Delta IP4$ | ... |

| Element temperature / IP | T1 | T2 | T3 | ... |
|---|---|---|---|---|
| IP1 | CHC11 | CHC21 | CHC31 | ... |
| IP2 | CHC12 | CHC22 | CHC32 | ... |
| IP3 | CHC13 | CHC23 | CHC33 | ... |
| ⋮ | ⋮ | ⋮ | ⋮ | |

$CH_4$ concentration (% by volume)

Oxygen concentration (% by volume)

(a)

EXHAUST GAS SENSOR AND SYSTEM THEREOF

RELATED APPLICATIONS

This application claims the priority of Japanese Patent Applications No. H8-358789 filed on Dec. 29, 1996, H9-85792 filed on Mar. 19, 1997, H9-123064 filed on Apr. 25, 1997, H9-246092 filed on Aug. 26, 1997 and H9-327080 filed on Nov. 12, 1997, which are incorporated herein by reference.

BACKGROUND OF THE INVENTION

The present invention relates to an exhaust gas sensor and an exhaust gas sensor system in which the sensor is used.

As a sensor for detecting a constituent of an exhaust gas from an automobile or the like, such as hydrocarbon (hereinafter referred to as "HC"), carbon monoxide (hereinafter referred to as "CO"), or nitrogen oxides (hereinafter referred to as "NOx") for example, a resistance type sensor has been known, in which oxide semiconductor such as $SnO_2$ is used as the detector element so that the content is detected on the basis of a change in the resistance of the oxide semiconductor which has absorbed the constituent to be detected. On the other hand, a CO sensor has been proposed in which Pt porous electrodes are formed on both surfaces of a zirconia element and in which one of the porous electrodes is covered with an oxidation catalyst. The exposure of the sensor to a gas containing CO and oxygen causes oxidation reaction of CO in the electrode that is not covered with the oxidation catalyst, the reaction causes the potential of the electrode to be a mixed potential influenced by the CO concentration; whereas, in the electrode that is covered with the oxidation catalyst, the exposure results in the complete oxidation of CO, so that a potential occurs which depends on the oxygen concentration in the gas. Thus taking the potential difference between the electrodes as an output allows the CO concentration in the gas to be detected on the basis of the potential difference.

The former resistance type sensor is characterized in that the output of the detector element made of oxide semiconductor varies with the concentration of oxygen of the exhaust gas. Accordingly, a problem occurs that, even with the same concentration of a constituent to be detected, the output value of the detector thus fluctuates in response to the concentration of oxygen in exhaust gas. For this reason, as disclosed in, e.g., Japanese Provisional Patent Publication No. 5-180794, the feeding of oxygen into exhaust gas by a pump element employing solid electrolyte has been proposed for increasing the oxygen concentration and for decreasing the relative fluctuation of the concentration of oxygen in the gas in order to improve the detection accuracy. This arrangement, however, has a problem that a large amount of change in the concentration of oxygen in exhaust gas makes insufficient the effect for suppressing the relative fluctuation of the concentration by the introduction of oxygen from the pump element and does not allow a sufficient detection accuracy to be obtained. On the other hand, the latter type of sensor using the mixed potential causes the similar problem because the potential of the electrode that is covered with the oxidation catalyst varies with the concentration of oxygen in the gas.

SUMMARY OF THE INVENTION

The present invention is intended to provide an exhaust gas sensor which is capable of detecting with a high accuracy the concentration of a constituent to be detected in exhaust gas even though oxygen concentration in the exhaust gas varies, and to provide an exhaust gas sensor system employing the sensor.

The present invention relates to a sensor for detecting a constituent to be detected which is contained in exhaust gas, and the arrangement of main parts of the sensor is as follows: The exhaust gas sensor comprises: an oxygen concentration cell element comprising solid electrolyte which has an oxygen-ion conductivity, and having on both surfaces electrodes which have an oxygen permeability, one of the electrodes facing a processing space; an oxygen pump element for pumping oxygen into or out of the processing space in such a direction that the absolute value of a concentration cell electromotive force generated in the oxygen concentration cell element decreases, the oxygen pump element comprising solid electrolyte which has an oxygen-ion conductivity, and having on both surfaces electrodes which have an oxygen permeability, one of the electrodes facing the processing space; and a heater element or heater elements for heating at least one of the oxygen pump element and the oxygen concentration cell element to a predetermined operating temperature of the sensor. The oxygen pump element serves to pump oxygen into or out of the space in such a direction that the absolute value of the concentration cell electromotive force generated in the oxygen concentration cell element decreases. Exhaust gas containing the constituent to be detected and oxygen is introduced into the processing space and into a space (an opposed space) that is across the oxygen concentration cell element from the processing space.

Here, the electrode facing the processing space on the oxygen pump element is referred to as a first electrode, the electrode facing the processing space on the oxygen concentration cell element is referred to as a second electrode, and the electrode on the side of the opposed space on the oxygen concentration cell element is referred to as a third electrode. The oxidation catalyst activities of the first to third electrodes are adjusted so that the constituent to be detected in the exhaust gas introduced into the processing space and into the opposed space is consumed by the reaction thereof with oxygen in the exhaust gas with at least any one of the first to third electrodes acting as oxidation catalyst in at least one of the processing space and the opposed space and so that a difference in the consumption of the constituent to be detected which is caused by the reaction with oxygen occurs between the processing space and the opposed space.

In a first arrangement of the exhaust gas sensor in accordance with the invention, the value of a current flowing through the oxygen pump element at the time when the absolute value of the concentration cell electromotive force of the oxygen concentration cell element reaches a target value EC of the electromotive force which is set within the range not more than 10 mV is taken as the information reflecting the concentration of the constituent to be detected in the exhaust gas.

In the second arrangement of the exhaust gas sensor in accordance with the invention, the absolute value of an offset electromotive force which is generated in the oxygen concentration cell element when test gas containing not less than 1 percent oxygen by volume and containing substantially no constituents which may react with oxygen at the operating temperature of the sensor is introduced into the processing space and the opposed space, is provided as EOS (in mV). Correspondingly, a target value EC of the electromotive force is set within the range not less than (EOS−5) mV and not more than (EOS+5) mV, and the value of a current flowing through the oxygen pump element at the time when the absolute value of the concentration cell electromotive force of the oxygen concentration cell element reaches the target value EC of the electromotive force is taken as the information reflecting the concentration of the constituent to be detected in the exhaust gas.

An exhaust gas sensor system in accordance with the invention (hereinafter simply referred to as "the sensor system") comprises the exhaust gas sensor; electromotive-force detecting means for detecting a concentration cell electromotive force generated in the oxygen concentration cell element; pump element voltage adjusting means for adjusting the voltage applied to the oxygen pump element so that oxygen is pumped into or out of the processing space in such a direction that the absolute value of the detected concentration cell electromotive force decreases; and output means for outputting the value of, or information reflecting, the current which flows through the oxygen pump element at the time when the absolute value of the concentration cell electromotive force reaches the target value EC of the electromotive force, as information reflecting the concentration of the constituent to be detected.

In the exhaust gas sensor or sensor system arranged as described above, exhaust gas containing the constituent to be detected and oxygen is introduced into the processing space and the opposed space on both sides of the oxygen concentration cell element, and the oxidation catalyst activities of the first and second electrodes facing the processing space and of the third electrode disposed on the side of the opposed space are adjusted so that a difference in the consumption of the constituent to be detected as a result of oxidation occurs between the processing space and the opposed space. The larger amount of oxygen is therefore consumed on the side where the larger amount of the constituent to be detected is consumed on the side where the in oxygen concentration occurs between both sides of the oxygen concentration cell element, and a concentration cell electromotive force according to the difference is generated. The oxygen pump element, for example, pumps oxygen into the processing space in the case that the processing space has the lower oxygen concentration, while the element pumps oxygen out of the processing space in the case that the processing space has the higher oxygen concentration; thus the concentration cell electromotive force is controlled so as to come to the target value EC of the electromotive force.

The current (hereinafter referred to as the "pump current") which flows through the oxygen pump element at the time when the concentration cell electromotive force reaches the target value EC of the electromotive force, generally reflects the concentration of the constituent to be detected in the exhaust gas, and therefore the concentration of the constituent to be detected can be detected on the basis of the pump current. The pump current is little influenced by the oxygen concentration in the exhaust gas, unless the concentration of the constituent to be detected in the exhaust gas changes. Besides, the pump current changes linearly in general with change in the concentration of the constituent to be detected. For this reason, the concentration of the constituent to be detected in the exhaust gas can be accurately detected, even though the oxygen concentration varies within a given range.

The oxygen pump element can be disposed so as to face the oxygen concentration cell element so that a space of a given width as the processing space where the passage of, e.g., exhaust gas is allowed is formed between the oxygen pump element and the oxygen concentration cell element. In this case, the width of the space is preferably set, for example, not more than 1 mm. The space having a width larger than 1 mm weakens the effect of the space for regulating fresh influx of exhaust gas and may lower the detecting accuracy of the sensor. Additionally, making the ratio Sp/Ss of the area Sp of the first electrode to the area Ss of the second electrode not less than one provides a constant oxygen concentration in the vicinity of the second electrode and thus improves the accuracy and stability of the sensor output.

When oxygen is pumped into or out of the processing space by the oxygen pump element so that the oxygen concentrations on both sides of the oxygen concentration cell element, i.e., the oxygen concentrations in the processing space and in the opposed space, are equal, the pump currents correspond directly to the differences between both the spaces in the consumption of the constituent to be detected. As a result, the concentration of the constituent to be detected can be detected more accurately, and the detection result can be readily analyzed. In this case, the equal oxygen concentrations on both sides of the oxygen concentration cell element should theoretically make the concentration cell electromotive force zero, and the oxygen pump element therefore should pump oxygen into or out of the processing space so that the concentration cell electromotive force makes zero. Even though the oxygen concentrations on both sides of the oxygen concentration cell element are equal, however, it is usual that the electromotive force of the oxygen concentration cell element does not become zero and that a given offset electromotive force remains.

The inventors et al. noticed that almost all oxygen-ion-conductive solid electrolytes generally used caused the absolute values of the offset electromotive forces of the oxygen concentration cell elements made of the solid electrolytes to be not more than 10 mV, and found that, in the first arrangement of the exhaust gas sensor of the invention, the concentration of a constituent to be detected in exhaust gas could be detected accurately by setting the target value EC of electromotive force not more than 10 mV, and by taking as the detection signal the current flowing through the oxygen pump element at the time when the absolute value of the concentration cell electromotive force reached the target value EC of electromotive force. In the case that the range of oxygen concentration in the atmosphere to be measured is known, however, the offset electromotive force corresponding to the maximum oxygen concentration in the range is preferably set as the target value of electromotive force.

On the other hand, as a result of close study, the inventors et al. obtained and completed the second arrangement of the invention, on the basis of the following finding: The offset electromotive force of the oxygen concentration cell element becomes more fluctuant with decrease in oxygen concentration in the exhaust gas associated with the detection, and therefore the setting of the target value EC of electromotive force on the basis of the offset electromotive force corresponding to an oxygen concentration not more than a given value makes the sensor outputs prone to be influenced by the oxygen concentration in the exhaust gas. In order to solve this problem, it is effective to provide as EOS (in mV) the absolute value of the offset electromotive force generated in the oxygen concentration cell element at the time when test gas containing not less than 1 volume percent oxygen and substantially no constituents which may react with oxygen at the operating temperature of the sensor is introduced into the processing space and the opposed spaces, and to set the target value. EC of electromotive force within the range not less than (EOS−5) mV and not more than (EOS+5) mV, by using EOS as the reference. The setting of the target value EC of electromotive force within the range results in more stable sensor outputs which are not influenced by the oxygen concentration in the exhaust gas. In this case, setting the target value EC of electromotive force as close to EOS as possible is preferable for improving the detecting accuracy of the sensor. As test gas for determining EOS, gas having oxygen concentration not less than 10% or the air is preferably used. With the target value EC of electromotive force set not more than 10 mV in the same manner as the first arrangement, more stable and more accurate sensor outputs can be obtained.

The exhaust gas sensor in accordance with the invention can be disposed downstream from an oxidation catalytic converter or a three way catalytic converter, e.g., for a gasoline internal combustion engine, in order to detect the deterioration of the three way catalyst in the converter. In this case, oxygen in exhaust gas is introduced into the exhaust gas sensor after a substantial portion of the oxygen is consumed for the oxidation of CO or HC by the action of the catalyst on the upstream side. Since the level of oxygen concentration in the exhaust gas associated with the detection is generally not more than 5000 ppm, the exhaust gas sensor is preferably adapted so as to be capable of accurately detecting a constituent to be detected in the state where oxygen concentration is substantially low as describe above. For that purpose, e.g., providing that a sensor output corresponding to an oxygen concentration of 100 ppm is Q100 and that a sensor output corresponding to an oxygen concentration of 1000 ppm is Q1000, the target value EC of electromotive force should be established so that the rate of change $\Delta$ (%) of the output which rate is defined by:

$$\{(Q100-Q1000)/Q100\} \cdot 100$$

is within ±30%, more preferably within ±10%.

As a referantial art, the air-fuel ratio sensor disclosed in Japanese Unexamined Patent Publication No. 61-95243 is an example of a sensor in which electrodes having different oxidation catalyst activities are formed on both sides of an oxygen concentration cell element and in which an oxygen pump element is disposed so as to face the oxygen concentration cell element and so as to form a space having a given width on one side of the oxygen concentration cell element. The sensor of the publication is, however, intended to detect as an air-fuel ratio the ratio of oxygen concentration to the concentration of combustible constituent(s) such as CO or HC in air-fuel mixture, and the object, function, and effect of the sensor are fundamentally different from those of the sensor of the invention which detects the amount of a constituent to be detected in exhaust gas irrespective of the oxygen concentration in the exhaust gas. As a matter of course, the exhaust gas sensor of the invention is characterized in that the target value EC of the electromotive force of the oxygen concentration cell element is established so as to fit the object of use which is unique to the invention and which is different from that of the air-fuel ratio sensor of the publication, and in that the oxygen pump element operates so as to approach the electromotive force of the oxygen concentration cell element to the target value EC of electromotive force. Those characteristics are not at all disclosed in the art of the publication.

The second and third electrodes formed on both surfaces of the oxygen concentration cell element can be arranged so as to have different oxidation catalyst activities on a constituent to be detected. This arrangement increases the difference in the consumption of the constituent to be detected between the processing space and the opposed space, increases the sensor output level, and improves the sensitivity of detecting the constituent to be detected. In this case, making the oxidation catalyst activity of the second electrode higher than that of the third electrode improves the linearity of the sensor output with respect to the concentration of the constituent to be detected in exhaust gas, and may further improve the accuracy of detecting the constituent to be detected. In this arrangement, the oxygen pump element pumps oxygen into the processing space so that the absolute value of the concentration cell electromotive force generated in the oxygen concentration cell element decreases. Making the oxidation catalyst activities on the constituent to be detected of the first and second electrodes higher than that of the third electrode further increases the difference in the consumption of the constituent to be detected between the processing space and the opposed space, and improve the sensitivity of detecting the constituent to be detected.

More specifically, the second and third electrodes which are to be used are preferably such that the difference between the electrodes in the conversion ratio $\eta$ of the constituent to be detected, which will be defined below, is not less than 20 percentage points. That is, a sample in which a disc-like porous electrode having a diameter of 8 mm is formed, with use of the same material and condition as the second or third electrode, on a disc of oxygen-ion-conductive solid electrolyte having a diameter of 12 mm and a thickness of 1 mm is placed in a cylindrical body having a gas inlet and a gas outlet, and is heated to the operating temperature of the sensor. In this state, test gas containing oxygen of 300 ppm, a constituent to be detected of 350 ppm, 3% water vapor and the residual parts of argon is introduced into the cylindrical body through the inlet at a flow rate of 100 ml/min. Provided that the concentration of the constituent to be detected in the test gas discharged through the outlet is given as Cs (in ppm), the conversion ratio $\eta$ (%) of the constituent to be detected is calculated from the following equation:

$$\eta = \{(350-Cs)/350\} \cdot 100 \tag{1}$$

When the constituent to be detected which is contained in the test gas is oxidized and consumed by the action of the electrode as the oxidation catalyst, the concentration Cs of the constituent to be detected in the discharged test gas decreases and the conversion ratio $\eta$ of the constituent to be detected thereby increases. Accordingly, the value $\eta$ can be used as a parameter representing the oxidation catalyst activity on the constituent to be detected of each electrode in the sensor, and as a parameter reflecting the consumption of the constituent to be detected in the processing space or the opposed space. Making the difference in the value $\eta$ between the second electrode and the third electrode not less than 20% increases the difference in the consumption of the constituent to be detected between the processing space and the opposed space, increases the sensor output level, and improves the sensitivity of detecting the constituent to be detected. In the case that, for example, the oxidation catalyst activity of the second electrode is higher than that of the third electrode, a preferable arrangement is such that the conversion ratio $\eta$ of the constituent to be detected that is achieved by the second electrode is larger by not less than 20% than that achieved by the third electrode. The difference in the value $\eta$ is more preferably not less than 30%.

The value $\eta$ achieved by an electrode varies with the operating temperature of the sensor. The operating temperature of the sensor is preferably established so that the difference in $\eta$ is not less than 20%, preferably not less than 30%. When the operating temperature of the sensor is established so that the pump current in the oxygen pump element is maximized with the voltage applied thereto being constant, the sensitivity of detecting the constituent to be detected is further improved.

In the case that the constituent to be detected is, e.g., CO or HC; the electrode(s) which are to have a relatively high catalytic activity on the reaction with oxygen, out of the first to third electrodes, may comprise metal (simple substance or alloy) based on any one of Pt, Pd, and Rh, alloy based on Pt—Rh, alloy based on Rh—Pd, alloy based on Pd—Ag, or the like (hereinafter those metals will be referred to as a high-activity metal group), while the electode(s) which are to have a relatively low catalytic activity may comprise metal (simple substance or alloy) based on any one of Au, Ni, and Ag, alloy based on Pt—Au, alloy based on Pt—Ni, alloy based on Pt—Ag, alloy based on Ag—Pd, alloy based on Au—Pd, alloy based on Pt—Pd or the like (hereinafter those metals will be referred to as a low-activity metal group). Any of the metals mentioned above has a high degree of reversible catalysis (hereinafter referred to as oxygen-dissociating catalysis) on the reaction of dissociating oxygen molecules for injecting oxygen into the solid electrolyte constituting the elements and on the recombination reaction of oxygen for discharging oxygen out of the solid electrolyte. There is, however, a great difference between the former group and the latter group in the catalytic activity on the reaction between a hydrocarbon-based constituent to be detected and oxygen. For example, the arrangement in which the first and second electrodes comprise a member of the high-activity metal group, such as metal based on any one of Pt, Pd, and Rh, and in which the third electrode comprises a member of the low-activity metal group, such as metal based on any one of Au, Ni, and Ag, increases the difference in the consumption of the constituent to be detected between the processing space and the opposed space, increases the sensor output level, and improves the sensitivity of detecting the constituent to be detected. The catalytic activities on the reaction between the constituent to be detected and oxygen remarkably differ between Pt or Pd and Au, in particular, and the employment of metals based on those elements as the materials of the electrodes is preferable for the improvement of the above effect.

In the case that the constituent to be detected is, e.g., methane, the detecting sensitivity and selectivity on the constituent to be detected may be significantly improved by, e.g., a combination of the materials of the electrodes. Above all, the selectivity on the detection of methane can be remarkably improved by the arrangement in which the electrode(s) having the higher oxidation catalyst activity comprise metal based on Pt or Pd and in which the electrode (s) having the lower oxidation catalyst activity comprise metal based on Au.

A third arrangement of the exhaust gas sensor in accordance with the invention is characterized in that, for the purpose of the selective detection of methane as the constituent to be detected, the third electrode comprises Pd which makes the oxidation catalyst activity on methane of the third electrode lower than, at least, that of the second electrode. That is, the addition of Pd constituent to the third electrode decreases the oxidation catalyst activity on methane of the electrode and improves the selectivity of the sensor on the detection of methane.

In this case, at least one of the first and second electrodes have to be composed of material which has a higher oxidation catalyst activity on methane than the material of the third electrode. For example, the compositions of both the first and second electrodes based on Pt provide a remarkable difference in oxidation activity on methane between the third electrode and the first and second electrodes, and thus further improve the selective detectivity on methane.

More preferably, the first and second electrodes are Pt porous electrtodes and the third electrode is a Pd-added Pt porous electrode. It is preferable that Pd in the third electrode is supported by carrier particles comprising inorganic material or the like, from the viewpoint of exerting the effects of homogeneous diffusion of Pd and of decrease in interface resistance. Such an electrode is produced, for example, as follows: In advance, Pd is supported by particles comprising the same solid electrolyte as constitutes the oxygen concentration cell element; and the particles supporting Pd, and porous particles of Pt are mixed and sintered.

Pd content in the third electrode is preferably adjusted within the range not more than 90% by weight. Pd content of more than 90% by weight may result in an insufficient selectivity on the detection of methane. Preferably, the third electrode is composed mainly of, e.g.,, Pt and contains not less than 0.1% Pd by weight. Pd content of less than 0.1% by weight in the third electrode also may result in an insufficient selectivity on the detection of methane, e.g., in the case that the first and second electrodes are composed mainly of Pt. The third electrode may contain, along with Pd, one or more of Au, Ag, Cu, Mn, Fe, Co, and Zn.

In the composition of an electrode having a relatively low oxidation catalyst activity on a constituent to be detected, a portion of the electrode that includes at least the surface contacting exhaust gas can be composed of material inert as a catalyst on the reaction between the constituent to be detected and oxygen. In this case, as a matter of course, the whole electrode can be composed of the material inert as the catalyst; however, only the surface of the portion contacting exhaust gas may be composed of the material inert as the catalyst. For example, in the production of such an electrode, the main body of the electrode may be formed of material having a catalytic activity and its surface may be coated with material inert as the catalyst. Such materials inert as the catalyst include materials belonging to the low-activity metal group such as metal based on any one of Au, Ni, and Ag, and oxides such as $SnO_2$, $ZnO$, $In_2O_3$, $WO_3$, and $Bi_2O_3$.

A gas holding member comprising metal meshes or porous metal can be interposed into the space (the processing space) formed between the oxygen pump element and the oxygen concentration cell element. In this arrangement, the gas holding member functions as a spacer for forming the space and thus improves the dimensional accuracy of the space. In the case of the gas holding member comprising metal meshes, the density of the meshes is preferably between 100 and 500 meshes.

A space-forming member for forming a space of a given width between itself and the oxygen concentration cell element may be disposed on the side of the oxygen concentration cell element where the third electrode is formed. This arrangement makes the absolute value of the offset electromotive force smaller and less fluctuant, and may increase the detection accuracy of the sensor. The space-forming member may be a plate-like heater element for heating the oxygen concentration cell element to the operating temperature of the sensor. Such a heater element doubling as the space-forming member allows the sensor to be made more compact.

A fourth arrangement of the exhaust gas sensor in accordance with the invention comprises: an oxygen concentration cell element comprising solid electrolyte which has an oxygen-ion conductivity, and having electrodes on both surfaces; an oxygen pump element comprising solid electrolyte which has an oxygen-ion conductivity, having electrodes on both surfaces, facing the oxygen concentration cell element to form between itself and the oxygen concentration cell element a space of a given width where the flow of exhaust gas from the atmosphere to be measured is allowed, and pumping oxygen into or out of the space in such a direction that the absolute value of a concentration cell electromotive force generated in the oxygen concentration cell element decreases; and a heater element or heater elements for heating at least one of the oxygen pump element and the oxygen concentration cell element to a predetermined operating temperature of the sensor. The arrangement is characterized in that the oxygen concentration cell element and the oxygen pump element are formed as a unitary sintered body in which those elements are laminated with the space formed therebetween.

In accordance with the above arrangement of the exhaust gas sensor, the oxygen concentration cell element and the oxygen pump element are formed as the unitary sintered body in which those elements are laminated together, and the following effects are therefore achieved:

① The integration of the oxygen concentration cell element and the oxygen pump element, which is performed simultaneously with the sintering of the elements, allows the assembly processes after the sintering to be omitted or simplified and thus increases the efficiency of producing the sensor;

② For example, in the arrangement in which the oxygen concentration cell element and the oxygen pump element are separately sintered and integrated by cementing or the like after the sintering, it may be difficult to make the width of the formed space constant, because of the deformation of the elements being sintered or other reasons, and thus there may occur a variation in output level among individual sensors. In the arrangement in which the integration is achieved by sintering, however, the easiness of controlling the width of the formed space restrains such a problem from occurring.

③ In the arrangement in which, for the purpose of rendering the sensor compact, the oxygen concentration cell element and the oxygen pump element are formed like thin plates (e.g., plates having thicknesses not more than 1 mm, more specifically, between 0.2 and 0.4 mm), sintered, and then integrated by cementing or the like; a fracture or cracks may be prone to occur in the elements, because of the insufficiency of mechanical strengths such as shock-resistance in the elements. The integration achieved by sintering, however, causes the elements to reinforce each other and improves the mechanical strengths of the elements.

Such an integrated structure as described above can be obtained efficiently, e.g., by the following method of production: Electrode patterns which are to be the electrodes are printed with use of powder paste as the materials of the electrodes, on both surfaces of a first ceramic powder compact which is to be the oxygen concentration cell element; and electrode patterns are similarly printed on both surfaces of a second ceramic powder compact which is to be the oxygen pump element. Subsequently, the first and second ceramic powder compacts are laminated together so that the electrode patterns which are to be the first and second electrodes face each other and so that the space is formed between the facing electrode patterns. By the sintering of the laminate, the oxygen concentration cell element and the oxygen pump element which are integrated together are obtained.

The above exhaust gas sensor can be formed as a unitary sintered body in which the heater element or heater elements are laminated on the side opposite to the space of at least one of the oxygen concentration cell element and the oxygen pump element and in which the oxygen concentration cell element, the oxygen pump element, and the heater element (s) are laminated together. This arrangement simplifies the processes of assembling the sensor including the heater element(s), allows the whole sensor to be made more compact, and further increases the mechanical strength of the whole sensor by the reinforcing effect of the integrated heater element(s).

The sensor with the arrangement described above can be produced efficiency by the above-mentioned method in which third ceramic powder compact(s) which are to be the heater element(s) are laminated on the side opposite to the space of at least one of the first and second ceramic powder compacts and in which the laminate is sintered to form the oxygen concentration cell element, the oxygen pump element, and the heater element(s) which are integrated together.

In the exhaust gas sensor of the fourth arrangement, the space may be formed so as to communicate with the outside space through communicating portions formed on the side edges of the laminate of the oxygen concentration cell element and the oxygen pump element. This arrangement allows exhaust gas to be introduced smoothly into the space through the communicating portions. In this case, the communicating portions can be composed of porous ceramic bodies which allow the flow of gas between the space and the outside space. This arrangement restrains contaminant particles such as soot or oil droplets contained in exhaust gas from entering the space, and thus prevents or restrains the deterioration of the first and second electrodes facing the space, which deterioration would be caused by the deposition of the contaminant particles. An example of the method of forming the communicating portions composed of the porous ceramic bodies is as follows: In the method mentioned formerly, communicating portion patterns which are to be the communicating portions are formed and interposed between the first and second ceramic powder compacts, by printing or the like method with use of paste comprising porous ceramic powder (such as porous $Al_2O_3$ powder) or such powder mixture or the like as will become the porous ceramic bodies after sintered, and then all the components are integrally sintered.

In the space between the oxygen concentration cell element and the oxygen pump element may be formed a prop or pros which define the distance of the space without impeding gas from flowing into and out of the space. For example, in the case that the oxygen concentration cell element and the oxygen pump element are formed like plates, so-called ceramic green sheets formed from ceramic powder and organic binder which have been kneaded are often used as the first and second ceramic powder compacts. In this case, the ceramic green sheets laminated with the space formed therebetween may deform and sag into the space by the sintering; as a result, there may occur a variation in the width of the space formed eventually and, in extreme cases, troubles may occur such as the crush of the space, which brings the facing electrodes into contact with each other. As described above, forming the prop(s) which define the distance of the space, between the oxygen concentration cell element and the oxygen pump element, allows the space of an expected width to be formed stably and thus prevents such problems as a variation in output among individual sensors which is caused by the variation in the width of the space.

The prop(s) can be formed efficiently by such a method as follows: Prop pattern(s) which are to be the prop(s) are formed with use of ceramic powder in the area corresponding to the space, on at least one of the first and second ceramic powder compacts. Subsequently, the first and second ceramic powder compacts are laminated together so as to form the space on the side where the prop pattern(s) are formed. By sintering the laminate, the prop(s) based on the prop pattern(s) are formed between the oxygen concentration cell element and the oxygen pump element. The prop pattern(s) can be formed by the disposition of ceramic powder compact(s) (such as ceramic green sheet(s)), pattern printing with use of ceramic powder paste, or the like method.

Specifically, the props can be arranged scatteringly or staggered in the area where the space is formed, or can be formed like partition wall(s) which partition the space into two or more parts adjoining in a direction that intersects the direction of the lamination of the oxygen concentration cell element and the oxygen pump element. The material of the prop(s) may comprise either the same ceramic material as of the oxygen concentration element and the oxygen pump element (i.e., solid electrolyte ceramic having an oxygen ion conductivity), or ceramic material different from the material of the elements (e.g., $Al_2 O_3$ (including porous form)); more preferably, the material of the prop(s) comprises material which can be integrated by sintering with the oxygen concentration cell element and with the oxygen pump element.

The oxygen concentration cell element and the oxygen pump element can be formed like elongated plates and can be disposed so as to face each other. In this arrangement, the first to third electrodes can be formed on one-end sides of the surfaces of the oxygen concentration cell element and the oxygen pump element. A spacer having a thickness generally equal to the width of the space can be interposed between the oxygen concentration cell element and the oxygen pump element on the other end sides of the surfaces so that the spacer, the oxygen concentration cell element and the oxygen pump element are integrated together by sintering. Disposing the spacer between the oxygen concentration cell element and the oxygen pump element allows the required space to be readily formed, and the integration of the spacer provides the reinforcement of the plate-like oxygen concentration cell element and oxygen pump element and thus improves the mechanical strength of the sensor.

The exhaust gas sensor with such an arrangement can be produced efficiently by such a method as follows: In the above-mentioned method, the first and second ceramic powder compacts are formed like elongated plates and are disposed so as to face each other. Electrode patterns are formed on one-end sides of the surfaces of the first and second ceramic powder compacts. A spacer compact which is to be the spacer is interposed between the first and second ceramic powder compacts on the other end sides of the surfaces. As a result of the sintering of the laminate of the spacer compact and the first and second ceramic powder compacts, the oxygen concentration cell element and the oxygen pump element are joined and integrated together through the medium of the spacer based on the spacer compact.

In this case, forming the above-mentioned prop or props in the space improves the dimensioned accuracy of the space. An additional spacer can be interposed between the oxygen concentration cell element and the oxygen pump element at a position which is longitudinally opposed to the spacer across the space. With this arrangement, the portions of the oxygen concentration cell element and of the oxygen pump element where the space is formed are supported at both sides with respect to the longitudinal direction by the spacer and the additional spacer, and therefore the mechanical strength of the space portion of the sensor can be significantly increased. On the other hand, the mechanical strength of the space portion of the sensor can be similarly increased by the arrangement in which reinforcing spacers are interposed between the integrated with the oxygen concentration cell element and the oxygen pump element so as to extend along part of the periphery of the space, e.g., along both longitudinal side edges of the elements. In these arrangements, the spacer, the prop(s), the additional spacer, and the reinforcing spacer may comprise the same ceramic material as of the oxygen concentration cell element and the oxygen pump element. In this case, between those spacers and prop(s) and at least one of the oxygen concentration cell element and the oxygen pump element are preferably interposed an insulating layer or insulating layers for preventing the current leakage between the oxygen concentration cell element and the oxygen pump element.

An example of more simple arrangement of the sensor is as follows: The oxygen concentration cell element and the oxygen pump element are formed like elongated plates and are disposed so as to face each other. The electrodes are formed on one-end portions of the surfaces of the oxygen concentration cell element and the oxygen pump element. In the space between the oxygen concentration cell element and the oxygen pump element are formed prop(s) which define the distance of the space without impeding gas from flowing into and out of the space. In the area except the space, the oxygen concentration cell element and the oxygen pump element are joined and integrated together through the medium of an insulating layer. With this arrangement, the space can be formed without use of spacer(s), and the sensor can be made more compact. Besides, the processes of the production, disposition and lamination of the spacer(s) can be omitted, and therefore the sensor can be produced more efficiently.

An example of the method of producing the sensor with the arrangement is as follows: In this method, first and second ceramic powder compacts are formed like elongated plates and are laminated together. Electrode patterns are formed on one-end sides of the surfaces of the first and second ceramic powder compacts. Prop patterns which are to be the prop(s) are formed with use of ceramic powder paste in the area which is to be the space between the first and second ceramic powder compacts. Additional supporting patterns are formed at positions which do not interfere with the prop patterns, in the are which is to be the space, with use of powder paste made from material which would burn or decompose (or would burn or decompose to vanish) by sintering. An insulating layer pattern is formed between the first and second ceramic powder compacts in the area except the area which is to be the space. By sintering the laminate, the space and the prop(s) based on the prop patterns are formed between the oxygen concentration cell element and the oxygen pump element and, in the area except the space, the oxygen concentration cell element and the oxygen pump element are joined together through the medium of an insulating layer based on the insulating layer pattern. The prop patterns and the additional supporting patterns can be formed by printing.

When the first and second ceramic powder compacts are laminated together, the prop patterns and additional supporting patterns which have been formed complimentarily by printing or the like method as described above prevent or restrain the crush of the prop patterns between both the compacts, on the basis of the reinforcement effect by the additional supporting patterns. Besides, the space having a given width can be formed accurately and very simply between the oxygen concentration cell element and the oxygen pump element, because the sintering causes the additional supporting patterns to burn or decompose to vanish. Even though the insulating layer pattern is formed so as to be considerably thinner than the prop patterns, the first and second ceramic powder compacts which are formed of, e.g., ceramic green sheets can be brought into intimate contact with each other through the medium of the insulating layer pattern by slight flexes of the compacts and can be integrated together by sintering, without a hitch.

The insulating layer pattern can be formed with use of paste of insulating ceramic powder such as $Al_2 O_3$ powder. In this case, the prop patterns formed with use of paste of insulating ceramic powder, such as $Al_2 O_3$ porous powder, which has larger particle diameters than the powder for the insulating layer pattern further resist being crush in the lamination. The additional supporting patterns can be formed with use of, e.g., paste composed mainly of carbon powder.

In the above-mentioned exhaust gas sensor, it is advantageous in the improvement of the detecting accuracy of the sensor to make the space between the oxygen pump element and the oxygen concentration cell element as small as possible (preferably not more than 1 mm) to obtain the maximum effect of the space for restricting the influx of new exhaust gas. Conversely, the space of too large width may cause an unstable reaction between HC and oxygen on the electrode(s) having catalytic activity and may decrease the electromotive force of the oxygen concentration cell, thus resulting in an insufficient sensor output. This tendency is remarkable especially in the case that oxygen concentration in the exhaust gas subjected to measurement widely fluctuates, or in the case that water vapor concentration in the gas is considerably high. In the case that a space-forming member for forming a space (another space) of a given width between itself and the oxygen concentration cell element is disposed on the side of the oxygen concentration cell element where the third electrode is formed, the width of the space is preferably made as small as possible (preferably not more than 1 mm) by the same reasons.

With the space(s) between the elements of too small width, however, a slight deformation which may occur in the production of the oxygen pump element, the oxygen concentration cell element, and the space-forming member by sintering may significantly influence the width(s) of the space(s) and may cause a variation in output among individual sensors. In order to solve such a problem, such a sensor structure as will be described below is effective: The electrode on the side of the space on the oxygen pump element will be referred to as a first electrode; the electrode on the side of the space on the oxygen concentration cell element will be referred to as a second electrode; and the electrode on the side of the opposed space on the oxygen concentration cell element will be referred to as a third electrode. Measuring chamber(s) are formed so as to contact at least one of the second and third electrodes, and gas communicating portion(s) are formed so as to penetrate wall portion(s) of the measuring chamber(s) from the side of the atmosphere to be measured to the side of the measuring chamber(s). The gas communicating portion(s) are configured as diffusion flow regulator(s) comprising at least nay one of small bores, slit(s), and porous communicating portion(s) which comprise porous ceramic or porous metal.

A fifth arrangement of the exhaust gas sensor in accordance with the invention comprises: an oxygen concentration cell element comprising solid electrolyte which has an oxygen-ion conductivity, and having electrodes on both surfaces; an oxygen pump element comprising solid electrolyte which has an oxygen-ion conductivity, having electrodes on both surfaces, facing the oxygen concentration cell element to form between itself and the oxygen concentration cell element a space of a given width where the flow of exhaust gas is allowed, and pumping oxygen into or out of the space in such a direction that the absolute value of a concentration cell electromotive force generated in the oxygen concentration cell element decreases; a heater element or heater elements for heating at least one of the oxygen pump element and the oxygen concentration cell element to a predetermined operating temperature of the sensor, a measuring chamber or measuring chambers formed so as to contact at least one of a second electrode and a third electrode, wherein a first electrode is the electrode on the side of the space on the oxygen pump element, the second electrode being the electrode on the side of the space on the oxygen concentration cell element, the first electrode being the electrode on the side of the opposed space on the oxygen concentration cell element; and a gas communicating portion or gas communicating portions formed so as to penetrate wall portion(s) of the measuring chamber(s) from the side of the atmosphere to be measured to the side of the measuring chamber(s). The gas communicating portion(s) are configured as diffusion flow regulator(s) comprising at least any one of small bores, slit(s), and porous communicating portion(s) which comprise porous ceramic or porous metal.

In accordance with such an arrangement, even with the width of the space larger than a certain degree, exhaust gas flows into the measuring chamber(s) through the diffusion flow regulator(s) with the diffusion of the gas regulated and, after introduced into the measuring chamber(s), the gas is discharged into the atmosphere to be measured, with the diffusion of the gas regulated by the diffusion flow regulator (s). Accordingly, the residence time of the introduced exhaust gas in the measuring chamber(s) is increased; even though the composition (especially, the amount of oxygen or water vapor) of exhaust gas in the atmosphere subjected to detection changes, the influence of the change upon the gas in the measuring chamber(s) is thus restrained and a stable, high output of the sensor is obtained. As a result, the detection accuracy of the sensor can be increased.

A set of the measuring chamber and the diffusion flow regulator may be formed either on the side of the second electrode or on the side of the third electrode on the oxygen concentration cell element. For the purpose of improving the sensor output, it is more preferable to form the set at least one the side of which the catalytic activity is the higher of the space between the oxygen pump element and the oxygen concentration cell element and of the opposed space, i.e., on the side where the reaction between oxygen and HC is the more active. More preferably, the above sets are formed on both sides of the oxygen concentration cell element.

The measuring chamber(s) and the diffusion flow regulator(s) are formed as follows: In the case that those are formed on the side of the space between the oxygen concentration cell element and the oxygen pump element, a wall portion may be formed so as to surround the second electrode and so as to define as the measuring chamber a space surrounded by the inside surfaces of the wall portion and by the surfaces facing each other of the oxygen concentration cell element and of the oxygen pump element. The diffusion flow regulator(s) are formed so as to penetrate at least one of the wall portion and the oxygen concentration cell element from the side of the atmosphere to be measured to the side of the measuring chamber, and may be formed as slit(s) or small bores which provide a communication between the atmosphere to be measured and the measuring chamber. The above-mentioned porous ceramic body (or porous metal body) which allows gas to flow between the space and the atmosphere to be measured is also capable of serving as the diffusion flow regulator.

In the case that the slit(s) are formed as the diffusion flow regulator(s), a wall-forming body constituting at least a part of the wall portion can be disposed, e.g., between the oxygen concentration cell element and the oxygen pump element, and the slit(s) can be formed between the wall-forming body and at least one of the oxygen concentration cell element and the oxygen pump element, so as to extend along surface(s) of the oxygen concentration cell element and/or the oxygen pump element. This arrangement allows exhaust gas to be introduced smoothly into the measuring chamber(s) through the slit(s) without spatial bias.

With the width (the distance) of the slit given as d and the size of the measuring chamber in the direction in which the oxygen concentration cell element and the oxygen pump element face (hereinafter referred to as the height of the measuring chamber) given as h, the ratio d/h is preferably adjusted within the range from 1/100 to 1/4. The ratio d/h larger than 1/4 may result in an insufficient effect of the slit for regulating the diffusion of exhaust gas and insufficient sensor outputs. The ratio d/h smaller than 1/100 may result in too low rate of gas flow into or out of the measuring chamber(s) and may lower the detection accuracy of the senor. The radio d/h is more preferably adjusted within the range from 1/20 to 1/8. By the same reasons, the ratio S/V of the total area S of the inner surfaces of the slit to the volume V of the space in the slit is preferably adjusted within the range from 4 to 100, more preferably from 20 to 50.

The absolute value of the slit width d is preferably adjusted within the range from 0.01 to 1.0 mm. The width d larger than 1.0 mm may result in an insufficient effect of the slit for regulating the diffusion of exhaust gas and insufficient sensor outputs. The width d smaller than 0.01 mm may result in too low rate of gas flow into or out of the measuring chamber(s) and may lower the detection accuracy of the sensor. The width d is more preferably set within the range from 0.02 to 0.05 mm.

The slit(s) can be formed in the middle portion of the thickness of the wall-forming body (the middle portion with respect to the direction in which the oxygen concentration cell element and the oxygen pump element are laminated); however, it is more advantageous in the production of the sensor to form the slit(s) between the wall-forming body and at least one of the oxygen concentration cell element and the oxygen pump element. In the former case, an increase in the number of the steps for the production is inevitable. For example, space(s) which are to be the slit(s) have to be previously bored through a ceramic compact (hereinafter referred to as a "wall-forming compact") which is to be the wall-forming body, or the ceramic compact has to be formed of two parts adjoining in the direction of the thickness and has to be sintered with a space formed between the parts. In the latter case, on the other hand, the exhaust gas sensor with the above structure can be produced simply by the formation of space(s) of given width(s) between the wall-forming compact and ceramic compact(s) (hereinafter referred to as "element-forming compact(s)") which are to be the oxygen concentration cell element and/or the oxygen pump element, and by the sintering of the compacts.

The slit(s) can be formed, e.g., by the interposal of layer(s) formed of material (such as carbon paste) which would burn up by sintering, between the wall-forming compact and the element-forming compact(s) in the area(s) where the slit(s) are to be formed, and by the sintering of the laminate, which causes the layer(s) to burn up. In this case, the width(s) of the slit(s) to be formed can be freely adjusted by the adjustment of the thickness(es) of the layer(s) to be formed.

The wall-forming body can be integrated by sintering with at least one of the oxygen pump element and the oxygen concentration cell element. The integration by sintering increases the mechanical strength of the sensor. In the case that the slit(s) are formed only between the wall-forming body and any one of the oxygen pump element and the oxygen concentration cell element; on the side where the slit(s) are not formed the wall-forming compact and the element-forming compact are integrated together over generally the entire area of the laminated surfaces. On the side where the slit(s) are formed, the slit(s) can be formed by the interposal of the layer between part of the laminated surfaces; the wall-forming compact and the element-forming compact can be integrated together in the area in the laminated surfaces where the layer is not interposed. In this case, even on the side where the slit(s) are formed, the wall-forming body and the oxygen pump element and/or the oxygen concentration cell element are integrated together in the area except the area where the slit(s) are formed, and therefore the strength of the sensor can be further increased.

In the case that the diffusion flow regulator is formed of small bores instead of cause exhaust gas to flow into the measuring chamber(s) without bias, in this case, it is preferably to form at given intervals a plurality of small bores, e.g., extending in direction(s) parallel with the surfaces of the plate-like oxygen pump element and oxygen concentration cell element. The small bores can be formed so as to penetrate the oxygen concentration cell element in the direction of the thickness. In this case, it is preferable in achieving the unbiased influx of exhaust gas to form a plurality of the small bores at given intervals along the periphery of the second or third electrode.

The oxygen pump element and the oxygen concentration cell element can be formed like elongated plates, and the diffusion flow regulator may comprise slits, or a plurality of small bore groups arranged at given intervals, the slits or the plurality of small bore groups formed on both longitudinal sides of the oxygen pump element and the oxygen concentration cell element. With this arrangement, the exhaust gas which has been flowed into the measuring chamber through the slit or the small bore groups on one side is discharged through those on the other side. As a result, exhaust gas is allowed to flow smoothly in the measuring chamber, and thus the responsivity of the sensor output can be improved.

In the above-mentioned exhaust gas sensor, a measuring chamber may be formed on the opposite side of the oxygen concentration cell element to the space, as follows: Such a space-forming member described above for forming another space between itself and the oxygen concentration cell element is disposed so as to face the opposite side of the oxygen concentration cell element. Between the space-forming member and the oxygen concentration cell element, a wall portion is formed so as to surround the third electrode, so that the measuring chamber is formed of the space surrounded by the inside surfaces of the wall portion and by the surfaces facing each other of the space-forming member and the oxygen concentration cell element.

In this case also, the diffusion flow regulator can be formed in generally the same manner as the measuring chamber formed between the oxygen pump element and the oxygen concentration cell element. The diffusion flow regulator is formed so as to penetrate at least one of the wall portion and the space-forming member from the side of the atmosphere to be measured to the side of the measuring chamber, and may be formed as slit(s) or small bores which provide a communication between the atmosphere to be measured and the measuring chamber. Between the space-forming atmosphere to be measured and the measuring chamber. Between the space-forming member and the oxygen concentration cell element, a wall-forming body constituting at least a part of the wall portion can be disposed, and the slit(s) can be formed between the wall-forming body and at least one of the space-forming member and the oxygen concentration cell element so as to extend along surface(s) of the space-forming member and/or the oxygen concentration cell element.

The wall-forming body can be integrated by sintering with at least one of the space-forming member and the oxygen concentration cell element. The space-forming member and the oxygen concentration cell element can be formed like elongated plates, and the diffusion flow regulator may comprise slits formed on both longitudinal sides of the space-forming member and the oxygen concentration cell element.

An exhaust gas sensor system employing the exhaust gas sensor of the invention can be provided with heat generation control means which controls the heat generation in the heater element(s) so as to approach the temperature of the oxygen concentration cell element to a predetermined temperature target value. In the sensor system, the operation of the oxygen pump element is controlled with reference to the concentration cell electromotive force generated in the oxygen concentration cell element; however, the concentration cell electromotive force varies with the temperature of the element, and therefore a change in the temperature of the oxygen concentration cell element causes a fluctuation of the concentration cell electromotive force and a fluctuation of the pump current as information on detected concentrated, even though the concentration of a constituent to be detected is constant. Such a fluctuation would result in an increase in measurement error. By the provision of such heat generation control means as described above, however, the heat generation in the heater element(s) is controlled so that the temperature of the oxygen concentration cell element approaches the predetermined temperature target value. As a result, the measurement error on the constituent to be detected, which error is caused by a change in the temperature of the element, can be decreased and thus the measurement accuracy can be improved.

The heat generation control means may comprise temperature detecting means for detecting the temperature of the oxygen concentration cell element, and energization control means for controlling the energization for the heater element (s) so as to approach the temperature of the oxygen concentration cell element to a temperature target value on the basis of the temperature detected by the temperature detecting means. By this arrangement, information on the pump current is corrected on the basis of the detected temperature, even in the case that the temperature of the oxygen concentration cell element is transiently changed by a sudden changed in the temperature of exhaust gas or the like reason. Accordingly, the accuracy of detecting the constituent to be detected can be maintained satisfactorily. The temperature of the oxygen concentration cell element may be measured with a temperature sensor provided additionally, such as thermistor and thermocouple; however, measuring the temperature by making use of the fact that the internal resistance of the oxygen concentration cell element varies with the temperature requires no additional temperature sensor and thus allows the arrangement of the measuring system to be simplified.

In this arrangement, the sensor system may comprise concentration information correcting means for producing information on the temperature-compensated concentration of a constituent to be detected, on the basis of the temperature detected by the temperature detecting means and on the basis of the pump current information, and corrected measurement output means for outputting the produced information on the concentration of the constituent to be detected, as a corrected measurement.

More specifically, the concentration information correcting means may comprise: correction reference information storing means for storing, as correction reference information, information on the relation between temperature deviation and pump current correct, which information provides the relation between temperature deviations from the temperature target value and corrections for pump current information (pump current correction); pump current correcting determining means for determining the correction for pump current which corresponds to the difference between the temperature detected by the temperature detecting means and the temperature target value, with reference to the correction reference information; and correction calculating means for calculating to correct the measured pump current, on the basis of the determined pump current correction. With this arrangement, the pump current information can be corrected on the basis of the conversion of a temperature deviation from the target temperature, to a pump current correction. As a result, the algorithm of the correction process can be simplified and thus the responsivity of outputting the correction for a measurement of the concentration of a constituent to be detected can be improved.

In this arrangement, the concentration information correcting means can be provided with pump current/concentration converting means for converting the pump current information into information on the concentration of the constituent to be detected. The corrected measurement output means is capable of outputting information on the converted concentration of the constituent to be detected, as the information on the temperature-compensated concentrated of the constituted to be detected. More specifically, the pump current/concentration converting means may comprise storage means for storing pump current/concentration information which represents the relation between the pump currents and the concentrations of a constituent to be detected; and concentration calculating means for calculating the concentration of the constituent to be detected which is indicated by the corrected pump current information, with reference to the pump current/concentration information which has been stored. The corrected measurement output means can be adapted so as to output the calculation result; however, the output means may be adapted so as to output the corrected pump current information just as it is.

Alternatively, the concentration information correcting means may comprise: correction reference information storing means for storing, as correction reference information, pump current/concentration information which represents, for various temperatures, relations between the pump currents and the concentrations of a constituent to be detected; and corrected concentration information producing means which refers to the correction reference information on the basis of the temperature detected by the temperature detecting means and the measured pump current, and thereby produces the value of the concentration of the constituent to be detected which corresponds to the temperature and the pump current, as the information on the temperature-compensated concentration of the constituent to be detected. In this arrangement, it is necessary to prepare the pump current/concentration information for various temperatures; however, the concentration of the constituent to be detected which corresponds to the temperature and pump current which have been measured can be directly determined without the calculation of the pump current correction from the detected temperature. Accordingly, the responsivity of outputting the concentration of the constituent to be detected can be further improved.

The temperature detecting means may comprise internal-resistance measuring means for measuring the internal resistance of the oxygen concentration cell element, temperature information producing means for producing information on the temperature of the oxygen concentration cell element on the basis of the measured internal resistance, and temperature information output means for outputting the produced information on the temperature. As described above, this arrangement does not require any additional temperature sensor or the like, and allows the arrangement of the system to be simplified.

More specifically, the internal-resistance measuring means may comprise detecting-current passing means for passing an internal-resistance detecting current of a constant value through the oxygen concentration cell element, and voltage information detecting means for detecting information (voltage information) which reflects the voltage applied to the oxygen concentration cell element during the passage of the internal-resistance detecting current; and may be adapted so as to measure the internal resistance of the oxygen concentration cell element on the basis of the detected voltage information. This arrangement allows the internal resistance of the oxygen concentration cell element to be measured simply from the applied voltage at the time of the passage of the constant current.

In the case that there is a difference in oxygen concentration between both sides of the oxygen concentration cell element, a concentration cell electromotive force is generated in the oxygen concentration cell element, and the information on the concentration cell electromotive force included in or superposed on the detected voltage information may cause an error. In the measurement of the internal resistance of the oxygen concentration cell element, it is effective in improving the accuracy of measuring the internal resistance to increase the voltage applied to the oxygen concentration cell element, by the setting of the internal-resistance detecting current not less than a given value, in order to make the influence of the concentration cell electromotive force relatively small. In order to eliminate or decrease the superposed or included influence of the concentration cell electromotive force, the following method is also effective: The internal-resistance measuring means is provided with concentration cell electromotive force measuring means for measuring the concentration cell electromotive force of the oxygen concentration cell element through which the internal-resistance detecting current is not passed, and with voltage information correcting means for correcting the content of the detected voltage information on the basis of the measured concentration cell electromotive force. More specifically, the influence of the concentration cell electromotive force can be effectively eliminated by subtracting the measurement of the concentration cell electromotive force given by the concentration cell electromotive force measuring means, from the detected voltage information.

When the current for the measurement of internal resistance is passed through the oxygen concentration cell element, oxygen is transported in the oxygen concentration cell element, opposite to the direction of the current passage (i.e., the element acts as an oxygen pump), and oxygen concentrations vary on both sides of the oxygen concentration cell element. As a result, the changes in oxygen concentrations may lead up to an error of the accuracy of measuring the concentration of the constituent to be detected, when the exhaust gas sensor resumes measuring the concentration of the constituent to be detected. On the other hand, a considerably high internal resistance of the oxygen concentration cell element may make difficult the travel of oxygen ions in the oxygen concentration cell element and may cause a polarization in the element upon the passage of the current. The accuracy of measuring the concentration of the constituent to be detected, which accuracy is achieved after the resumption, can be improved and the polarized state of the oxygen concentration cell element can be terminated by the following operation: After the internal-resistance detecting current is passed through the oxygen concentration cell element and the internal resistance of the element is measured, a correction current is passed by correction current passing means through the oxygen concentration cell element, opposite in direction to the internal-resistance detecting current. By the current passage, oxygen is transported opposite to the above direction of the transportation, so that the oxygen concentrations which have changes approach the levels which had been given before the measurement of the internal resistance. The level of the correction current and the period of time for which the current is to be passed are preferably set so that oxygen of generally the same amount as considered to be transported during the passage of the internal-resistance detecting current is reversely transported by the passage of the correction current. For example, a current generally as much as the internal-resistance detecting current is preferably passed for generally as long period of time as the internal-resistance detecting current has been passed.

There can be additionally provided pump current controlling means which compares the concentration cell electromotive force of the oxygen concentration cell element with a predetermined control reference value and outputs to the oxygen pump element a pump current according to the difference between the concentration cell electromotive force and the target value EC of the electromotive force. By this arrangement, the pump current is controlled so that the concentration cell electromotive force approaches the target value EC of the electromotive force. In this regard, the internal-resistance measuring means can be provided with pump current interrupting means for interrupting with predetermined timing the pump current output from the pump current controlling means to the oxygen pump element, and the detecting current passing means can be adapted so as to pass the internal-resistance detecting current through the oxygen concentration cell element in the state where the pump current output is interrupted. By this arrangement, the interference between the internal-resistance detecting current and the pump current can be prevented and the internal resistance of the oxygen concentration cell element can be accurately detected.

In the case that the pump current output is interrupted for a considerably long period of time, the concentration cell electromotive force may deviate from the target value EC of the electromotive force and may become unstable, thus hindering the achievement of the fundamental object of the apparatus of the invention, i.e., the detection of the concentration of a constituent to be detected in exhaust gas. For that reason, the pump current interrupting means of the internal-resistance measuring means can be adapted so as to interrupt the pump current output from the pump current controlling means periodically at predetermined time intervals, so that the internal-resistance measuring means periodically measures the internal resistance of the oxygen concentration cell element, in accordance with the periodical interruption of the pump current output. By this arrangement, the frequency of measuring the internal resistance can be increased without long-lasting interruption of the pump current output. As a result, a measurement of the concentration of a constituent to be detected can be temperature-compensated with higher accuracy, and the temperature of the heater element(s) can be controlled more accurately by the heat generation control means which uses the internal resistance value as temperature information.

BRIEF DESCRIPTION OF THE DRAWINGS

FIG. 3A is a representation illustrating an example of assembly structure of the same;

FIG. 3B is a cross sectional view of FIG. 3A;

FIG. 19A is a representation illustrating an example of assembly structure of the same;

FIG. 19B is a cross sectional view of FIG. 19A;

FIG. 20 is an exploded view in perspective illustrating a method of producing the exhaust gas sensor of FIG. 17;

FIG. 26 is an exploded view in perspective illustrating a method of producing the exhaust gas sensor of FIG. 25;

FIG. 28 is an exploded view in perspective illustrating a method of producing the exhaust gas sensor of FIGS. 27A–27E;

FIG. 40A is a profile illustrating an example of measurement of a change in pump current caused by hard acceleration or hard deceleration of an engine;

FIG. 40B is a graph illustrating an example of the relation between the element temperatures and the correction of pump current;

FIG. 40C is a conceptual representation of a map illustrating the relation between the element temperatures and the correction of pump current;

FIG. 44A is a conceptual representation of a map illustrating the relation between the internal resistance of the oxygen concentration cell element and the correction of pump current;

FIG. 44B is a conceptual representation of a two-dimensional map illustrating the relation between the element temperatures and the pump currents and HC concentrations;

FIG. 57 is a schematic representation illustrating a laminate formed in the assemblage of the sensor of FIG. 53;

FIG. 58 is a schematic representation illustrating an experimental arrangement used in Experiment Example 1;

FIG. 59A is a graph illustrating the dependence of the conversion ratio h of methane upon temperature in a Pd porous electrode and in an Au porous electrode in Experiment Example 1;

FIG. 59B is a graph illustrating the dependence of the output of an exhaust gas sensor employing the electrodes upon temperature;

FIG. 60 is a graph illustrating the dependence of the output of the exhaust gas sensor of Experiment Example 1 upon methane concentration;

FIG. 61 is a graph illustrating the dependence of the electromotive force of the oxygen concentration cell element of the sensor upon methane concentration, for various combinations of electrodes;

FIG. 62 is a graph illustrating the influence which interfering gases exert upon the output of the exhaust gas sensor of Experiment Example 1;

FIG. 63 is a graph illustrating the influence which oxygen concentration exerts upon the output of the exhaust gas sensor of Experiment Example 1;

FIG. 64 is a graph illustrating the dependence of the output of an exhaust gas sensor of Experiment Example 2 upon methane concentration;

FIG. 65 is a graph illustrating the influence which oxygen concentration exerts upon the output of the exhaust gas sensor of Experiment Example 2;

FIG. 66 is a graph illustrating the dependence of the output of an exhaust gas sensor of a modification of Experiment Example 2 upon methane concentration;

FIG. 67 is a graph illustrating the dependence of the offset electromotive force of the oxygen concentration cell element of an exhaust gas sensor of Experiment Example 3 upon oxygen concentration;

Figure 68:
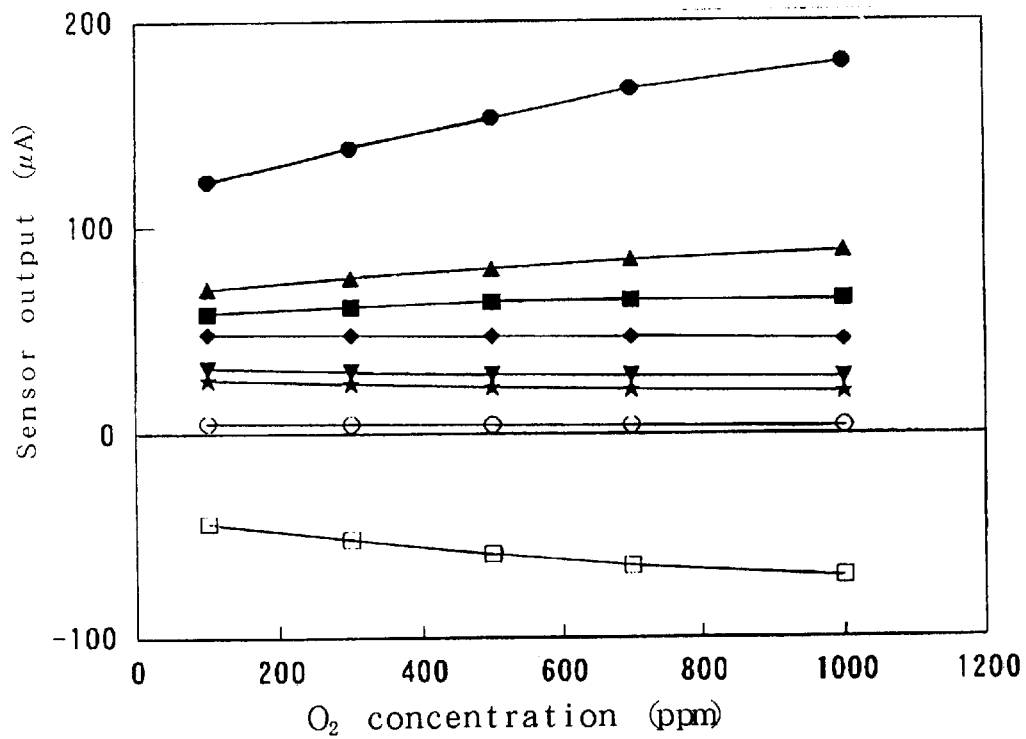
Figure 69:
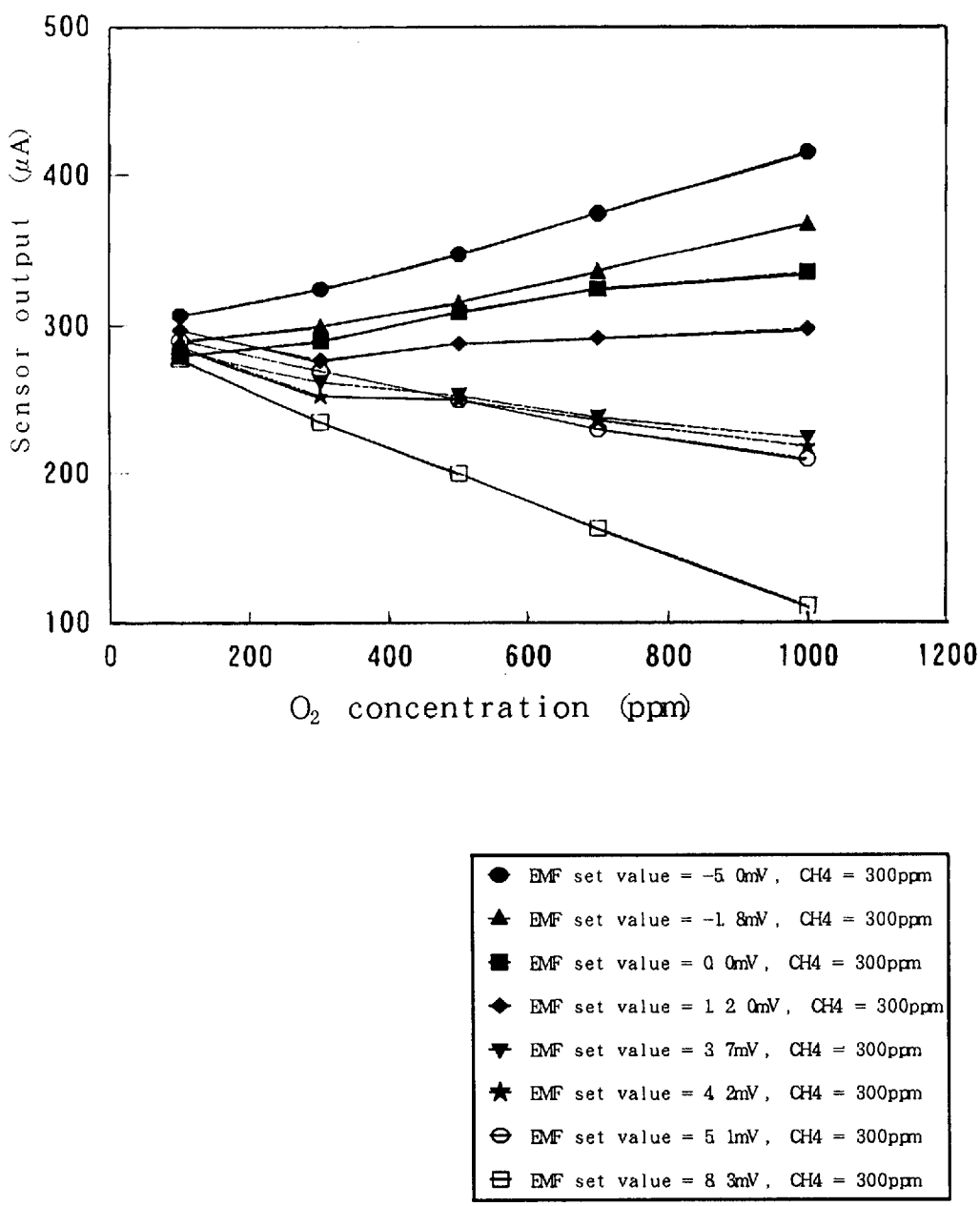
Figure 70:
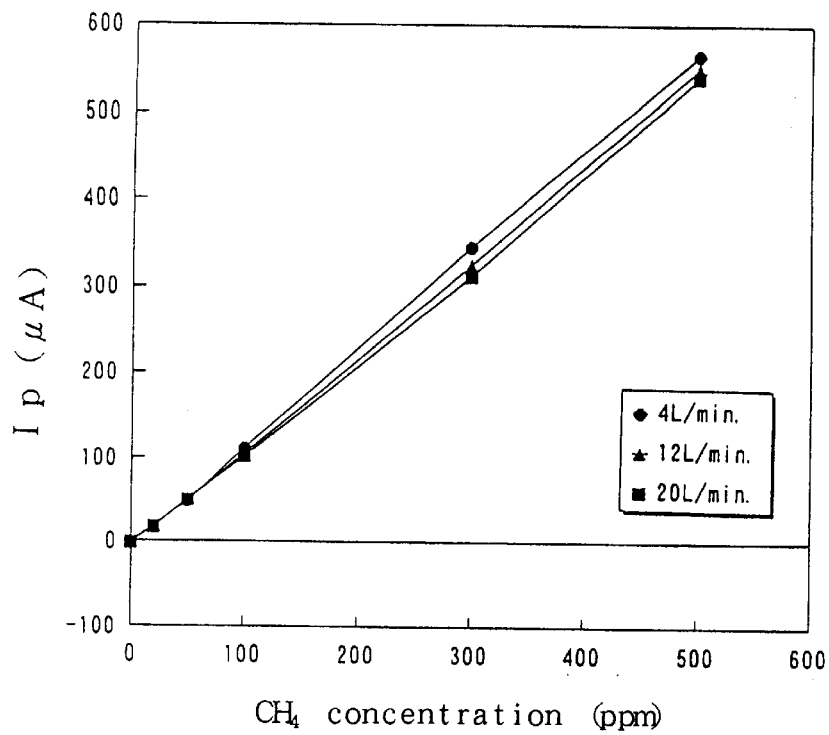
Figure 71:
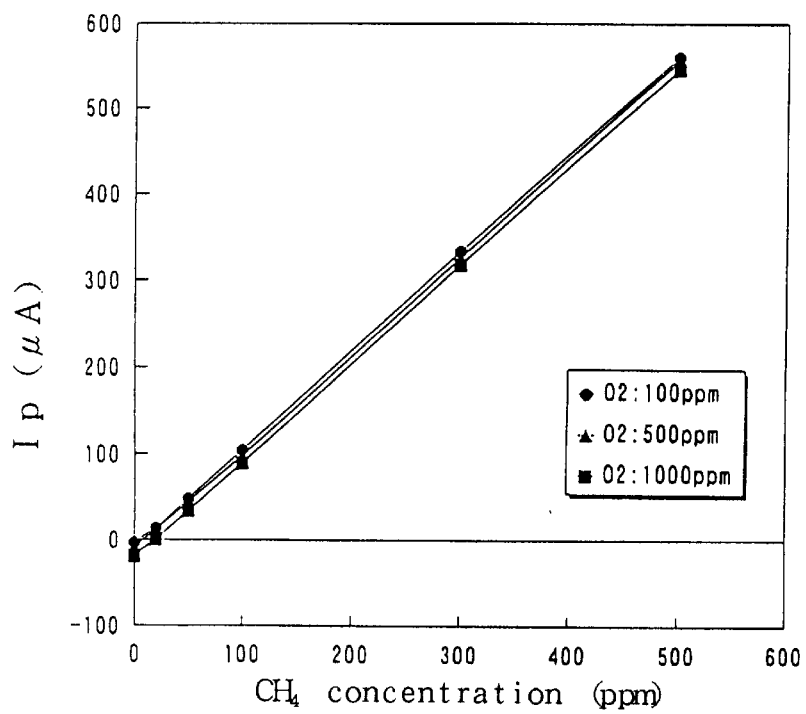
Figure 72:
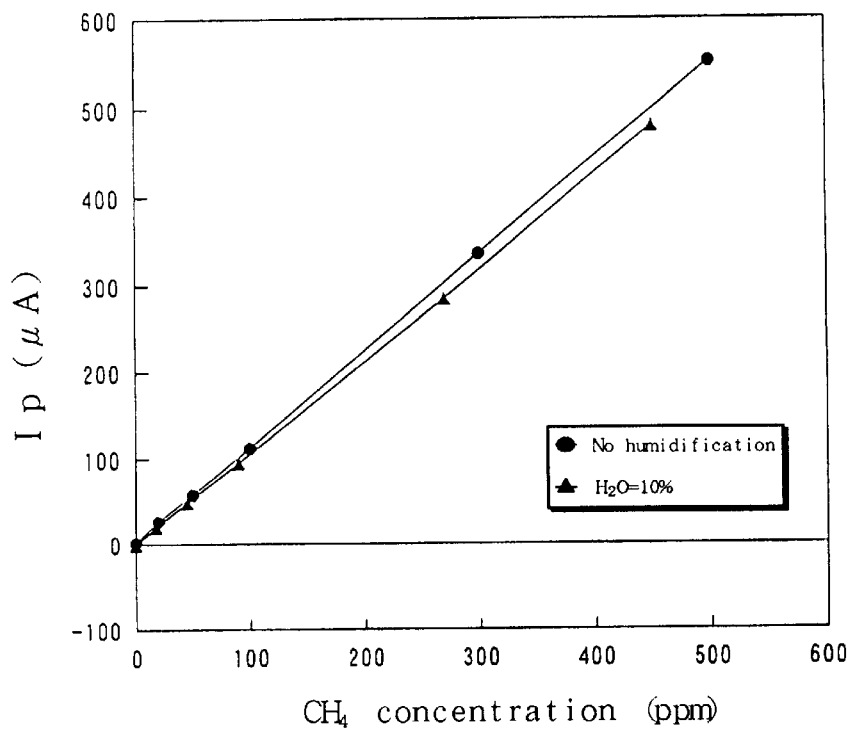
Figure 73:
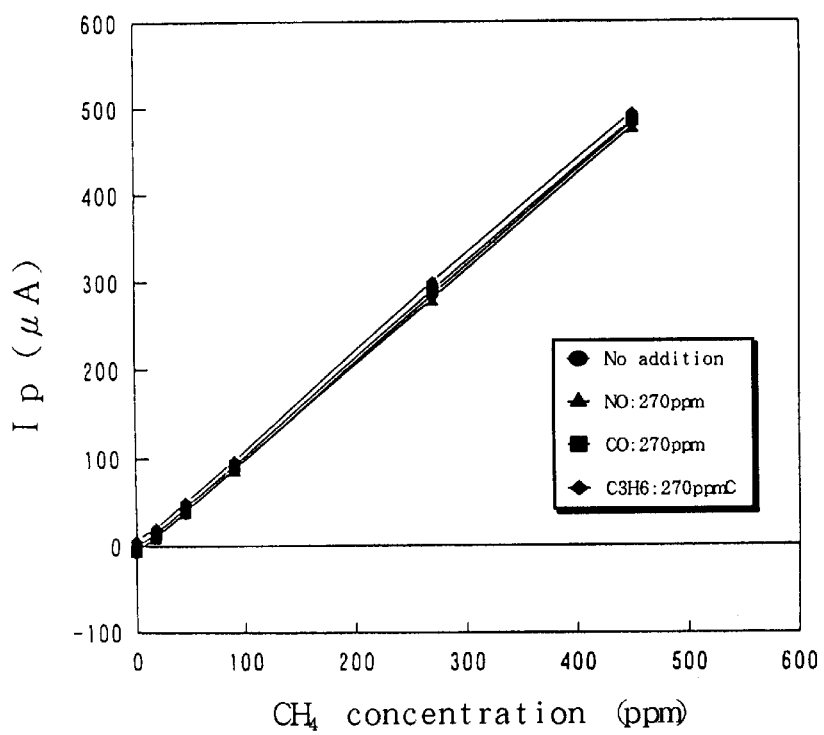
Figure 74:
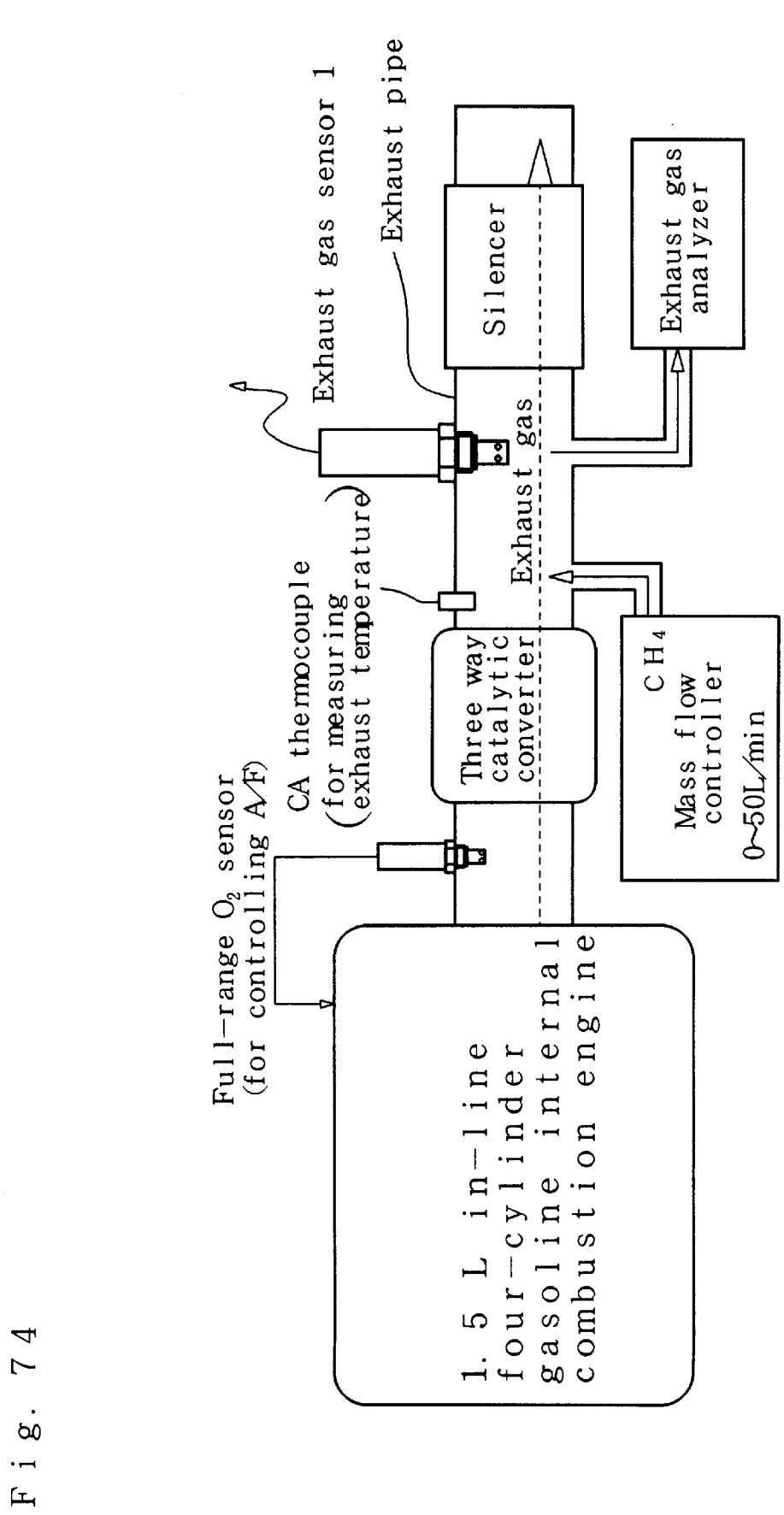
Figure 75:
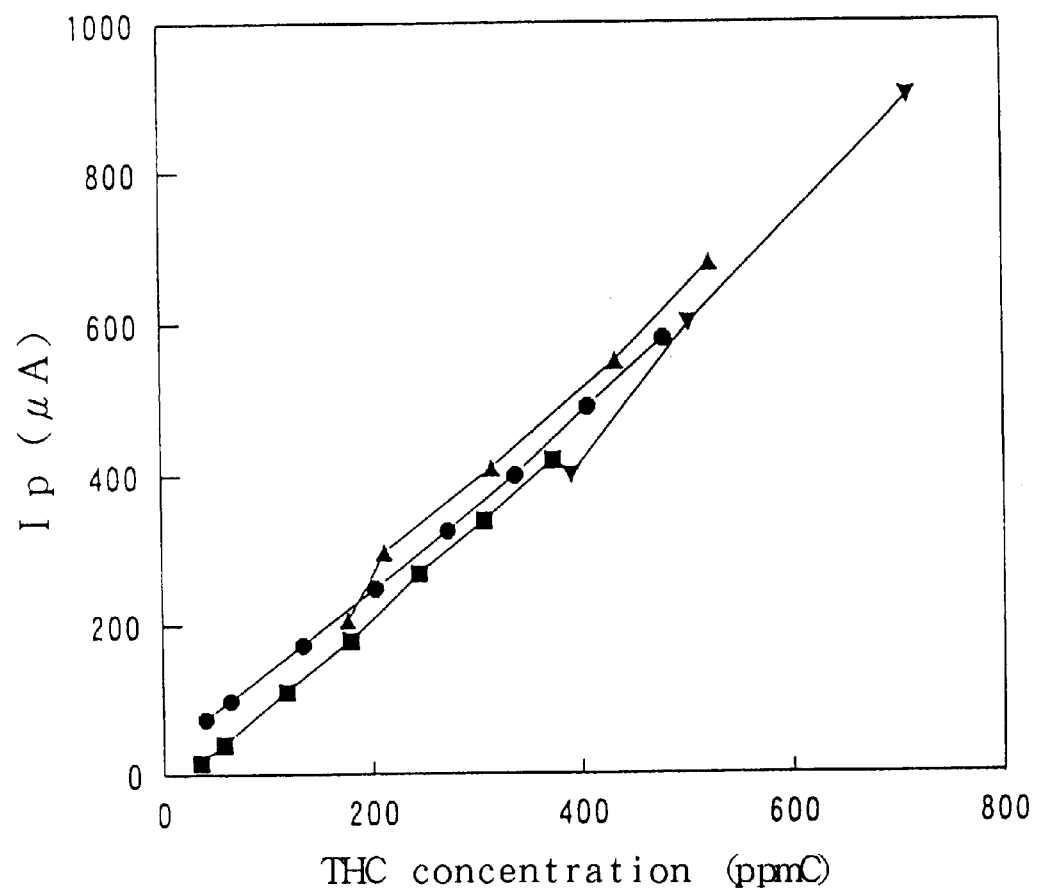
Figure 76:
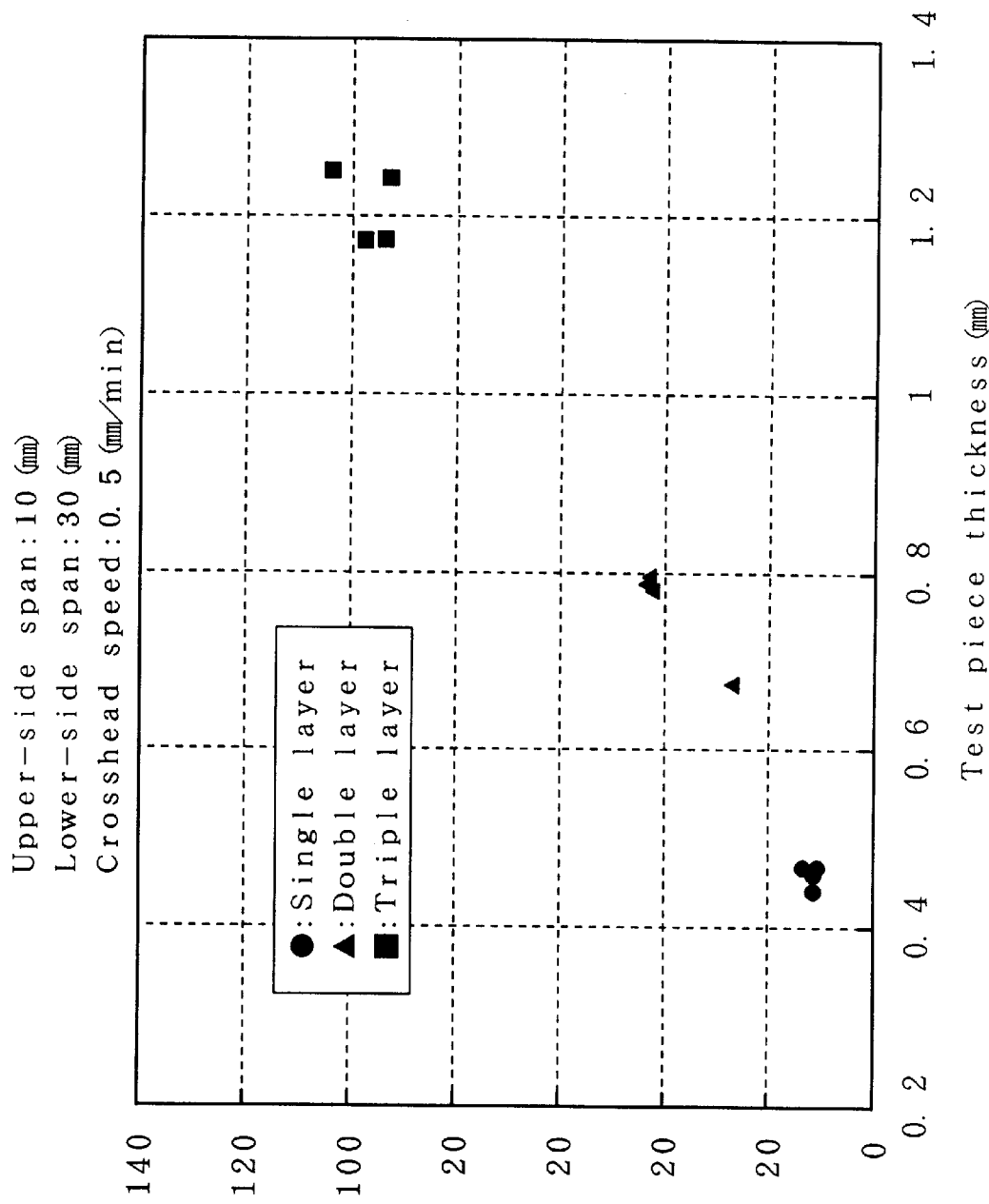
Figure 77A:
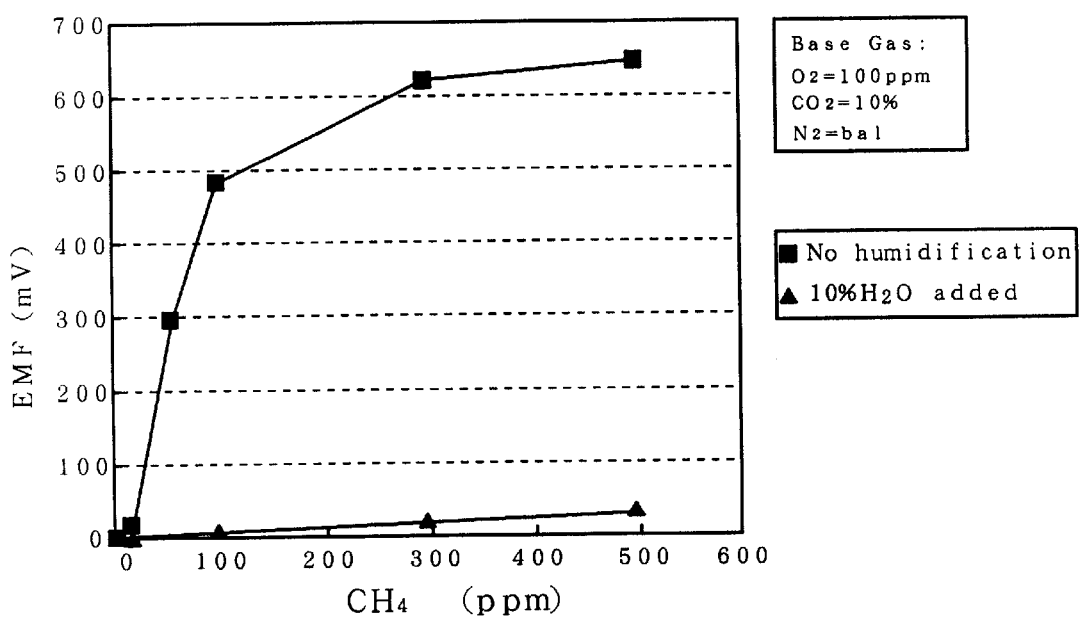
Figure 77B:
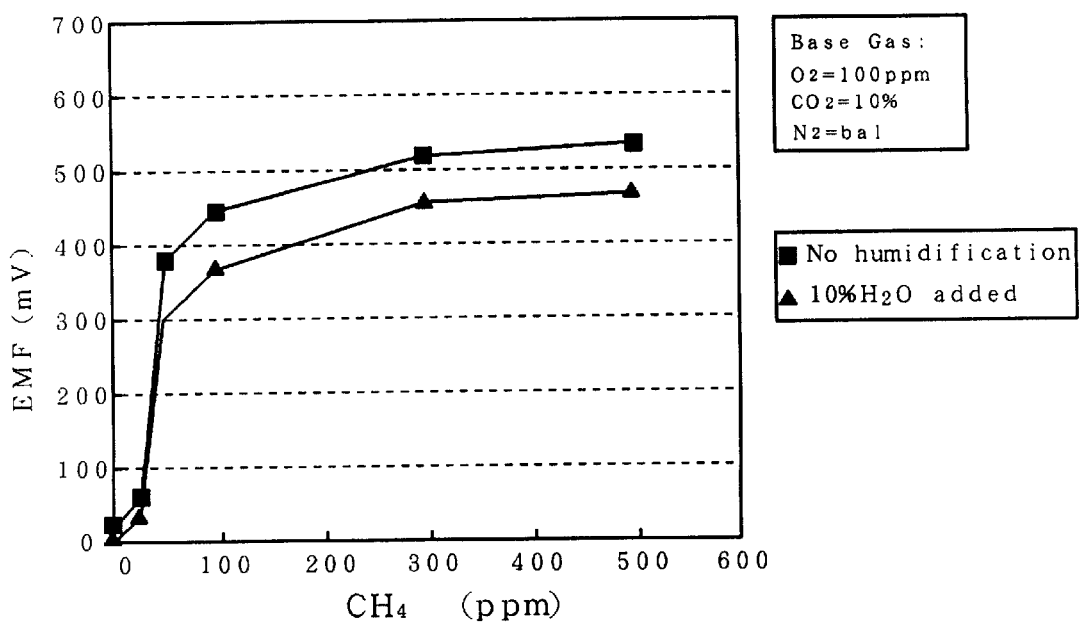
Figure 78A:
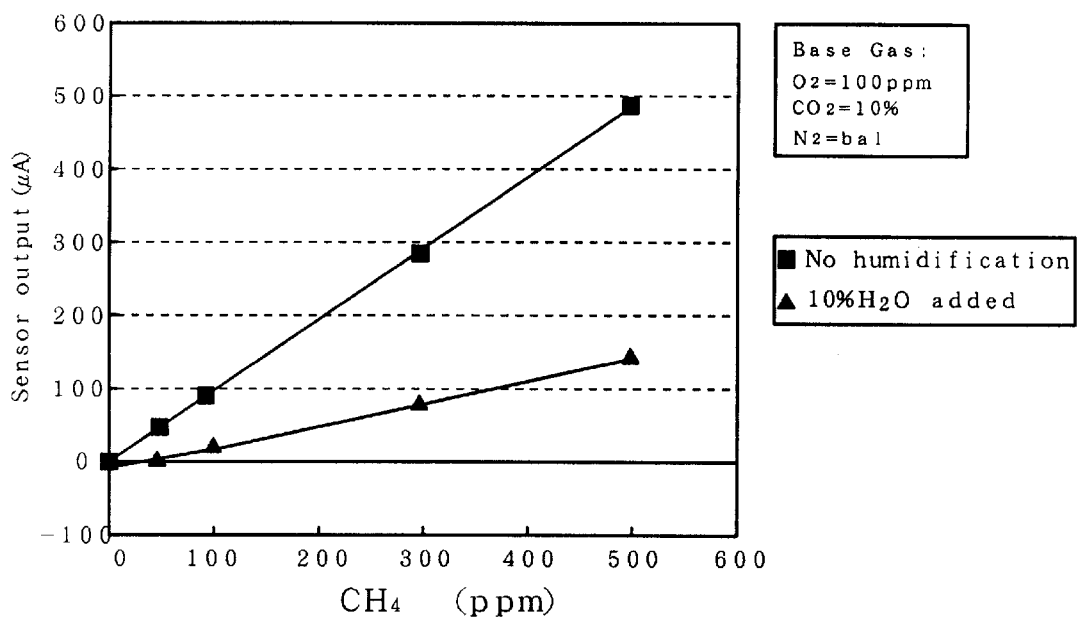
Figure 78B:
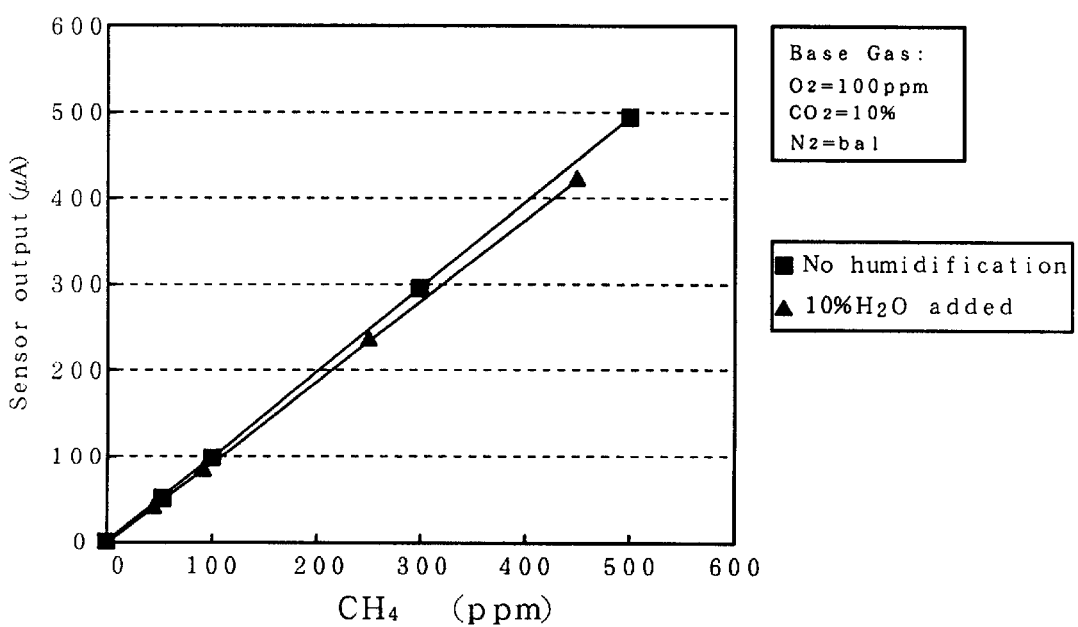
Figure 79A:
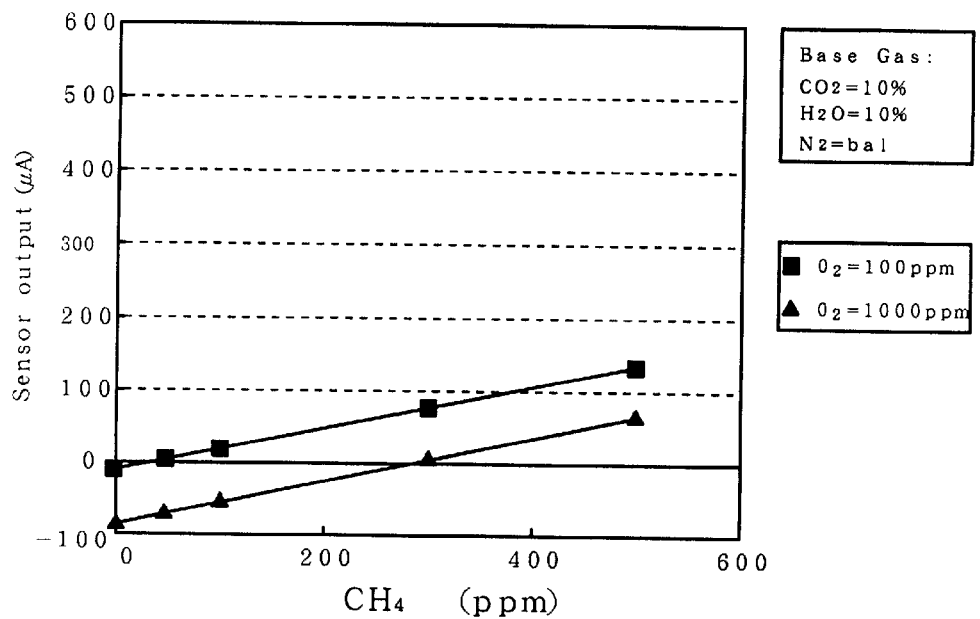
Figure 79B:
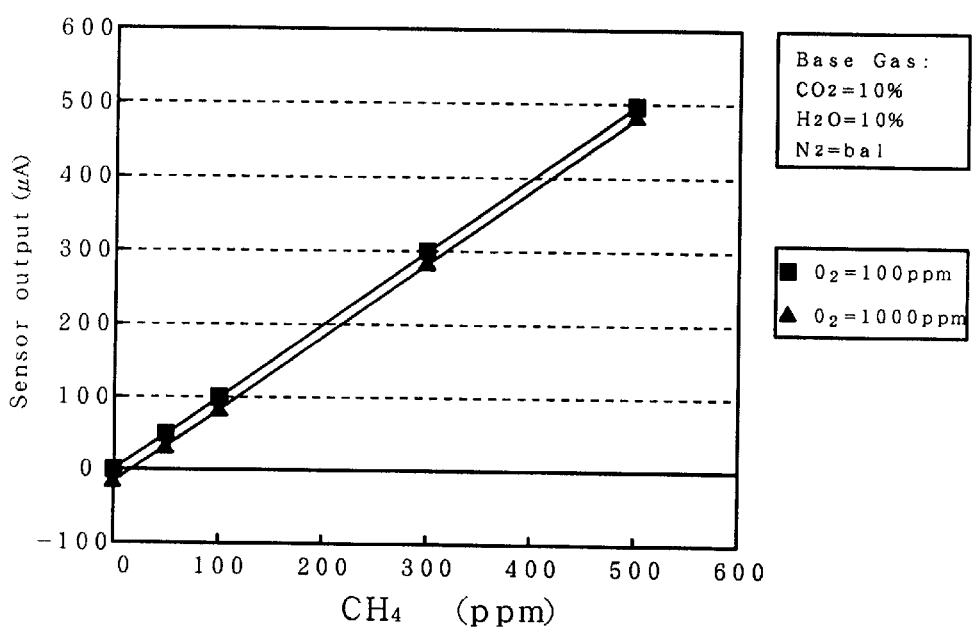
Figure 80A:
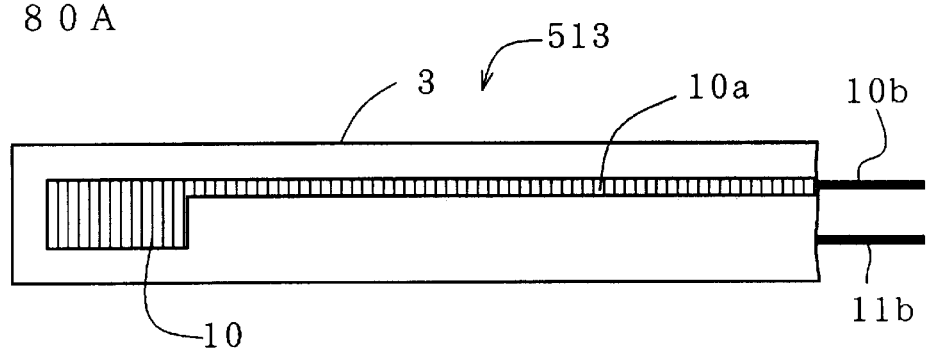
Figure 80B:
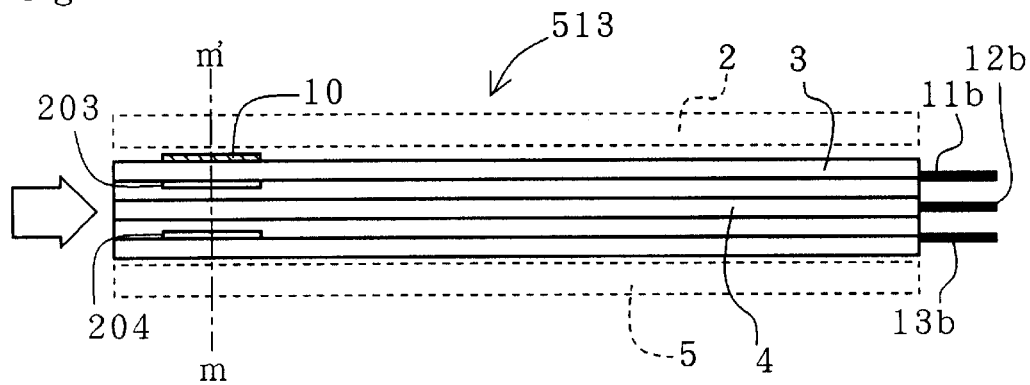
Figure 80C:
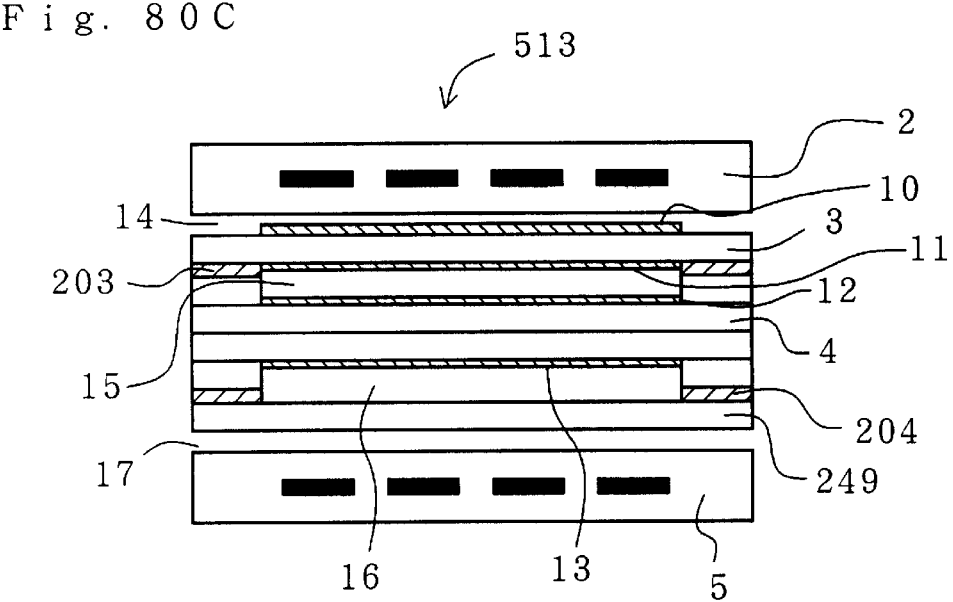
Figure 81:
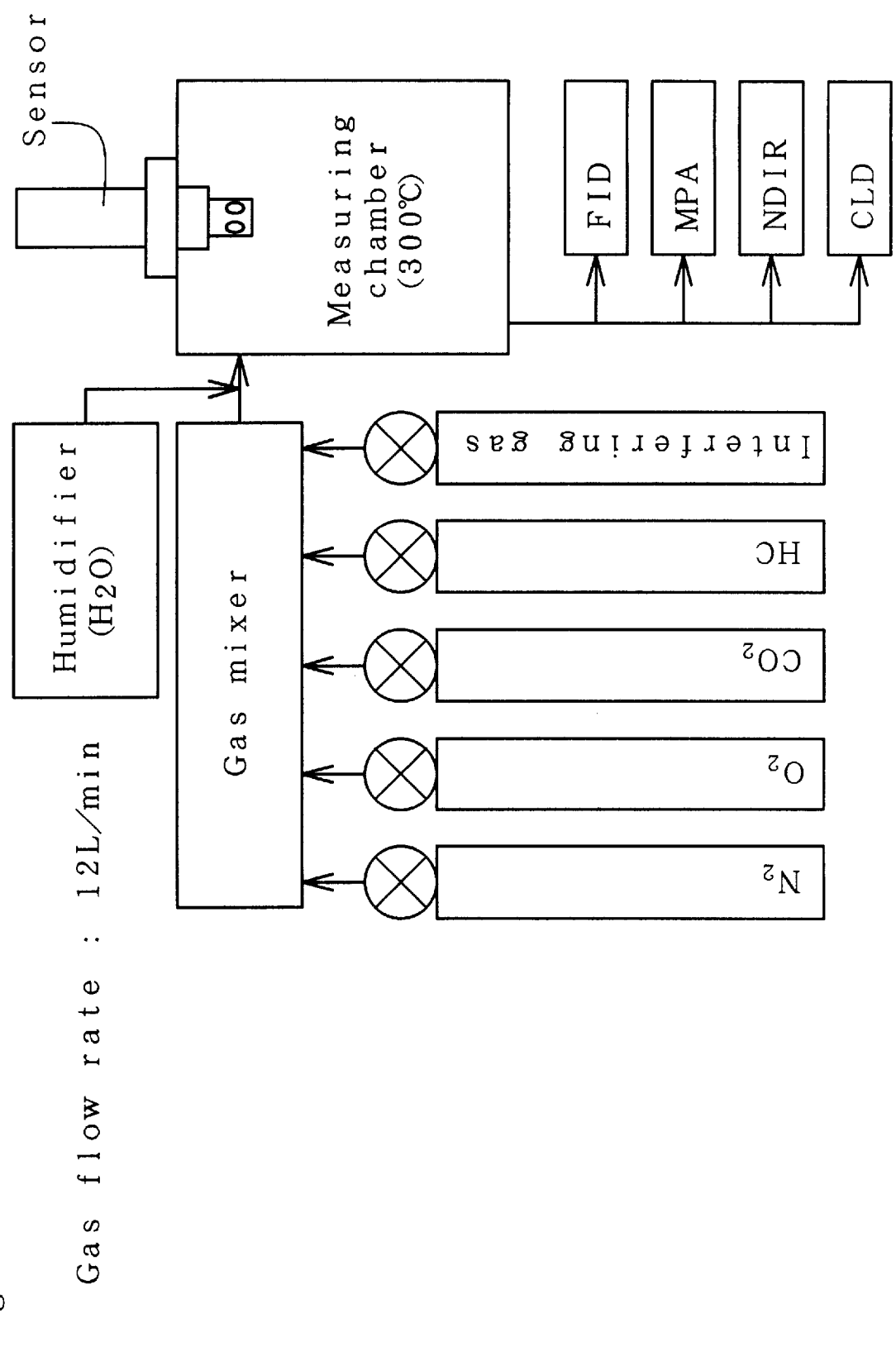
Figure 82:
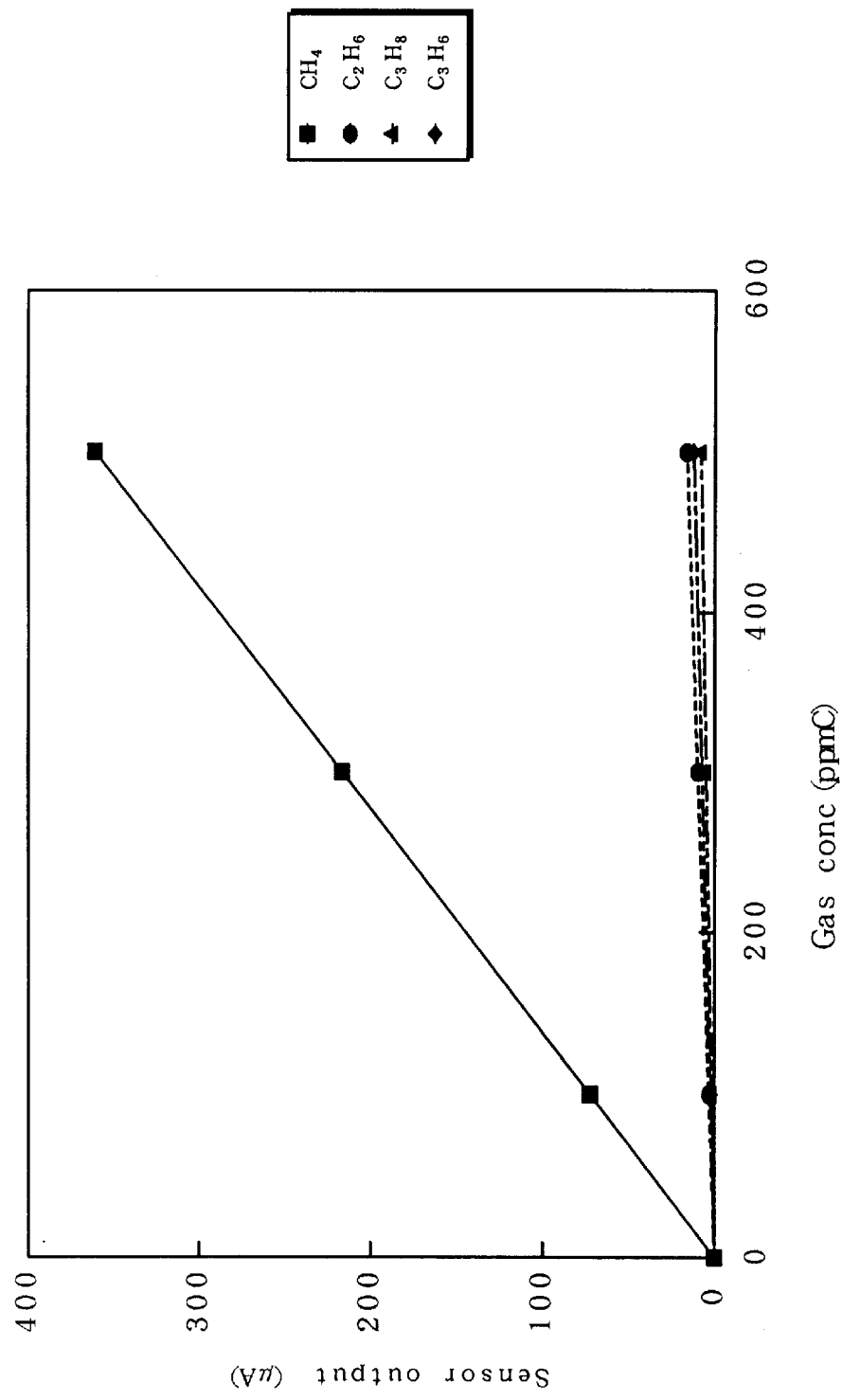
Figure 83:
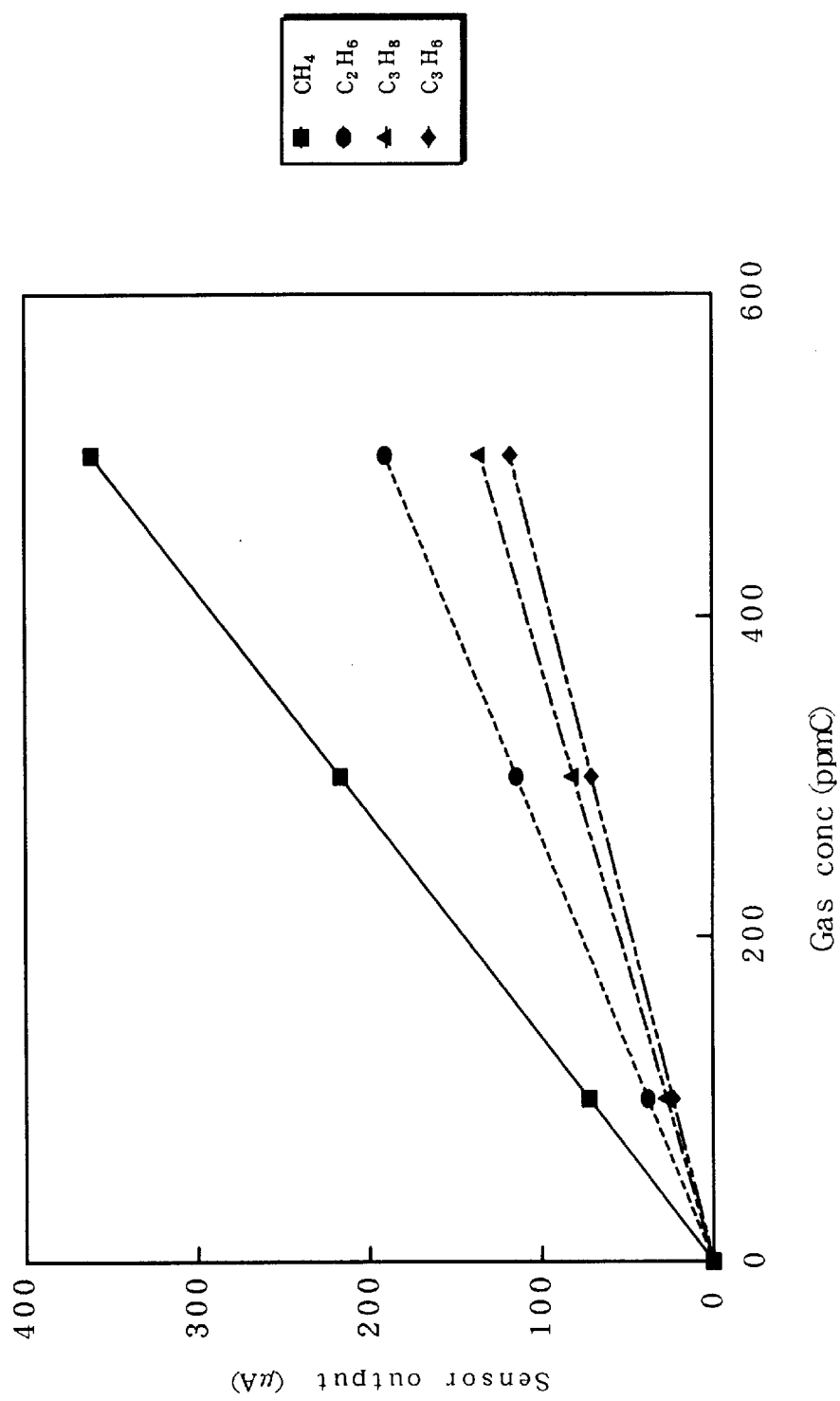

FIG. 68 is a graph illustrating the dependence of the output of the exhaust gas sensor of Experiment Example 5 upon oxygen concentration in the case that the target value of electromotive force is set at various values (with methane concentration of 0 ppm);

FIG. 69 is a graph illustrating the dependence of the output of the exhaust gas sensor of Experiment Example 3 upon oxygen concentration in the case that the target value of electromotive force is set at various values (with methane concentration of 300 ppm);

FIG. 70 is a graph illustrating the experiment result of Experiment Example 4;

FIG. 71 is a graph illustrating the experiment result of Experiment Example 5;

FIG. 72 is a graph illustrating the experiment result of Experiment Example 6;

FIG. 73 is a graph illustrating the experiment result of Experiment Example 7;

FIG. 74 is a schematic representation illustrating the arrangement of a system used in an experiment of Experiment Example 8;

FIG. 75 is a graph illustrating the experiment result of Experiment Example 8;

FIG. 76 is a graph illustrating the experiment result of Experiment Example 10;

FIG. 77A is a 1st graph illustrating the experiment result of Experiment Example 11;

FIG. 77B is a 2nd graph illustrating the experiment result of Experiment Example 11;

FIG. 78A is a 3rd graph illustrating the experiment result of Experiment Example 11;

FIG. 78B is a 4th graph illustrating the experiment result of Experiment Example 11;

FIG. 79A is a 5th graph illustrating the experiment result of Experiment Example 11;

FIG. 79B is a 6th graph illustrating the experiment result of Experiment Example 11;

FIG. 80A is a representation illustrating an exhaust gas sensor used in Experiment Example 12 (a plan view of the sensor from which heaters are removed);

FIG. 80B is a longitudinal section of the sensor of FIG. 80A;

FIG. 80C is a section along the line m-m' of FIG. 80B;

FIG. 81 is a block diagram illustrating a system for evaluating characteristics of gas sensor in Experiment Example 12;

FIG. 82 is a graph illustrating the evaluation result on an exhaust gas sensor of an embodiment in Experiment Example 12; and FIG. 83 is a graph illustrating the evaluation result on an exhaust gas sensor for reference in Experiment Example 12.

DETAILED DESCRIPTION OF THE PREFERRED EMBODIMENTS

Hereinafter, preferred embodiments of the invention will be described referring to some embodiments shown in the appended drawings.

Embodiment 1

Figure 1:
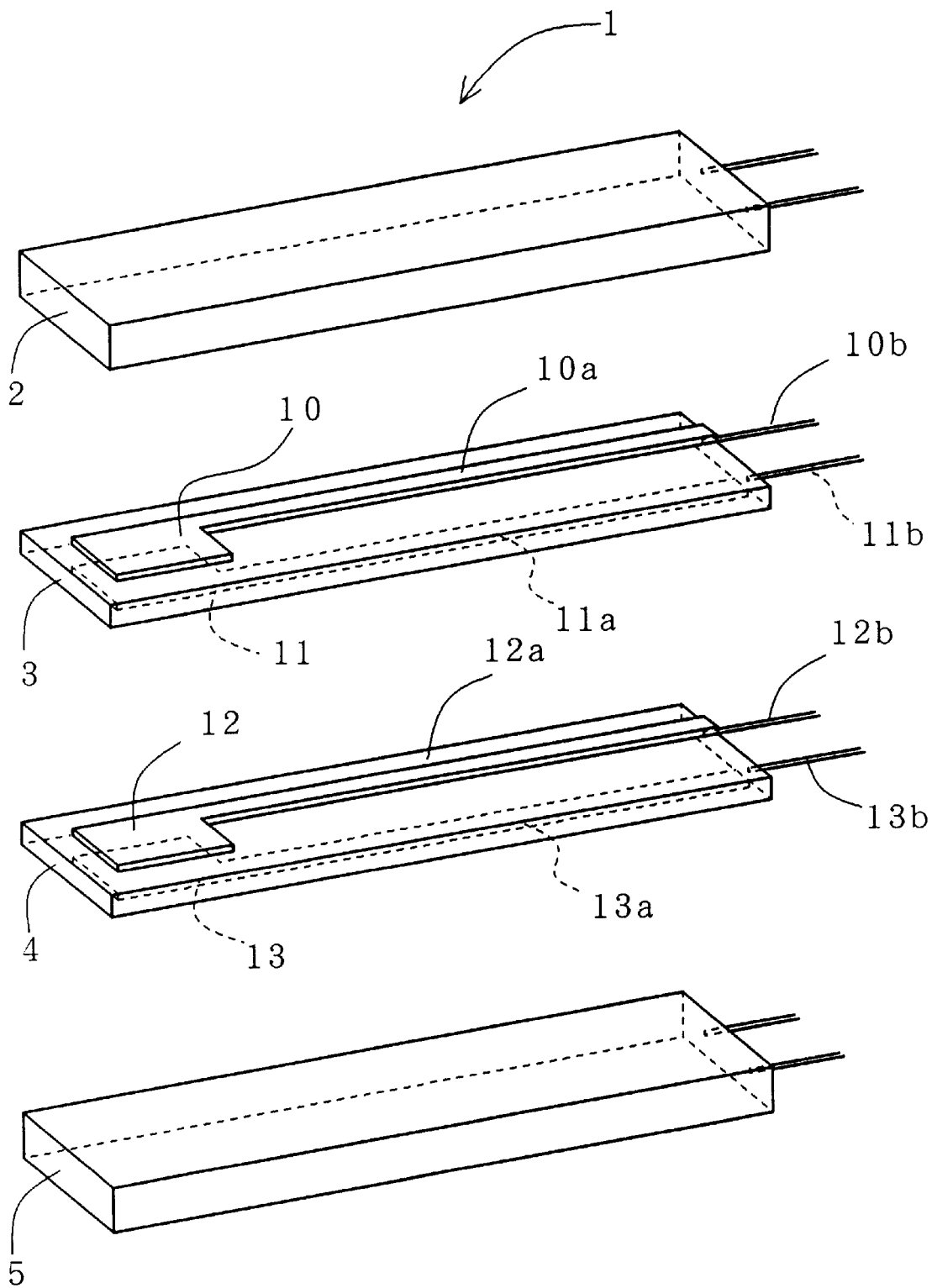
FIG. 1 is an exploded view in perspective illustrating main parts of an exhaust gas sensor in accordance with Embodiment 1 of the invention.
Figure 2A:
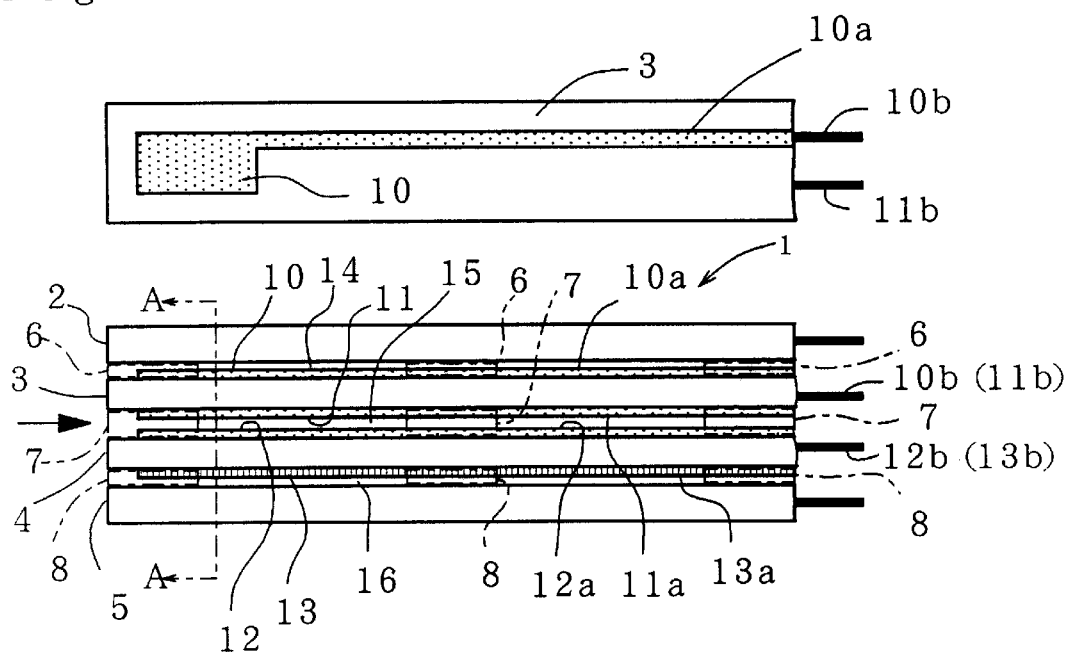
FIG. 2A is a first representation illustrating the detailed structure of the same.
Figure 2B:
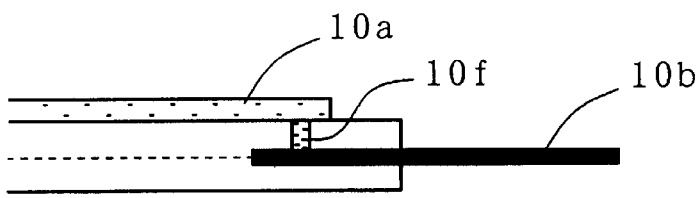
FIG. 2B is a second representation illustrating the detailed structure of the same.
Figure 2C:
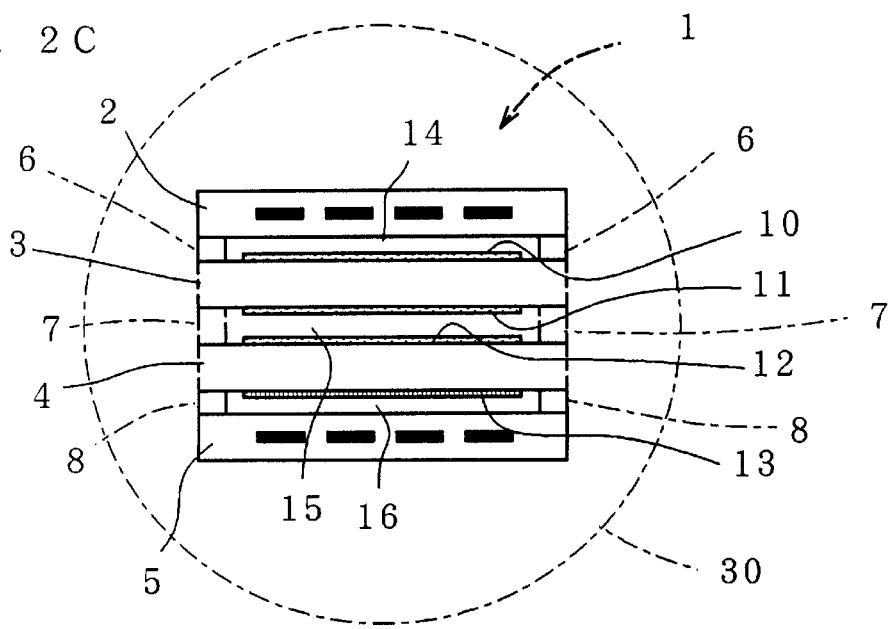
FIG. 2C is a third representation illustrating the detailed structure of the same.

FIG. 1 is an exploded view in perspective illustrating the arrangement of main parts of an exhaust gas sensor 1 in accordance with Embodiment 1 of the invention. The exhaust gas sensor 1 comprises a first heater 2 (a heater element), an oxygen pump element 3, an oxygen concentration cell element 4, and a second heater 5 (a heater element), which have been formed like elongated plates and have been laminated in the listed order. As shown in FIGS. 2A to 2C, spacers 6, 7, and 8 comprising glass, cement, or the like are interposed between the first heater 2 and the oxygen pump element 3, between the oxygen pump element 3 and the oxygen concentration cell element 4, and between the oxygen concentration cell element 4 and the second heater 5, respectively. Besides, spaces 14 to 16 each having a given size are provided between the above elements. The space 15 corresponds to a "processing space" i.e., the space between the oxygen pump element and the oxygen concentration cell element, and the space 16 corresponds to an "opposed space". The second heater 5 also serves as a space-forming member.

The oxygen pump element 3 and the oxygen concentration cell element 4 each comprise a solid electrolyte having an oxygen-ion conductivity. A typical example of such a solid electrolyte is $ZrO_2$ in which $Y_2O_3$ or CaO is solidly solved; however, solid solution of other alkaline earth metal oxide(s) or other rare earth metal oxide(s) and $ZrO_2$ may be used. $ZrO_2$ as the base may contain $HfO_2$. The first and second heaters 2 and 5 comprise a ceramic heater which is publicly known.

The oxygen pump element 3 is formed like an elongated plate. On both surfaces of one longitudinal end portion of the element 3 are formed porous electrodes 10 and 11 each having an oxygen molecule dissociability. Similar porous electrodes 12 and 13 are formed on both surfaces of the oxygen concentration cell element 4 at the positions corresponding to the electrodes 10, 11 on the oxygen pump element 3. The above-mentioned spacers 6 to 8 are disposed at positions which may not interfere with the porous electrodes 10 to 13, for example, so that the spacers extend intermittently along the edges of the element 3 or 4. Exhaust gas EG is thus allowed to be introduced into the spaces 14 to 16. The electrode 11 on the oxygen pump element 3 and the electrode 12 on the oxygen concentration cell element 4 are disposed so as to face each other across the space 15.

Electrode lead portions 10a and 11a extend from the porous electrodes 10 and 11, respectively, on the oxygen pump element 3 along the length of the element 3 toward the mounting end of the exhaust gas sensor 1; the electrode lead portions 10a and 11a are formed integrally with the porous electrodes 10 and 11, respectively. At the mounting end, one-side ends of connector terminals 10b and 11b are embedded in the oxygen pump element 3. As shown in FIG. 2B, for example, the connector terminals 10b and 11b are electrically connected to the ends of the electrode lead portions 10a and 11a, respectively, by way of conducting portions 10f formed as sinters of metal paste. Electrode lead portions 12a and 13a are similarly formed integrally with the porous electrodes 12 and 13, respectively, on the oxygen concentration cell element 4, and connector terminals 12b and 13b are connected to the lead portions 12a and 13a, respectively.

FIG. 3A illustrates an example of the general arrangement of the exhaust gas sensor 1, and FIG. 3B illustrates the inner structure of the same. The first heater 2, the oxygen pump element 3, the oxygen concentration cell element 4, and the second heater 5 are laminated with the spacers 6 to 8 interposed therebetween, so as to form a laminate 31. A ceramic stopper 30 having a rectangular through hole 30a is fitted over the laminate 31. The laminate 31 is disposed in a ceramic insulating tube 32 which is open at one end and which has its bottom portion 32b provided with a through hole 32a at the other end, so that the end portion 31a (hereinafter referred to as a detector end) of the laminate 31 where the electrodes 10 to 13 are formed protrudes from the through hole 32a. The space between the insulating tube 32 and the laminate 31 is filled with glass G. The ceramic stopper 30 has its end surface in contact with the inner surface of the bottom portion 32b of the insulating tube 32 and thereby serves to define the degree of the protrusion of the laminate 31 from the insulating tube 32.

The outside of the insulating tube 32 is covered with a metallic outer tube 33 and with a metal fitting body 34 which is integrated with the outer tube 33 by a crimping connection 34a. On the outer circumferential surface of the metal fitting body 34 is formed a male thread portion 34b for mounting the sensor 1 to a mounting (not shown) of an exhaust pipe or the like. The detector end 31a of the laminate 31 protrudes from an opening 34c formed at one end of the metal fitting body 34. A protector mounting sleeve 34d shaped like a ring is formed integrally with the circumference of the opening 34c of the metal fitting body 34. A cylindrical protector 35 which covers the detector end 31a and which has a plurality of through holes 35a allowing the inflow of exhaust gas to the detector end 31a is fitted over the protector mounting sleeve 34d and joined into one piece with the sleeve by spot welding or the like method. A crimping metal fitting 36 for receiving a machining force in the crimping is disposed adjacent to the crimping connection 34a in the space formed between the middle portion of the insulating tube 32 and the metal fitting body 34, and the remaining space is filled with filler material 80.

Leads 37 are joined by welding or the like with the connector terminals (see, e.g. FIG. 1) of the elements 2 to 5 constituting the laminate 31. The end portions of the leads extend outward from one end of the insulating tube 32 and the outer tube 33. The middle portions of the leads 37 are covered with a seal member 38 comprising elastic material such as rubber, and a protecting outer tube 39 made of the metal is fitted over the seal member 38. One end side of the protecting outer tube 39 is crimped onto and integrated with the outer tube 33.

Figure 4A:
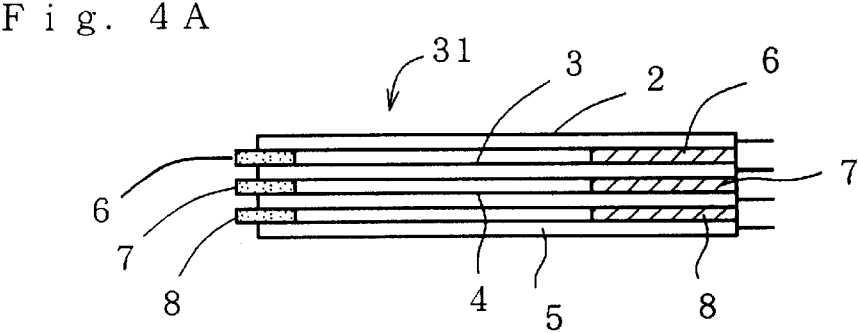
FIG. 4A is a representation illustrating the steps of a process of assembling the same.
Figure 4B:
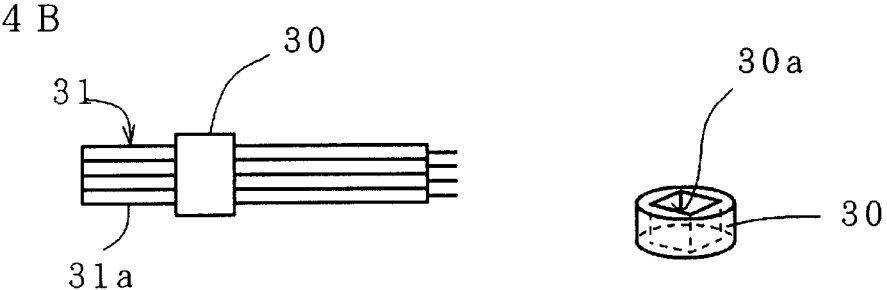
FIG. 4B is an illustrative representation following FIG. 4A.
Figure 4C:
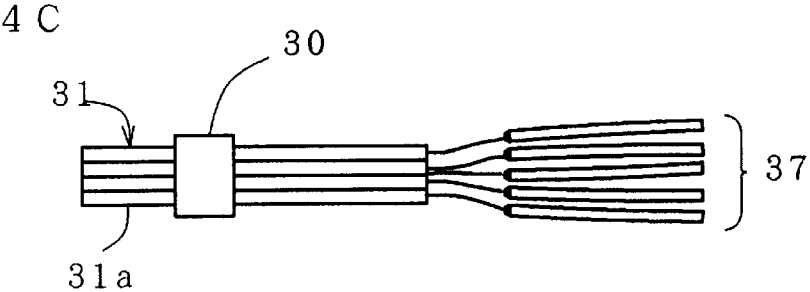
FIG. 4C is an illustrative representation following FIG. 4B.
Figure 4D:
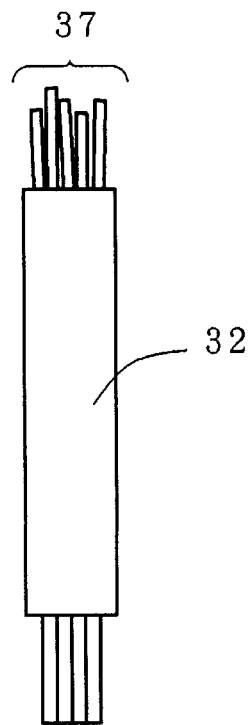
FIG. 4D is an illustrative representation following FIG. 4C.

The assemblage of the exhaust gas sensor 1 can be performed, e.g., in the following steps. As shown in FIG. 4A, the elements 2 to 5 are laminated with the spacers 6 to 8 interposed therebetween so as to form the laminate 31; as shown in FIG. 4B, the ceramic stopper 30 is fitted over the laminate; then, as shown in FIG. 4C, the leads 37 made of e.g., stainless steel are joined by welding with the connector terminals of the elements 2 to 5; as shown in FIG. 4D, the laminate 31 is inserted into the insulating tube 32, the inside of the tube 32 is filled with glass powder, and the space between the insulating tube 32 and the laminate 31 is sealed with the glass by melting the glass powder with the heating up to about 800° C. in a given furnace.

Figure 5A:
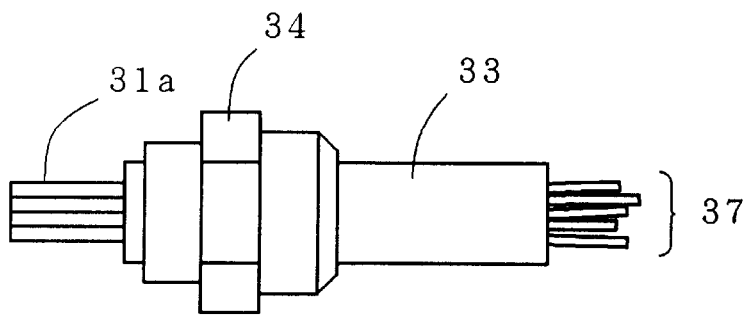
FIG. 5A is an illustrative representation following FIG. 4D.
Figure 5B:
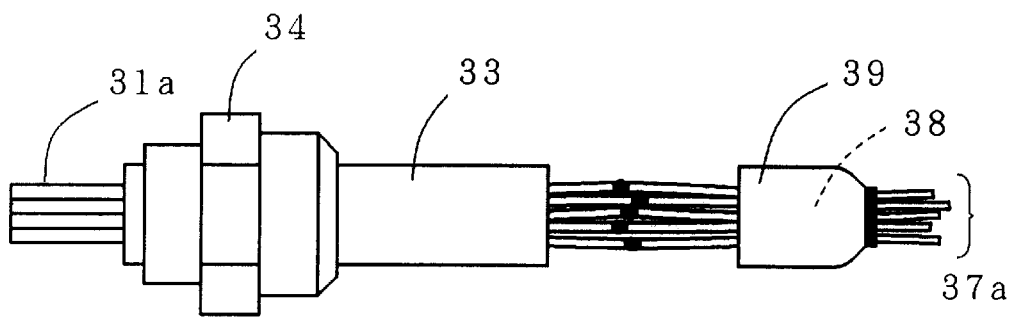
FIG. 5B is an illustrative representation following FIG. 5A.
Figure 5C:
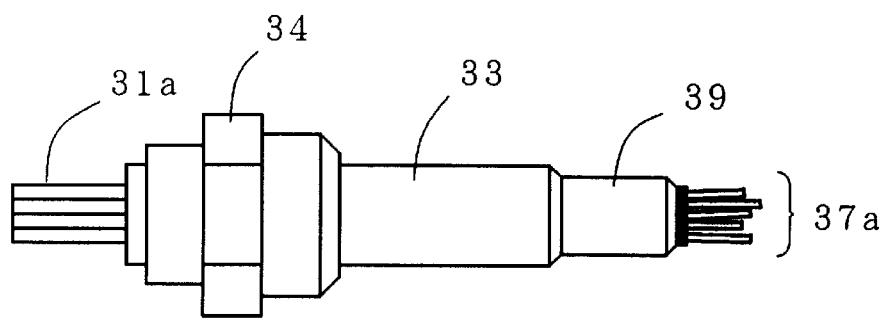
FIG. 5C is an illustrative representation following FIG. 5B.
Figure 5D:
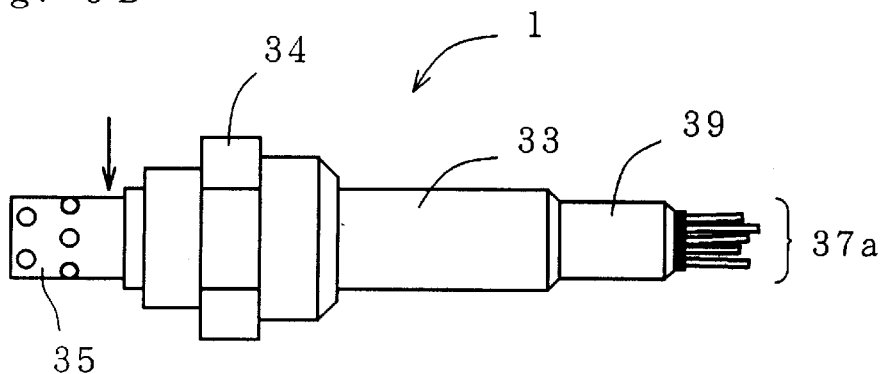
FIG. 5D is an illustrative representation following FIG. 5C.

As shown in FIG. 5A, the insulating tube 32 integrated with the laminate 31 is subsequently disposed in the metal fitting body 34, and the filler material 80 and the crimping metal fitting 36 are inserted between the insulating tube 32 and the metal fitting body 34. The outer tube 33 is then fitted over the exposed portion of the insulating tube 32, i.e., the portion which is not covered with the metal fitting body 34. By crimping the metal fitting body 34 onto the outer tube 33 while heating, the crimping connection 34a is formed, so that the metal fitting body 34 and the outer tube 33 are integrated together. After that, as shown in FIG. 5B, a bundle of other leads 37a integrated with the seal member 38 and with the protecting outer tube 39 are respectively welded to the corresponding leads 37 (hereinafter, reference numeral 37 will be given to the integrated leads). The seal member 38 and the protecting outer tube 39 are then slid on the leads 37 so that one end portions of the member 38 and of the tube 39 are inserted into the outer tube 33. After that, crimping the outer tube 33 onto the tube 39 results in the state shown in FIG. 5C. When the protector 35 is welded to the metal fitting body 34, the assemblage of the exhaust gas sensor 1 is completed as shown in FIG. 5D.

Figure 6:
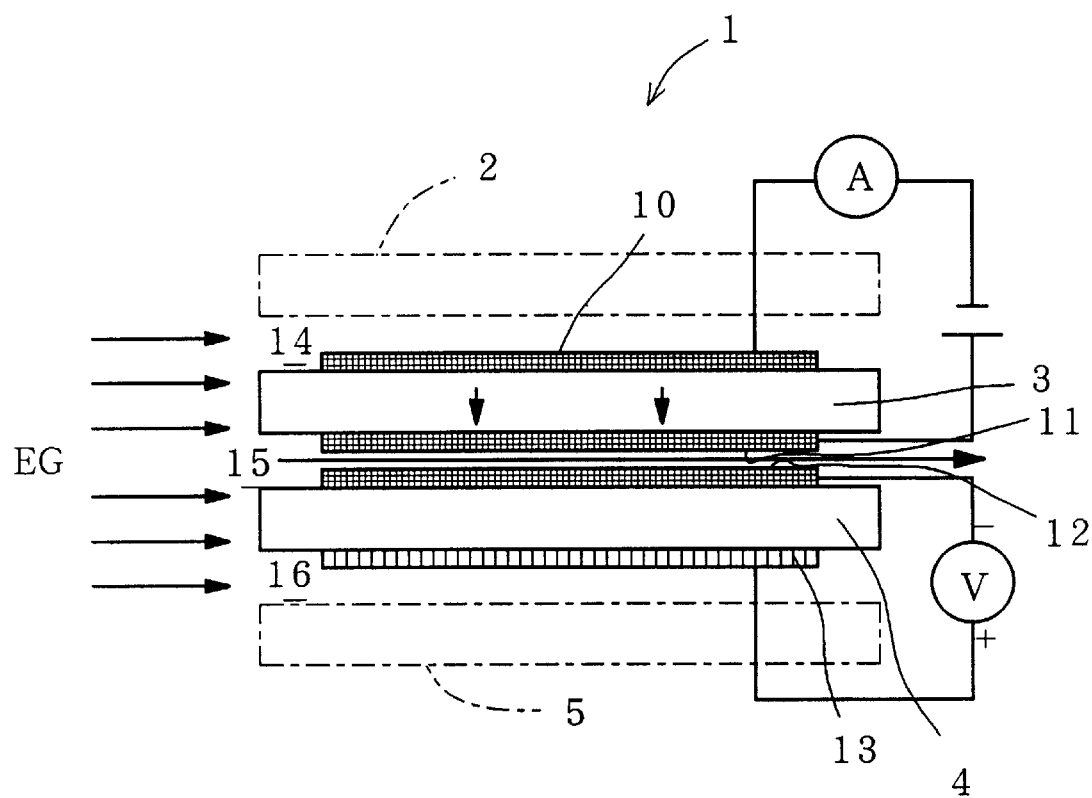
FIG. 6 is a representation illustrating the operation of the sensor.

The exhaust gas sensor is mounted to a mounting provided on e.g., an exhaust pipe so that the portion including the protector 35 of the sensor is positioned in the exhaust pipe. In this state, as shown in FIG. 6, a voltage is applied to the oxygen pump element 3 through the leads 37 (see FIG. 3) so that one of the porous electrodes 10, 11 is positive and so that the other is negative. Oxygen molecules in the exhaust gas in contact with the positive porous electrode are dissociated on the electrode, and the dissociated oxygen in the form of ions is driven by the applied voltage into the element 3. The oxygen ions transported through the element 3 by the application of the voltage receive electrons on the negative porous electrode and recombine into oxygen molecules, which are released into the atmosphere.

To the porous electrodes 12, 13 on the oxygen concentration cell element 4 is applied no voltage. Oxygen molecules in the exhaust gas in contact with the electrodes 12, 13 are dissociated on the electrode 12, 13 and diffused in the form of ions into the element 4. Any difference in oxygen concentration between the side of the electrode 12 and the side of the electrode 13 would result in a concentration gradient of oxygen ion in the element 4, and a concentration cell electromotive force according to the concentration gradient is generated between the electrodes 12 and 13. Hereinafter, with respect to the space 15 formed between the oxygen pump element 3 and the oxygen concentration cell element 4, the porous electrode 10 on the oxygen pump element 3 which electrode does not face the space 15 will be referred to as an "outside electrode," and the porous electrode 11 facing the space 15 will be referred to as a "first electrode." On the other hand, the porous electrode 12 facing the space 15 on the oxygen concentration cell element 4 will be referred to as a "second electrode," and the porous electrode 13 not facing the space 15 will be referred to as a "third electrode."

At least some of the porous electrodes 10 to 13 not only perform the dissociation and recombination of oxygen molecules but also serve as oxidation catalyst for promoting the binding reaction between a constituent to be detected which is based on hydrocarbon and oxygen in the exhaust gas in contact with the electrodes, that is, for promoting the combustion reaction of the constituent to be detected. In the exhaust gas sensor according to the invention, the oxidation catalyst activities on the constituent to be detected of the first electrode 11, the second electrode 12 and the third electrode 13 out of the four electrodes 10 to 13 are adjusted so that a difference in the consumption of the constituent to be detected which is caused by the reaction with oxygen occurs between both sides of the oxygen concentration cell element 4 (i.e., between the side of the space 15 and the side of the space 16).

More specifically, referring to FIG. 6, the first electrode 11 and the second electrode 12 each comprise, e.g., a Pt porous electrode having a relatively high oxidation catalyst activity on hydrocarbon, and the third electrode 13 comprises an Au porous electrode having a relatively low oxidation catalyst activity on hydrocarbon. The sizes of the space 15 and the space 16 are adjusted within the range not more than 1 mm by the adjusting of the heights of the spacers 7 and 8. The area Sp of the first electrode 11 is set to be equal to or larger than the area Ss of the second electrode 12.

The oxygen pump element 3 and the oxygen concentration cell element 4 can be produced, for example, in the following method. Green compacts which have a shape corresponding to the oxygen pump element 3 or the oxygen concentration cell element 4 are produced with use of material in which solid electrolyte powder and organic binder are kneaded. The ends of the connector terminals 10b to 13b are embedded in the green compacts. With use of paste in which a given amount (e.g., on the order of 10 percent by weight) of ceramic powder made from the same material as the solid electrolyte constituting the element 3 or 4 is mixed with metal powder such as Pt, the print patterns of the electrodes 10 to 13 (and of the electrode lead portions 10a to 13a) are formed on both sides of the green compacts. By sintering those compacts, the oxygen pump element 3 and the oxygen concentration cell element 4 are obtained. The sintered print patterns thus form the electrodes 10 to 13 and the electrode lead portions 10a to 13a. In the case that, however, metal such as Au, Ag, Pd and the alloys thereof, having a lower melting point than the sintering temperature of ceramics (solid electrolyte) is used as the material of the electrodes, the material may be paste-printed after the sintering of the green compacts and may be baked at a temperature lower than the sintering temperature of ceramics.

The method of using the exhaust gas sensor 1 will be described below.

As shown in FIG. 6, the exhaust gas sensor 1 is mounted to an exhaust pipe, and exhaust gas containing a constituent to be detected based on hydrocarbon and containing oxygen is introduced into the space 15 between the oxygen pump element 3 and the oxygen concentration cell element 4 and into the space 16 (the opposed space) between the oxygen concentration cell element 4 and the heater 5. At this time, the consumption of the constituent to be detected in the exhaust gas, which is caused by the oxidation of the constituent, on the side of the space 15 is larger than that on the side of the space 16, because the electrodes 11, 12 on the side of the space 15 comprise Pt and the electrode 13 on the side of the space 16 comprises Au. Since the larger consumption of the constituent to be detected leads to the larger consumption of oxygen in the exhaust gas Eg, oxygen concentration in the space 16 is higher than that in the space 15, so that a concentration cell electromotive force is generated in the oxygen concentration cell element 4, with the side of the space 16 positive.

When oxygen is pumped from the side of the space 14 to the side of the space 15 by the oxygen pump element 3 so that the absolute value of the concentration cell electromotive force is a constant value, e.g., a constant value not more than 10 mV, the current flowing through the oxygen pump element 3 (hereinafter referred to as "oxygen pump current" or "pump current") has a value reflecting the amount of oxygen which has been consumed for the oxidation of the constituent to be detected. When the concentration of the constituent to be detected in the exhaust gas Eg increases, the amount of oxygen which is consumed with the oxidation of the constituent also increases and, as a result, the pump current increases. Accordingly, the measurement of the pump current provides the concentration of the constituent to be detected in the exhaust gas Eg.

Figure 7:
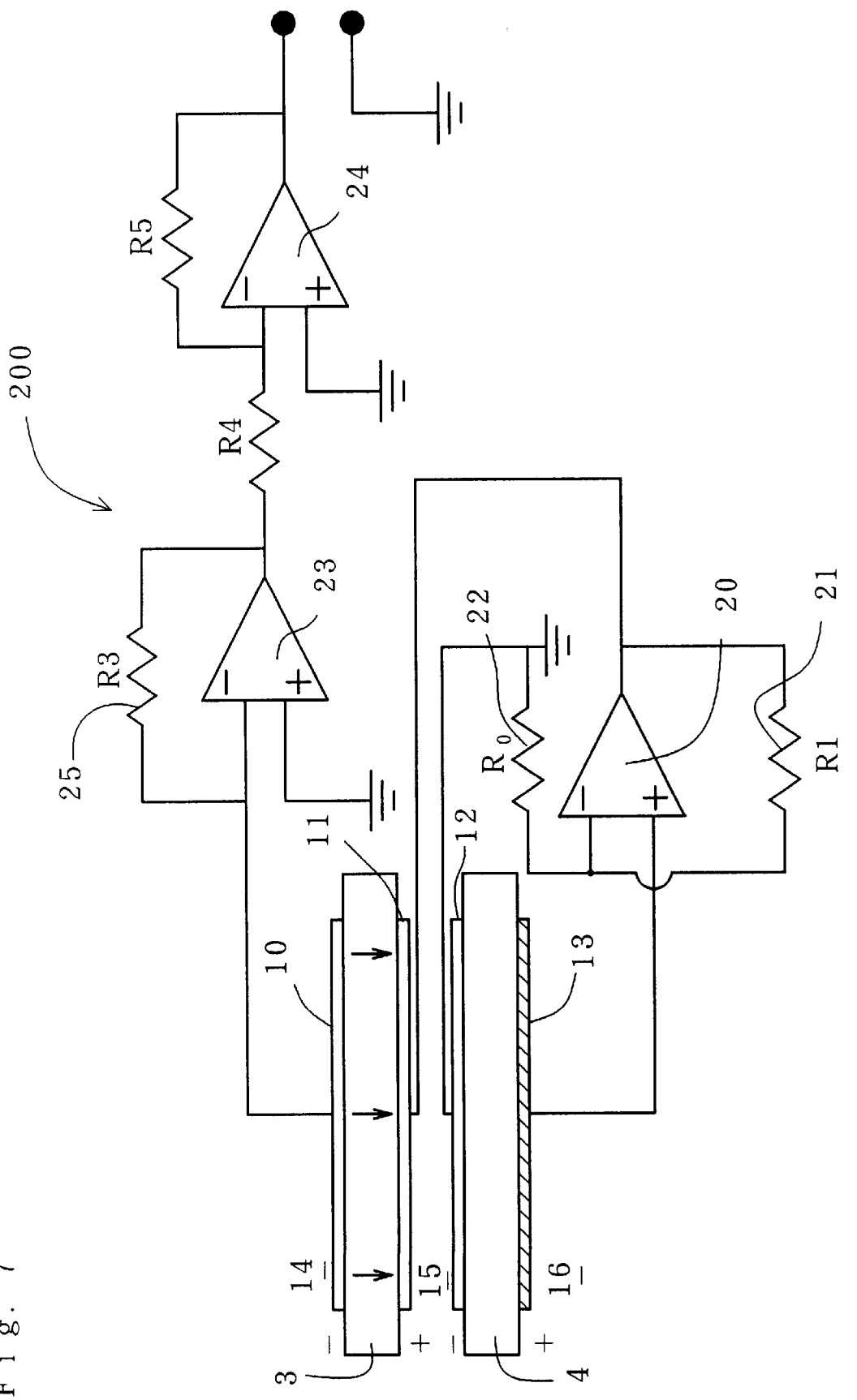
FIG. 7 is a block diagram illustrating an example of a control circuit for the sensor.

FIG. 7 is a block diagram illustrating an example of the arrangement of a sensor system in accordance with the invention for detecting the concentration of a constituent to be detected in exhaust gas on the basis of the above-mentioned principle. In the sensor system 200, the second electrode 12 and the third electrode 13 on the oxygen concentration cell element 4 in the exhaust gas sensor 1 are connected to the negative terminal (earthing terminal) and the positive terminal, respectively, of a noninverting amplifier 20 (means for adjusting pump element voltage, and means for detecting electromotive force). The concentration cell electromotive force generated in the element 4 is thereby amplified with a gain of R1/R0, wherein R0 is the electric resistance of a resistor 22 connected to the ground side of the noninverting amplifier 20 and wherein R1 is the electric resistance of a resistor 21 connected in the same way with negative feedback.

The output of the noninverting amplifier 20 is connected to the first electrode 11 on the oxygen pump element 3, and the amplified concentration cell electromotive force is applied to the oxygen pump element 3. At this time, the concentration cell electromotive force generated in the oxygen concentration cell element 4 is such that the side of the third electrode 13 is positive, because the oxygen concentration on the side of the space 16 is higher than that on the opposite side. The concentration cell electromotive force is amplified by the noninverting amplifier 20 without the inversion of polarity and applied to the first electrode 11 on the oxygen pump element 3. The oxygen pump element 3 thus carries the pump current with the side of the first electrode 11 positive, so that oxygen in the space 14 is pumped to the side of the space 15 as indicated by the arrows in the drawing. The pump current is amplified by an inverting amplifier 23 (output means) and taken out as a sensor output reflecting the methane concentration in the exhaust gas Eg. Provided that the internal resistance of the oxygen pump element 3 is Ri and that the electric resistance of a resistor 25 connected with negative feedback to the inverting amplifier 23 is R3, the gain of the inverting amplifier 23 is R3/Ri. In this embodiment, the polarity of the output of the inverting amplifier 23 is inverted by the noninverting amplifier 24 having a gain of 1 (R4=R5).

In accordance with the above circuit arrangement, when a decrease in oxygen concentration in the space 15 causes an increase in the concentration cell electromotive force, the oxygen pump current increases and the pumping of oxygen to the space 15 by the oxygen pump element 3 is promoted. The concentration cell electromotive force then decreases by degrees, and therefore the oxygen pump current is so controlled as to decrease. As a result, the oxygen pump current is controlled so that the concentration cell electromotive force is eventually brought approximately to zero. From the equilibrium value of the oxygen pump current at that time, the concentration of the constituent to be detected can be obtained. In this case, the target value EC of the electromotive force can be considered to be generally equal to zero.

Theoretically, the concentration cell electromotive force of zero indicates that oxygen concentrations on both sides of the oxygen concentration cell element 4 (i.e., in the spaces 15 and 16) are equal. This means that the pump current corresponds directly to the difference in the consumption of the constituent to be detected between the spaces 15 and 16; therefore, the concentration of the constituent to be detected can be detected accurately and the detection results can be readily analyzed. Even though oxygen concentrations in the spaces 15 and 16 are equal, however, it is often that the actual electromotive force of the oxygen concentration cell element 4 does not become zero and that a given offset electromotive force remains. In this case, the target value EC of the electromotive force corresponding to the offset electromotive force is set within the range not more than 10 mV and the current flowing through the oxygen pump element 3 at the time when the absolute value of the concentration cell electromotive force reaches the target value EC is taken as the detection signal; thus the concentration of a constituent to be detected in exhaust gas can be detected more accurately.

The offset electromotive force of the oxygen concentration cell element 4 becomes more fluctuant with decrease in the oxygen concentration in the exhaust gas associated with the detection. Accordingly, the setting of the target value EC of the electromotive force on the basis of the offset electromotive force corresponding to an oxygen concentration not more than a given value makes the sensor outputs prone to be influenced by the oxygen concentration in exhaust gas. It is therefore effective to provide as EOS (in mV) the absolute value of the offset electromotive force at the time when test gas containing e.g., not less than 1 volume percent (preferably not less than 10 volume percent) oxygen and substantially no constituents which may react with oxygen at the operating temperature of the sensor is introduced into the spaces 15 and 16, and to set the target value EC of the electromotive force within the range not less than (EOS−5) mV and not more than (EOS+5) mV, by using EOS as the reference.

Figure 8:
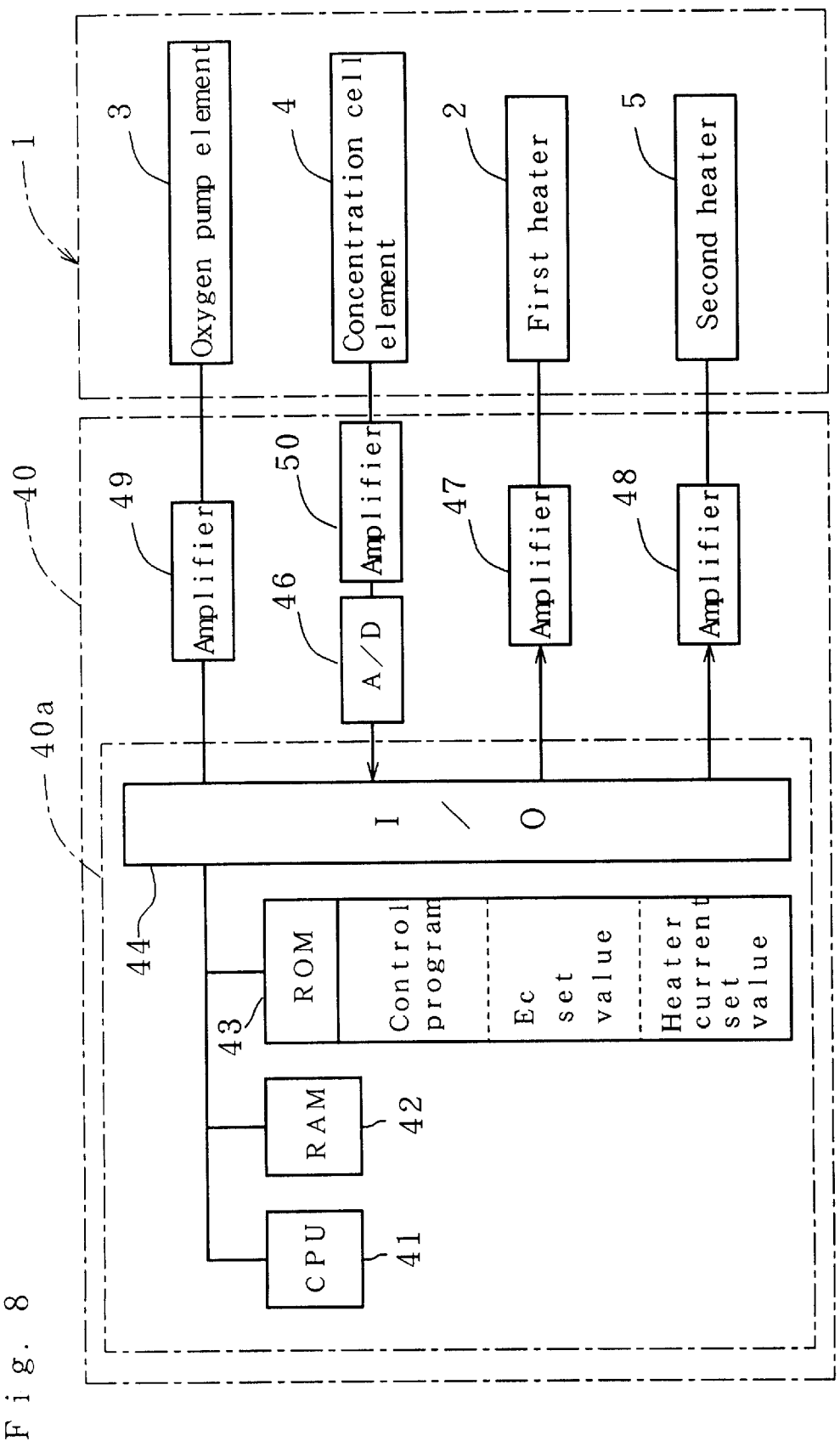
FIG. 8 is a block diagram illustrating another example of the same.

FIG. 8 illustrates an example of the arrangement of a sensor system in which the target value EC of the electromotive force can be freely set according to the offset electromotive force. In this arrangement, the exhaust gas sensor 1 mentioned above is connected to a sensor controlling section 40 including a microprocessor 40a. The microprocessor 40a comprises a CPU 41, a RAM 42, a ROM 43 and an I/O port 44 to which the former components are connected. To the I/O port 44 are connected the oxygen pump element 3 through an amplifier 49, the oxygen concentration cell element 4 through an A/D converter 46 and through an amplifier 50, and the first and second heaters 2 and 5 through amplifiers 47 and 48, respectively. The ROM 43 is stored with a control program for controlling the operation of the sensor 1, the target value EC of the electromotive force, and the set value of a heater current. The CPU 41 is the main constituent of the means for adjusting pump element voltage and of the means for detecting electromotive force. The RAM 42 serves as the work area for the CPU 41.

The voltage to be applied to the oxygen pump element 3 is outputted through the I/O port 44 and through the amplifier 49, at a value specified by the CPU 41. The electromotive force of the oxygen concentration cell element 4 is amplified by the amplifier 50, digitized by the A/D converter 46 and inputted into the I/O port 44. In this embodiment, a control dead zone having a width of ±δ is set with respect to a target value EC of the electromotive force. The control of the energization of the heaters 2 and 5 is performed by the sensor controlling section 40.

Figure 9:
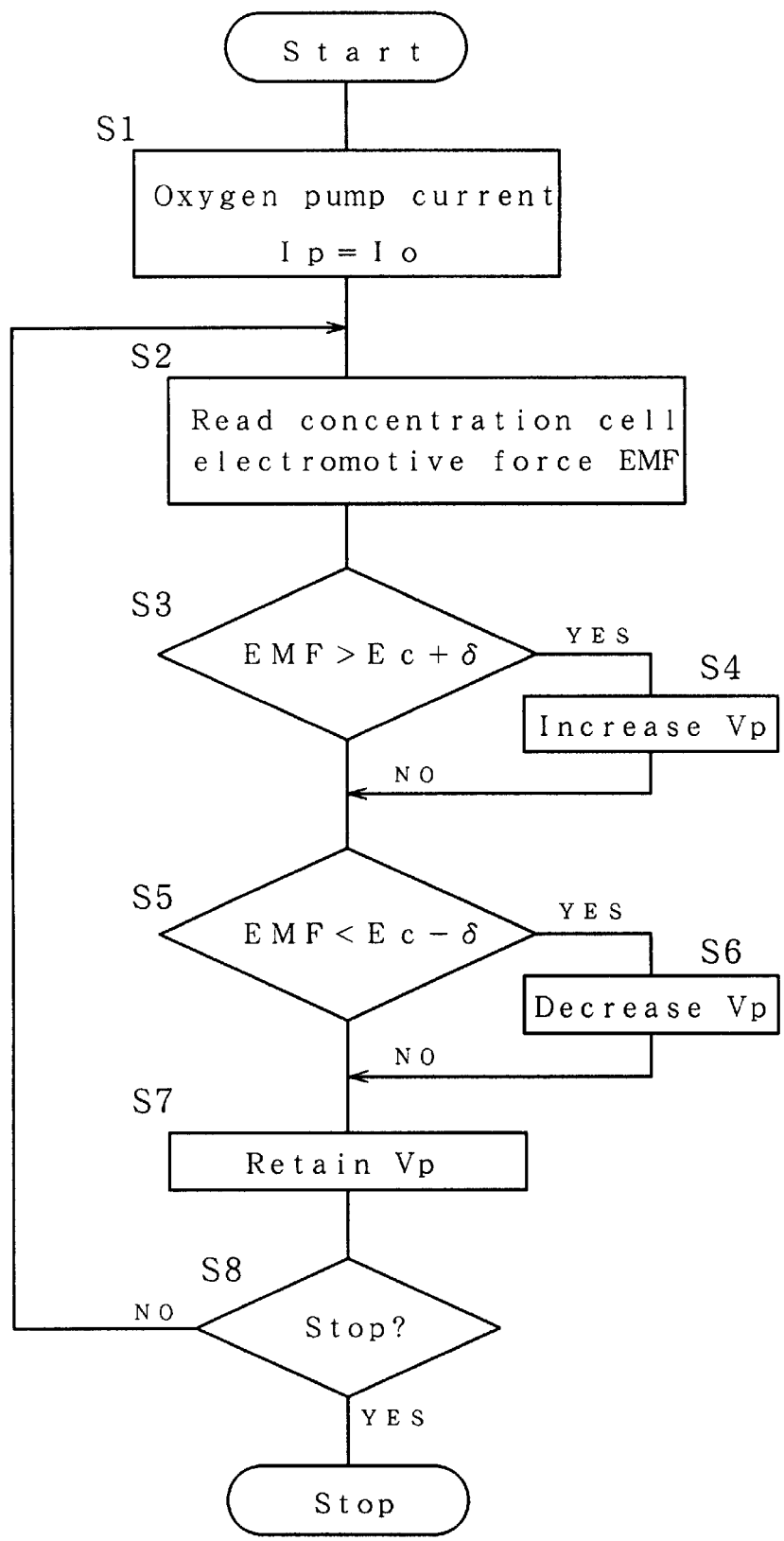
FIG. 9 is a flow chart illustrating a flow of the control which is exercised by the control circuit of FIG. 8 on the operation of the sensor.

FIG. 9 illustrates a flow of controlling the operation of the sensor on the basis of the control program. When the control program is started, the voltage to be applied to the oxygen pump element 3 is outputted at a value of Vp, in S1, so that the oxygen pump current Ip equals an initial value Io. In S2, the inputted value of the electromotive force EMF of the concentration cell is read in. In the case that EMF is out of the control tolerance EC±δ, VP(i.e., Ip) is increased or decreased (in S3 to S6) so that EMF goes within the tolerance, in the case that EMF is within the control tolerance, the value of Vp(i.e., Ip) at that time is retained in S7 and the flow returns to S2 and repeats the same processes. The electromotive force EMF of the concentration cell is thereby maintained in the vicinity of EC. The value of the output current from the oxygen pump element 3 at that time can be taken as the sensor output.

The side of the oxygen pump element 3 having the outside electrode may be isolated from exhaust gas and the air may be introduced there.

Figure 10A:
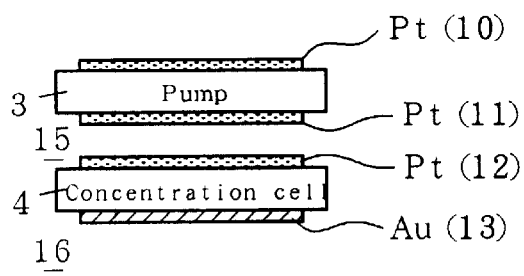
FIG. 10A is a schematic representation illustrating the 1st modification of the arrangement of electrodes.
Figure 10B:
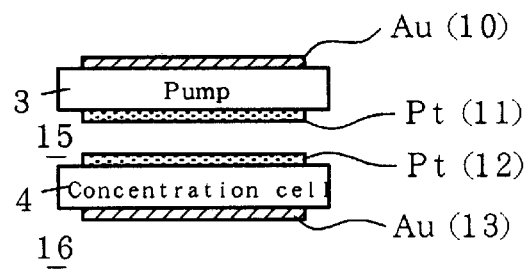
FIG. 10B is a schematic representation illustrating a 1st modification of the arrangement of electrodes.
Figure 10C:
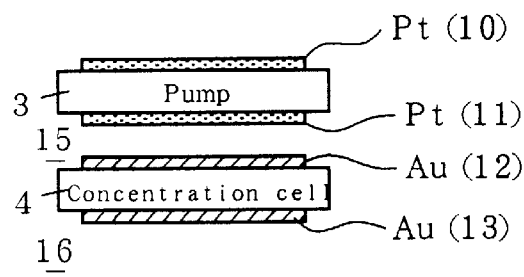
FIG. 10C is a schematic representation illustrating a 2nd modification of the arrangement of electrodes.
Figure 10D:
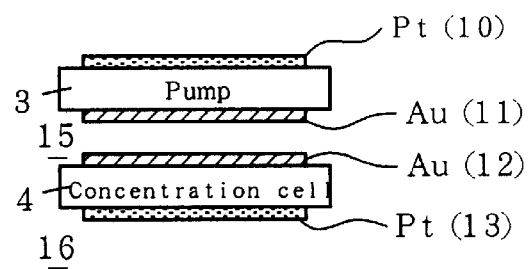
FIG. 10D is a schematic representation illustrating a 3rd modification of the arrangement of electrodes.
Figure 10E:
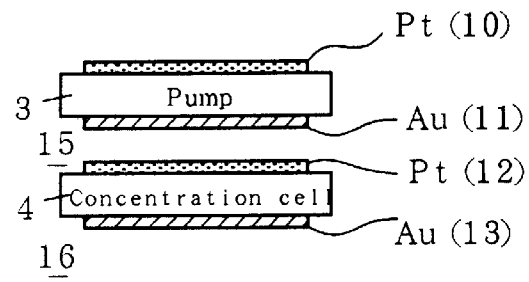
FIG. 10E is a schematic representation illustrating a 4th modification of the arrangement of electrodes.
Figure 10F:
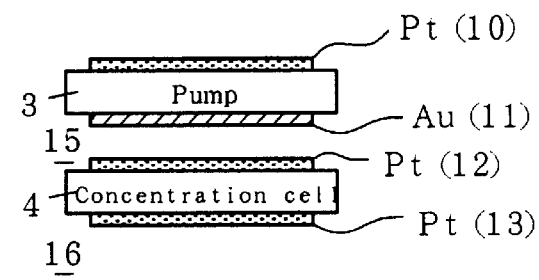
FIG. 10F is a schematic representation illustrating a 5th modification of the arrangement of electrodes.

Instead of the above-mentioned combination of the materials of the electrodes 10 to 13 on the oxygen pump element 3 and the oxygen concentration cell element 4, which combination is shown in FIG. 10A, various combinations may be employed which would cause a difference in the consumption with oxidation of a constituent to be detected between both sides of the oxygen concentration cell element 4. FIG. 10B illustrates an example in which the outside electrode 10 on the oxygen pump element 3 comprises an Au porous electrode having a lower oxidation catalyst activity. FIGS. 10C and 10E illustrate examples in which one of the first electrode 11 and the second electrode 12 both facing the space 15 comprises an Au porous electrode. FIG. 10D illustrates an example in which both the first electrode 11 and the second electrode 12 comprise an Au porous electrode having a lower oxidation catalyst activity and in which the third electrode comprises a Pt porous electrode having a higher oxidation catalyst activity. In this case, the consumption of a constituent to be detected on the side of the space 16 is larger than that on the side of the space 15, and the oxygen pump element 3 therefore operates to pump oxygen out from the space 15. FIG. 10F illustrates an example in which the first electrode 11 of the arrangement is replaced by an Au porous electrode.

Figure 11A:
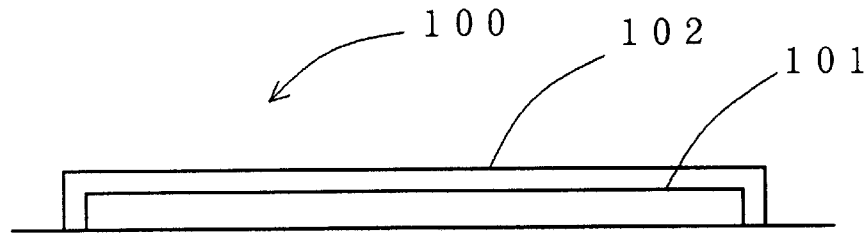
FIG. 11A is a representation illustrating a 1st example of a method of producing by coating an electrode which is inert as catalyst.

With regard to an electrode having a lower oxidation catalyst activity, as shown in FIG. 11A, a main body 101 of a porous electrode may be formed of Pt, Rh, Pd, Ir or the like which belong to the group of metals having a relatively high activity, and a coating 102 of a material which is inert as catalyst (e.g., a material belonging to a lower-activity metal group such as a metal containing Au or Ag as its principal constituent, or an oxide such as $SnO_2$, $ZnO$, $In_2O_3$, $WO_3$, and $Bi_2O_3$) may be applied onto the surface of the main body which will contact exhaust gas, so as to form a finished electrode.

Figure 11B:
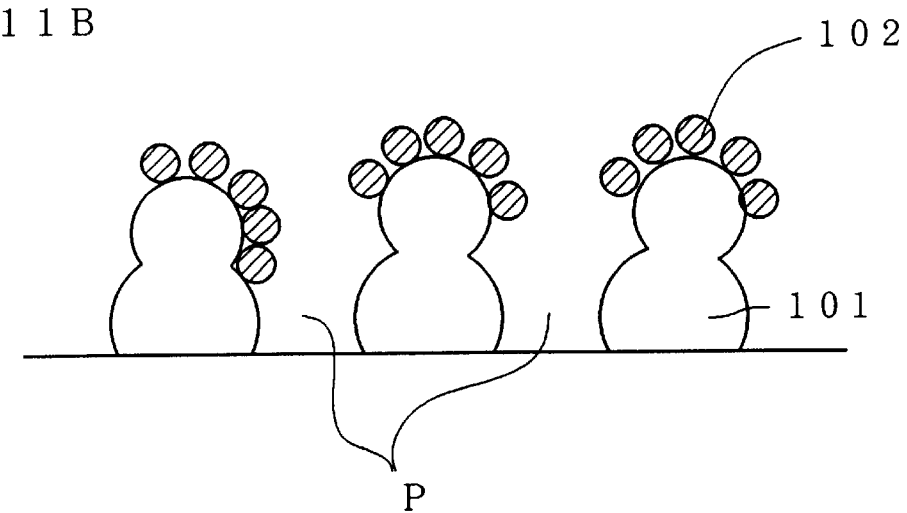
FIG. 11B is a representation illustrating a 2nd example of a method of producing by coating an electrode which is inert as catalyst.
Figure 11C:
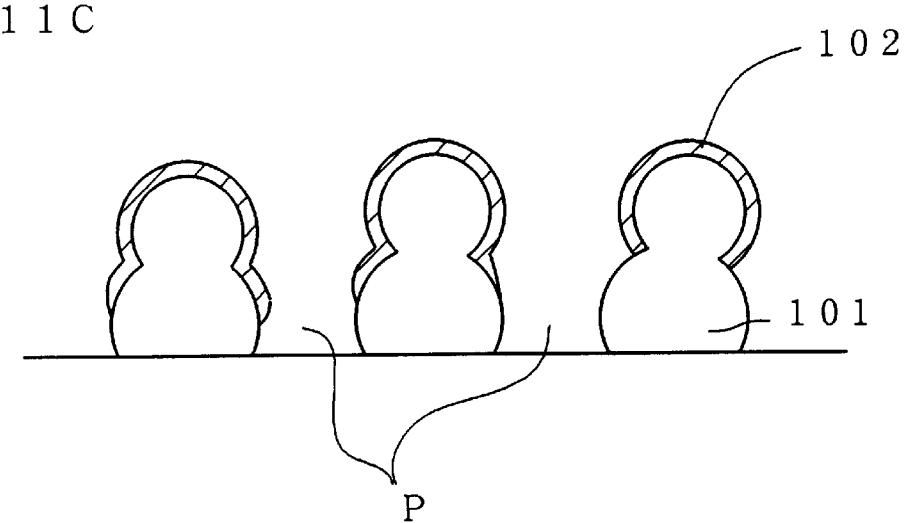
FIG. 11C is a representation illustrating a 3rd example of a method of producing by coating an electrode which is inert as catalyst.

In this case, e.g., as shown in FIG. 11B, the coating 102 can be formed by the method in which paste which contains particles of the material inert as catalyst is applied onto the main body 101 and resintered; alternatively, as shown in FIG. 11C, the coating 102 can be formed by vapor deposition such as vacuum deposition or sputtering. As shown in FIGS. 11B or 11C, a large number of gaps P are formed in the porous main body 101 so as to run deep into the body; the coating 102 therefor may not necessarily be formed at great depth of such gaps P. Such uncoated areas could be permitted, provided that the catalytic activity on the reaction between the constituent to be detected and oxygen could be made sufficiently low.

Figure 12A:
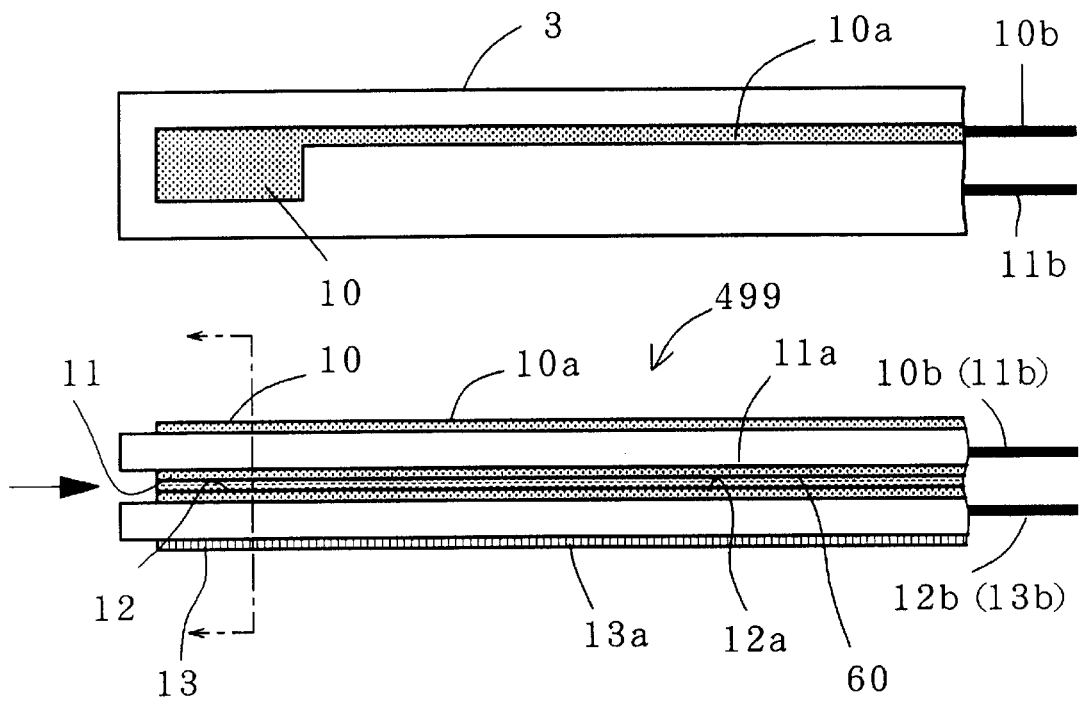
FIG. 12A is a schematic representation illustrating an example in which a gas holding member is interposed between an oxygen pump element and an oxygen concentration cell element.
Figure 12B:
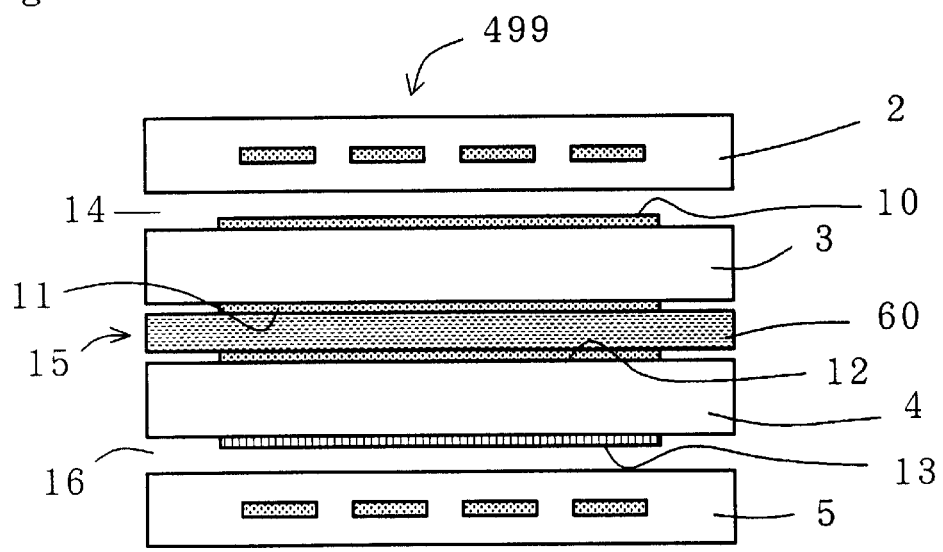
FIG. 12B is a schematic representation following FIG. 12A.

As shown in FIG. 12, a gas holding member 60 comprising metal meshes or porous metal (such as of Pt) can be interposed into the space 15 formed between the oxygen pump element 3 and the oxygen concentration cell element 4. In the case of the gas holding member 60 comprising metal meshes, the density of the meshes to be used is preferably between 100 and 500 meshes.

Figure 13A:
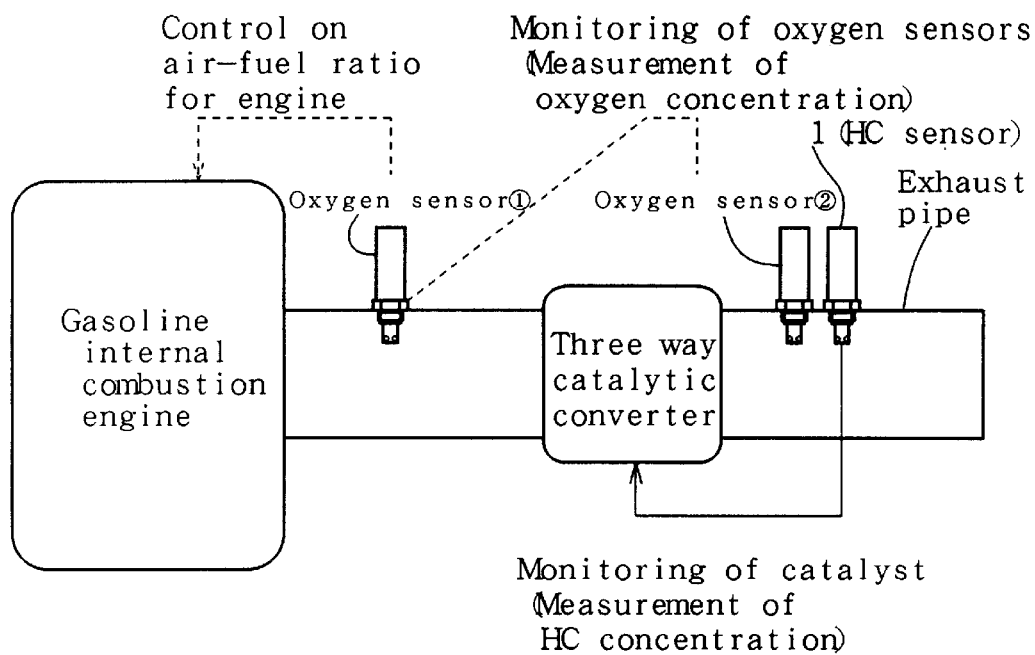
FIG. 13A is a schematic representation illustrating an application of an exhaust gas sensor in accordance with the invention.

An example of the application of the exhaust gas sensor 1 in accordance with the invention will be described below. FIG. 13A schematically illustrates an exhaust gas purifying system for gasoline internal combustion engine. To an exhaust pipe are mounted an oxygen sensor ① for controlling the air-fuel ratio for the engine, a three way catalytic converter for simultaneously performing the oxidation of HC and the reduction of NOx in exhaust gas to purify the gas, and an oxygen sensor ② for measuring the oxygen concentration in the purified exhaust gas, which are arranged in the listed order, the nearest to the engine first. The exhaust gas sensor 1 of the invention is disposed downstream from then, and measures the HC concentration in the purified exhaust gas, e.g., for detecting the deterioration of the catalyst.

Figure 13B:
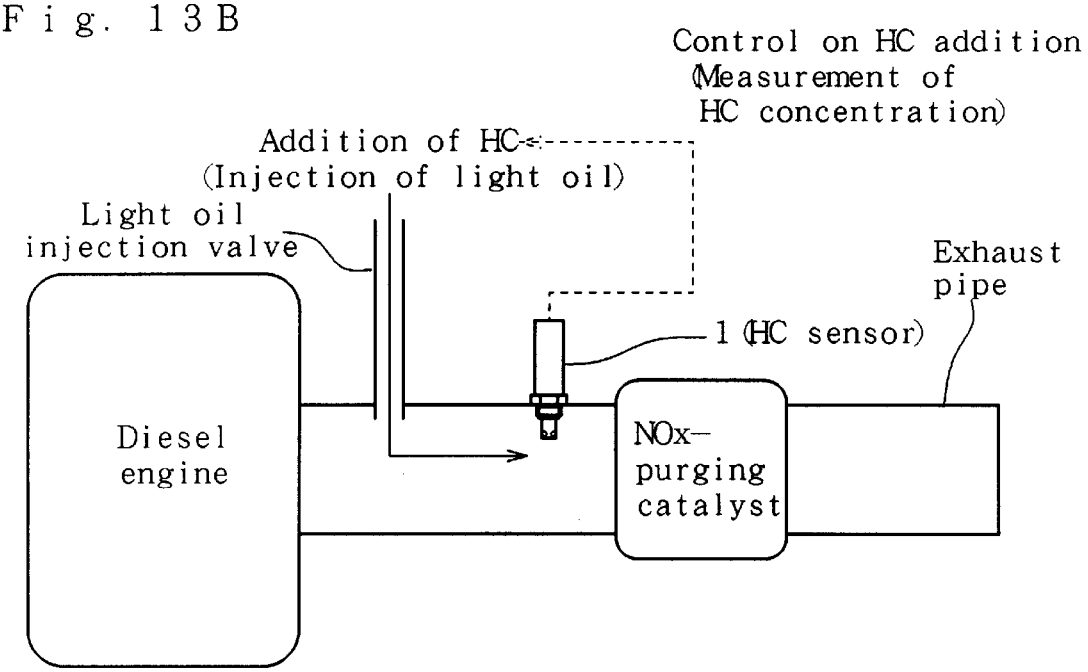
FIG. 13B is a schematic representation illustrating another application of an exhaust gas sensor in accordance with the invention.

FIG. 13B schematically illustrates an exhaust gas purifying system for diesel engine. In an exhaust pipe are provided a light oil injection valve for injection light oil as HC source into exhaust gas, and NOx-purging catalyst, which are arranged in the listed order, the nearer to the engine first. The NOx-purging catalyst serves to decompose NOx into nitrogen and oxygen with use of HC as reducing agent added by the injection of light oil, to purge the gas of NOx. The exhaust gas sensor 1 of the invention is disposed upstream from the NOx-purging catalyst and serves to monitor the HC concentration in the exhaust gas into which light oil has been injected, in order to feed back and control the amount of light oil to be injected into the exhaust gas.

Figure 14A:
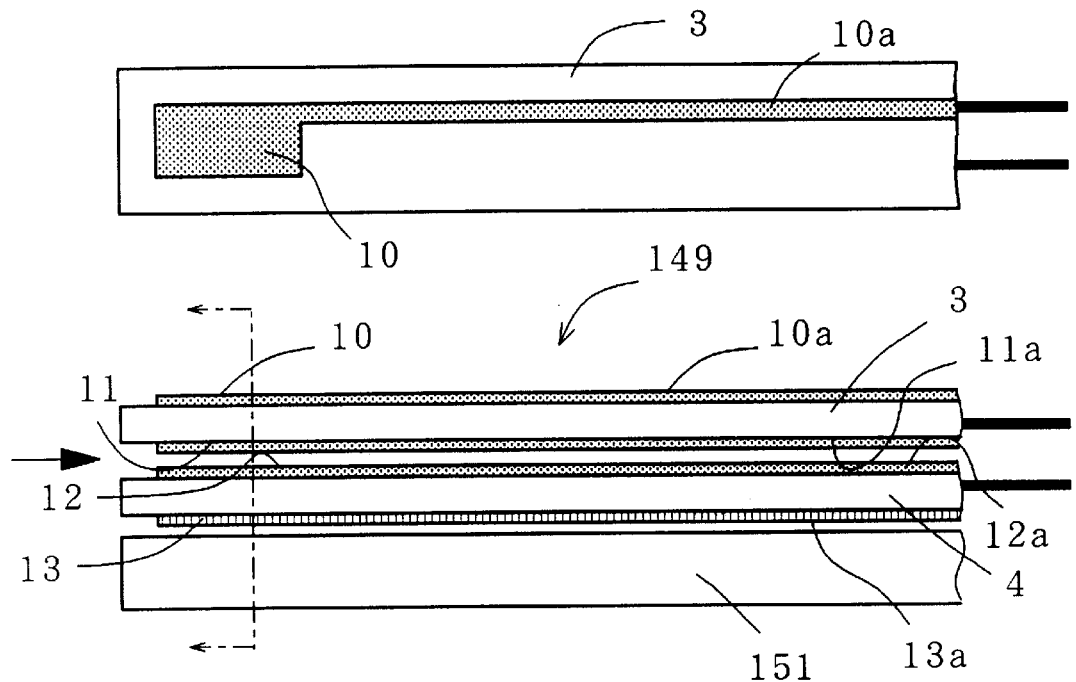
FIG. 14A is a representation illustrating a 1st example of a composite sensor in which an exhaust gas sensor in accordance with the invention as used.
Figure 14B:
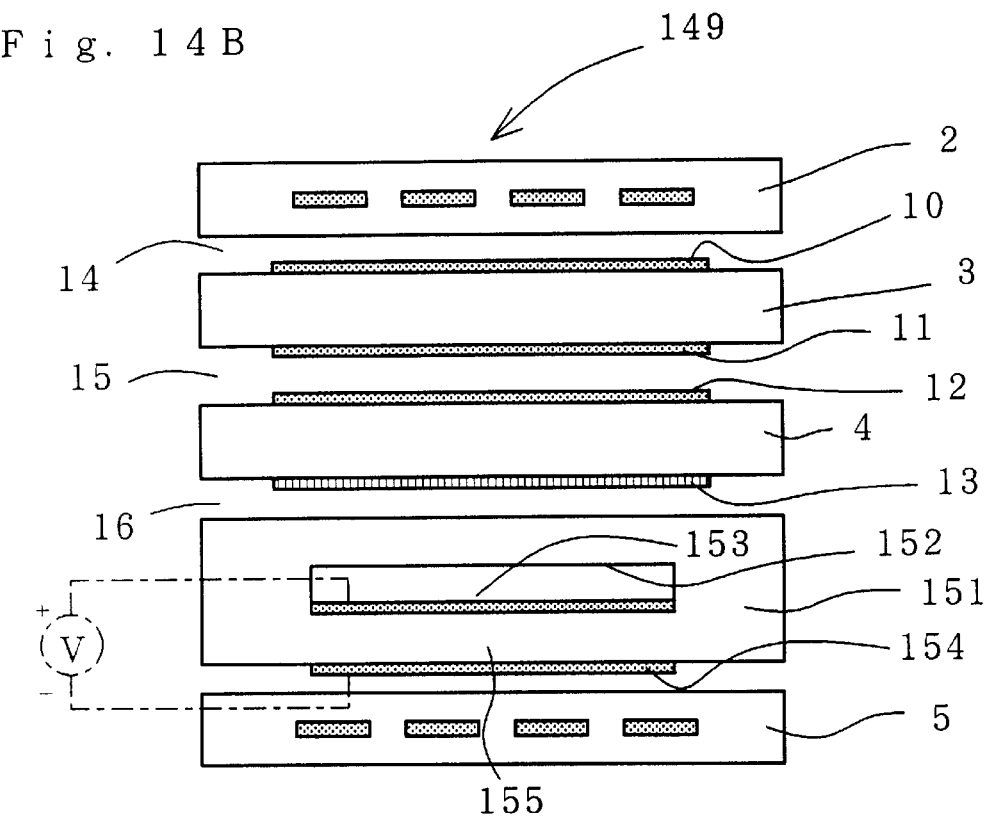
FIG. 14B is a schematic representation following FIG. 14A.

FIGS. 14A, and 14B illustrates an example of a composite sensor into which a plate-like oxygen sensor 151 is incorporated, as an example of the application of an exhaust gas sensor in accordance with the invention. In the composite sensor 149, the plate-like oxygen sensor 151 is disposed between a second heater 5 and an oxygen concentration cell element 4 and a space 16 is formed between the plate-like oxygen sensor 151 and the oxygen concentration cell element 4. The plate-like oxygen sensor 151 comprises a solid electrolyte having an oxygen-ion conductivity such as $ZrO_2$, and an atmosphere introducing chamber 152 is formed in the sensor 151. Porous electrodes 153 and 154 are formed on both sides of a wall 155 which is positioned across the atmosphere introducing chamber 152 from the oxygen concentration cell element 4. When exhaust gas is brought into contact with the electrode 154, the atmosphere (the air) introduced into the atmosphere introducing chamber 152 acts as the reference gas, and a concentration cell electromotive force according to the oxygen concentration in the exhaust gas occurs in the wall 155. The oxygen concentration in the exhaust gas can be known by taking the electromotive force as the sensor output. With use of the composite sensor 149, e.g., in FIG. 13A, the oxygen sensor ② and the exhaust gas sensor 1 of the invention can be integrated into one sensor.

Figure 15A:
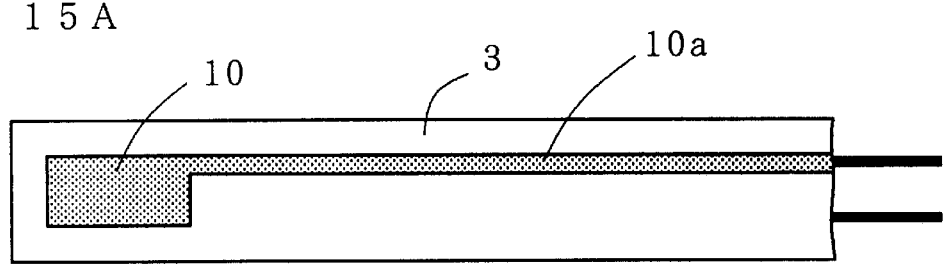
FIG. 15A is a representation illustrating a 2nd example of a composite sensor in which an exhaust gas sensor in accordance with the invention as used.
Figure 15B:
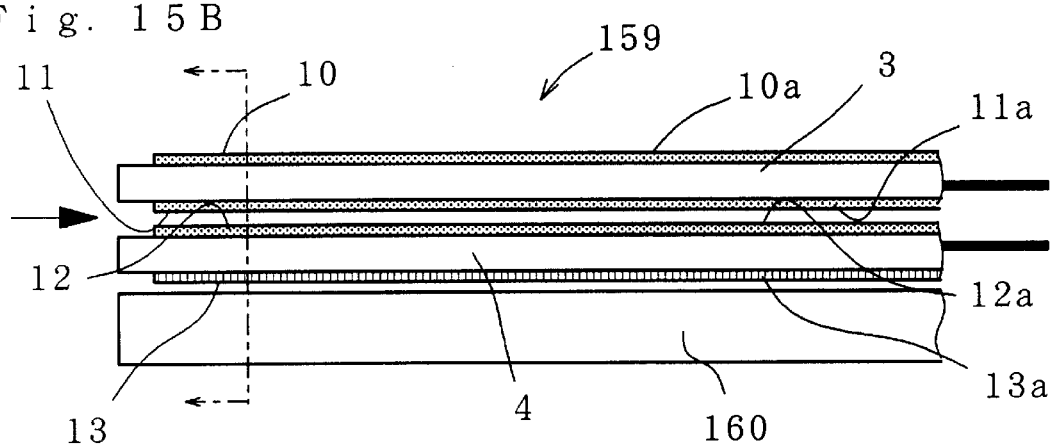
FIG. 15B is a side view of FIG. 15A.
Figure 15C:
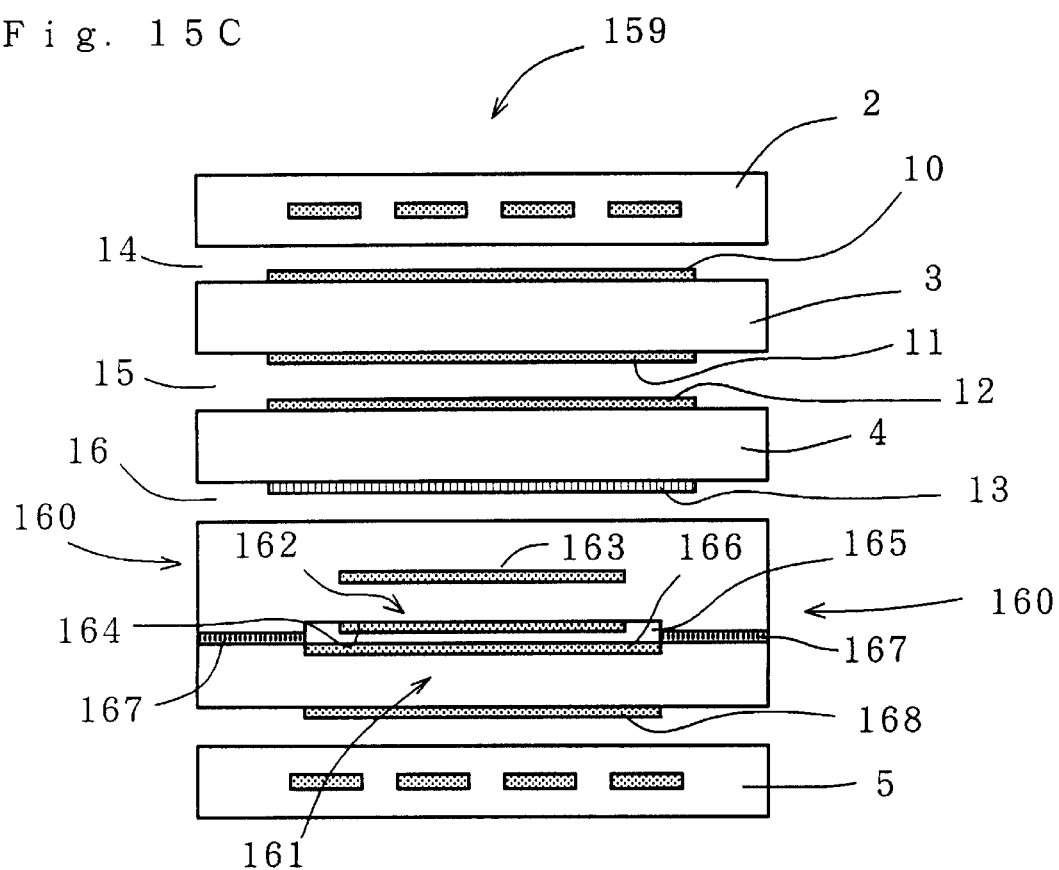
FIG. 15C is a sectional view of FIG. 15B.

FIGS. 15A, 15B and 15C illustrate an example of a composite sensor with which a full-range oxygen sensor is combined. A composite sensor 159 has the same arrangement as shown in FIG. 14 except that the plate-like oxygen sensor 151 is replaced by a full-range oxygen sensor 160. The full-range oxygen sensor 160 comprises a solid electrolyte having an oxygen-ion conductivity and has a structure in which an oxygen pump element 161 and an oxygen concentration cell element 162 are so disposed as to face each other across a measuring chamber 165. Exhaust gas is introduced into the measuring chamber 165 through diffusion holes 167 formed with use of porous ceramic or the like. The oxygen concentration in the measuring chamber 165 is measured by the oxygen concentration cell element 162 on the basis of the concentration cell electromotive force which occurs between an electrode 163 as the oxygen reference electrode embedded in the element 162 and an electrode 164 on the side of the measuring chamber 165.

On the other hand, a voltage is applied to the oxygen pump element 161 through electrodes 166 and 168 by an external power source not shown. The oxygen pump element 161 pumps oxygen into or out of the measuring chamber 165 at a rate determined by the direction and magnitude of the voltage. The operation of the oxygen pump element 161 is controlled by a control section (not shown) on the basis of the oxygen concentration in the measuring chamber 165 detected by the oxygen concentration cell element 162 so that the oxygen concentration in the measuring chamber 165 is held constantly at a concentration corresponding to the theoretical air-fuel ratio. The air-fuel ratio (A/F) of the exhaust gas can be known on the basis of the pump current in the oxygen pump element 161 at that time. With use of the composite sensor 159, in FIG. 13A, the oxygen sensor ② and the exhaust sensor 1 of the invention can be integrated into one sensor in the same way as the composite sensor 149 in FIG. 14; in addition to that, the accuracy of measuring oxygen concentration can be further improved. When the composite sensor 159 is used as the sensor for controlling light oil injection shown in FIG. 13B, the control of diesel combustion can be performed on the basis of the measurement of the oxygen concentration in the exhaust gas.

Figure 16A:
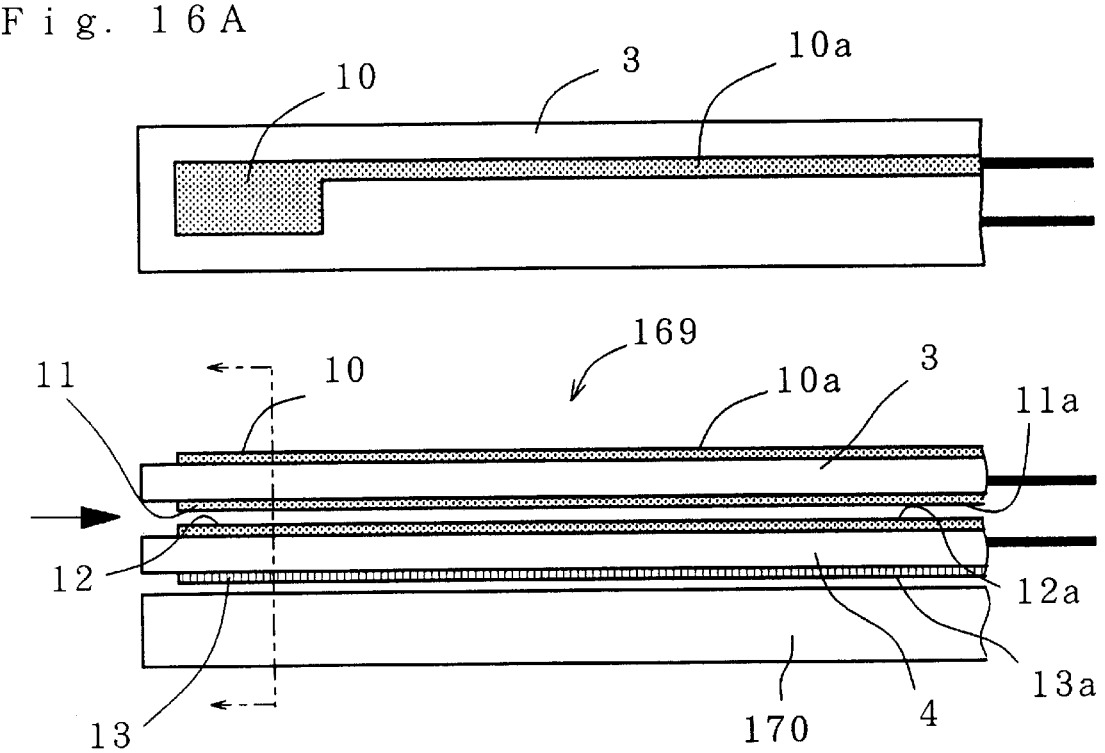
FIG. 16A is a representation illustrating a 3rd example of a composite sensor in which an exhaust gas sensor in accordance with the invention as used.
Figure 16B:
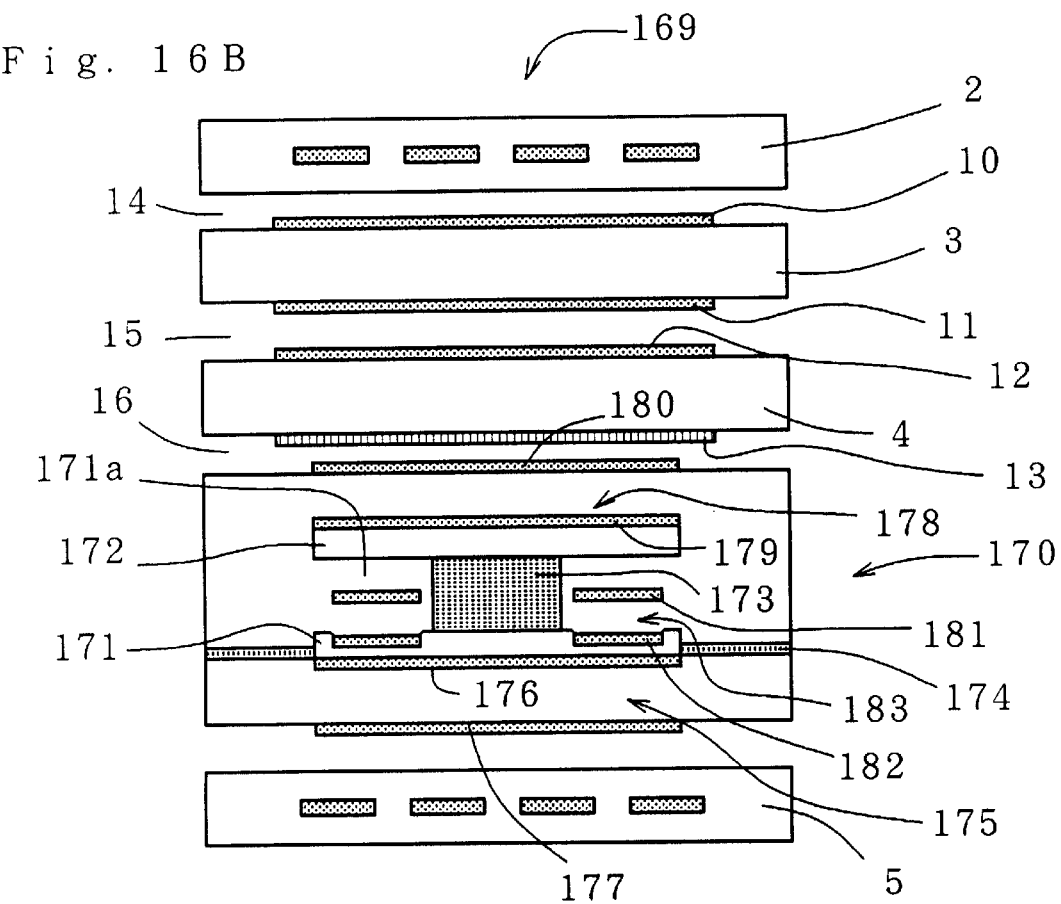
FIG. 16B is a schematic representation following FIG. 16A.

FIG. 16 illustrate an example of a composite sensor with which as NOx sensor of two-chamber type is combined. A composite sensor 169 has the same arrangement as shown in FIG. 14 except that the plate-like oxygen sensor 151 is replaced by NOx sensor 170. The NOx sensor 170 comprises a solid electrolyte having an oxygen-ion conductivity such as $ZrO_2$, and first and second measuring chambers 171, 172 are formed in the sensor 170 so as to sandwich a partition wall 171a and so as to adjoin each other in the direction of the thickness of the sensor. In the partition wall 171a is formed a second diffusion hole 173 which is formed with use of porous ceramic or the like and which allows both the chambers to communicate with each other. The first measuring chamber 171 communicates with the ambient atmosphere by way of first diffusion holes 174. A first oxygen pump element 175 having electrodes 176 and 177 is disposed on the opposite side of the first measuring chamber 171 to the wall 171a, and a second oxygen pump element 178 having electrodes 179 and 180 is disposed on the opposite side of the second measuring chamber 172 to the wall 171a. In the partition wall 171a is formed an oxygen concentration cell element 183 (having an oxygen reference electrode 181 in the partition wall 171a and having an opposing electrode 182 facing the first measuring chamber 171) for detecting the oxygen concentration in the first measuring chamber 171.

In the operation of the composite sensor 169, first, the ambient atmosphere gas is introduced into the first measuring chamber 171 through the first diffusion holes 174. From the introduced gas, oxygen is pumped out by the first oxygen pump element 175. The oxygen concentration in the measuring chamber is detected by the oxygen concentration cell element 183. On the basis of the detected value, the oxygen pumping operation of the first oxygen pump element 175 is controlled by a control section (not shown) so that the oxygen concentration in the gas in the first measuring chamber 171 is of a constant value which will not cause the decomposition of NOx. The gas in which the oxygen concentration has been lowered flows through the second diffusion hole 173 into the second measuring chamber 172, where oxygen is pumped out by the second oxygen pump element 178 so that NOx and oxygen in the gas are completely separated. NOx concentration in the gas can be detected on the basis of the pump current in the second oxygen pump element 178 at that time.

With use of the composite sensor 169 as mentioned above, the concentrations of HC, NOx and oxygen in the exhaust gas can be measured with one sensor.

EMBODIMENT 2

Hereinafter, another embodiment of an exhaust gas sensor in accordance with the invention will be described.

Figure 17A:
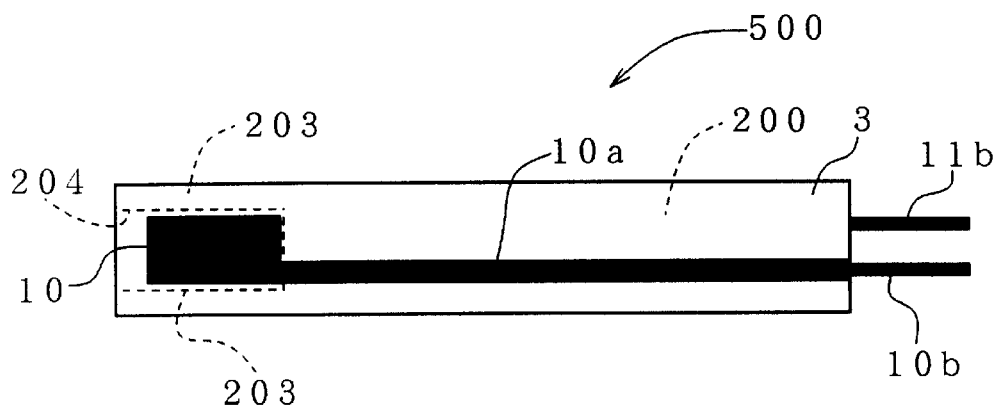
FIG. 17A is a plan view of an exhaust gas sensor in accordance with Embodiment 2 of the invention.
Figure 17B:
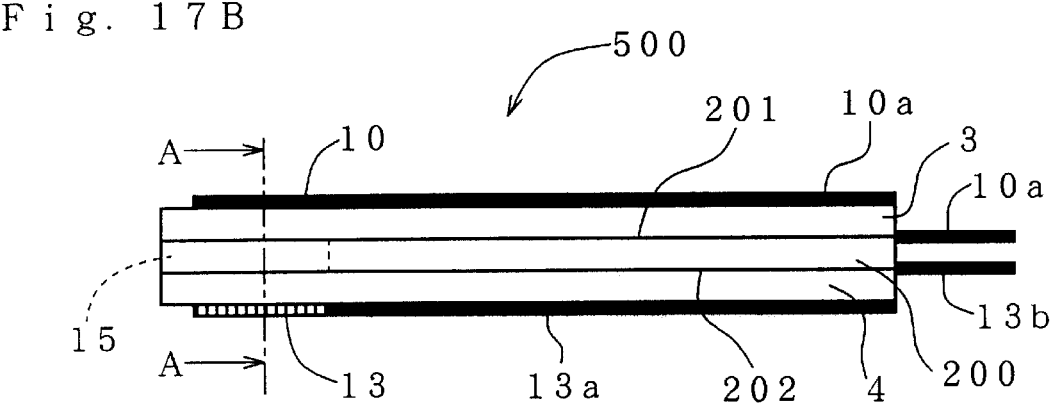
FIG. 17B is a side view illustrating main parts of an exhaust gas sensor in accordance with Embodiment 2 of the invention.
Figure 17C:
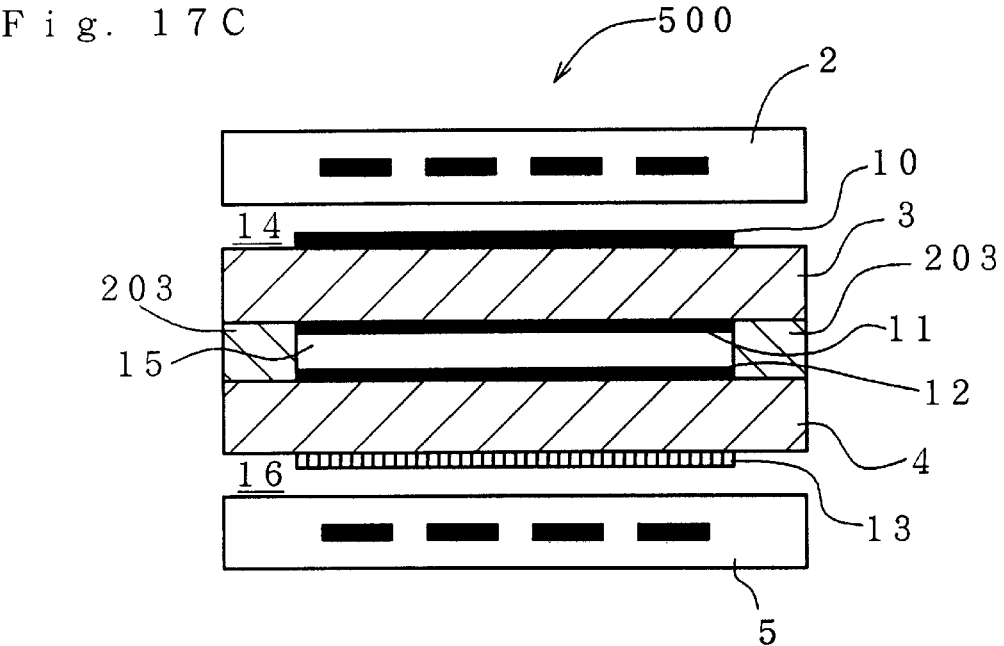
FIG. 17C is a A—A sectional view of FIG. 17B.

An exhaust gas sensor 500 shown in FIG. 17 comprises a first heater 2 (a heater element), an oxygen pump element 3, an oxygen concentration cell element 4, and a second heater 5 (a heater element), which have been formed like elongated plates and have been laminated in the listed order, in the same manner as the exhaust gas sensor of the embodiment 1.

The oxygen pump element 3 is formed like an elongated plate. On both sides of one longitudinal end portion of the element 3 are formed porous electrodes 10 and 11 having an oxygen molecule dissociability. Similar porous electrodes 12 and 13 are formed on both sides of the oxygen concentration cell element 4 (which also serves as temperature detecting means) at the positions corresponding to the electrodes 10, 11 on the oxygen pump element 3. Between the oxygen pump element 3 and the oxygen concentration cell element 4, except the area where the electrodes 10 to 13 are formed, is interposed a plate-like spacer 200 comprising the solid electrolyte ceramic which is the same as the material of the elements. Both sides of the spacer 200 are integrated by sintering with the oxygen pump element 3 and with the oxygen concentration cell element 4 through the medium of insulating layers 201, 202 comprising $Al_2O_3$ or the like. A space 15 is thereby formed between the electrode 11 on the oxygen pump element 3 and the electrode 12 on the oxygen concentration cell element 4. Elongated reinforcing spacers 203 integrated with the spacer 200 are interposed between and integrated with the oxygen concentration cell element 4 and the oxygen pump element 3 in the space 15 so as to extend along both longitudinal side edges of the elements. The space 15 communicates with the outside space at the end faces of the oxygen concentration cell element 4 and the oxygen pump element 3 via an opening 204 as a communicating portion which opens between both the reinforcing spacers 203; exhaust gas is thereby allowed to flow into and out of the space 15.

Spacers 6 and 8 (see FIG. 18) comprising glass, cement, or the like are interposed between the first heater 2 and the oxygen pump element 3, and between the oxygen concentration cell element 4 and the second heater 5, respectively. Besides, spaces 14 to 16 each having a given size are provided between the elements. The space 15 corresponds to a "space between the oxygen pump element and the oxygen concentration cell element", and the space 16 corresponds to an "opposed space". The second heater 5 also serves as a space-forming member.

Figure 18A:
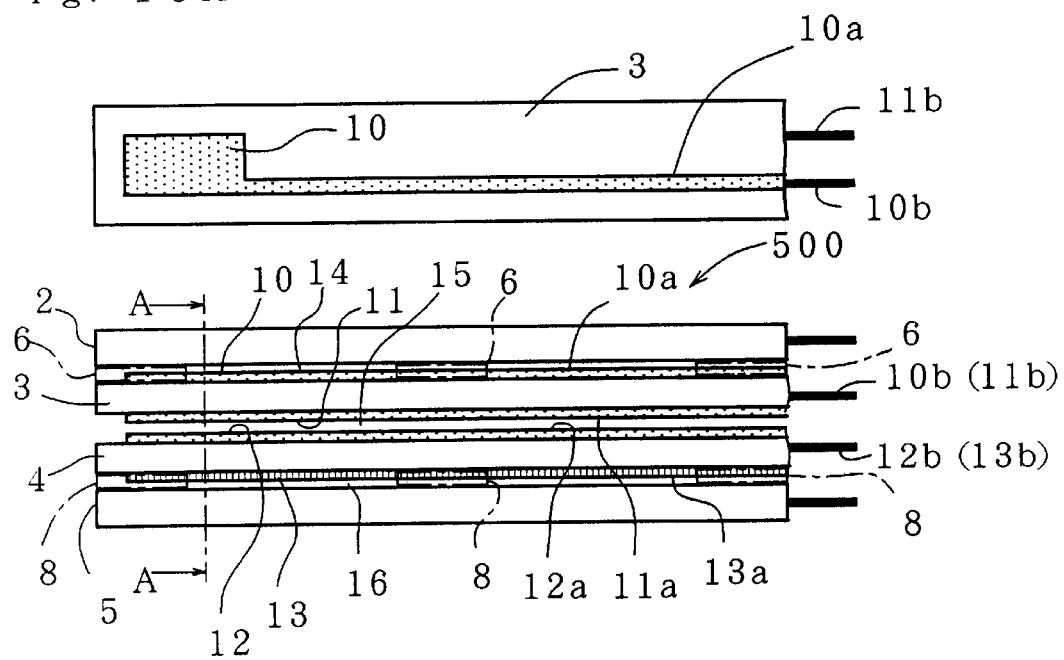
FIG. 18A is a representation illustrating the detailed structure of the same.
Figure 18B:
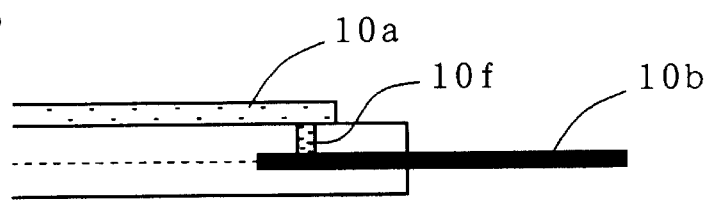
FIG. 18B is a schematic representation following FIG. 18A.
Figure 18C:
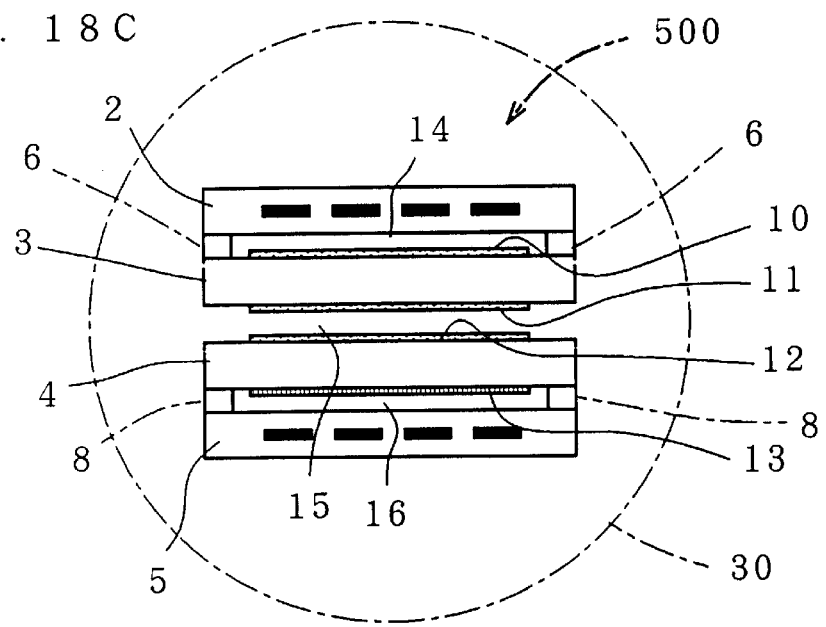
FIG. 18C is a schematic representation following FIG. 18B.
Figure 21A:
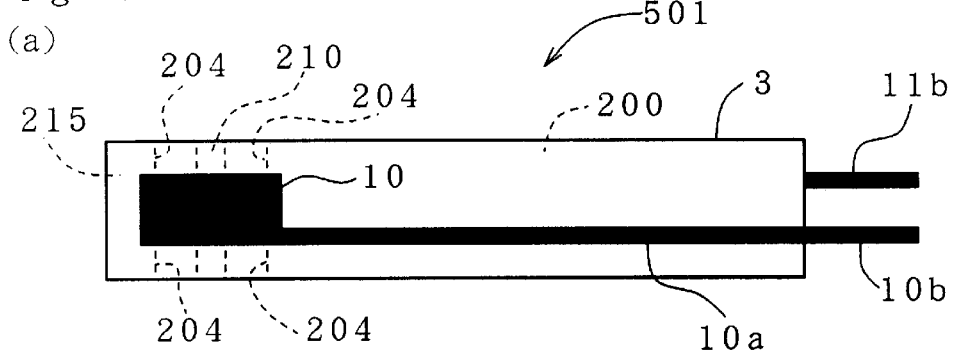
FIG. 21A is a plan view illustrating a 1st modification of the exhaust gas sensor of FIGS. 17A–17C.
Figure 21B:
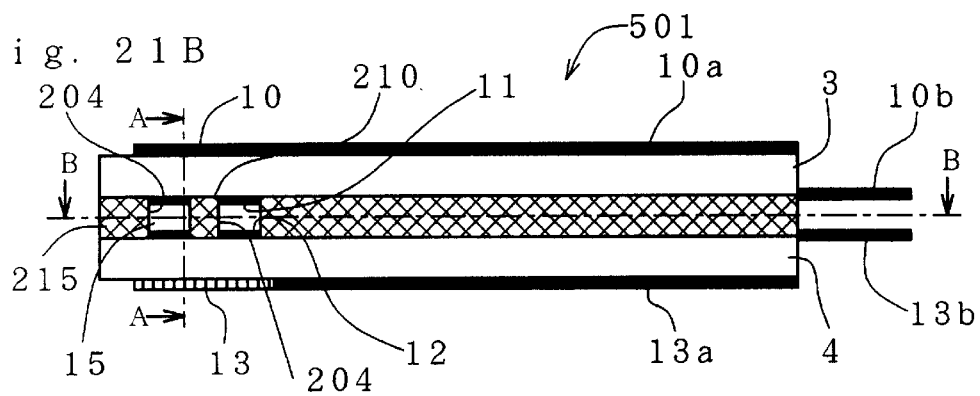
FIG. 21B is a side view of FIG. 21A.
Figure 21C:
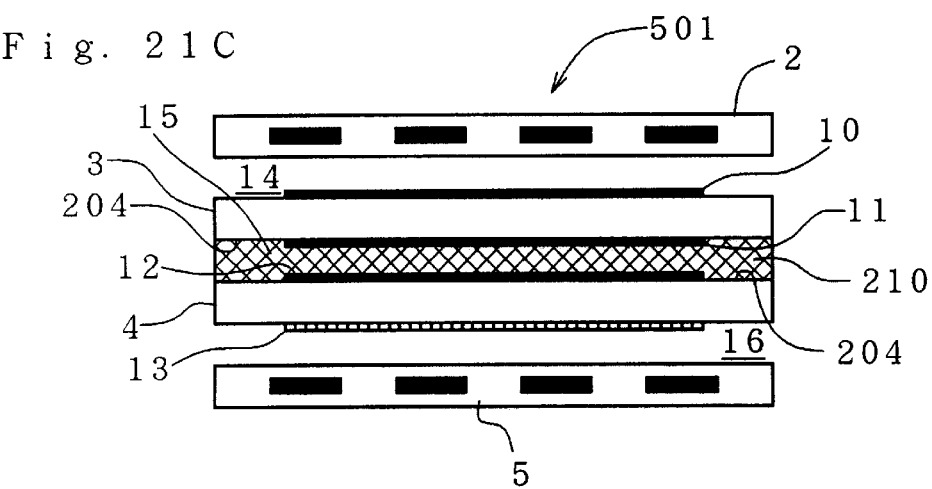
FIG. 21C is an A—A sectional view of FIG. 21B.
Figure 21D:
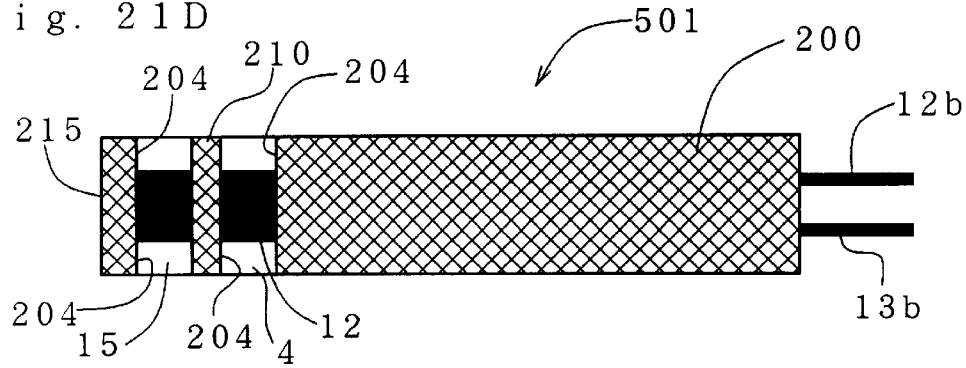
FIG. 21D is a B—B sectional view of FIG. 21B.

FIG. 18 are representations for illustrating the internal structure of the exhaust gas sensor 500 depicted with the spacer 200 and the reinforcing spacers 203 omitted. The main part of the oxygen pump element 3 and of the oxygen concentration cell element 4 have the same structures as the exhaust gas sensor of the embodiment 1; the common elements are therefore designated by the same reference numerals, and the detailed description on the elements is omitted. FIG. 19A illustrates an example of the arrangement of the exhaust gas sensor 500 as a whole and FIG. 19B illustrates the internal structure of the sensor. In the sensor, except that the laminate 31 forming the main parts of the sensor is arranged as shown in FIG. 17, the other elements are the same as the exhaust gas sensor 1 of the embodiment 1 in FIGS. 3; therefore, the common elements are designated by the same reference numerals, and the detailed description on the elements is similarly omitted.

A method of integrally sintering the oxygen pump element 3 and the oxygen concentration cell element 4 will be described below referring to FIG. 20. An unsintered assembly 310 for forming an integral sintered body consists of a first portion 211 (corresponding to a first ceramic powder compact) for forming the oxygen pump element 3, a second portion 212 (corresponding to a second ceramic powder compact) for forming the oxygen concentration cell element 4, and a third portion 213 for forming the space 15. The first portion 211 comprises $ZrO_2$ green sheet 220 which has been formed with use of a material in which $ZrO_2$ powder and organic binder are kneaded and which is to be the main body of the oxygen pump element 3. Insulating coats (insulating layer patterns) 221 and 222 for achieving the insulation between lead portions 10a, 11a and the oxygen pump element 3 are formed with use of $Al_2O_3$ paste or the like on both surfaces of the $ZrO_2$ green sheet 220 except the areas where the electrodes 10, 11 (see e.g., FIG. 18) are to be formed. After the formation of the insulating coats 221 and 222, there are printed and formed electrode patterns 223 and 224 for forming the electrodes 10, 11 and the lead portions 10a, 11a, with use of Pt paste or the like. On the electrode pattern 223 which is to be the outside electrode 10 is formed a protecting overcoat 225 with use of $Al_2O_3$ paste or the like.

In the second portion 212, similarly, insulating coats (insulating layer patterns) 231 and 232 are formed on both surfaces of a $ZrO_2$ green sheet 230 which is to be the main body of the oxygen concentration cell element 4. On the side of the insulating coat 231 is formed an electrode pattern 233 for forming the electrode 12 and its lead portion 12a. On the side of the insulating coat 232, however, is formed only an electrode lead portion pattern 234 for forming the lead portion 13a, because the electrode 13 (the third electrode) comprising Au and having a relatively low melting point cannot be sintered integrally with $ZrO_2$. On the pattern 234, a protecting overcoat 235 is applied with use of $Al_2O_3$ paste.

The third portion 213 principally comprises a $ZrO_2$ green sheet 240 in which a portion 200a to be the spacer 200 (a spacer forming body) and a portion 203a to be the reinforcing spacer 203 are integrally formed. On both surfaces of the green sheet 240 are formed cementing coats 241 and 242 with use of $Al_2O_3$ paste or the like. The cementing coats 241 and 242, together with the insulating coats 222 and 231, are sintered to form the insulating layers 201 and 202, respectively, and thus serve to cement together the spacer 200 and the reinforcing spacer 203 and the oxygen pump element 3 and the oxygen concentration cell element 4.

Between the first portion 211 and the third portion 213, which are to be laminated together, are interposed one-end sides of Pt—Rh alloy wires 243a, 243b for forming terminals 10b and 11b (see FIG. 2), corresponding to the ends of the lead portions 10a and 11a. At a position in the $ZrO_2$ green sheet 220 corresponding to the end of the lead portion 10a is provided a through hole 220a, which is to be filled with paste when the pattern of the lead portion 10a is formed. As shown in FIG. 18B, the filled paste is sintered by sintering to form a conducting portion 10f, which provides continuity between the terminal 10b (Pt—Rh alloy wire 243b) and the lead portion 10a. The pattern of the lead portion 11a and the Pt—Rh alloy wire 243a are sandwiched between the $ZrO_2$ green sheets 220 and 240 so as to directly contact each other.

The second portion 212 is laminated with the third portion 213 on the side opposite to the first portion 211, and one-end sides of Pt—Rh alloy wires 244a, 244b for forming terminals 12b and 13b (see FIG. 18) are interposed therebetween so as to correspond to the ends of the lead portions 12a and 13a, respectively. With this lamination, the unsintered assembly 310 is completed. At a position in the $ZrO_2$ green sheet 230 corresponding to the end of the lead portion 13a is provided a through hole 230a, in the same manner as the through hole 220a in the first portion 211, so that a conducting portion based on the paste which is filled in the through hole 230a provides continuity between the terminal 13b and the lead portion 13a. The pattern of the lead portion 12a and the Pt—Rh alloy wire 244a which is to be the terminal 12b are sandwiched between the $ZrO_2$ green sheets 240 and 230 so as to directly contact each other.

Sintering the unbaked assembly 310 provides an integral sintered body shown in FIGS. 17 and 18 of the oxygen pump element 3 and of the oxygen concentration cell element 4 on which the third electrode 13 has not yet been formed. Subsequently, as shown in FIG. 20, a pattern 245 is paste-printed with use of Au powder paste at the corresponding position on the oxygen concentration cell element 4, and baked at a temperature (e.g., between 850 and 1000° C.) lower than the sintering temperature of ceramics, as a secondary metallizing treatment. The third electrode 13 is thus formed and the main parts of the exhaust gas sensor are finished.

As shown in FIG. 27, in the space 15 between the oxygen concentration cell element 4 and the oxygen pump element 3 may be formed props 210 which define the distance of the space 15 without impeding gas from flowing into and out of the space 15. In an example shown in FIG. 21, a prop 210 is formed of the solid electrolyte ceramic which is the same as the material of the oxygen pump element 3 and the oxygen concentration cell element 4, in the form of a partition wall which partitions the space 15 into two parts in the middle of the length of the space 15. An additional spacer 215 is also interposed between and integrated with the elements 3, 4 on the side opposite to the spacer 200 across the space 15. The space 15 communicates with the outside space through openings 204, as the communicating portions, which are formed on both longitudinal side surfaces of the laminate of the oxygen pump element 3 and of the oxygen concentration cell element 4 and on both sides of the prop 210. This arrangement allows exhaust gas to flow into and out of the space 15.

Figure 22:
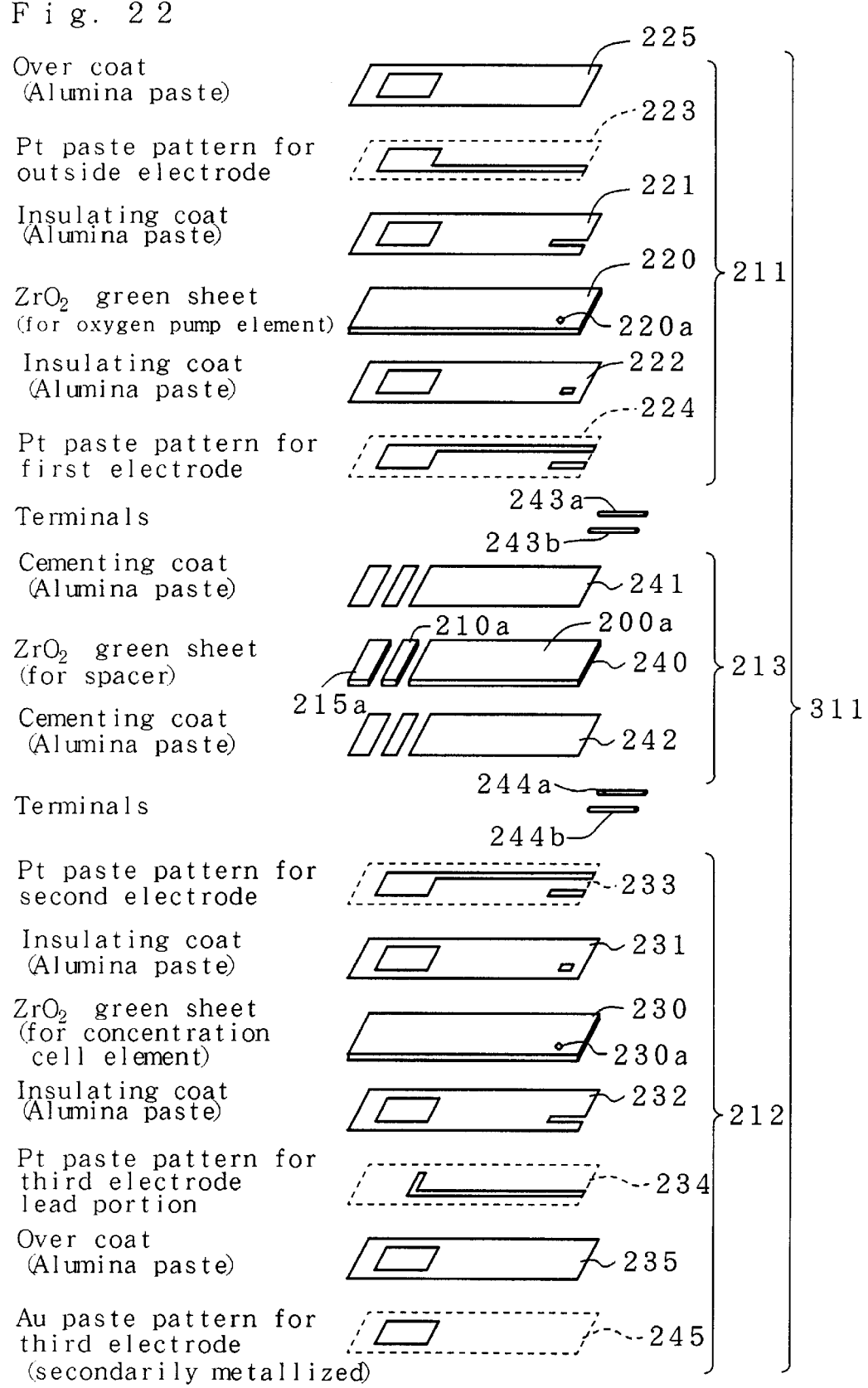
FIG. 22 is an exploded view in perspective illustrating a method of producing the exhaust gas sensor of FIG. 21.
Figure 23A:
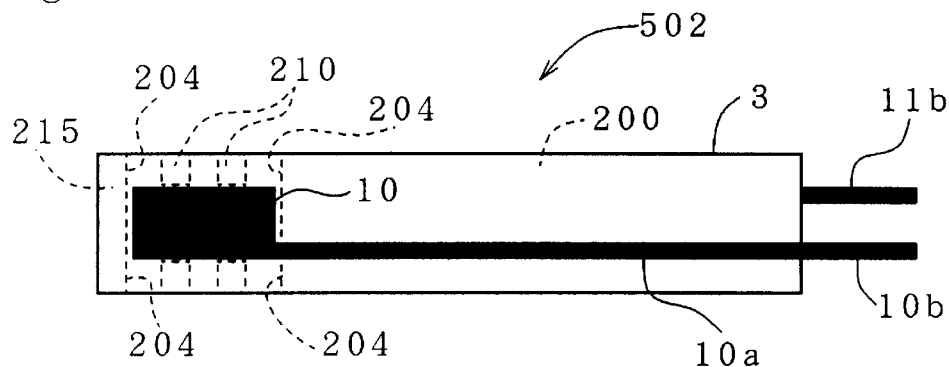
FIG. 23A is a plan view illustrating a 2nd modification of the exhaust gas sensor of FIGS. 17A–17C.
Figure 23B:
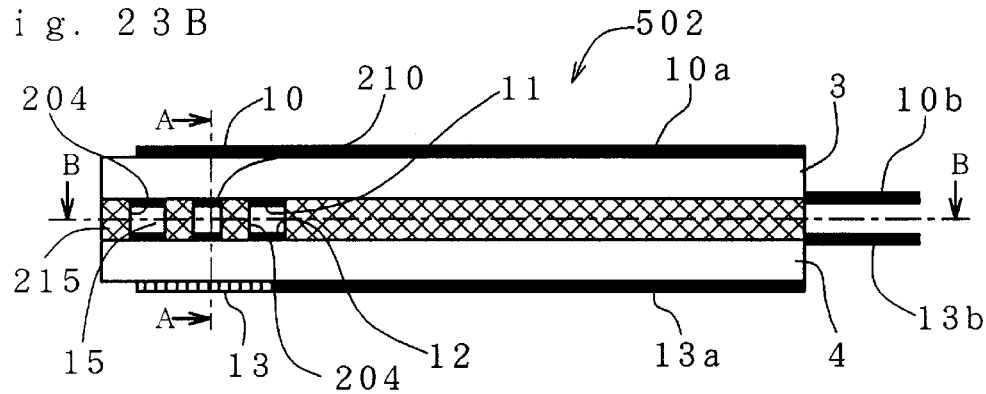
FIG. 23B is a side view of FIG. 23A.
Figure 23C:
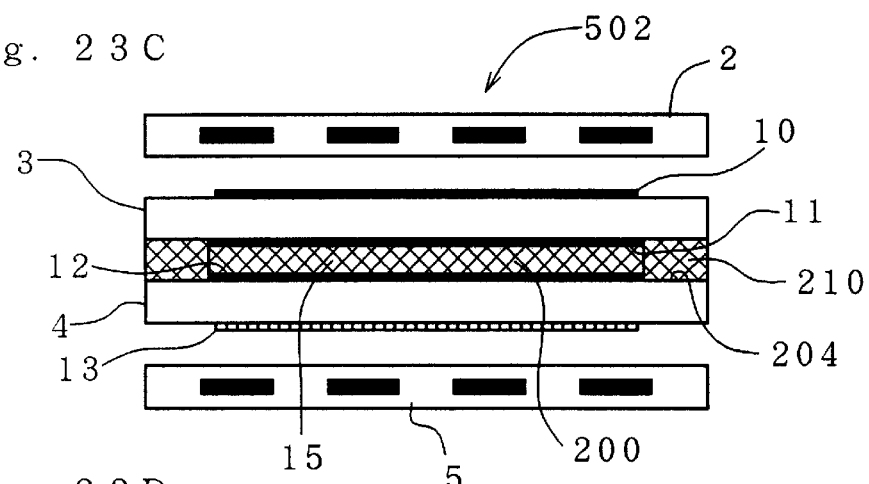
FIG. 23C is an A—A sectional view of FIG. 23B.
Figure 23D:
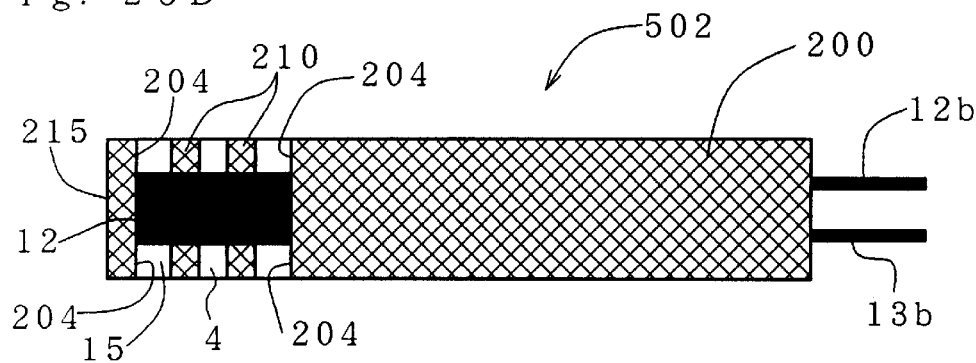
FIG. 23D is a B—B sectional view of FIG. 23B.
Figure 24A:
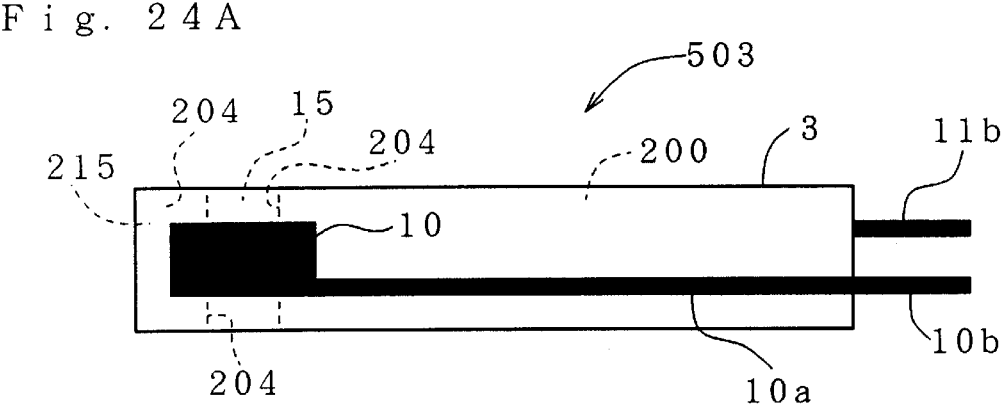
FIG. 24A is a plan view illustrating a 3rd modification of the exhaust gas sensor of FIGS. 17A–17C.
Figure 24B:
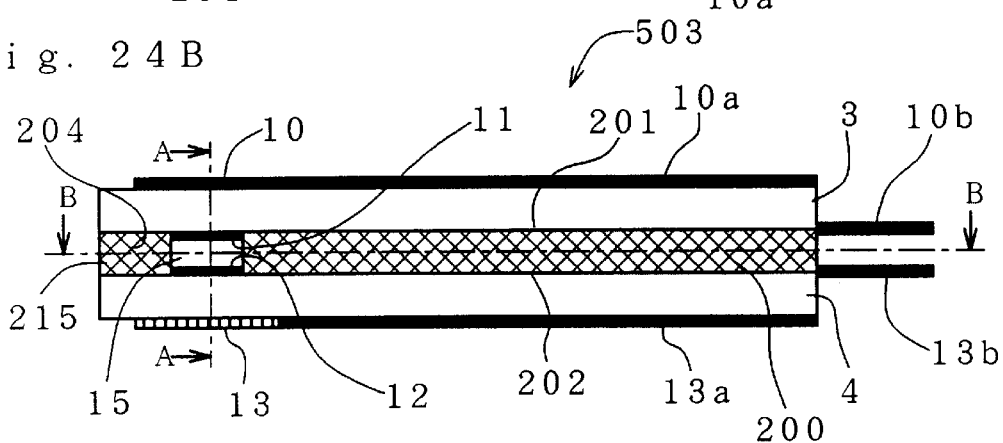
FIG. 24B is a side view of FIG. 24A.
Figure 24C:
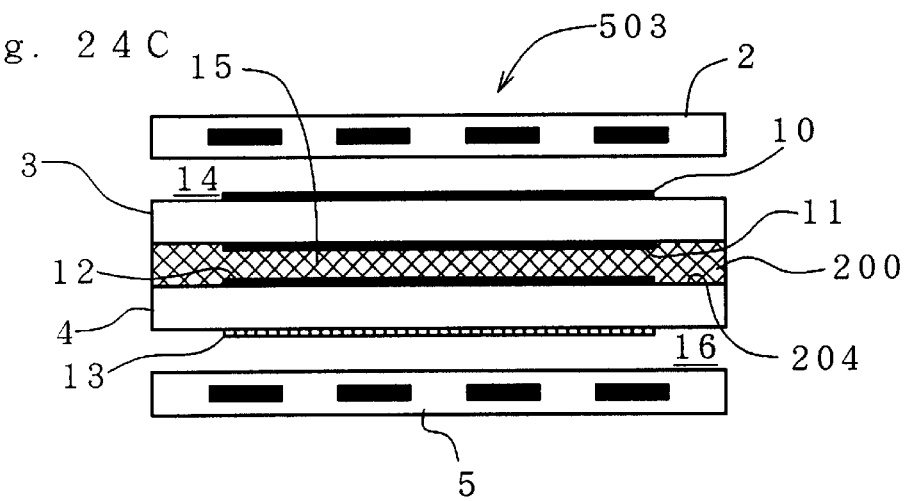
FIG. 24C is an A—A sectional view of FIG. 24B.
Figure 24D:
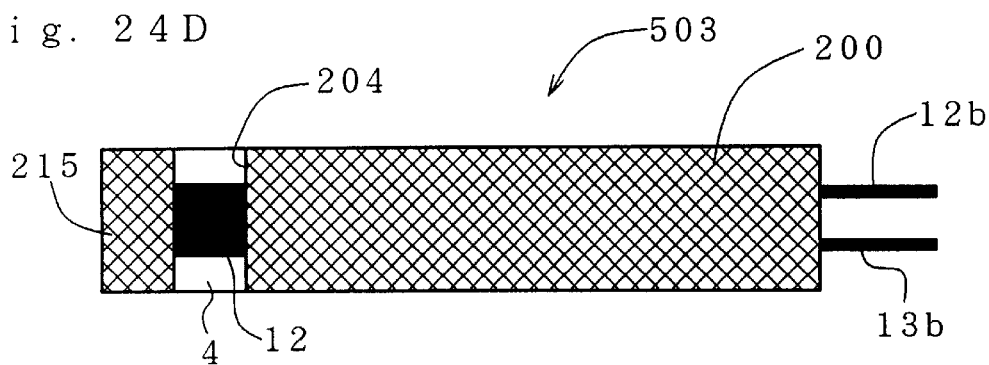
FIG. 24D is a B—B sectional view of FIG. 24B.

The prop 210 can be formed integrally with the oxygen pump element 3 and with the oxygen concentration cell element 4 by the sintering of an unsintered assembly 310 shown in FIG. 22. The unsintered assembly 310 in FIG. 22 is constituted in the same manner as shown in FIG. 20 except for the third portion 213. In the third portion 213 are formed a spacer compact 200a for forming the spacer 200, an additional spacer compact 215a for forming the additional spacer 215 which is disposed on the opposite side of the area that is to be the space 15, and a prop compact 210a as the pattern of the prop disposed therebetween, with use of the $ZrO_2$ green sheet 240. The first portion 211 and the second portion 212 are laminated on both sides of the compacts.

By the sintering of the laminate, the prop 210 based on the prop compact 210a is formed between the oxygen concentration cell element 4 and the oxygen pump element 3. In the sintering, the interposed prop compact 210a prevents the $ZrO_2$ green sheets laminated with the space formed therein from deforming and sagging into the space, so that the space 15 of an expected size can be formed stably. In the example shown in FIG. 21, the prop 210 is so formed as to extend across the electrodes 11 and 12 widthwise; however, as shown in FIG. 23, the props 210 may be formed in the positions which may not provide interference with the electrodes 11 and 12. In the drawing, a plurality of props 210 are disposed at given intervals along both longitudinal sides of the oxygen concentration cell element 4 and the oxygen pump element 3. In the case that the length of the space 15 along the lengths of the oxygen concentration cell element 4 and the oxygen pump element 3 is not so large, the prop(s) 210 can be omitted as shown in FIG. 24.

Figure 25A:
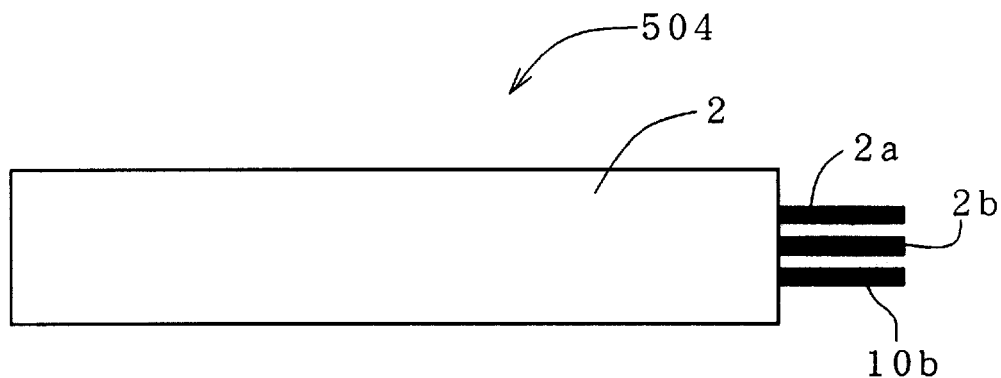
FIG. 25A is a plan view illustrating a 4th modification of the exhaust gas sensor of FIGS. 17A–17C.
Figure 25B:
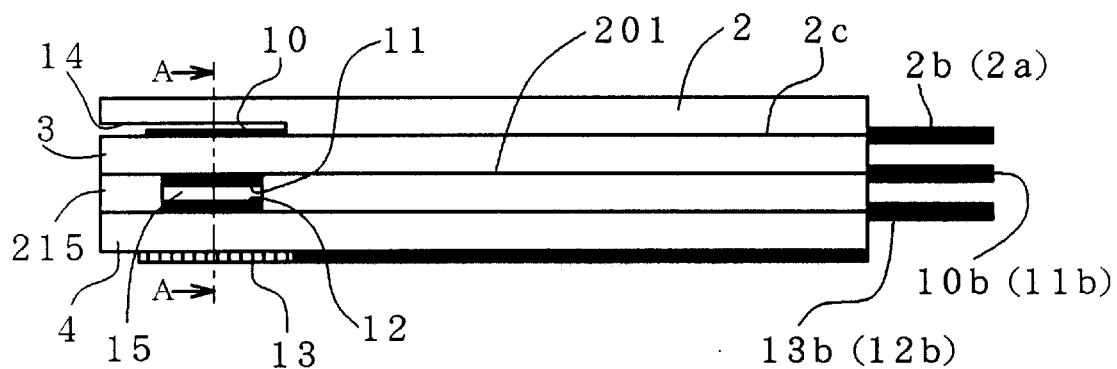
FIG. 25B is a side view of FIG. 25A.
Figure 25C:
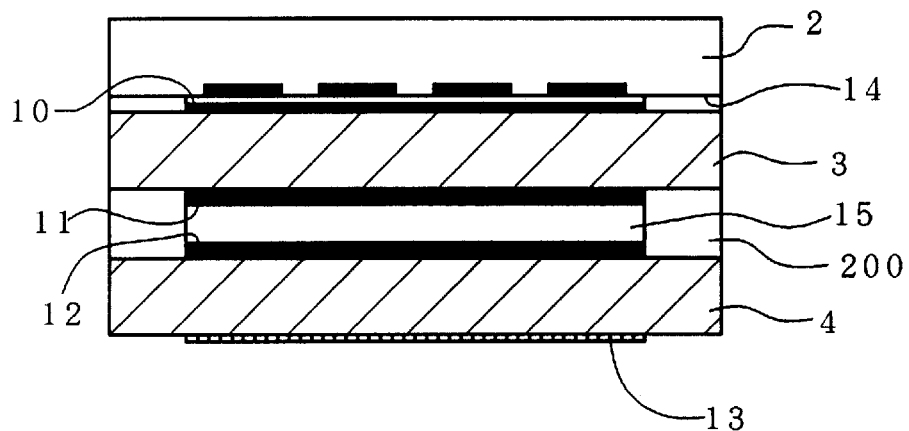
FIG. 25C is an A—A sectional view of FIG. 25B.

At least one of the first and second heaters 2 and 5 can be integrated by sintering with the oxygen concentration cell element 4 and with the oxygen pump element 3. FIG. 25 illustrate an example of such an arrangement. The first heater 2 is laminated on the opposite side of the oxygen pump element 3 to the space 15. The oxygen pump element 3, the oxygen concentration cell element 4, and the first heater 2 are laminated together so as to form an integral sintered body. The second heater 5 is omitted here. The space 14 is formed between the first heater 2 and the outside electrode 10, and the first heater 2 and the oxygen pump element 3 are joined together in the area except the space 14, through the medium of an insulating layer 2c comprising $Al_2O_3$ or the like.

As shown in FIG. 26, the above sensor structure is achieved, in such an unsintered assembly as generally shown in FIG. 22, by laminating a fourth portion (a third ceramic powder compact) 214 that is to be the first heater 2, on the side of the first portion 211 opposite to the third portion 213, and by sintering the unsintered assembly 312 obtained as the laminate. The difference from FIG. 22 will be described below: The overcoat 225 in FIG. 22 is omitted from the first portion 211. The fourth portion 214 is formed by the lamination of Pt—Rh alloy wires 257a, 257b which are to be terminals 2a1, 2b (see FIG. 25) for energizing the heater, a cementing coat 256 (made of $Al_2O_3$ paste or the like), an additional supporting pattern 255 for forming space (made of carbon paste or the like), an overcoat 254 (made of $Al_2O_3$ paste or the like), a heater pattern 253 (made of Pt paste or the like), an insulating coat 252 (made of $Al_2O_3$ paste or the like), a $ZrO_2$ green sheet 251 (which is to be the main body of the heater), and an overcoat 250 (made of $Al_2O_3$ paste or the like), which are laminated in the listed order from the nearest to the electrode pattern 223. The props 210 are omitted in the same way as the arrangement in FIG. 24. The additional supporting pattern 255 for forming space is formed selectively in the area corresponding to the outside electrode 10 of the electrode pattern 223, and the pattern 255 vanishes in the sintering to form the space 14 between the main body of the heater 2 based on the $ZrO_2$ green sheet 251 and the oxygen pump element 3, as shown in FIG. 25.

FIG. 27 illustrate an example of the arrangement of an exhaust gas sensor in which spacers are not used, as a more simple arrangement. In the exhaust gas sensor 505, an oxygen pump element 3 and an oxygen concentration cell element 4 are formed like elongated plates and disposed so as to face each other. Electrodes 10 to 13 are formed on one longitudinal end portions of the surfaces of the oxygen pump element 3 and of the oxygen concentration cell element 4. Props 210 are formed in a space 15 between the oxygen pump element 3 and the oxygen concentration cell element 4, while, in the area except the space 15, the oxygen pump element 3 and the oxygen concentration cell element 4 are joined and integrated together through the medium of an insulating layer 260 having a thickness smaller than the height of the props 210. The sensor is provided with at least one of first and second heaters 2 and 5; however, FIG. 27 are depicted with the heaters omitted.

Figure 27A:
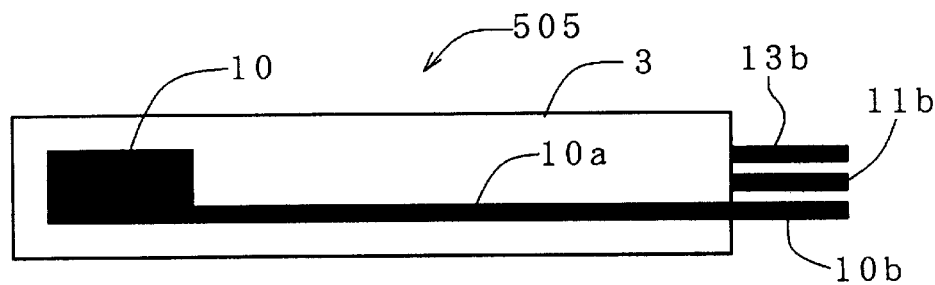
FIG. 27A is a plan view illustrating a 5th modification of the exhaust gas sensor of FIGS. 17A–17C.
Figure 27B:
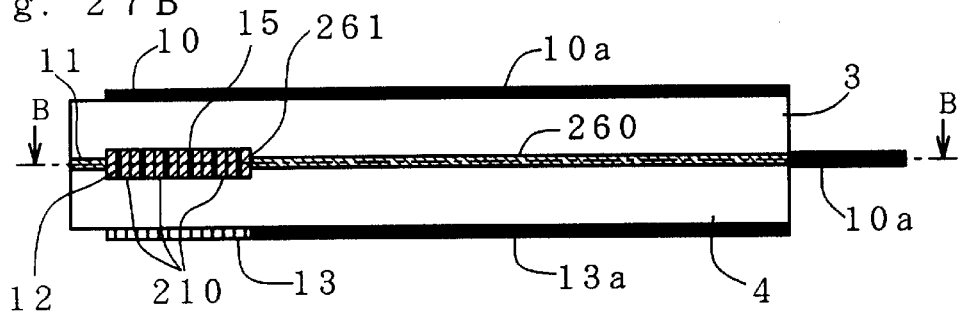
FIG. 27B is a side view of FIG. 27A.
Figure 27C:
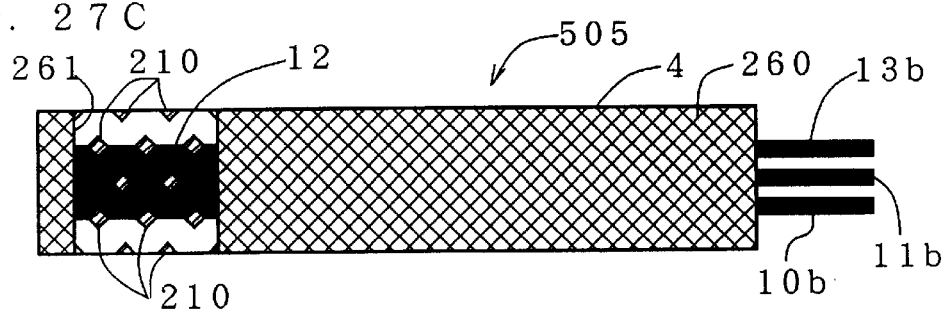
FIG. 27C is an B—B sectional view of FIG. 27B.
Figure 27D:
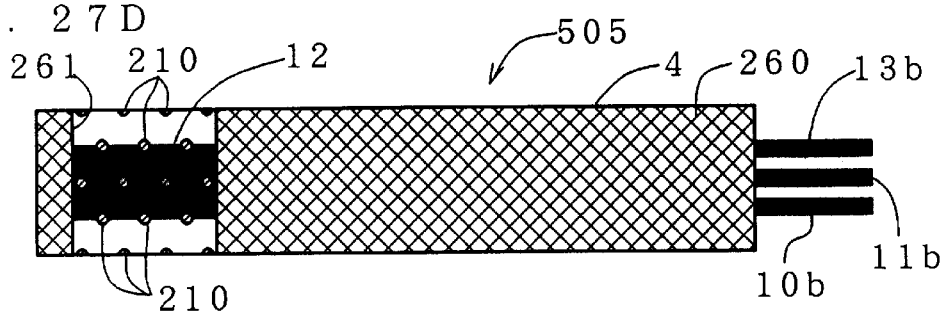
FIG. 27D is a sectional view illustrating a modification of props of the sensor.
Figure 27E:
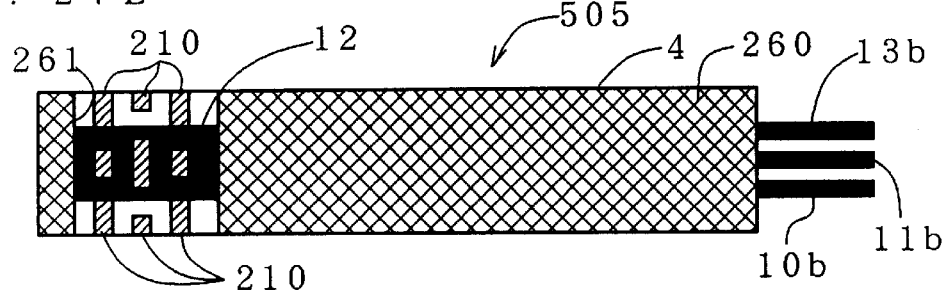
FIG. 27E is a sectional view illustrating another modification of props of the sensor.

The space 15 opens on both longitudinal side surfaces of the laminate of the oxygen pump element 3 and of the oxygen concentration cell element 4 to from communicating portions 261 which allow exhaust gas to flow into and out of the space 15. Terminals 10b, 11b, and 13b of the electrodes 10 to 13 protrude from one end surfaces of the oxygen pump element 3 and of the oxygen concentration cell element 4, with the base ends thereof interposed between the elements. The form of the connection of the terminals 10b and 13b to the electrodes 10 and 13 is the same as shown in FIG. 18B. The electrodes 11 and 12 are commonly grounded as described below, and the terminal 11b is therefore shared between the electrodes 11 and 12, with the terminal 12b in the arrangement of FIG. 18 omitted. As shown in FIG. 27C, the props 210 having a rectangular section are arranged scatteringly or staggered; however, the props may have a circular section as shown in FIG. 27D or may have rectangular sections of different lengths as shown in FIG. 27E.

A method of producing the above sensor structure will be described with use of FIG. 28. In this case, the production is also achieved basically by the sintering of the unsintered assembly 315 comprising the first portion 211 and the second portion 212; however, the differences in producing method from the sensor structure shown in FIG. 17 and others are as follows. First, the third portion including the $ZrO_2$ green sheet for forming the spacer is omitted. In place of that, prop patterns 266a and 266b which are to be props 210 are formed in the area which is to be the space 15, on the surfaces facing each other of the first portion 211 and of the second portion 212, with use of ceramic powder paste (e.g., porous $Al_2O_3$ powder paste). Additional supporting patterns 267a and 267b are formed at positions which do not interfere with the prop patterns 266a and 266b, in the area which is to be the space 15, with use of powder paste made from a material which burns or decomposes by sintering (e.g., carbon paste). In the area other than the area which is to be the space 15, a cementing coat 269 as an insulating layer pattern is formed of $Al_2O_3$ powder paste or the like with its thickness smaller than the sum of the heights of the prop patterns 266a and 266b.

Figure 30A:
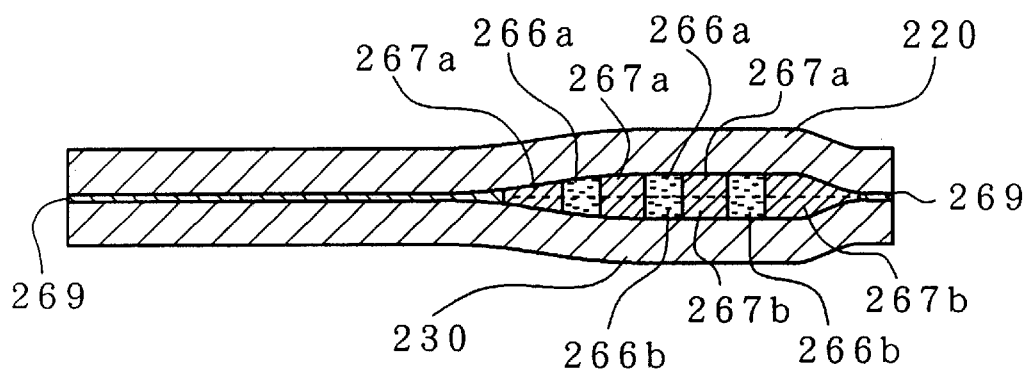
FIG. 30A is a representation illustrating the function of the additional supporting pattern.
Figure 30B:
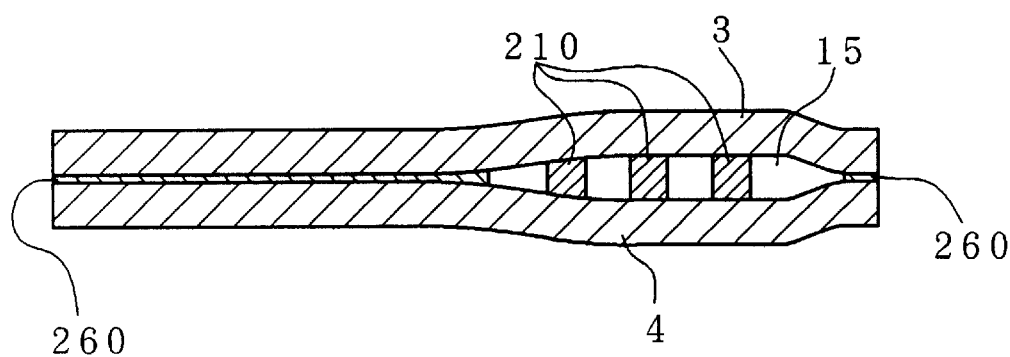
FIG. 30B is a schematic representation following FIG. 30A.

By the sintering of the unsintered assembly 315, as shown in FIG. 30, the additional supporting patterns 267a and 267b vanish, the prop pattern 266a and 266b are integrated together to form the props 210, and the space 15 of which the size is defined by the props 210 is formed, between the oxygen concentration cell element 4 and the oxygen pump element 3. In the area other than the space 15, the oxygen concentration cell element 4 and the oxygen pump element 3 are joined together through the medium of an insulating layer 260 based on the cementing coat 269.

Figure 29A:
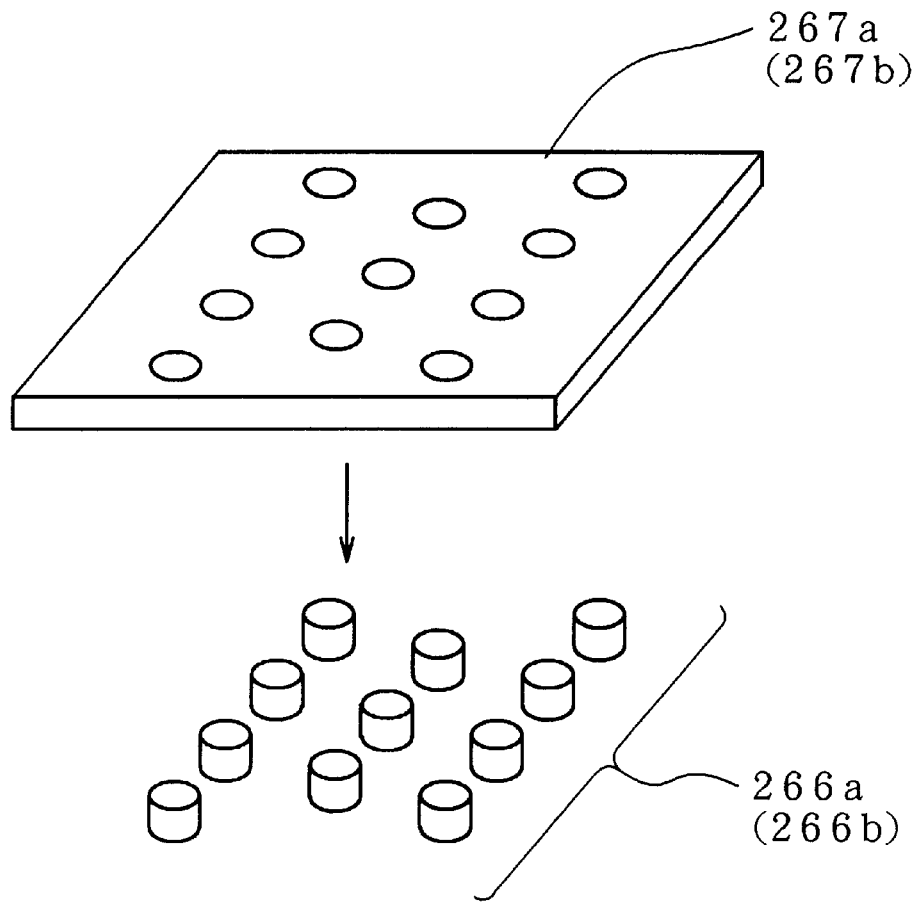
FIG. 29A is a representation schematically illustrating the relation between prop pattern and additional supporting pattern in the sensor.
Figure 29B:
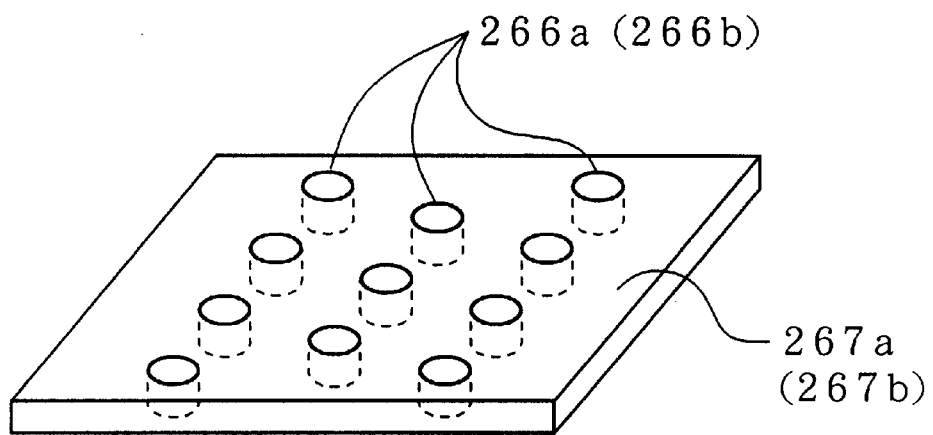
FIG. 29B is a schematic representation following FIG. 29A.

As shown in FIG. 29, the prop patterns 266a and 266b and the additional supporting patterns 267a and 267b are formed complementarily so as to generally fill a plane. When the first portion 211 and the second portion 212 are laminated, the crush of the prop patterns 266a and 266b between both the portions is prevented or restrained by the reinforcement effect by the additional supporting patterns 267a and 267b. Even though the thickness of the cementing coat 269 is considerably smaller than the sum of the thicknesses if the prop patterns 266a and 266b as exaggeratively shown in FIG. 30A, the first portion 211 and the second portion 212, of which the main parts are formed of the $ZrO_2$ green sheets 220 and 230, can be brought into intimate contact with each other through the medium of the cementing coat 269, by slight flexes of the $ZrO_2$ green sheets 220 and 230, and can be integrated together without a hitch by sintering.

Figure 31A:
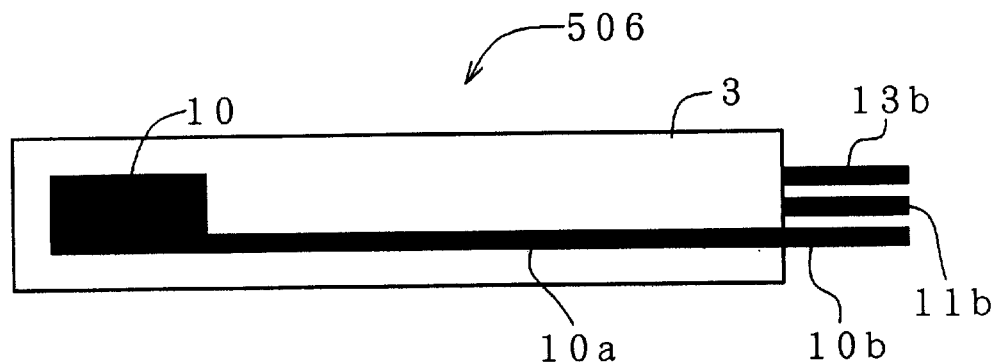
FIG. 31A is a plan view illustrating a 6th modification of the exhaust gas sensor of FIGS. 17A–17C.
Figure 31B:
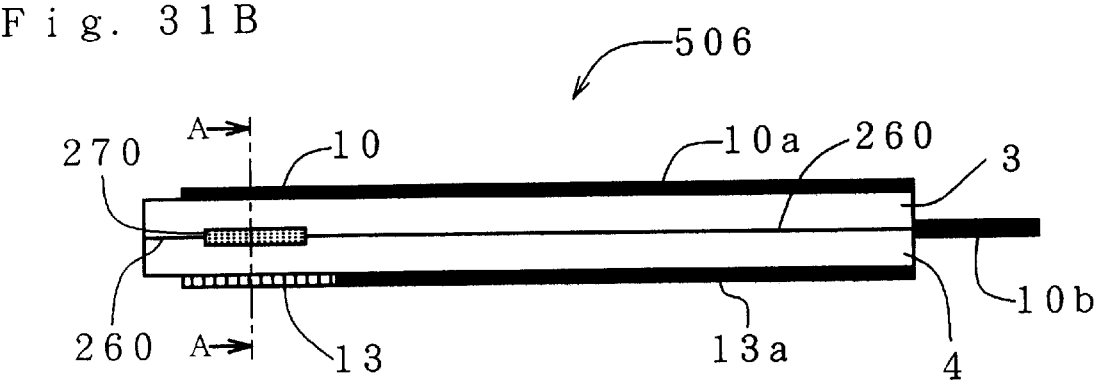
FIG. 31B is a side view of FIG. 31A.
Figure 31C:
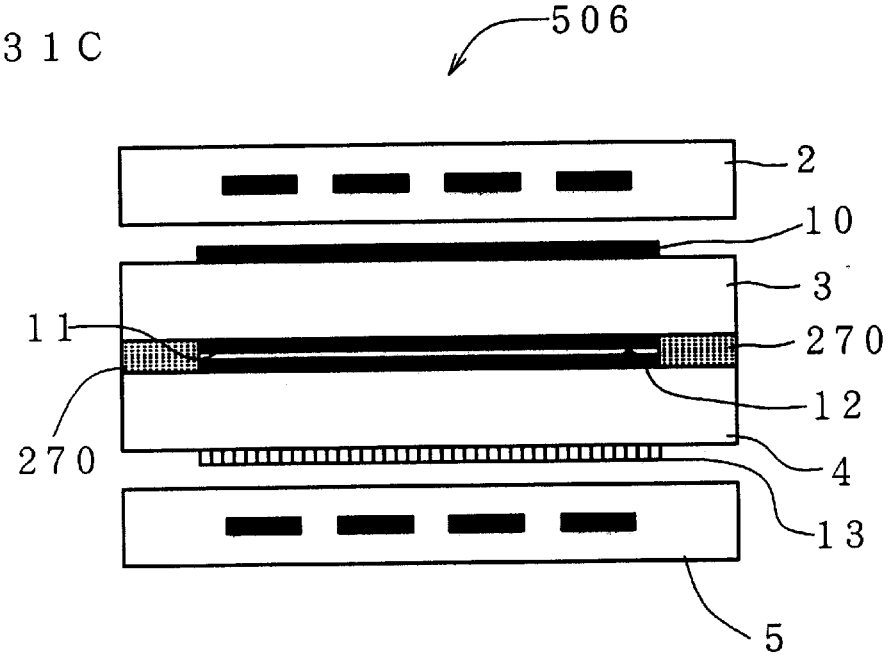
FIG. 31C is an A—A sectional view of FIG. 31B.

FIG. 31 illustrate an example of a modified sensor structure which can be obtained by a producing method similar to that shown in FIG. 28. In this arrangement, communicating portions of a space 15 are not formed as openings but formed as porous ceramic bodies 270 which are made of porous $Al_2O_3$ sintered bodies. The props 210 are not formed.

Figure 32:
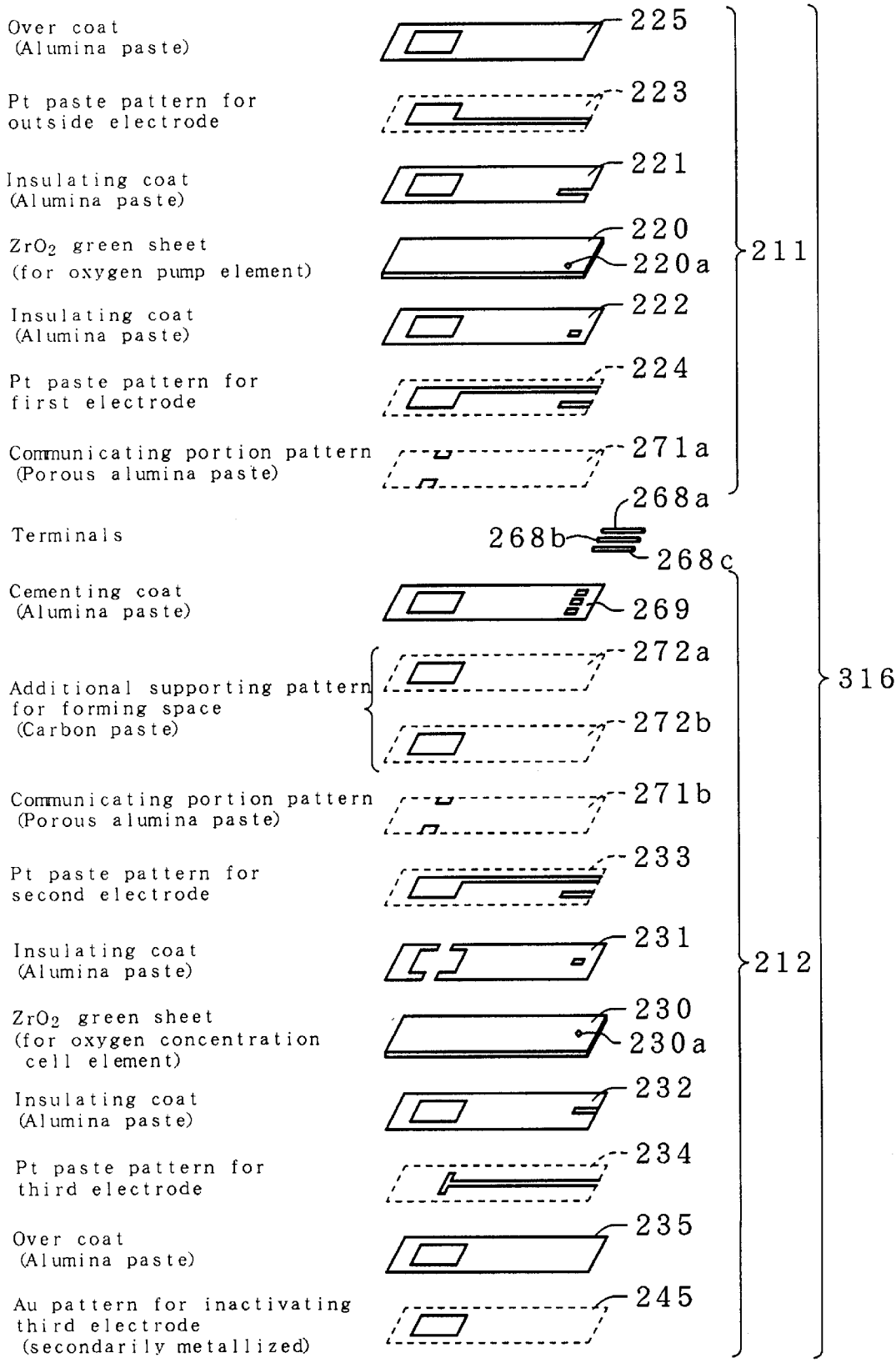
FIG. 32 is an exploded view in perspective illustrating a method of producing the exhaust gas sensor of FIGS. 31.

A method of producing the above structure will be described with use of FIG. 32, chiefly on the differences from FIG. 28. In place of the prop patterns 266a, 266b in FIG. 28, communicating portion patterns 271a and 271b for forming the porous ceramic bodies 270 are formed of porous $Al_2O_3$ powder paste. In the same way as shown in FIG. 28, in the space forming portion are formed additional supporting patterns 272a and 272b for forming space, which are made of carbon paste. By sintering, the communicating portion patterns 271a and 271b are integrated together to form the porous ceramic bodies 270, and the additional supporting patterns 272a and 272b for forming space vanish to form the space 15.

A sensor system with use of the above exhaust gas sensor will be described below.

Figure 33:
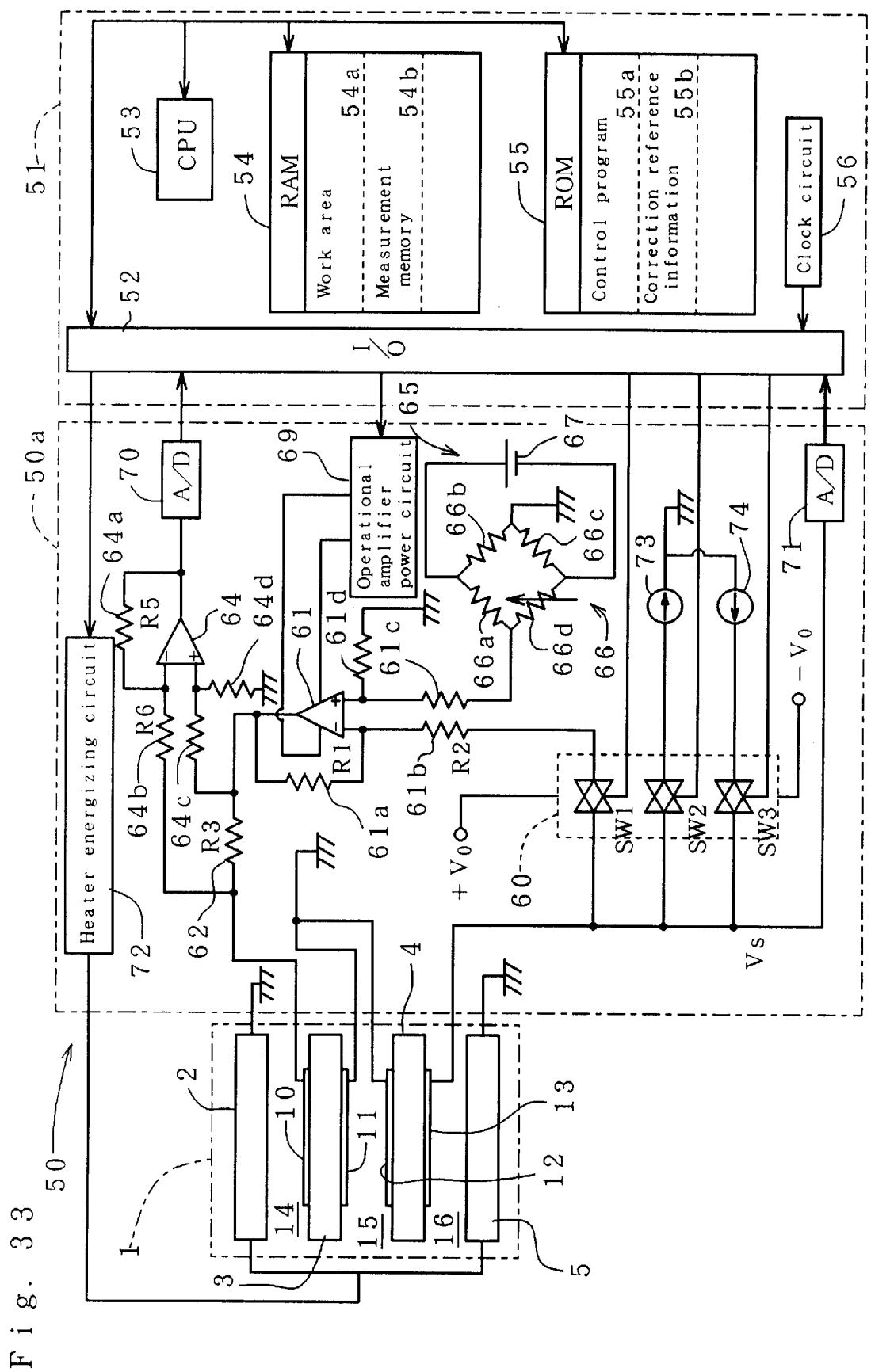
FIG. 33 is a block diagram illustrating the electrical arrangement of an example of an exhaust gas sensor system in accordance with the invention.

FIG. 33 is a block diagram illustrating the electrical arrangement of an example of a sensor system using the exhaust gas sensor 1. The sensor system 50 comprises the exhaust gas sensor 1, a microprocessor 51, and a peripheral circuit 50a providing a connection between the exhaust gas sensor 1 and the microprocessor 51. With use of control program 55a stored in a ROM 55, a CPU 53 of the microprocessor 51 acts as the main constituent of means for correcting the information on the concentration of a constituent to be detected, means for controlling energization, means for determining the correction of pump current, correction calculating means, means for producing corrected concentration information, means for measuring internal resistance, temperature information producing means, means for measuring concentration cell electromotive force, and voltage information correcting means.

In the oxygen concentration cell element 4 of the exhaust gas sensor 1, the second electrode 12 is grounded, and the third electrode 13 is connected to the negative terminal of an operational amplifier 61 (pump current controlling means) for inverting amplification, through a switching system, e.g., a switch SWI of a bipolar analog switching circuit 60 comprising CMOS-ICs or the like. To the positive terminal of the operational amplifier 61 is connected a power circuit 65 for providing a target value EC of electromotive force. The power circuit 65 is arranged so that the setting of the target value EC of electromotive force can be changed within a given range. In the example shown in the drawing, for example, the power circuit 65 comprises a bridge circuit 66 which has three fixed resistors 66a to 66c and one variable resistor 66d on the sides thereof, and a power source 67 connected to the bridge circuit 66. With the resistance range of the variable resistor 66d given as Rmin to Rmax, the resistances of the fixed resistors 66a to 66c have been adjusted so that, at a resistance value Re (Rmin<Re<Rmax) of the resistor 66d, the bridge is balanced and the output voltage to the terminal of the operational amplifier 61 becomes zero. The target value EC of electromotive force can be varied from 0 V toward positive side or negative side within a given range by the deviation of the resistance value of the variable resistor 66d from Re toward Rmin or Rmax.

The operational amplifier 61, together with peripheral resistors 61a to 61d, constitutes a differential amplifier, the output of which is connected to the outside electrode 10 on the oxygen pump element 3 through a resistor 62 for detecting current. The first electrode 11 on the oxygen pump element 3 and the second electrode 12 on the oxygen concentration cell element 4 are commonly grounded. The operational amplifier 61 thereby inverts and amplifies the voltage difference (Em−Ec) between an input Em of a concentration cell electromotive force of the oxygen concentration cell element 4 and the target value EC of electromotive force, and applies the voltage to the first electrode 11 on the oxygen pump element 3. Provided that the electric resistances of the resistors 61a and 61d are given as R1 and R2, respectively, the voltage gain of the operational amplifier 61 is A1=R1/R2.

Figure 34:
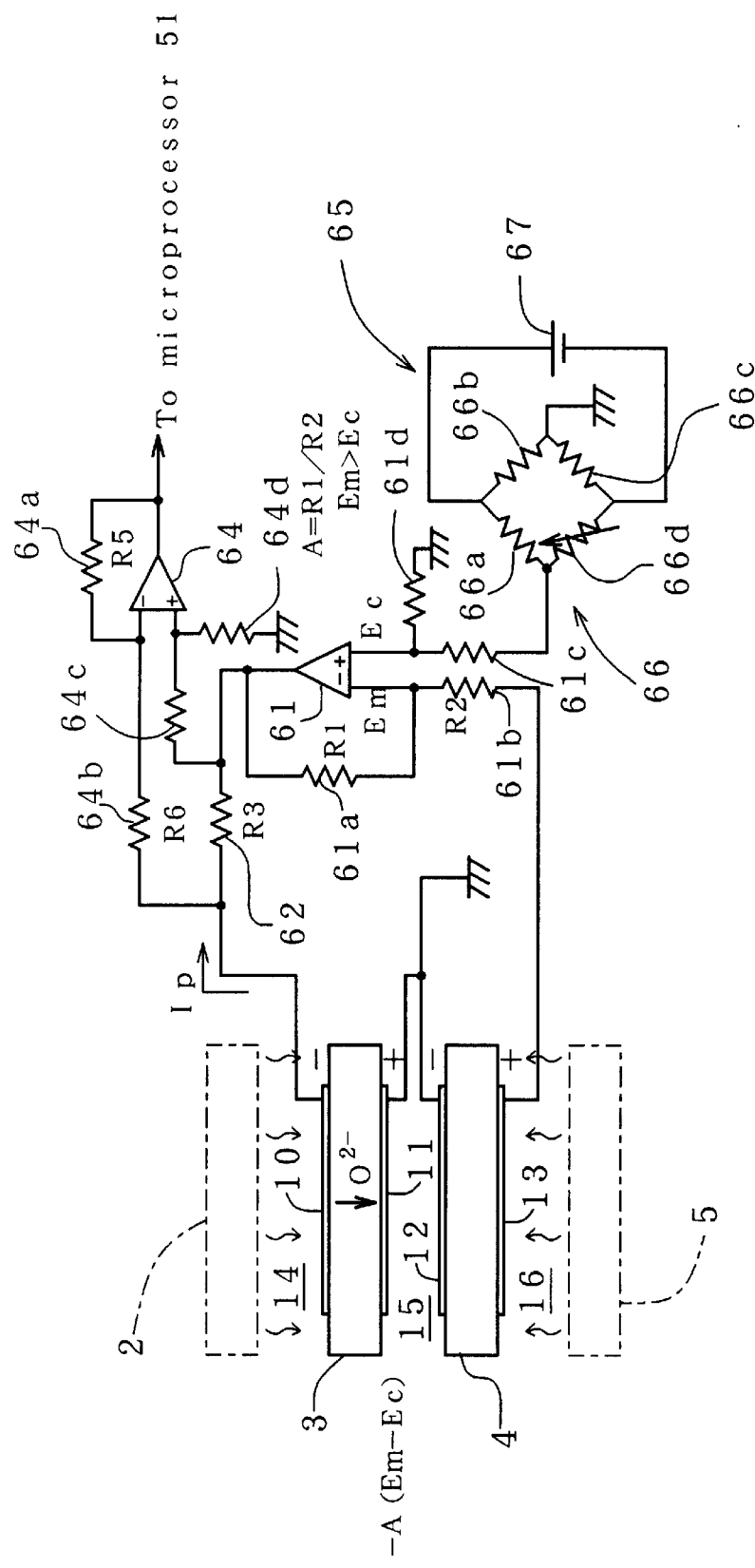
FIG. 34 is a block diagram illustrating the operation of a circuit of the sensor system in a mode of measuring hydrocarbon concentration.

In the case that Em is greater than Ec (i.e., Em−Ec>0) and the output voltage −A1 (Em−Ec) of the operational amplifier 61 is therefore negative, as shown in FIG. 34, the voltage is applied to the oxygen pump element 3 so as to make the side of the first electrode 11 negative, and a pump current Ip flows through the oxygen pump element 3 in such a direction that oxygen is pumped into the space 15. The pump current Ip is taken out as a voltage signal, in the form of the voltage difference across the resistor 62 (having a resistance of R3) for detecting current, by an operational amplifier 64 which, together with peripheral resistors 64a to 64 d, constitutes a differential amplifier. As shown in FIG. 33, the signal is digitized by a dipolar A/D converter 70 and inputted into the microprocessor 51. Reference numerals 64a and 64b designate resistors (having resistances R5 and R6, respectively) for adjusting the gain of the operational amplifier 64.

As shown in FIG. 33, constant-current power circuits 73 and 74 which have a current value of IC and have different polarities are connected to the third electrode 13 on the oxygen concentration cell element 4 through SW2 and SW3, respectively, of the analog switching circuit 60. A voltage signal Vs on the side of the third electrode 13 is digitized by a dipolar A/D converter 71 and inputted into the microprocessor 51. The switches SW1 to SW3 in the analog switching circuit 60 are respectively turned on or off in response to control signals from the microprocessor 51.

Figure 35A:
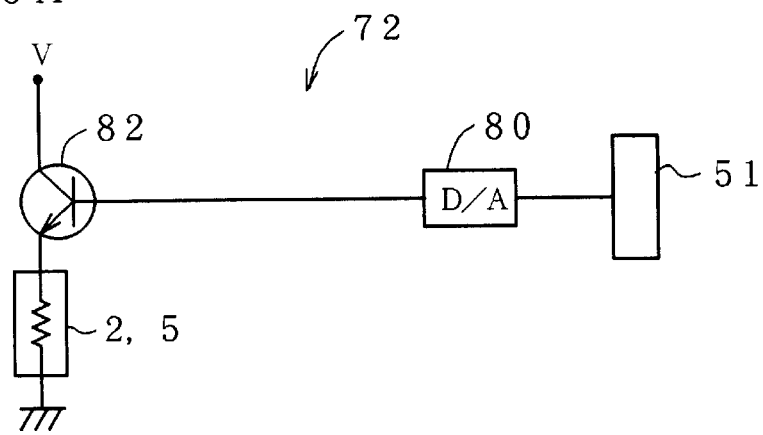
FIG. 35A is a block diagram illustrating a 1st example of a heater energizing circuit.

The first and second heaters 2 and 5 in the exhaust gas sensor 1 are connected to the microprocessor 51, e.g., through a common heater energizing circuit 72. FIG. 35A illustrates an example of the heater energizing circuit 72. The heater energizing circuit 72 comprises a D/A converter 80 for converting into analog form a heater control value provided by the microprocessor 51, and a transistor 82 connected to the D/A converter 80. The transistor 82, to which the heaters 2 and 5 are connected, operates in its active region and increases the energizing current for the heaters 2, 5 in response to the provided heater control value.

Figure 35B:
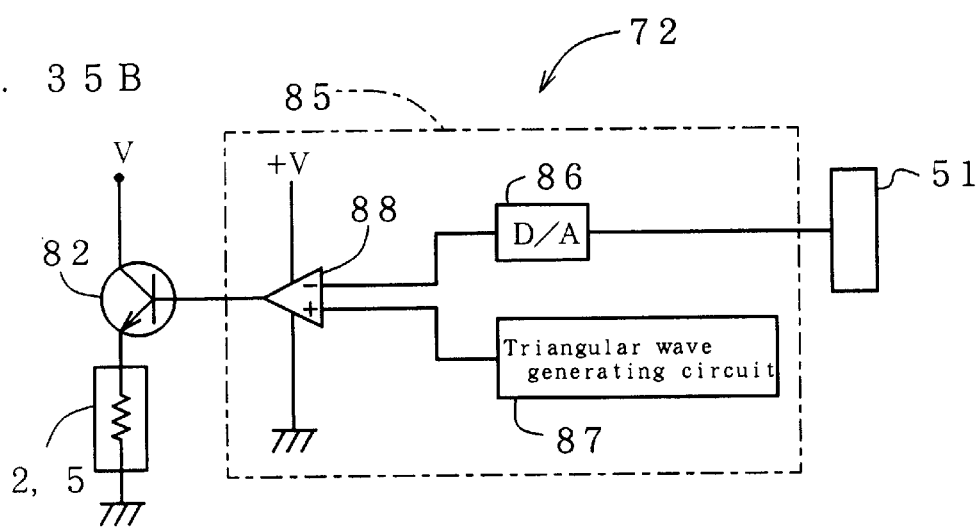
FIG. 35B is a block diagram illustrating a 2nd example of a heater energizing circuit.

FIG. 35B illustrates an example of the heater energizing circuit 72 in which the PWM (pulse width modulation) control method is employed. The main constituent of the circuit 72 is a PWM control circuit 85, which comprises a D/A converter 86 for converting into analog form a heater control value provided by the microprocessor 51, a triangular wave (or sawtooth wave) generating circuit 87, and a single-power operational amplifier 88 into which the outputs of the D/A converter 86 and of the triangular wave generating circuit 87 are inputted. The single-power operational amplifier 88 operates as a comparator which outputs either zero or a predetermined voltage V other than zero on the basis of the quantitative comparison between the heater control value and the inputted value of the triangular wave (in the embodiment, the inputted value of the triangular wave larger than the heater control value causes an output of +V, while the heater control value larger than the inputted value of the triangular wave causes an output of zero). Hereinafter, the operational amplifier 88 will be referred to as a comparator 88.

Figure 35C:
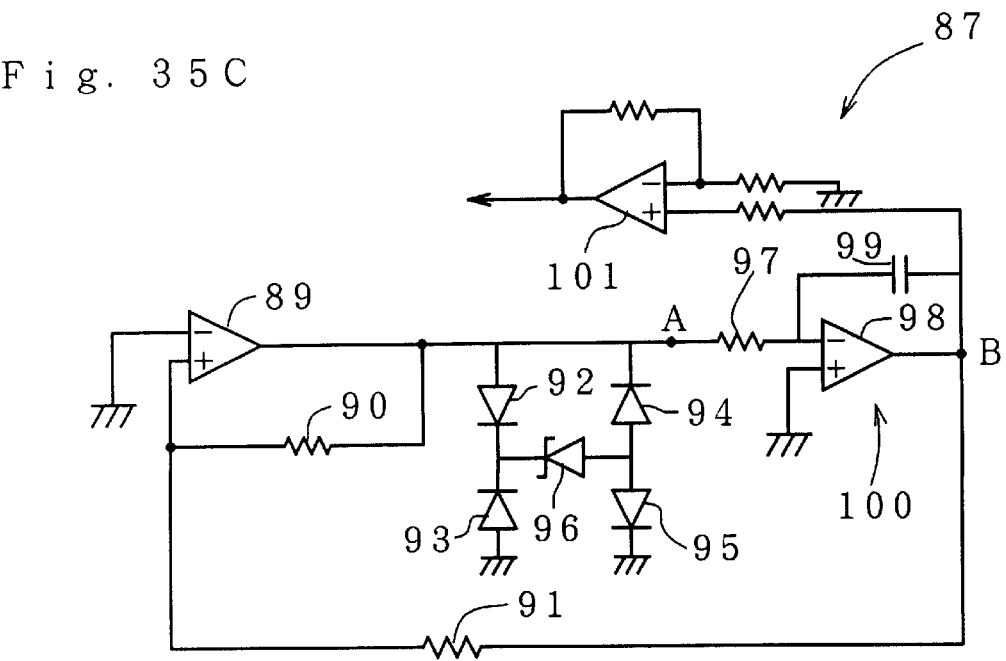
FIG. 35C is a block diagram illustrating a 3rd example of a heater energizing circuit.

FIG. 35C illustrates an example of the triangular wave generating circuit 87, which mainly comprises an operational amplifier 89 functioning as a comparator and an integrating circuit 100 having an operational amplifier 98, a resistor 97 and a capacitor 99. The operational amplifier 89 outputs a positive or negative maximum voltage, depending on whether the sum of the voltages at the points A and B in the drawing is positive or negative. With use of a group of diodes 92 to 95 and a Zener diode 96, the output voltage of the operational amplifier 89 forms a rectangular wave having its positive and negative voltages of a constant value VZD relative to 0 V, which wave is converted by the integrating circuit 100 into a triangular wave having a positive and negative maximum amplitude of VZD relative to 0 V. The cycle λ of the triangular wave (see FIGS. 36) can be adjusted according to the resistance value of the resistor 97 and the capacitance of the capacitor 99 in the integrating circuit 100. The generated triangular wave is amplified by an operational amplifier 101 so as to have a predetermined amplitude and outputted to the comparator 88 shown in FIG. 35B.

Figure 36A:
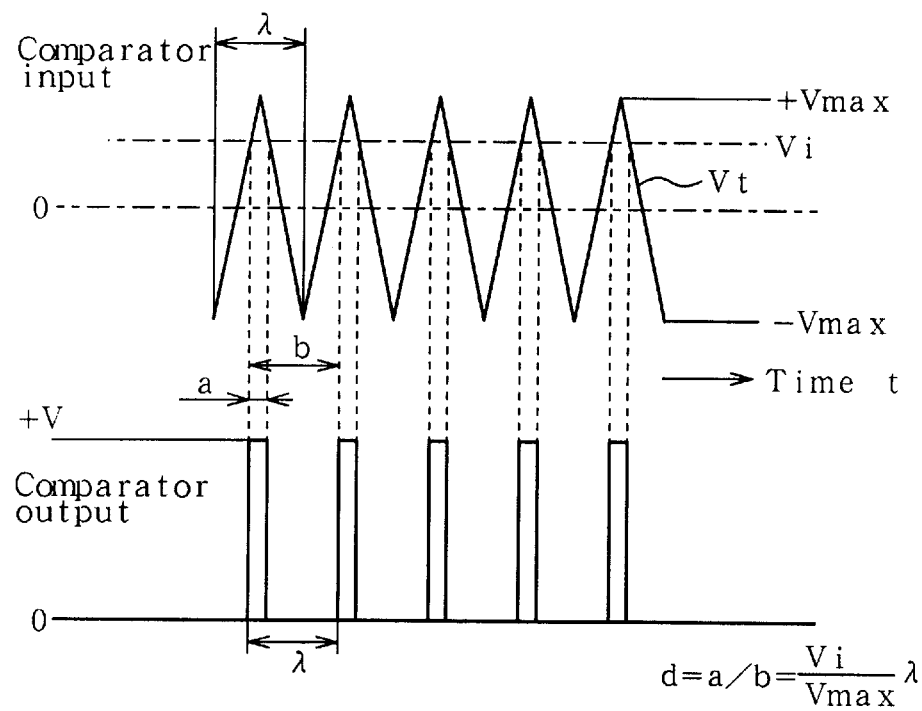
FIG. 36A is a representation illustrating the PWM control on heaters.
Figure 36B:
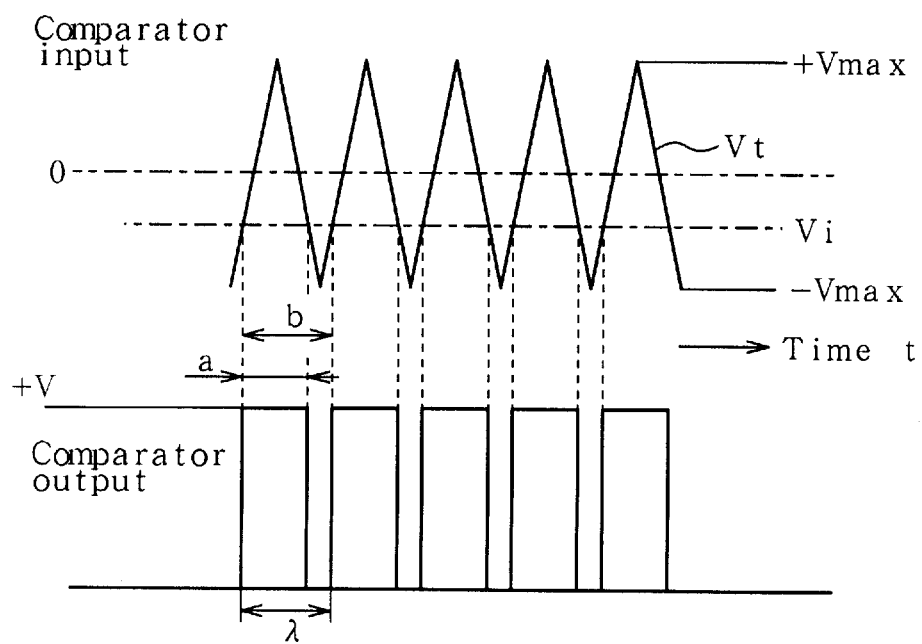
FIG. 36B is a representation following FIG. 36A.

FIGS. 36 are representations illustrating the operation of the PWM control circuit 85. When a heater control voltage Vi is smaller than the input Vt of the triangular wave at the input of the comparator 88, the output of the comparator 88 is of +V; when not smaller, the output is of zero. The comparator 88 thereby outputs a PWM wave having a duty ratio of $\{(Vi+Vmax)/2Vmax\}\lambda$ (wherein, $-Vmax \leq Vi \leq +Vmax$, Vmax is the maximum amplitude in the inputs of the triangular wave). The transistor 82 shown in FIG. 35B is switched at high rate by the output of the PWM wave, and the heaters 2, 5 are intermittently energized according to the duty ratio. The duty ratio varies in response to the heater control voltage Vi, and the heat of the heaters 2, 5 is thereby adjusted.

The microprocessor 51 shown in FIG. 33 comprises an I/O port 52 functioning as the input/output interface to the peripheral circuit 50a, and comprises the CPU 53, a RAM 54, the ROM 55, a clock circuit 56 and the like, which are connected to the I/O port 52. In the RAM 54 are formed a work area 54a for the CPU 53 and a measurement memory area 54b for storing various measurement data captured in the processes which will be described later and for storing various counter values generated in the control processes which will be described later. The ROM 55 is stored with the control programs 55a which manage the calculation for determining an output on a constituent to be detected by the sensor system 50 and manage the control on the output, and is stored with correction reference information 55b (of which the contents will be described later) used by the control programs 55a. The CPU 53 achieves a timer function for measuring time, by the count of the clock pulse which is generated by the clock circuit 56 at a constant cycle; the timer function is used in the processes which will be described later.

Figures 39A, 39B:
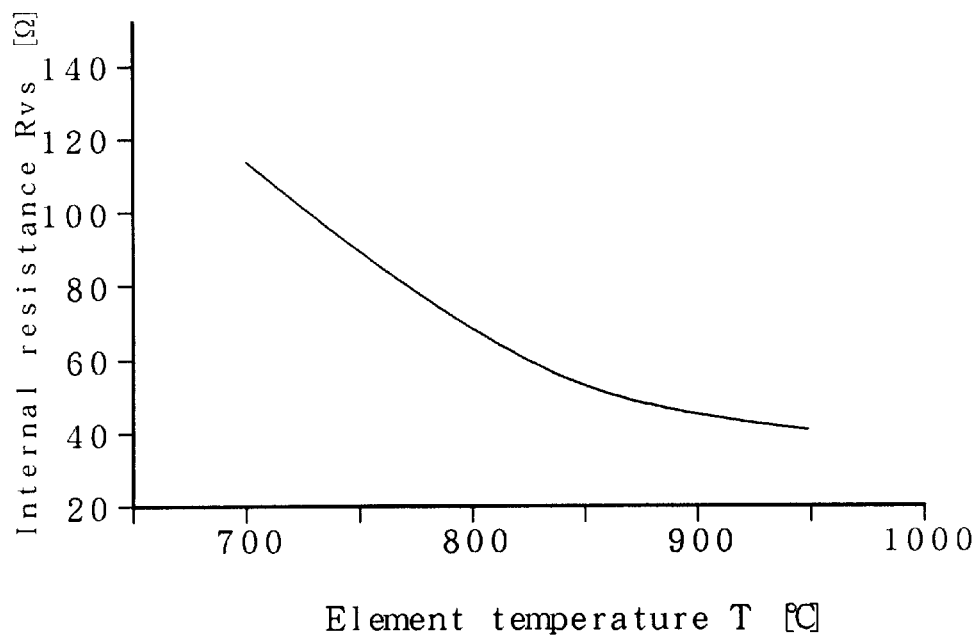
FIG. 39A is a graph illustrating an example of the relation between element temperatures and the internal resistance of the oxygen concentration cell element.
FIG. 39B is a conceptual representation of a map illustrating the relation between the internal resistance of the oxygen concentration cell element and the element temperatures.
Figure 45:
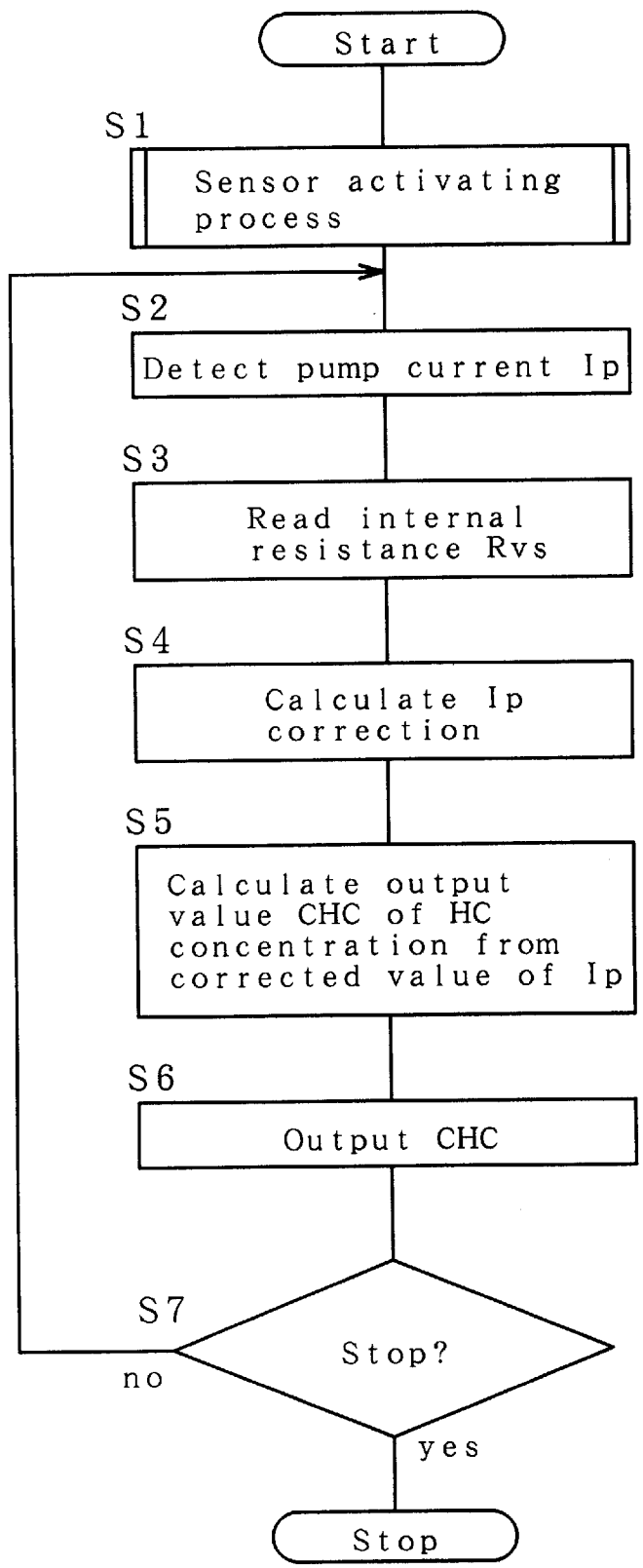
FIG. 45 is a flow chart illustrating the flow of control in a microprocessor in the system of FIG. 33.
Figure 46:
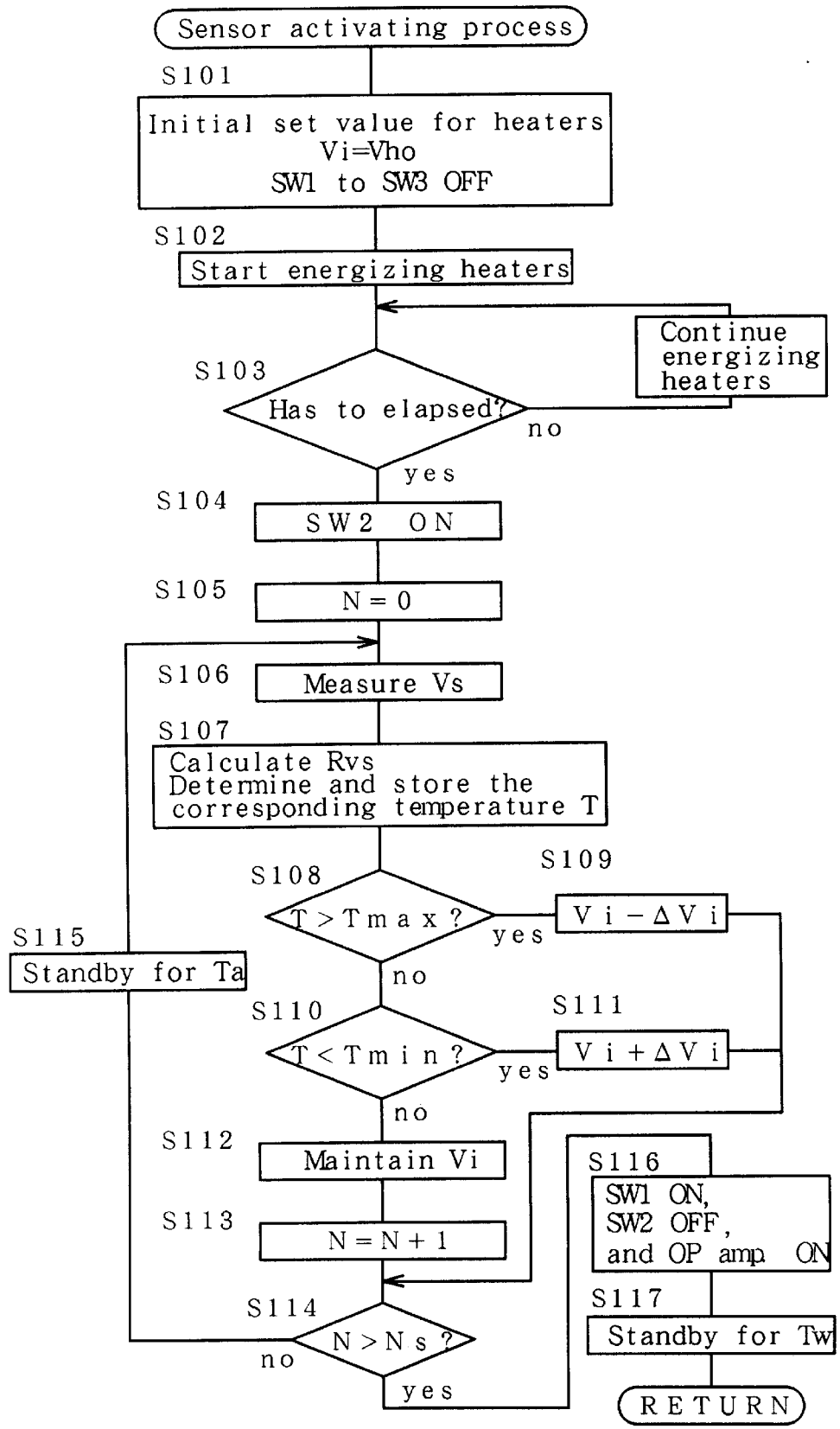
FIG. 46 is a flow chart illustrating the details of a sensor activating process in the flow of FIG. 45.
Figure 47:
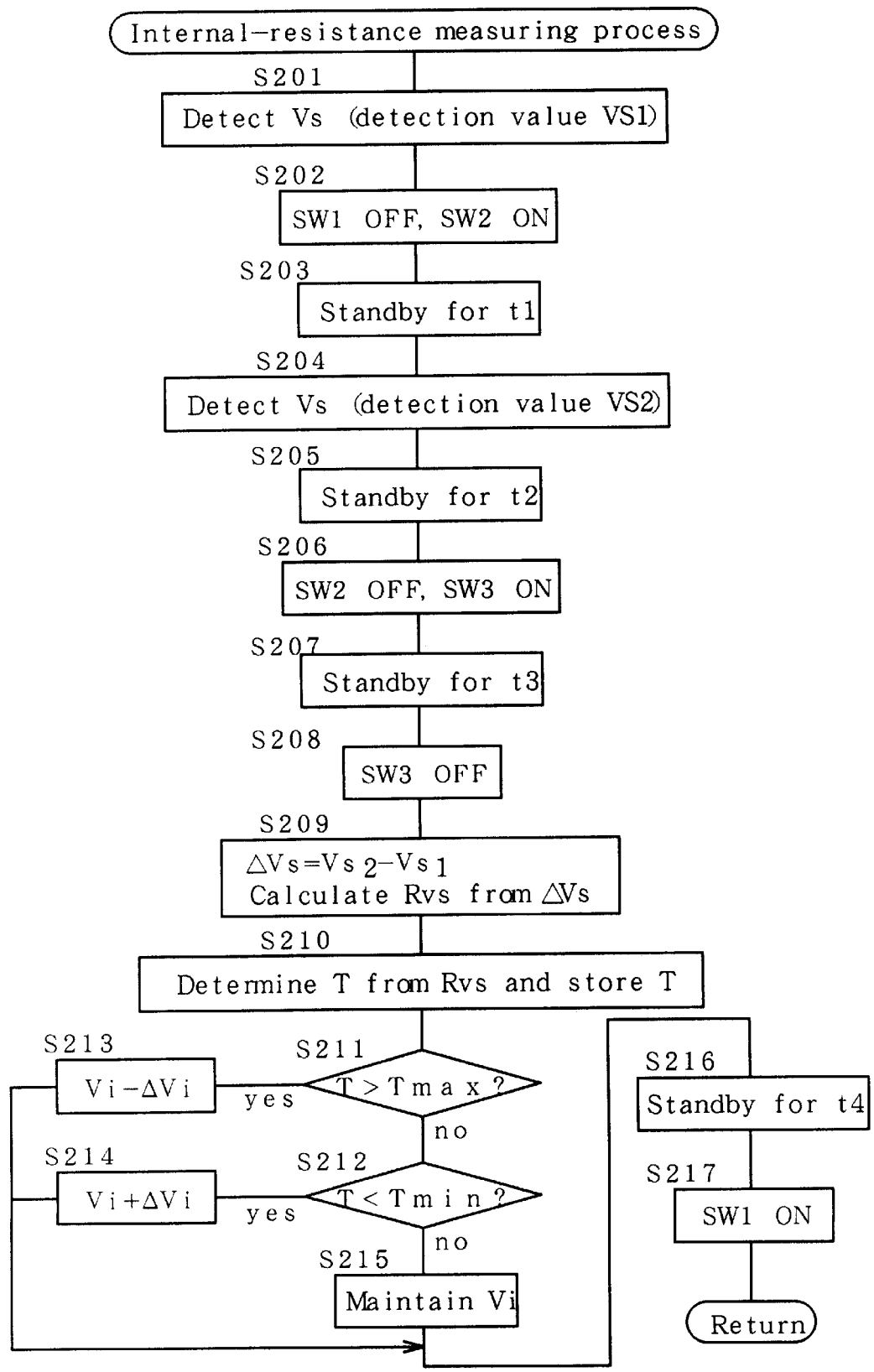
FIG. 47 is a flow chart illustrating the details of an internal-resistance measuring process in the flow of FIG. 45.

The operation of the sensor system 50 shown in FIG. 33 will be described below, on the basis of the flow of processes in the CPU 53 of the microprocessor 51. FIGS. 45 to 47 are the flow charts of the processes. In S1 in FIG. 45, a process for activating the exhaust gas sensor 1 is performed. The object of the activating process is to start to energize the heaters 2, 5 and to stabilize the temperatures of the oxygen pump element 3 and of the oxygen concentration cell element 4 at a predetermined operating temperature. The temperatures of the elements are detected by the measurement of the internal resistance of the oxygen concentration cell element 4, with use of a given dependence of the internal resistance Rvs upon temperature as shown in FIG. 39A.

FIG. 46 illustrates the activating process in detail. In S101, the control value Vi for the heater energizing circuit 72 is set at an initial set value Vho. At this time, all of SW1 to SW3 in the analog switching circuit 60 are turned off and the operational amplifier 61 is also turned into non-operating state. In this state, outputting the initial set value Vho of the heater control voltage value Vi to the heater energizing circuit 72 causes the energization of the heaters to start in S102. Once a predetermined period of time t0 has elapsed in S103 since the start of the energization, a temperature control process is started. In S104, SW2 in the analog switching circuit 60 is turned on. In S105, a counter value N for judging activation is cleared.

Figure 37:
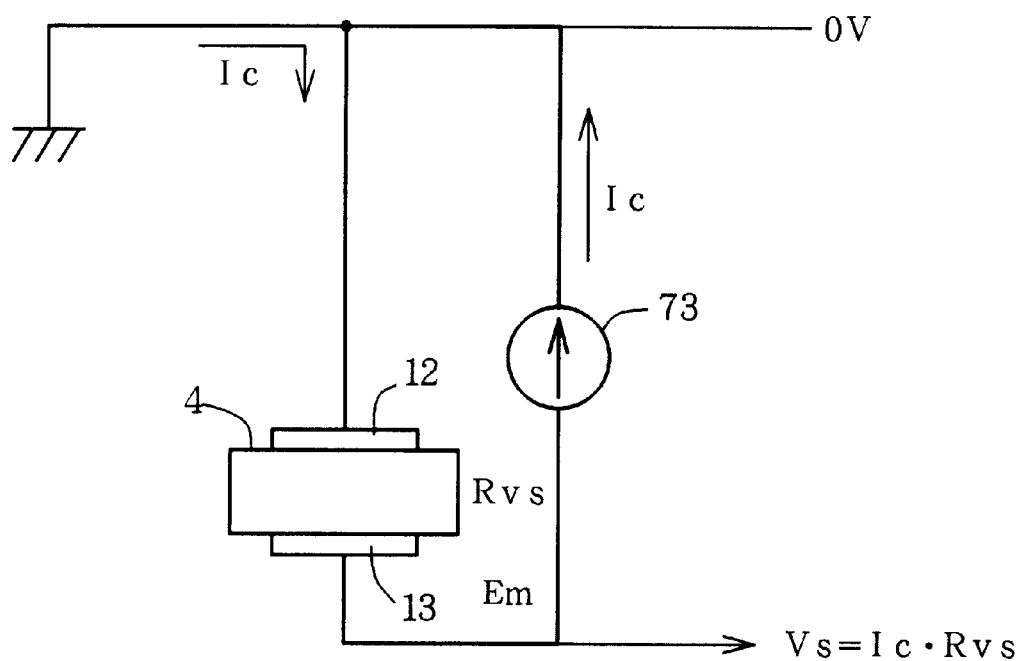
FIG. 37 is a block diagram illustrating the operation of a circuit in the measurement of the internal resistance of the oxygen concentration cell element.

In S106, the voltage value Vs on the side of the third electrode 13 in the oxygen concentration cell element 4 is captured via the A/D converter 71 (see FIG. 33). In S107, the internal resistance RVs of the oxygen concentration cell element 4 is calculated from Vs. Since SW1 is off and the operational amplifier 61 is not operating at this time, the operation of the constant-current power source 73 (having a current Ic: a current for detecting internal resistance) produces the energizing path to the oxygen concentration cell element 4 which path is shown in FIG. 37. Here the second electrode 12 on the oxygen concentration cell element 4 is grounded, and therefore the voltage Vs on the side of the third electrode 13 is represented by:

$$Vs = IC \cdot Rvs \quad (1)$$

(wherein Rvs is the internal resistance of the oxygen concentration cell element 4) Herein, Vs serves as the information on the voltage applied to the oxygen concentration cell element 4. The internal resistance Rvs can be calculated as:

$$Rvs = VS/IC \quad (2)$$

Strictly, on the voltage VS is superposed the concentration cell electromotive force Em of the oxygen concentration cell element 4; however, the superposition is not corrected in the activating process because the current Ic is sufficiently large and because the concentration cell electromotive force Em can be ignored in comparison with the partial pressure applied to the oxygen concentration cell element 4. Such a correction may be made by the method which will be described later.

As described above and shown in FIG. 39A, Rvs values has a given relation to the element temperatures T of the oxygen concentration cell element 4. Accordingly, storing the ROM 55 (see FIG. 33) with that relation as the correction reference information 55b allows the element temperature T to be determined from Rvs. Alternatively, Rvs value itself can be used as the temperature information. In the embodiment, for convenience of explanation, as shown in FIG. 39B, a map 301 in which various internal resistance values Rvs and various element temperature values T are listed so as to correspond to each other is stored in the ROM 55, so that the temperature T corresponding to Rvs is determined by interpolation with reference to the map 301 (S107). The calculated internal resistance value Rvs is stored into the measurement memory area 54b shown in FIG. 33. When an internal resistance Rvs is newly detected and calculated, the stored value is overwritten and updated.

In S108 and S110 of FIG. 46, it is judged whether the determined element temperature T is within the set temperature range between the maximum Tmax and the minimum Tmin or not. In the case that the element temperature T is higher than the maximum Tmax, the heater control voltage Vi decreases by a given value ΔVi to reduce the heat of the heaters 2, 5; in the case that the temperature T is lower than the minimum Tmin, the heater control voltage Vi increases by ΔVi to promote the heat-producing of the heaters 2, 5 (S109 and S111). In the case of Tmin≦T≦Tmax, the present value of Vi is maintained and the counter value N for judging activation is incremented (S112 and S113).

Until the counter value N for judging activation reaches, e.g., a set value Ns, the processes in S106 to S113 are repeated at uniform time intervals Ta (S114, S115). When N reaches Ns, it is judged that the element temperature T has been maintained generally within the set temperature range, and SW2 in the analog switching circuit 60 shown in FIG. 33 is turned off, SW1 turned on. Besides, the operational amplifier 61 is turned into the operating state and warmed up for a predetermined period of time Tw, and then the activating process is completed (S116, S117).

Referring to FIG. 45, upon the completion of the activating process S1, the detection of the pump current Ip in the oxygen pump element 3 is started in S2. In this state, only SW1 is turned on in the analog switching circuit 60, and therefore the energizing path is as shown in FIG. 34. With the contact of the sensor 1 with exhaust gas, the reaction between hydrocarbon (hereinafter referred to as HC) such as methane, as the constituent to be detected, and oxygen in the space 15 decreases the oxygen concentration in the space 15, and generates in the oxygen concentration cell element 4 an concentration cell electromotive force Em with the side of the third electrode 13 positive. Assuming that the target value EC of electromotive force inputted into the operational amplifier 61 is, for example, zero (i.e., Em−Ec>0), the output voltage −A1(Em−Ec) of the operational amplifier 61 is negative, and the voltage is applied to the oxygen pump element 3 so as to make the side of the first electrode 11 negative. At this time, a pump current Ip flows through the oxygen pump element 3 in such a direction that oxygen is pumped into the space 15. The pumping of oxygen into the space 15 by the oxygen pump element 3 decreases the concentration cell electromotive force Em by degrees, and the oxygen pump current Ip is therefore controlled so as to decrease. As a result, the oxygen pump current is controlled so that the concentration cell electromotive force Em is eventually brought approximately to zero; the concentration of the constituent to be detected can be obtained from the equilibrium value of the oxygen pump current Ip at that time. The signal of the pump current Ip is converted into a voltage signal, on the basis of the voltage difference across the resistor 62 for detecting current, which difference is taken by the operational amplifier 64 as described above. The signal is then digitized by the A/C converter 70 and inputted into the microprocessor 51.

As described above, the target value EC of electromotive force does not necessarily make zero, by the influence of the offset electromotive force. The description has been already done on the preferred set value of EC, and the detail is therefore omitted. The target value of electromotive force can be changed or adjusted by the adjustment of the variable resistor 66d in the power circuit 65, as described above. Even though the offset electromotive force of the oxygen concentration cell element 4 is different for each oxygen concentration cell element 4, it mostly retains a stable value in the same oxygen concentration cell element 4 for a comparatively long period of time. Accordingly, there is every reason to assume that it is not necessary to change the resistance value of the variable resistor 66d which has been adjusted, e.g., at the time of the shipment of the system 50, corresponding to the inherent offset electromotive force of the oxygen concentration cell element 4 that is being used. In this case, it is convenient for the variable resistor 66d to comprise a trimming potentiometer.

Referring to FIG. 45, once the value of the pump current Ip is detected, the concentration of the constituent to be detected which corresponds to the pump current Ip is determined; however, the pump current Ip varies depending on the element temperature T and is therefore corrected as follows: The internal resistance Rvs of the oxygen concentration cell element 4 stored in the RAM 54 (see FIG. 33) is read and the corresponding temperature T is determined with reference to the map 301 (see FIGS. 39) (FIG. 45: S3). The pump current corrections ΔIp to be made to the pump current Ip for various temperatures can be experimentally determined e.g., as shown in FIG. 40B. Accordingly, once a map 302 in which various values of ΔIp and various values of element temperature T are listed so as to correspond to each other is produced on the basis of the experiment results and stored in the ROM 55 (means for storing correction reference information), a pump current correction ΔIp can be determined by interpolation with reference to the map 302 (information on the relation between temperature deviation and pump current correction) (FIG. 45: S4). As shown in FIG. 44A, a map 302a may be stored in which the internal resistance Rvs and the pump current corrections ΔIp correspond directly to each other so that a correction ΔIp is determined directly from an internal resistance Rvs.

Figure 42:
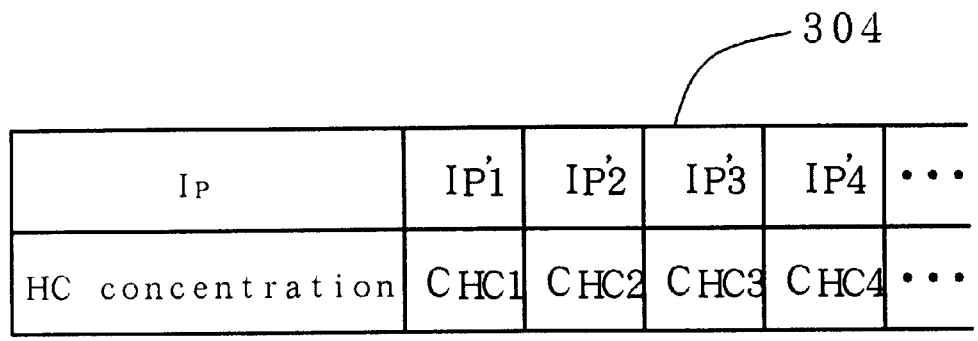
FIG. 42 is a conceptual representation of a map illustrating the relation between the pump currents and HC concentrations.

In S5, the measured pump current Ip is corrected by the addition of the pump current correction ΔIp, and hydrocarbon concentration CHC as the concentration of the constituent to be detected which corresponds to the corrected pump current Ip' is determined. The hydrocarbon concentrations CHC corresponding to various pump currents Ip' can be determined by interpolation with reference to such a map 304 (stored in the ROM 55) as shown in FIG. 42, which provides the relation between the pump current Ip' and the hydrocarbon concentration CHC. In S6, the hydrocarbon concentration CHC thus determined is outputted as the temperature-compensated detection value of the concentration. Subsequently, the process in S2 and later processes are repeated.

As shown in FIG. 44B, the hydrocarbon concentration CHC corresponding to the set of the detected pump current Ip and of the element temperature T may be directly determined by two-dimensional interpolation with reference to a two-dimensional map 302b (information on the relation between pump current information and the concentration of the constituent to be detected) in which pump currents Ip and hydrocarbon concentrations CHC for various element temperatures T are listed so as to correspond to each other. Alternatively, the pump current Ip which has been temperature-compensated by the above method may be outputted, just as it is.

Figure 38:
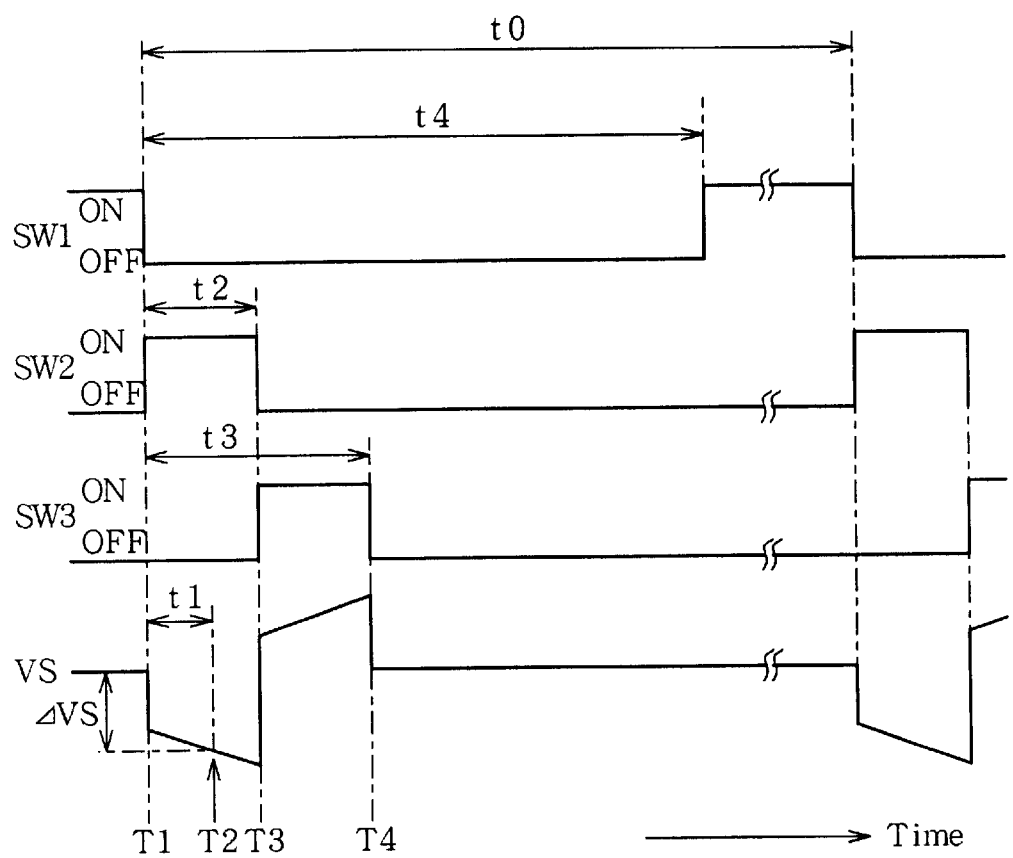
FIG. 38 is an operation timing diagram of switches in the measurement of the internal resistance of the oxygen concentration cell element.

After the element temperature T is set in the activating process, the control on the temperature T is continued in parallel with the above-mentioned process for detecting hydrocarbon concentration. The flow of the control process is illustrated in FIG. 47. The CPU 53 periodically executes this process routine as an interrupt-service routine in the routine shown in FIG. 45, on the basis of the time measurement based on a clock pulse (generated by the clock circuit 56 (see FIG. 33)). The cycle of the execution can be set e.g., within the range of 0.3 to 1 ms. The execution cycle longer than 1 ms may not ensure a sufficient accuracy of measuring temperature or detecting concentration by the sensor. On the other hand, the cycle shorter than 0.3 ms may not ensure a sufficient accuracy of detecting concentration, because of too large ratio of the temperature measuring process time to the processing time of the CPU 53 and because of an increase in the quiescent time of the oxygen pump element. There is, however, a possibility that the execution cycle can be set not more than the above value by the employment of the CPU 53 which provides high-speed processing e.g., based on a high clock frequency. FIG. 38 illustrates an operation timing diagram of SW1 to SW3 in the analog switching circuit 60 in the process, in correspondence with the detected voltage signal Vs on the side of the third electrode 13 in the oxygen concentration cell element 4.

In S201, the voltage signal Vs on the side of the third electrode 13 in the oxygen concentration cell element 4 is read, with SW1 in the analog switching circuit 60 (FIG. 33) remaining ON, and is stored as a detection value VS1 into the measurement memory area 54b in the RAM 54. The voltage signal Vs corresponds to the concentration cell electromotive force Em inputted into the operational amplifier 61. In S202, SW1 is turned off and SW2 is turned on. The energizing path then comes into the state shown in FIG. 37, and the constant current Ic for the detection of the internal resistance is passed through the oxygen concentration cell element 4. Upon the elapse of a given period of time t1 since the start of the passage of the constant current Ic, the voltage signal VS is read and stored as a detection value VS2 into the measurement memory area 54b in the RAM 54 (S203, S204). As described above, the voltage signal VS at this time reflects the internal resistance of the oxygen concentration cell element 4; however, the concentration cell electromotive force Em of the oxygen concentration cell element 4 is superposed on or included in the voltage signal VS. The influence of the concentration cell electromotive force Em can be eliminated by the obtainment of the difference between VS2 and VS1 (S209).

The reason shy VS is measured after the elapse of the given period of time t1 from the start of the passage of the constant current Ic is as follows: When the constant current Ic is passed through the oxygen concentration cell element 4, oxygen is transported in the oxygen concentration cell element 4, opposite to the direction of the current passage (i.e., from the side of the space 16 toward the side of the space 15), and the oxygen concentrations vary on both sides of the oxygen concentration cell element 4. As a result, as shown in FIG. 38, the concentration cell electromotive force Em and the value of VS vary with the continuation of the passage of the current Ic. In order to ensure a sufficient accuracy of measuring the internal resistance, it is important to make constantly and generally uniform the change in VS which is inevitably caused by the current passage. Since the constant current Ic is used as the current for the measurement of the internal resistance, the control which provides the constant energizing time t1 before the measurement of VS makes generally constant the amount of transported oxygen, i.e., the changes in the oxygen concentrations on both sides of the oxygen concentration cell element 4. Consequently, the change in the concentration cell electromotive force Em and the change in VS can be made generally constant. In the case that the switching speed of the analog switching circuit 60 is sufficiently high and that a sufficiently quick stabilization of the current level is achieved after the switching of the energizing path, VS may be measured immediately after the passage of the constant current Ic is started.

Figure 49:
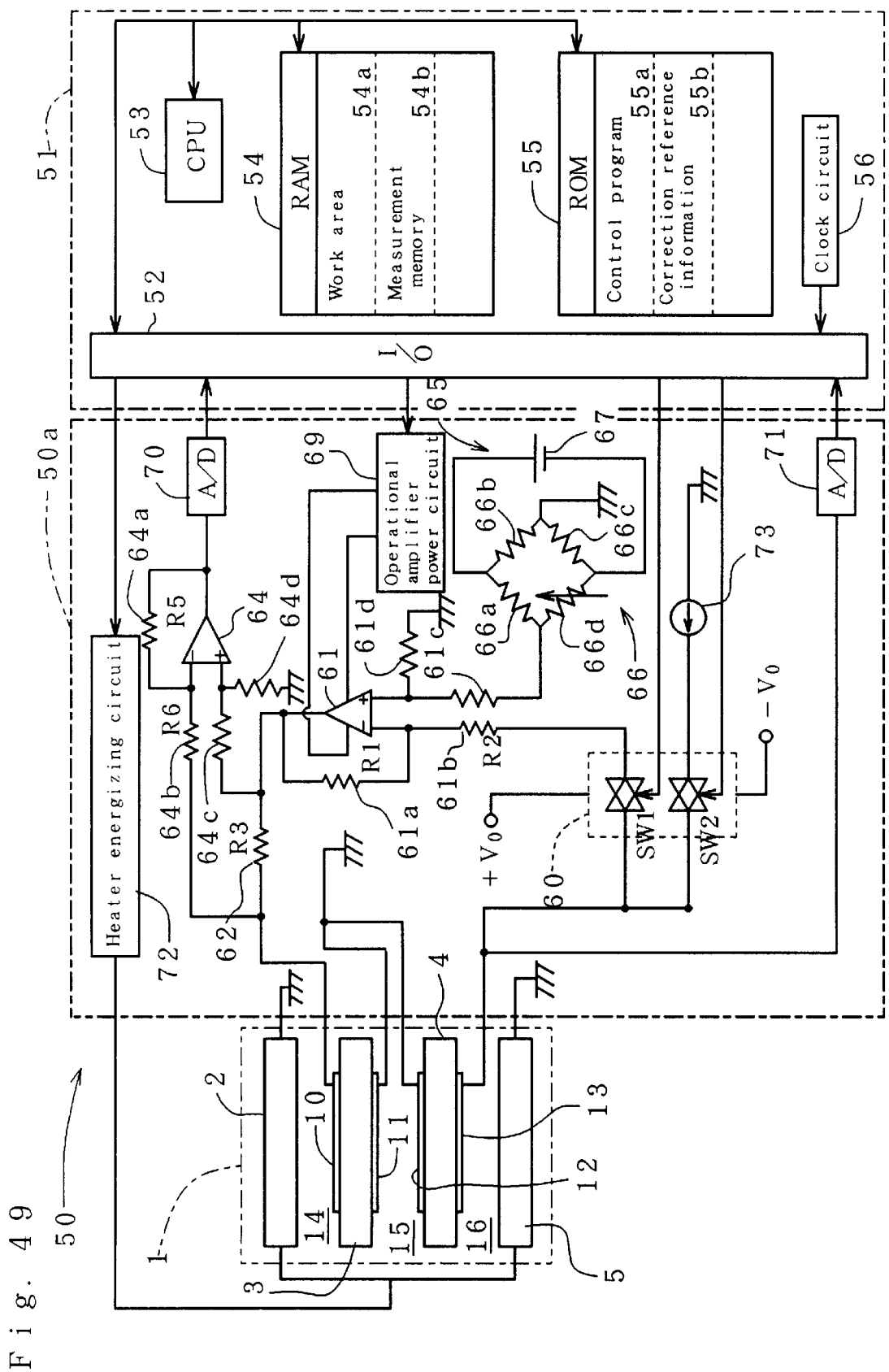
FIG. 49 is a block diagram illustrating the system of FIG. 33 in which a power supply for supplying correction current is omitted.

Another problem is that the changes in the oxygen concentrations on both sides of the oxygen concentration cell element 4 which are caused by the passage of the constant current Ic may influence the accuracy of measuring the concentration of the constituent to be detected when the HC concentration is measured afresh with the exhaust gas sensor 1. On the other hand, a relatively high internal resistance of the oxygen concentration cell element 4 may make difficult the travel of oxygen ions in the oxygen concentration cell element 4 and may cause a polarization with the passage of the current. In order to solve these problems, the embodiment employs the following method. In S205 to S208 in FIG. 47, upon the elapse of a given period of time t2 after the last detection of VS, SW2 is turned off to complete the passage of the constant current Ic, while SW3 is turned on to pass a correction current IA opposite in direction to and as large as Ic from the constant-current power source 74 (correction current passing means) having the opposite polarity, for a period of time t3 which is generally equal to the total time t1+t2 of the passage of Ic. After the period t3, SW3 is turned off. By this operation, oxygen of generally the same amount as described previously is transported in the opposite direction in the oxygen concentration cell element 4 and, as it were, oxygen which has been pumped from the space 16 into the space 15 by the passage of Ic is pumped back, so that the oxygen concentrations which have been changed can be brought back into the levels which were given before the measurement of the internal resistance. In the case that the influence on the changes in the oxygen concentrations on both sides of the oxygen concentration cell element 4 is considered to be considerably small, such as the case that the period of time for the passage of the current Ic for the measurement of the internal resistance of the oxygen concentration cell element 4 can be made sufficiently short, the constant-current power source 74 for generating the correction current IA can be omitted as shown in FIG. 49 (correspondingly, the analog switching circuit 60 having a small number of switching channels is preferably used).

Referring to FIG. 47, upon the completion of the passage of the correction current IA, the difference ΔVS between Vs2 and Vs1 is calculated as described above in S209, and Rvs is calculated from the equation (2) with ΔVS considered as Vs. The processes from S210 to S215 for determining the element temperature T from Rvs and for thereby determining the heater control voltage Vi are generally the same as the processes from S107 to S112 in the sensor activating process of FIG. 46, and the description on the processes is therefore omitted. Subsequently, after the standby for a period of time t4 in S216, SW1 is turned on in S217 to complete the internal-resistance measuring process. After that, the routine of the process for measuring hydrocarbon concentration in FIG. 45 is performed afresh. The measurement value of the element temperature T is updated every time the internal-resistance measuring process is performed, and the updated element temperature T is used at all times in the routine of the process for measuring hydrocarbon concentration in FIG. 45. The heater temperature is corrected periodically on the basis of the measurement of the element temperature T.

With this operation, the temperature of the oxygen concentration cell element 4 is maintained accurately at the set value by the heaters 2, 5, and the accuracy of measuring carbide concentration in exhaust gas is improved. Besides, as shown in FIGS. 40, even though the temperature of exhaust gas and, correspondingly, the temperature T of the oxygen concentration cell element 4 suddenly change by hard acceleration or hard deceleration of an automobile engine or the like, the measurement of HC concentration with a relatively high accuracy can be continued by the correction of the oxygen pump current Ip which correction corresponds to the change in the temperature, without the wait for the return of the element temperature T.

Figure 48:
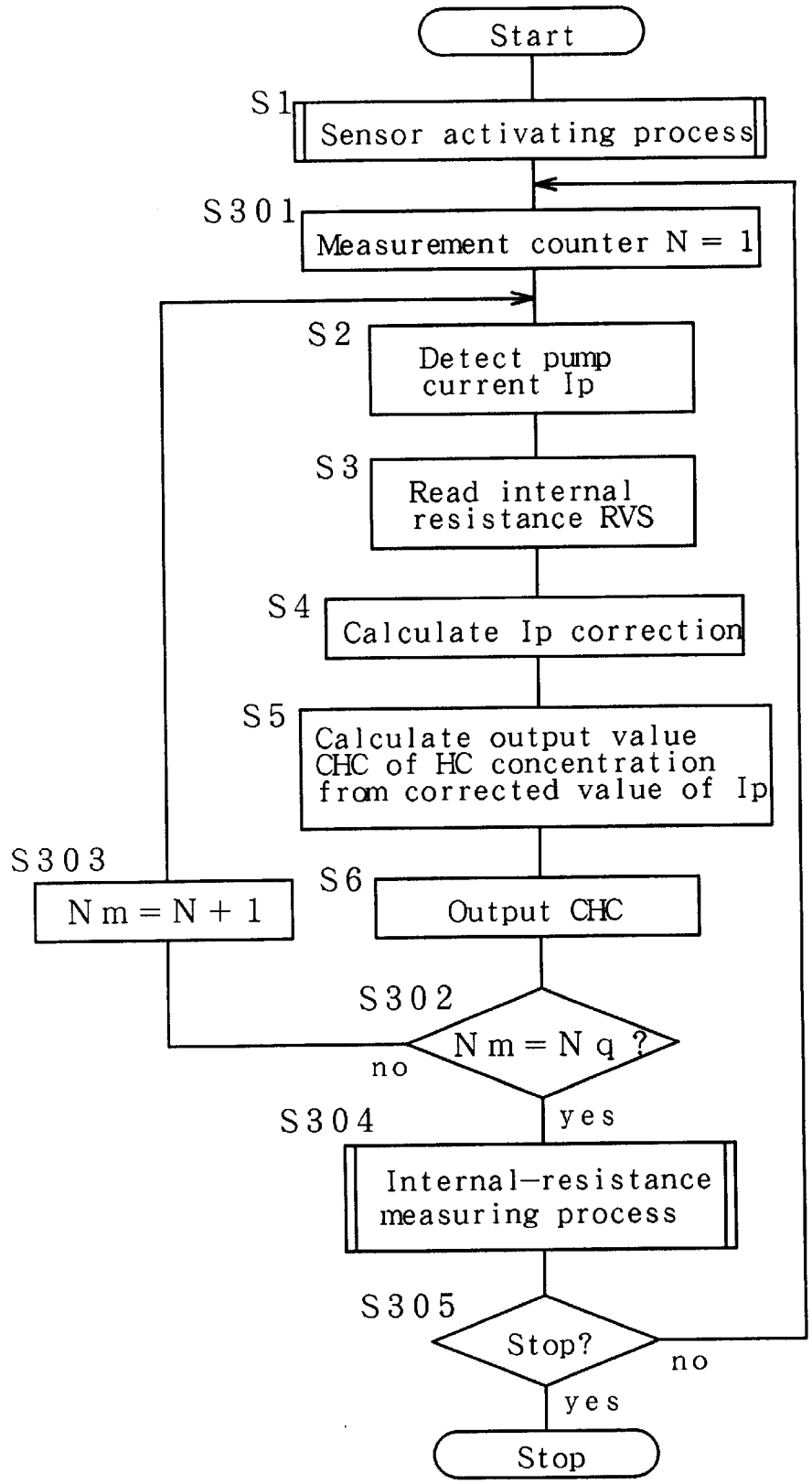
FIG. 48 is a flow chart illustrating the flow of another control scheme in the microprocessor in the system of FIG. 33.

The internal-resistance measuring process may be performed as a subroutine of the routine of the process for measuring HC concentration, instead of as an interrupting routine in the routine of the measuring process. FIG. 48 illustrates an example of a flow chart in this case. The processes for determining and outputting HC concentration in S1 to S6 are exactly the same as in FIG. 45 except that steps from S301 to S303 are added for counting up a measurement counter Nm every time a measurement is completed. When Nm reaches a given count Nq in S302, the internal-resistance measuring process which is exactly the same as shown in FIG. 47 is performed in S304. After the internal-resistance measuring process, the flow returns to S301 to reset the measurement counter Nm to 1, and the same processes are then performed afresh. This method is the same as the former method in that the internal-resistance measuring process is cyclically performed, but is characterized in that the internal-resistance measuring process is not necessarily performed at uniform time interval but performed every time the process for measuring HC concentration is completed a given number of times. With this arrangement, the process for measuring HC concentration is prevented from being interrupted by the internal-resistance measuring process, and the frequency of occurrence of errors or the like is reduced.

Figure 43:
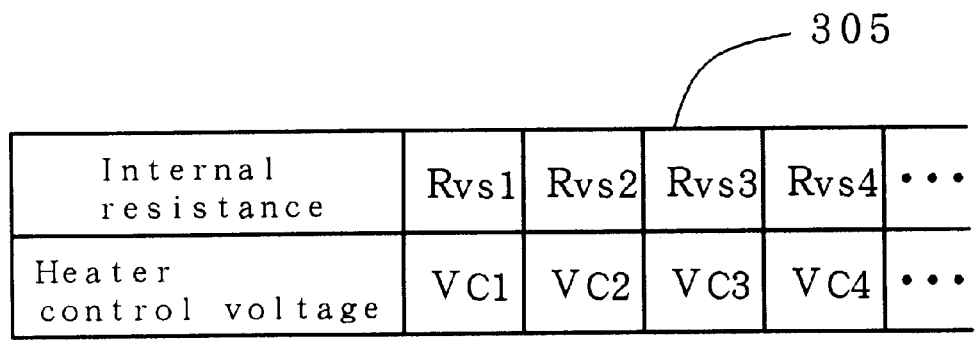
FIG. 43 is a conceptual representation of a map illustrating the relation between the internal resistance of the oxygen concentration cell element and heater control voltages.

As shown in FIG. 43, a map 305 may be stored which is stored with the control voltage values Vi to be applied to the heater energizing circuit 72, which voltage values correspond to various values of the internal resistance Rvs; with reference to the map 305, a control voltage Vi may be determined according to an internal resistance Rvs (i.e., an element temperature T), irrespective of the present voltage value.

Figure 50:
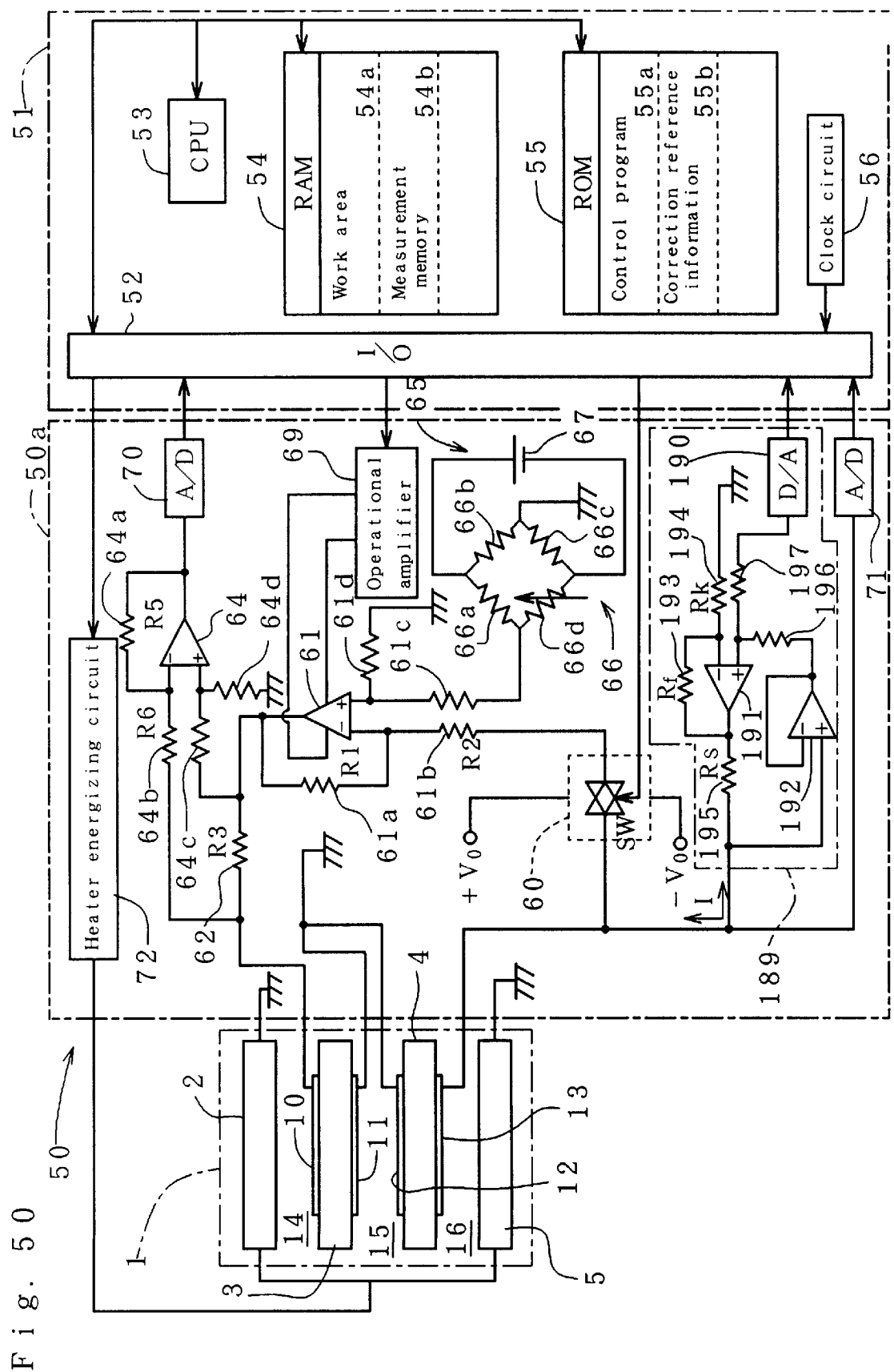
FIG. 50 is a block diagram illustrating the system of FIG. 33 in which a constant-current supply for measuring internal resistance and the constant-current supply for supplying correction current are replaced by a voltage-current converting circuit.

Instead of the two constant-current generating circuits 73 and 74 shown in FIG. 33, one circuit may be used of which the polarity is arbitrarily switched by a polarity switching circuit not shown. Alternatively, there may be used a circuit which is capable of generating a current according to the current value and polarity specified by the microprocessor 51. FIG. 50 illustrates an example of such a circuit. In this arrangement, a voltage-current converting circuit 189 is used instead of the constant-current generating circuits 73 and 74.

In the circuit 189, a current-specifying voltage Vi from the microprocessor 51 is inputted into an operational amplifier 191 through a D/A converter 190 (of dipolar type), and a resistor 195 for the detection of current is connected to the output of the operational amplifier 191. Besides, the voltage drop across the resistor 195 resulted from the output of the operational amplifier 191 is fed back through a voltage follower 192. With this arrangement, the voltage drop across the resistor 195, i.e., a current Io is maintained at a constant value according to the input voltage Vi, irrespective of the load connected thereto. Provided that the resistance of resistors 193 and 194 in the drawing are Rf and Rk, respectively, and that the resistance of the resistor 195 is Rs, the following equation holds:

$$Io=(Vi \cdot Rf)/(Rk \cdot Rs) \qquad (3)$$

In this case, a current Ic for the measurement of internal resistance can be generated by a given magnitude of the current-specifying voltage Vi, and a correction current can be generated as a current opposite in direction to the current Ic by the application of a current-specifying voltage Vi' opposite in polarity to the voltage Vi. The current level to be generated and the current-carrying time can be freely established by the adjustment of the value of the current-specifying voltage from the microprocessor 51 and by the adjustment of the period of time for which the voltage is outputted.

Hereinafter, several modifications of the exhaust gas sensors in accordance with the invention will be illustrated.

The side of the outside electrode on the oxygen pump element 3 may be isolated from exhaust gas atmosphere and the air may be introduced there.

In the exhaust gas sensor 500 shown in FIGS. 17 and the like, it is advantageous in the improvement of the detecting accuracy of the sensor 1 to make the space 15 between the oxygen pump element 3 and the oxygen concentration cell element 4 as small as possible (preferably not more than 1 mm) to obtain the maximum effect of the space 15 for restricting the influx of new exhaust gas. Conversely, the space 15 of too large size may cause an instable reaction between HC and oxygen on electrode(s) having a catalytic activity (the first electrode 11 and the second electrode 12, in this embodiment) and may decrease the electromotive force of the oxygen concentration cell, thus resulting in an insufficient sensor output. With the space 15 between the elements 3 and 4 of too small size, however, a slight deformation which may occur in the production of the oxygen pump element 3 and of the oxygen concentration cell element 4 by sintering may influence significantly on the size of the space 15 formed thereby and may cause variations in output among individual sensors. A sensor structure which is effective in solving this problem will be described below (the parts common with the sensor structure described above will be designated by the same reference numerals and the detailed description of the parts will be omitted).

Figure 51A:
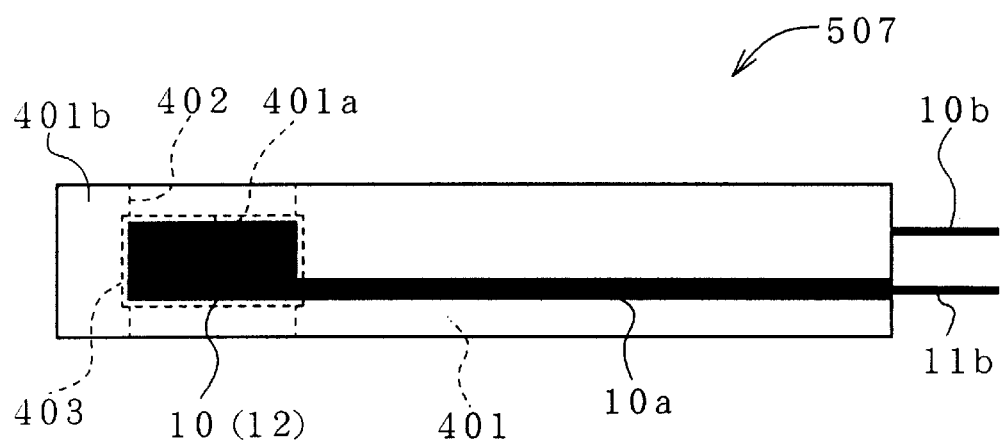
FIG. 51A is a plan view illustrating a 1st example of a sensor in which exhaust gas is introduced into a measuring chamber through slits.
Figure 51B:
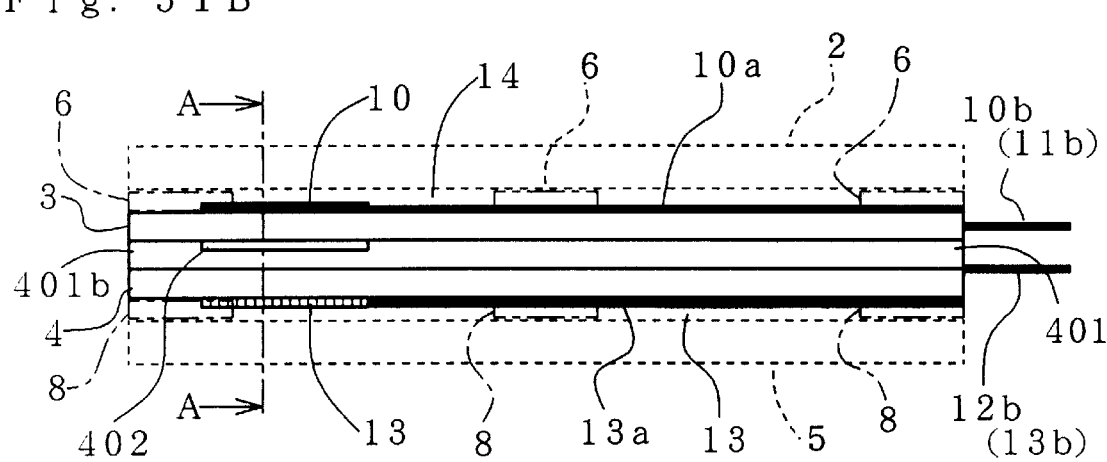
FIG. 51B is a side view of FIG. 51A.

That is, in an exhaust gas sensor 400 shown in FIGS. 51, between an oxygen concentration cell element 4 and an oxygen pump element 3 is interposed a spacer 401 as a wall-forming body, in which a spacer window 401a penetrating the spacer along the thickness is formed at the position corresponding to electrodes 11 and 12. With the provision of the window 401a, the spacer 401 forms a wall 401b surrounding the electrodes 11, 12. A measuring chamber 403 (a space 15) is formed as a space surrounded by the inside surfaces of the wall 401b and by the surfaces facing each other of the oxygen concentration cell element 4 and of the oxygen pump element 3. Between the wall 401b and the oxygen pump element 3 at the positions corresponding to the measuring chamber 403 are formed slits 402, as a diffusion flow regulator, for providing communications between the measuring chamber 403 and the outside atmosphere subjected to detection on both longitudinal sides of the oxygen pump element 3.

Figure 51C:
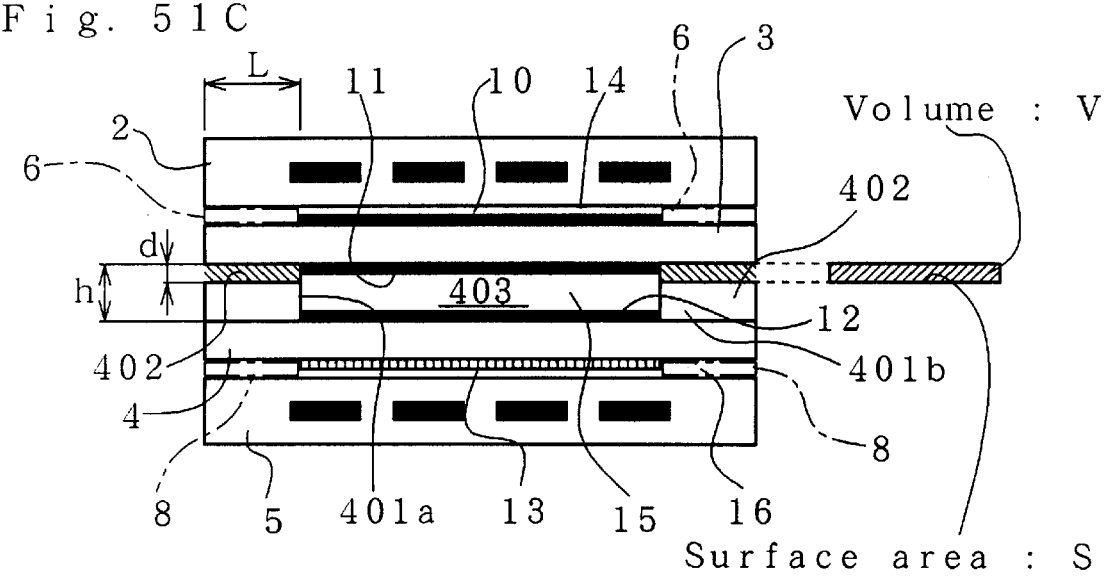
FIG. 51C is an A—A sectional view of FIG. 51B.

As shown in FIG. 51C, the slits 402 are formed in such a way that portions of the wall 401b on the side of the surface to be laminated onto the oxygen pump element 3 are cut out by a given depth on both longitudinal sides of the second electrode 12. Besides, as shown in FIG. 51A, the slits 402 extend along the corresponding edges of the electrode 12, in the longitudinal direction of the oxygen pump element 3. The width d of the slits 402 is so set as to be smaller than the height h of the measuring chamber 403. More specifically, the width d is set so that d/h is within the range from $1/100$ to $1/4$, more preferably from $1/20$ to $1/8$. The absolute value of the slit width d is set within the range from 0.01 to 1.0 mm, more preferably from 0.02 to 0.05 mm. The ratio S/V of the total area of the inner surfaces of the slit to the volume V of the space in the slit 402 is adjusted within the range from 4 to 100, more preferably from 20 to 50. The slits 402 may be formed between the wall 401b and the oxygen concentration cell element 4, in the same form.

The spacer 401 (the wall 401b) is integrated by sintering with the oxygen concentration cell element 4 in generally the entire area of the laminated surface, and is integrated by sintering with the oxygen pump element 3 in generally the entire area of the laminated surface except the areas where the slits 402 are formed. A first heater 2 and a second heater 5 are laminated on the oxygen pump element 3 and the oxygen concentration cell element 4 through the medium of spacers 6 and 8, respectively.

The integrated laminate of the oxygen pump element 3, the spacer 401 and the oxygen concentration cell element 4, forming the main body of the exhaust gas sensor 400, can be produced by the lamination and sintering of ceramic green sheets (compacts) which are to be the elements 3, 401 and 4, in the same method as shown in FIG. 20 and other drawings. The slits 402 can be formed simply by the interposal of layers of a given thickness formed of a material which would burn up at a sintering temperature (e.g., carbon paste), between the green sheet (ceramic compact) that is to be the oxygen pump element 3 and the green sheet that is to be the spacer, in the areas where the slits 402 are to be formed, and by sintering that causes the layers to burn up.

In accordance with the above-mentioned sensor structure, even with the height h of the measuring chamber 403 (i.e., the size of the space 15) larger than a certain degree, exhaust gas flows into the measuring chamber 403 with the dispersion of the gas regulated by the slits 402 and, after introduced into the measuring chamber 403, the gas is discharged into the atmosphere to be measured, through the slits 402 with the dispersion of the gas regulated. Accordingly, the residence time of the introduced exhaust gas in the measuring chamber 403 is increased; even though the composition (especially, the amount of oxygen or water vapor) of the exhaust gas in the atmosphere to be investigated is changed, the influence of the change upon the gas in the measuring chamber is thus decreased and the output of the sensor 400 is improved. As a result, the detection accuracy of the sensor 400 can be increased. Additionally, the oxygen pump element 3 and the oxygen concentration cell element 4 are integrated through the medium of the spacer 401, and the mechanical strength of the sensor 400 is therefore increased.

Figure 52A:
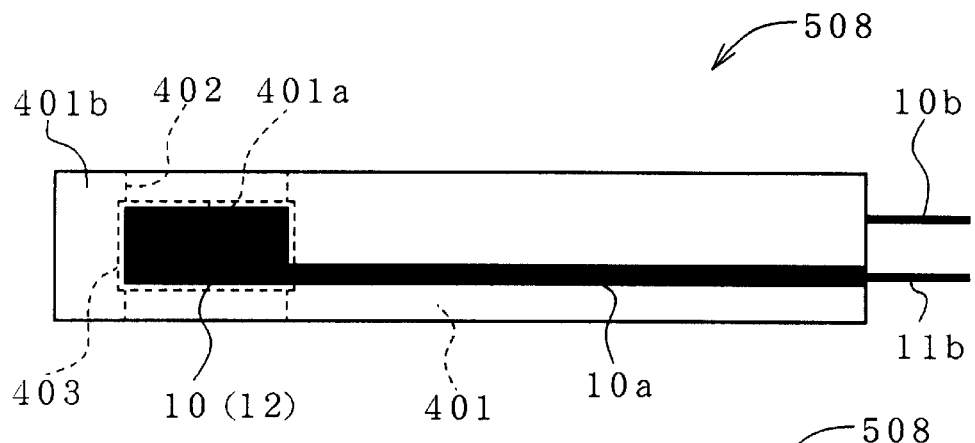
FIG. 52A is a plan view illustrating a 2nd example of a sensor in which exhaust gas is introduced into a measuring chamber through slits.
Figure 52B:
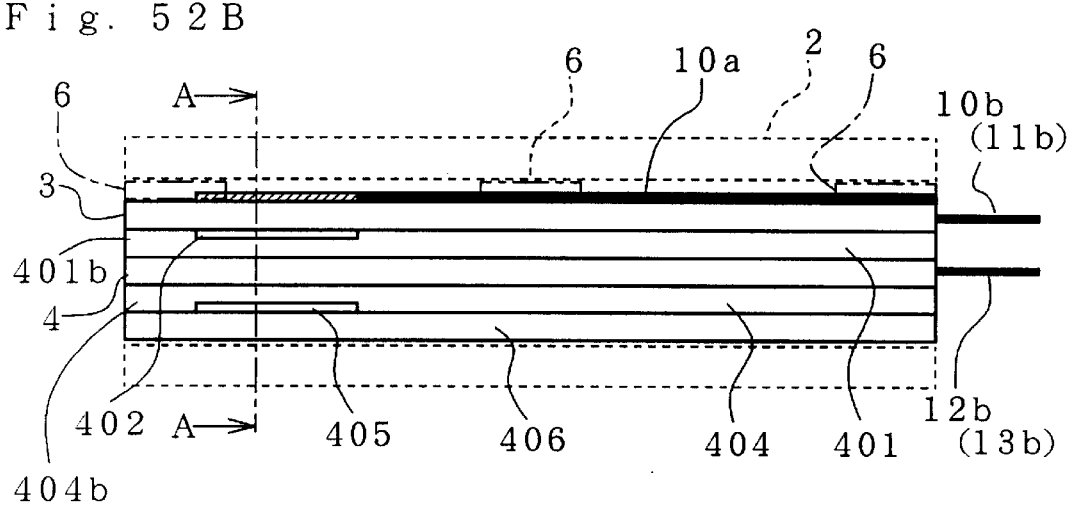
FIG. 52B is a side view of FIG. 52A.
Figure 52C:
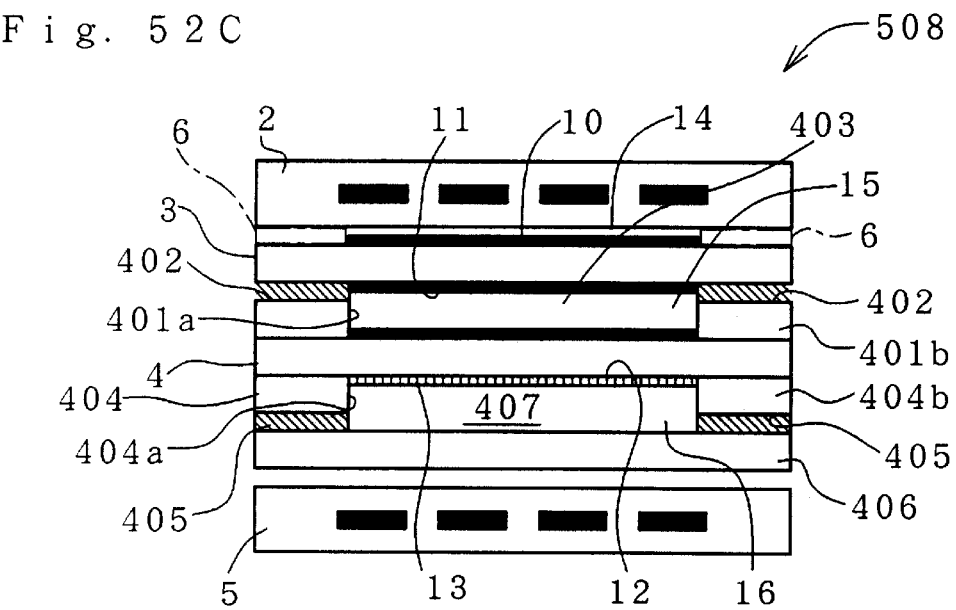
FIG. 52C is an A—A sectional view of FIG. 52B.

Another measuring chamber having the same structure may be formed on the side of the third electrode 13 on the oxygen concentration cell element 4. FIGS. 52 illustrate an example of such an arrangement. With a sensor 508 shown in FIGS. 52 is integrated a space-forming ceramic plate 406 as a space forming member, through the medium of a spacer 404 which is similar to the spacer on the side of the second electrode 12 and which has a window 404a. A measuring chamber 407 is defined by the inside surfaces of a wall 404b of the spacer 404 and by the surfaces facing each other of the oxygen concentration cell element 4 and of the space-forming ceramic plate 406. Between the wall 404b and the oxygen concentration cell element 4 at the positions corresponding to the measuring chamber 407 are formed slits 405 which are similar to the slits on the side of the second electrode 12. The second heater 5 is laminated on the space-forming ceramic plate 406. In accordance with the arrangement, the sensor which is more stable and which has a higher output can be obtained.

Figure 55A:
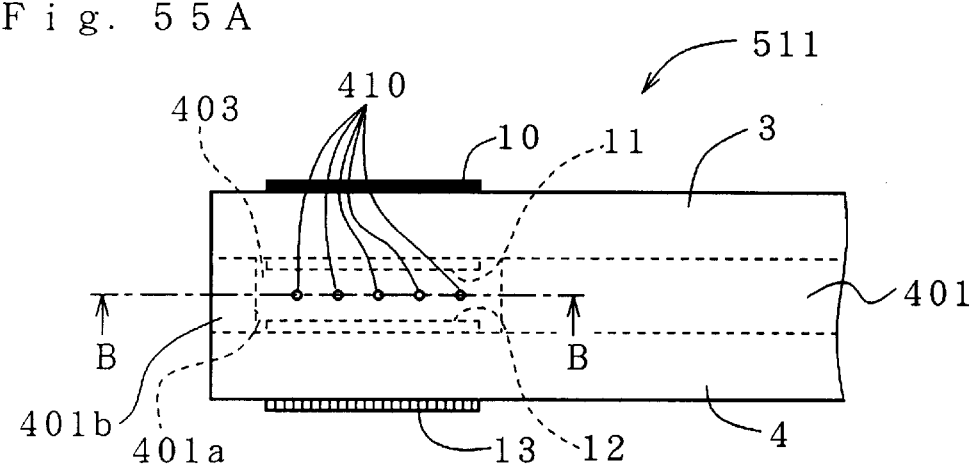
FIG. 55A is a fragmentary plan view illustrating an example of a sensor in which exhaust gas is introduced into a measuring chamber through small bores.
Figure 55B:
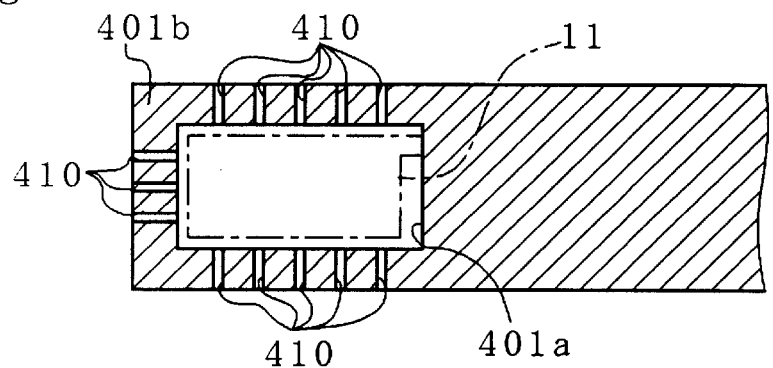
FIG. 55B is a B—B sectional view of FIG. 55A.
Figure 56A:
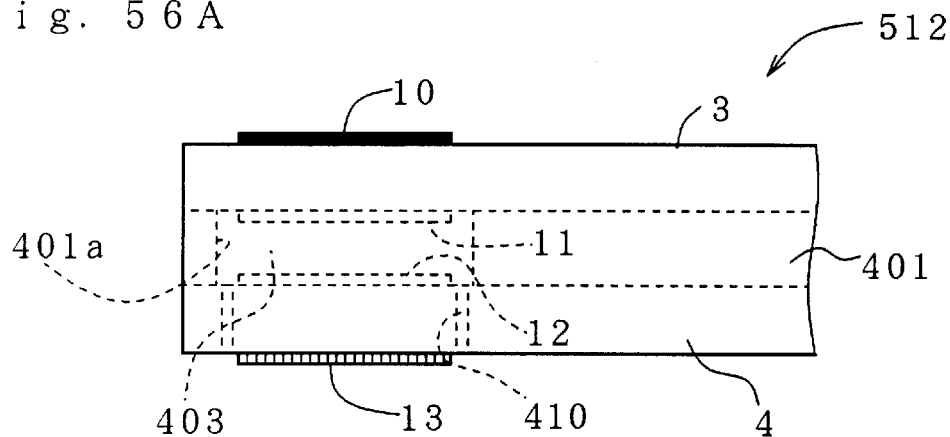
FIG. 56A is a fragmentary plan view illustrating a modification of the sensor.
Figure 56B:
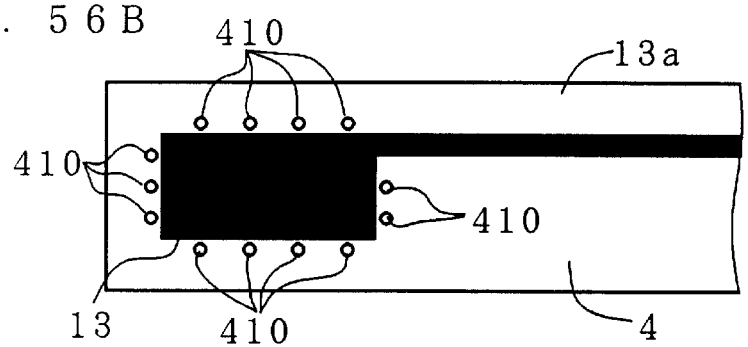
FIG. 56B is a bottom view of FIG. 56A.

The diffusion flow regulator can be configured by small bores instead of the slits. For example, in an example shown in FIGS. 55, a plurality of small bores 410 penetrating a wall 401b in directions parallel with the surfaces of the oxygen pump element 3 and of the oxygen concentration cell element 4 are formed at given intervals along the peripheries of the first and second electrodes 11, 12. In an example shown in FIGS. 56, a plurality of small bores 410 penetrating the oxygen concentration cell element 4 in the direction of the thickness are formed at given intervals along the periphery of the third electrode 13.

Figure 53A:
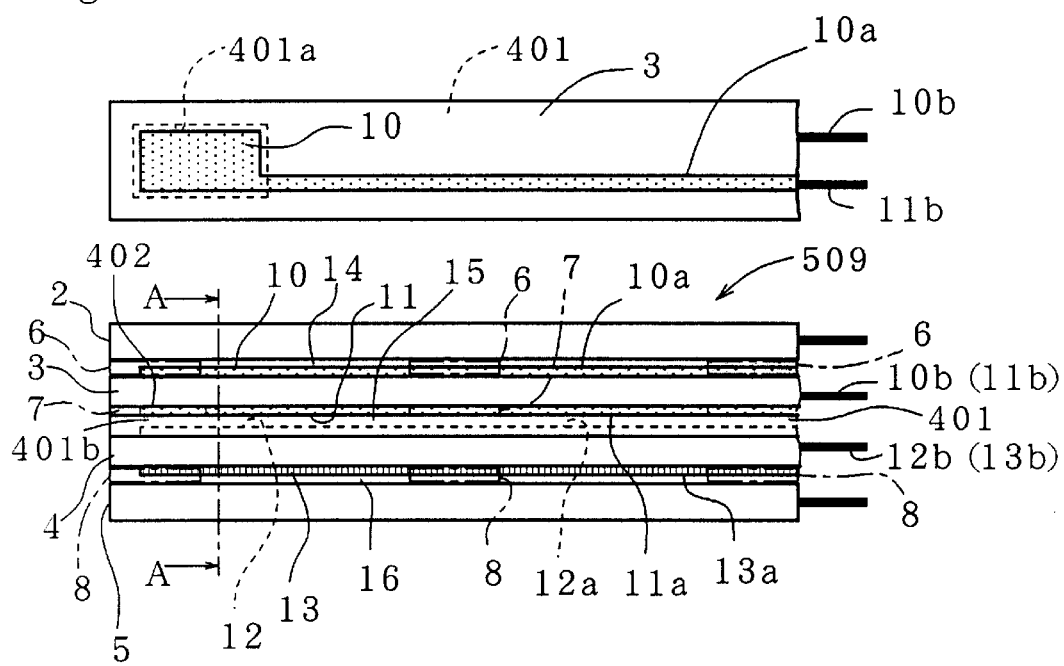
FIG. 53A is a plan view illustrating a 3rd example of a sensor in which exhaust gas is introduced into a measuring chamber through slits.
Figure 53B:
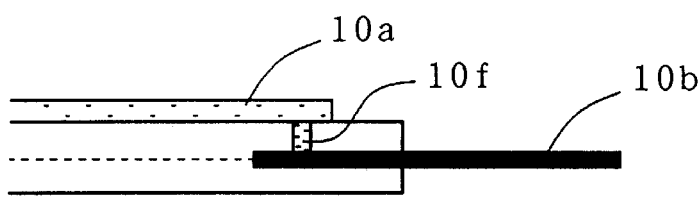
FIG. 53B is a side view of FIG. 53A.
Figure 53C:
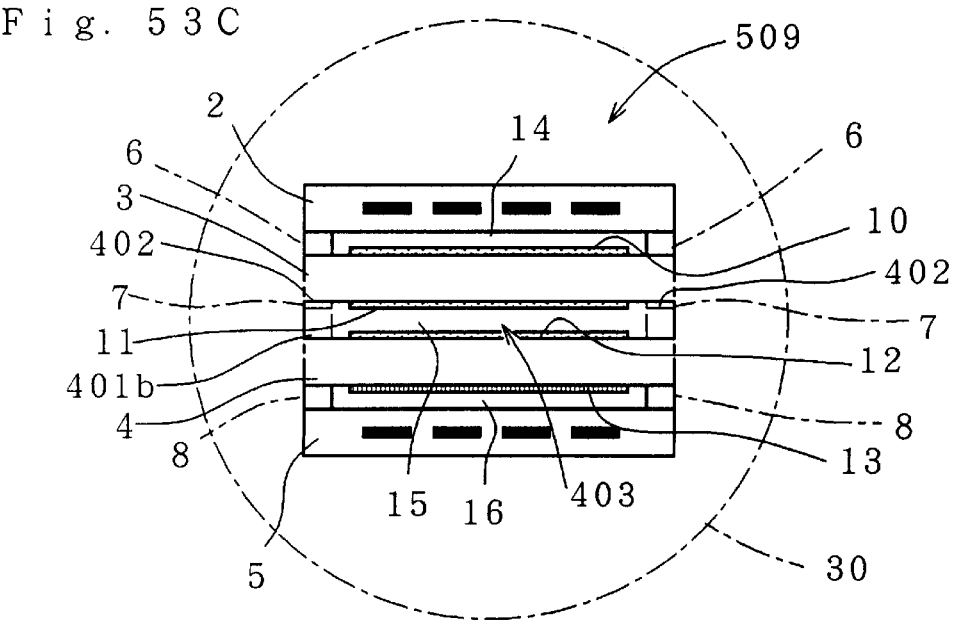
FIG. 53C is an A—A sectional view of FIG. 53B.
Figure 57:
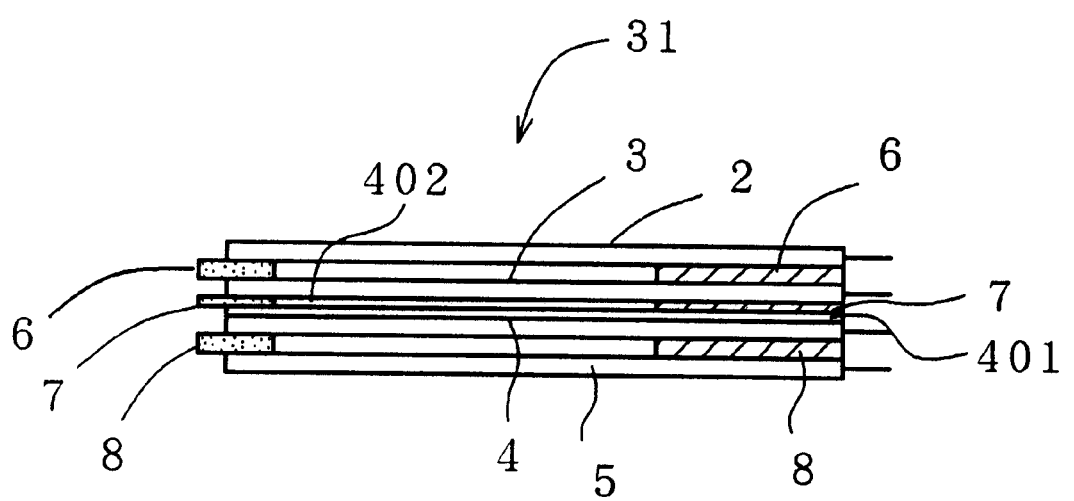

FIGS. 53 illustrate an example of an arrangement in which the above-mentioned spacer 401 is integrated with the oxygen concentration cell element 4 by sintering and in which the oxygen pump element 3 is not integrated with but separated from the element 4. In this case, the slits 402 are formed between a surface of the oxygen pump element 3 and the surface of the wall 401b facing the surface of the element 3. The first heater 2, the oxygen pump element 3, the oxygen concentration cell element 4 and the second heater 5 are laminated through the medium of the spacers 6 to 8 to form a laminate 31, and a ceramic stopper 30 having a rectangular through hole 30a is fitted over the laminate 31. As shown in FIG. 57, the spacer 7 is interposed between the spacer 401 and the oxygen pump element 3 so as to serve to form therebetween the slits 402 having a given size.

Figure 54A:
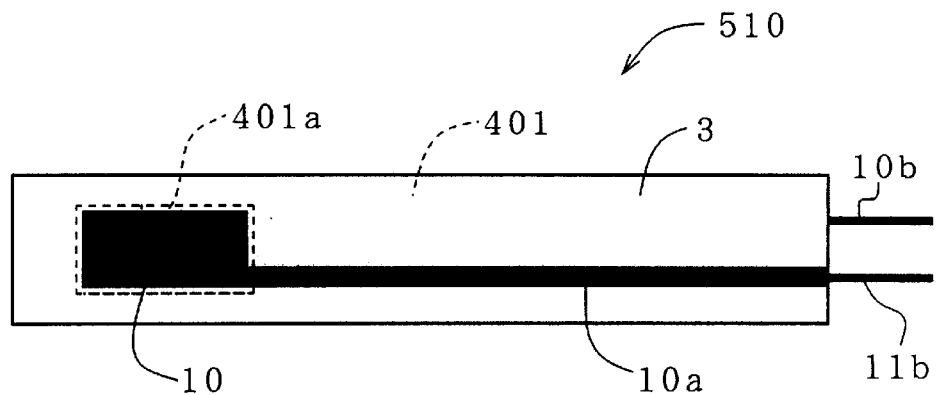
FIG. 54A is a plan view illustrating a 4th example of a sensor in which exhaust gas is introduced into a measuring chamber through slits.
Figure 54B:
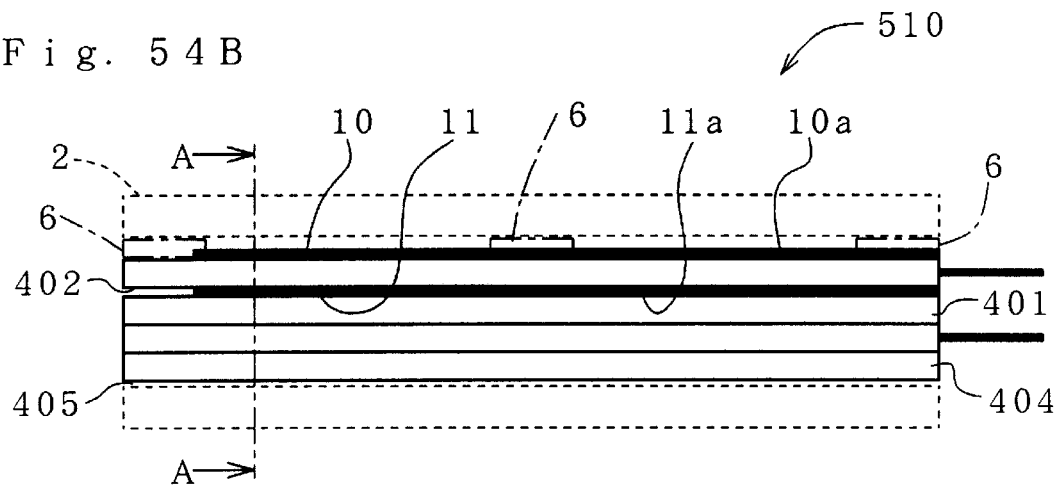
FIG. 54B is a side view of FIG. 54A.
Figure 54C:
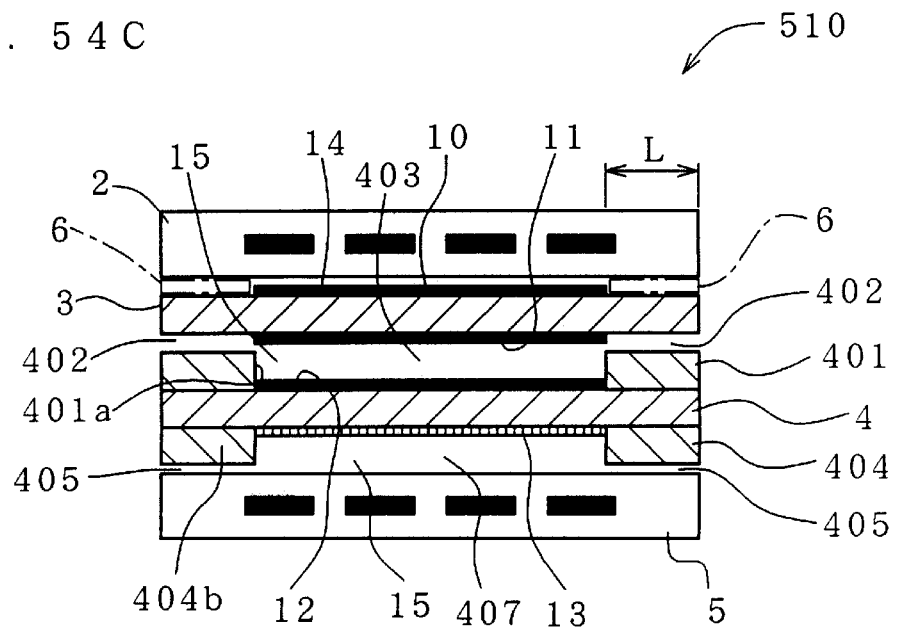
FIG. 54C is an A—A sectional view of FIG. 54B.

In this case also, as shown in FIGS. 54, another measuring chamber 407 may be formed on the side of the third electrode 13. With the sensor 510 shown in the drawings is integrated the spacer 404 for forming the measuring chamber 407 on the side of the third electrode 13 on the oxygen concentration cell element 4. the measuring chamber 407 is defined by the inside surfaces of the wall 404b of the space r 404 and by the surfaces facing each other of the oxygen concentration cell element 4 and of the second heater 5. Between the spacer 404 and the second heater 5 are formed the slits 405 which are similar to the slits on the side of the second electrode 12. In this arrangement, the second heater 5 serves as a space-forming member.

EXPERIMENT EXAMPLE 1

① Experiment 1

Figure 58:
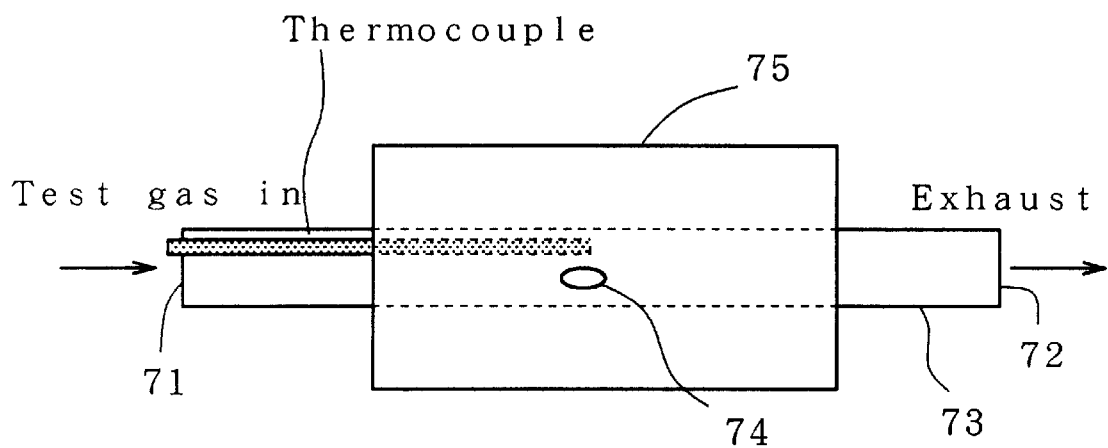
Figure 59A:
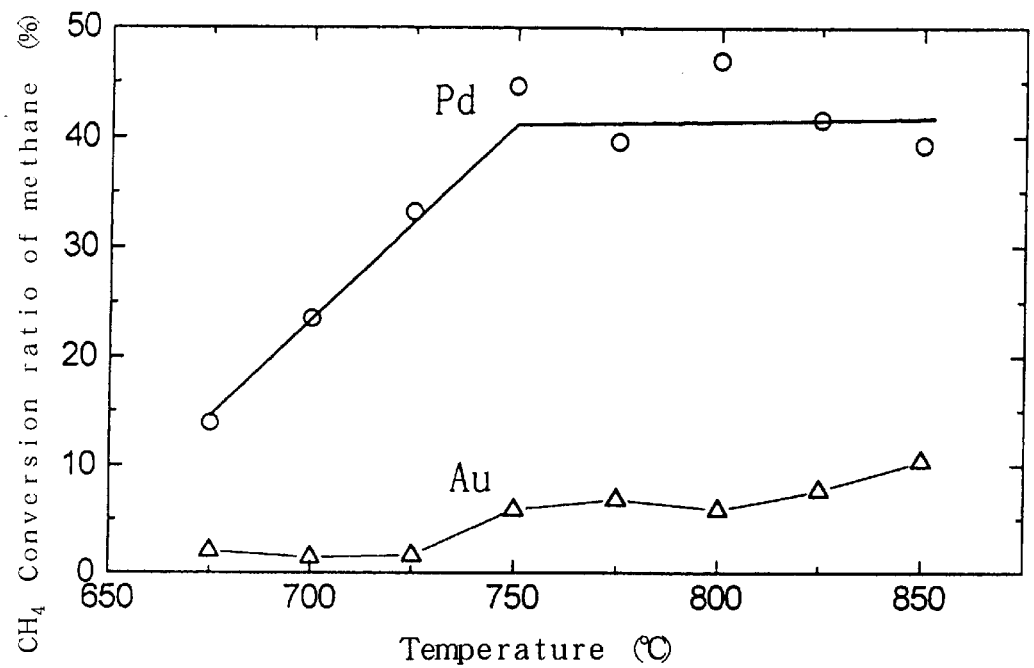

A ceramic green sheet comprising $Y_2O_3$ powder and $ZrO_2$ powder was stamped into discs. On a surface of each disc, a circular electrode pattern was formed of paste in which a given amount of $ZrO_2$ powder had been blended with alloy powder consisting of Pd (52% by weight) and Ag (48% by weight) or Au powder (and in which the average particle size of the metal powder is 1.0 $\mu$m). By sintering of the discs at 1470° C., samples were produced in each of which a disc-like Pd porous electrode or Au porous electrode having a diameter of 8 mm was formed on a disc of solid electrolyte having a diameter of 12 mm and a thickness of 1 mm and comprising a $ZrO_2$ sinter containing 5 mole percent $Y_2O_3$ (hereinafter referred to as YSZ). As shown in FIG. 58, the samples 74 were placed in a cylindrical body 73 having a gas inlet 71 and an outlet 72, in which body the temperature was maintained at various points between 675° C. and 850° C. with use of an electric furnace 75. In that state, test gas containing oxygen of 300 ppm, methane of 350 ppm as the constituent to be detected, 3% water vapor and the residual parts of Ar was introduced through the inlet 71 at a flow rate of 100 ml/min and discharged through the outlet 72. At the various temperatures, the methane concentrations Cs (in ppm) in the discharged test gas were measured and the conversion ratios η of methane defined by:

$$\eta\{(350-Cs)/350\}\cdot 100 \text{ (in \%)}$$

were obtained. FIG. 59A illustrates the measurement result of the conversion ratios η of methane at the various temperatures. The sample with use of the Au porous electrode provided the lower conversion ratios η which were mostly not more than 10%, while the sample with use of the Pd porous electrode provided the ratios η which increased with increase in temperature. The differences in η between both samples were found to be about 20% at 700° C. and from 30 to 40% at the temperatures not less than 750° C.

② Experiment 2

Disc-like Au porous electrodes having a diameter of 8 mm as an outside electrode and as a first electrode were formed on both surfaces of a solid electrolyte disc which was of the same material and of the same size as in Experiment 1, under the same condition as in Experiment 1, and an oxygen pump element was thus produced. On the other hand, a Pd porous electrode having a diameter of 8 mm as a second electrode was formed on one surface of the similar solid electrolyte disc and an Au porous electrode having a diameter of 3 mm as a third electrode was formed on the other surface of the disc; an oxygen concentration cell element was thus produced. Both the elements were laminated together so that the first and second electrodes faced each other, with Pt or Au meshes of 100 to 500 mesh interposed therebetween, and a sensor was thus produced.

The elements (i.e., the oxygen pump element 3 and the oxygen concentration cell element 4) were connected to a circuit which was the same as shown in FIG. 7 and, with use of the arrangement shown in FIG. 58, heated to 750° C. at which the difference in η measured in Experiment 1 between the Pd porous electrode and the Au porous electrode had been maximized. In this state, test gases consisting of methane of various concentrations from 50 to 700 ppm as the constituent to be detected, oxygen of 300 ppm, 3% water vapor (by volume) and the residual parts of argon were passed at a flow rate of 100 ml/min, and the electromotive forces of the oxygen concentration cell element in equilibrium were measured. Subsequently, the oxygen pump element was operated so that the electromotive forces EMF came to a target value EC of electromotive force, and pump currents Ip were then measured.

Figure 59B:
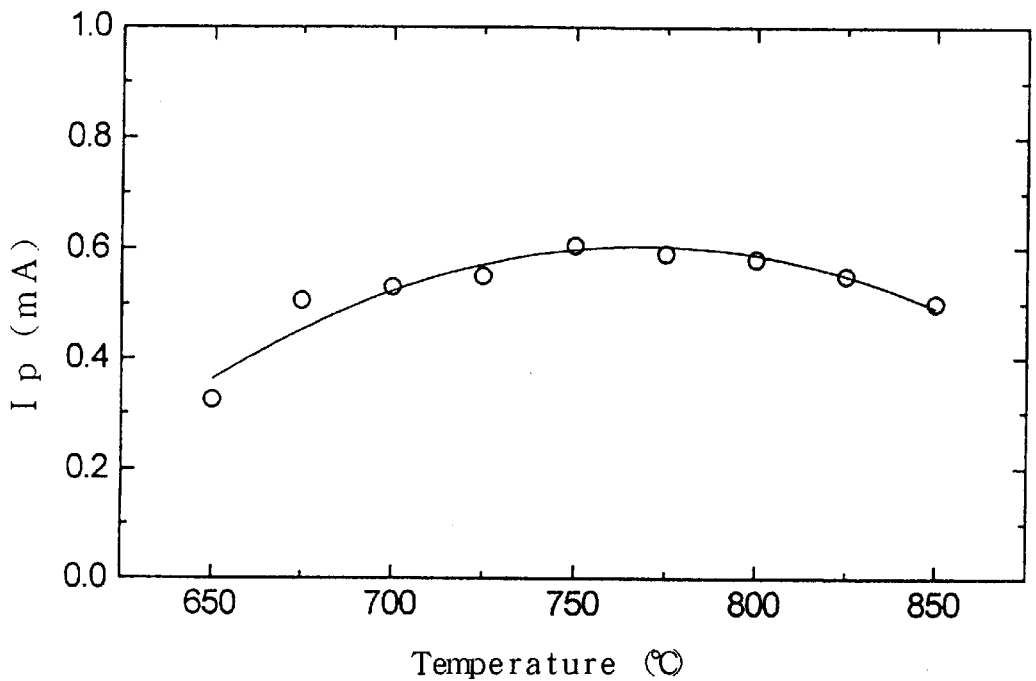
Figure 60:
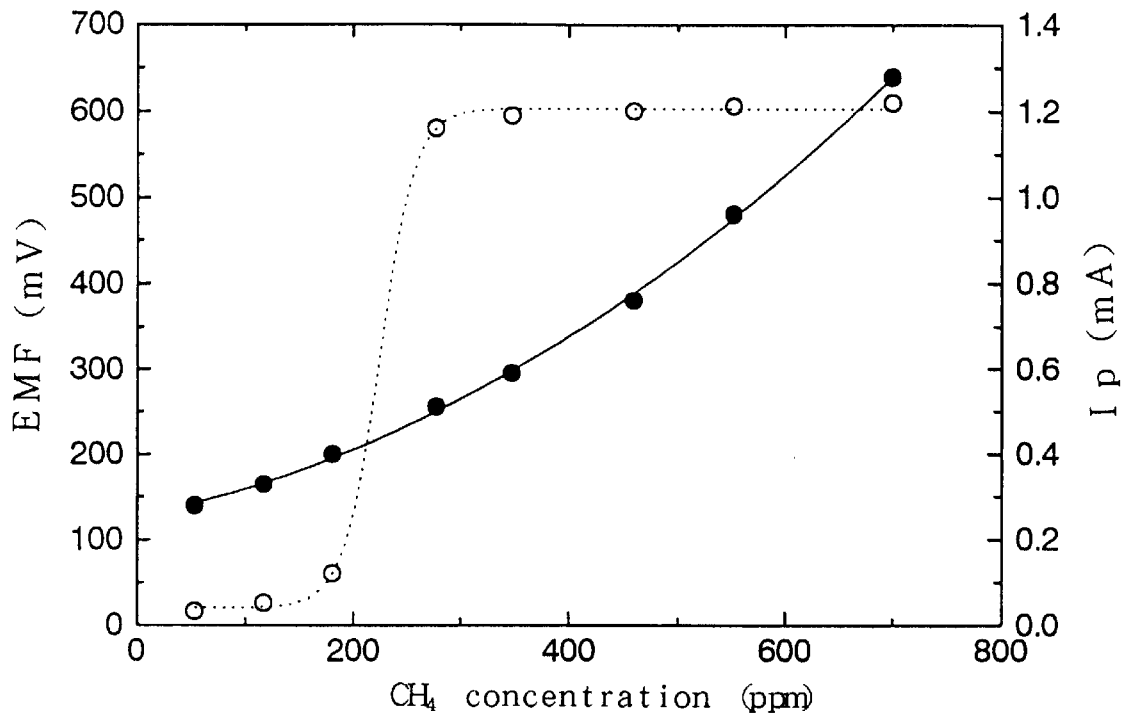
Figure 61:
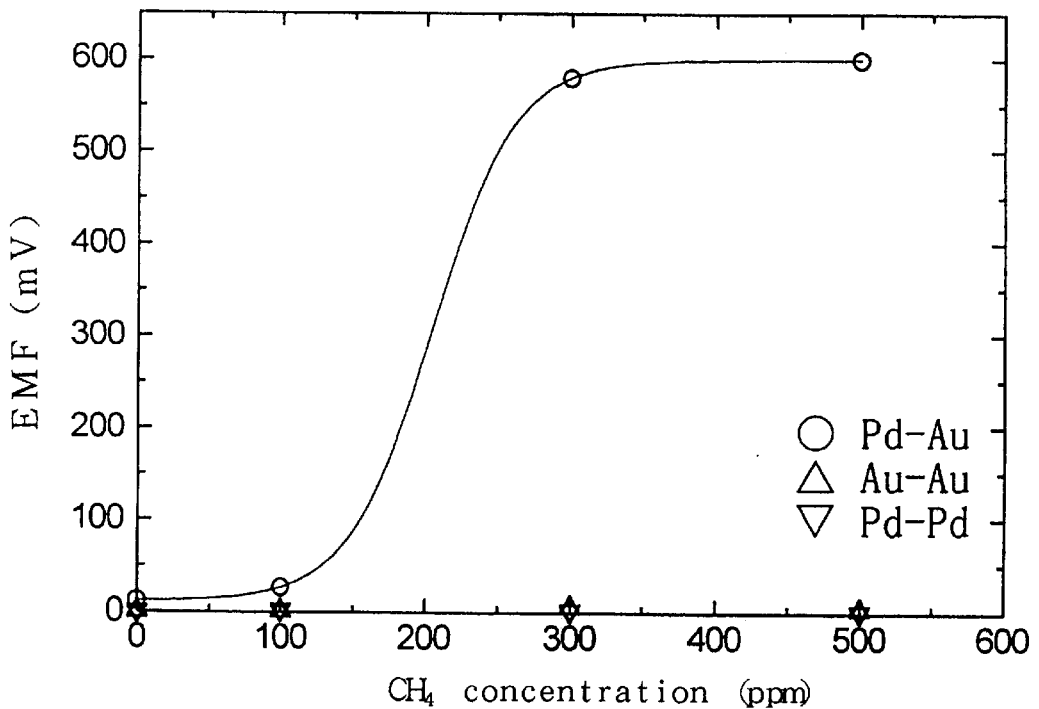

As a result, as shown in FIG. 60, the pump current Ip (shown by "●" in the drawing) increased linearly in general with the methane concentration in the test gases, it was therefore found that a methane concentration can be detected from Ip. As shown in FIG. 59B, the measurement in which methane concentration was fixed at 300 ppm and in which the sensor temperature was varied between 650° C. and 850° C., exhibited the maximum value of the sensor output in the vicinity of 750° C. at which the difference in η had been maximized. It was therefore found that the operation of the sensor at the temperature maximizing the difference in η is effective in improving the sensitivity of the sensor. For reference, the electromotive forces of the oxygen concentration cell element in the case that the oxygen pump element was not operated were measured for various concentrations of methane (the results are shown by "○" in FIG. 60). As a result, it was found that the electromotive force steeply increased in the vicinity of a methane content (about 200 ppm) of which the ratio to the oxygen concentration in the test gases was generally equal to the theoretical air-fuel ratio. This result means that, with the methane contents not less than the above value, a substantial difference in oxygen concentration occurred between both sides of the oxygen concentration cell element because almost all methane was oxidized and consumed on the side of the second electrode (i.e., on the space side) comprising Pd which has a higher oxidation catalyst activity on methane and because methane was not consumed so much on the side of the third electrode (i.e., on the opposed-space side) comprising Au which has a lower oxidation catalyst activity. On the other hand, a sample with an oxygen concentration cell element in which both the second and third electrodes were Au porous electrodes and a sample with an oxygen concentration cell element in which both the electrodes were Pd porous electrodes were produced, and the same experiment was performed with use of the samples. As a result, as shown in FIG. 61, those samples generated substantially no electromotive force, irrespective of methane concentration.

Figure 62:
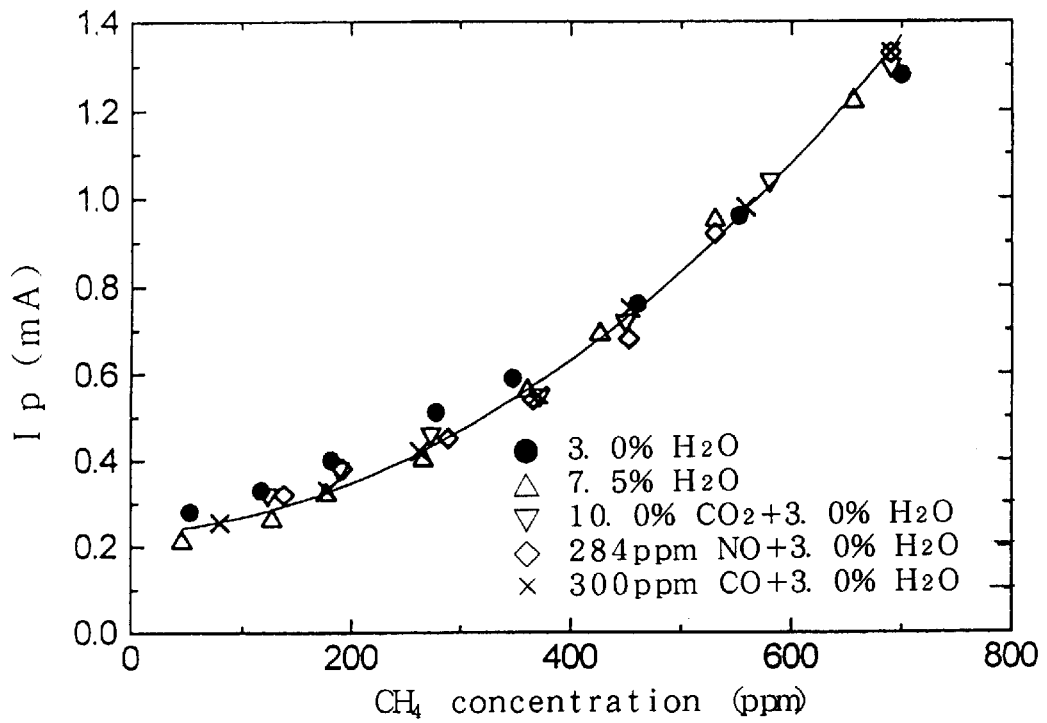

The influence was also investigated that the test gas with which any one of water vapor (7.5%), carbon dioxide (10.0%), nitrogen monoxide (284 ppm) and carbon monoxide (300 ppm) was mixed as an interfering gas exerted upon the dependence of the pump current Ip on methane concentration. The result shown in FIG. 62 indicates that the interfering gases exerted substantially no influence upon the dependence of Ip on methane concentration and that the selectivity on the detection of methane was sufficient in any case.

Figure 63:
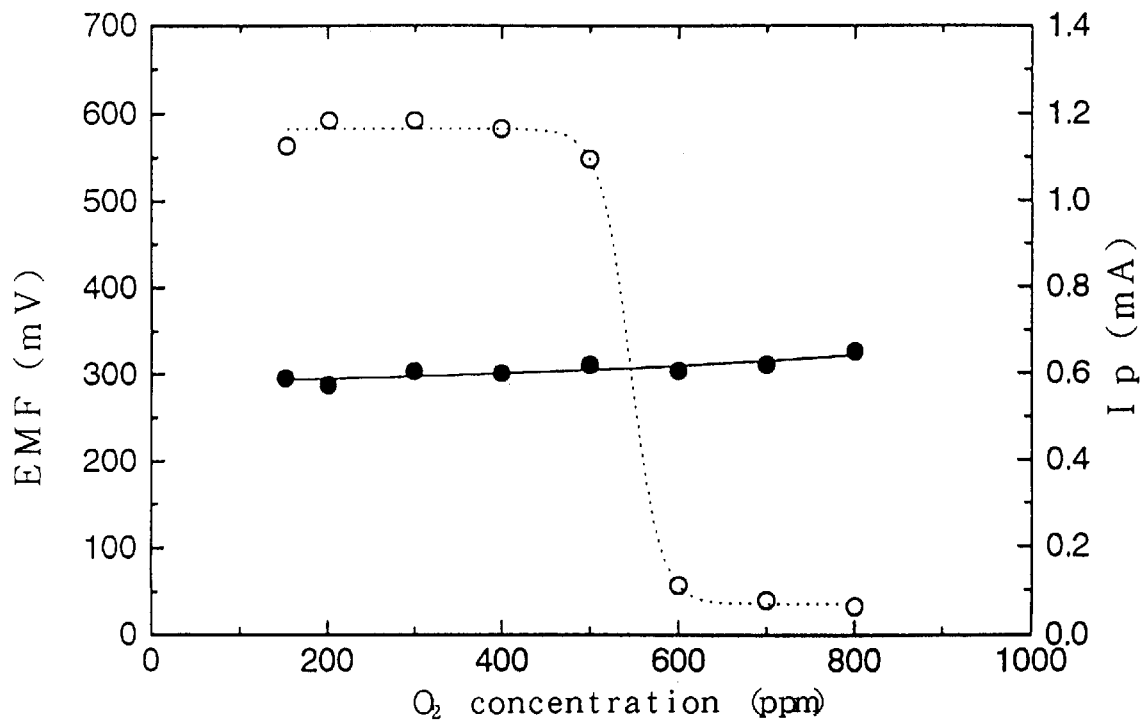

FIG. 63 illustrates the result of the same experiment in which methane concentration in the test gas was fixed at 350 ppm and in which oxygen concentration in the gas was varied between 100 and 800 ppm. The pump currents Ip exhibited generally a uniform value, irrespective of the oxygen concentrations in the test gases, and Ip as the sensor output was thus found to be little influenced by the oxygen concentration in the test gas.

EXPERIMENT EXAMPLE 2

Disc-like Au porous electrodes having a diameter of 8 mm as outside electrodes and first electrodes were formed on both surfaces of solid electrolyte discs which were of the same material and of the same size as in Experiment 1 in Experiment Example 1, under the same condition as in Experiment 1, and oxygen pump elements were thus produced. On the other hand, a Pd porous electrode and an Au porous electrode (an example for comparison) having a diameter of 8 mm as second electrodes were respectively formed on one-side surfaces of the similar solid electrolyte discs and Au porous electrodes having a diameter of 3 mm as third electrodes were formed on the other-side surfaces of the discs; oxygen concentration cell elements were thus produced. Both the elements were laminated together so that the first and second electrodes faced each other, with Pt or Au meshes of 100 to 500 mesh interposed therebetween, and sensors were thus produced.

Figure 64:
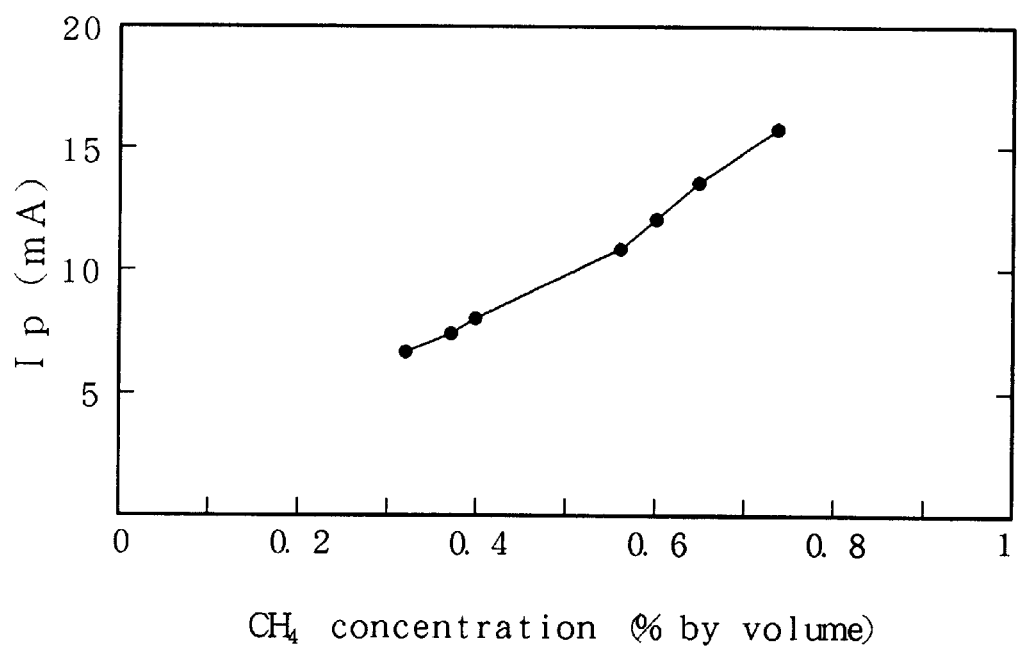

The elements (i.e., the oxygen pump element 3 and the oxygen concentration cell element 4) were connected to a circuit which was the same as shown in FIG. 7 and, with use of the arrangement shown in FIG. 58, heated to a temperature between 850° C. and 900° C. Simultaneously, test gases consisting by volume of methane of various concentrations between 0.3 and 0.8% as the constituent to be detected, 0.5% oxygen, 5% water vapor and the residual parts of argon were passed through the furnace at a flow rate of 100 ml/min, and the electromotive forces of the oxygen concentration cell element in equilibrium were measured. Subsequently, the oxygen pump element was operated so that the electromotive forces EMF came to the target value EC of electromotive force, and the pump currents Ip were then measured. It was found that the pump current Ip, as shown in FIG. 64, increased linearly in general with methane concentration in the test gases and that a methane concentration can be detected from Ip.

Figure 65:
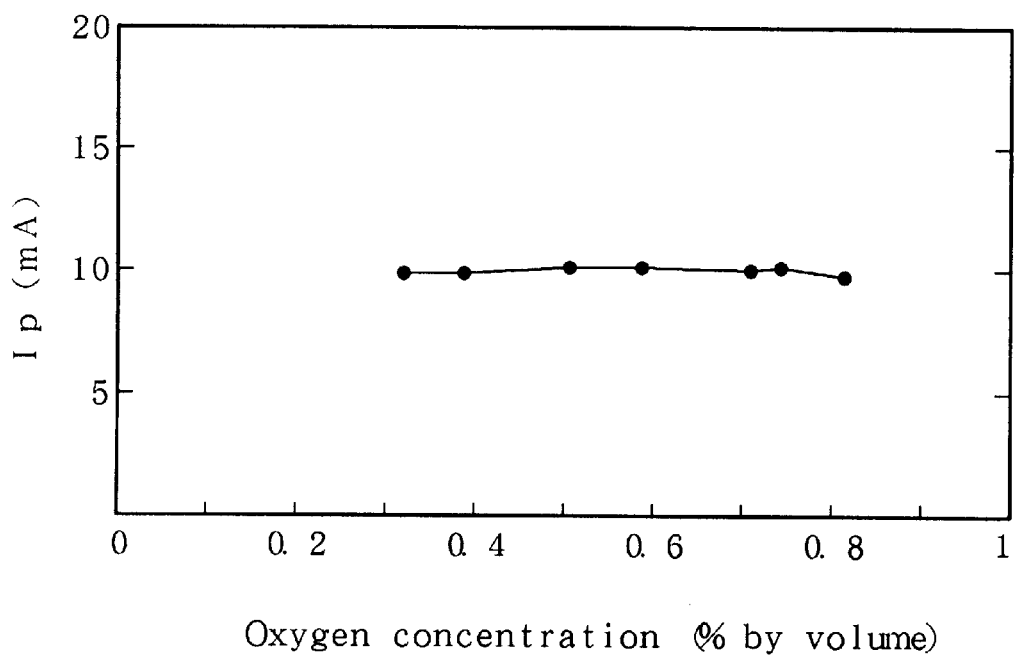

FIG. 65 illustrates the result of the same experiment in which methane concentration in the test gas fixed at 0.5% and in which oxygen concentration in the gas was varied between 0.3 and 0.8% by volume. The pump currents Ip exhibited generally a uniform value, irrespective of oxygen concentrations in the test gases, and Ip as the sensor output was thus found to be little influenced by oxygen concentration in the test gas.

Figure 66:
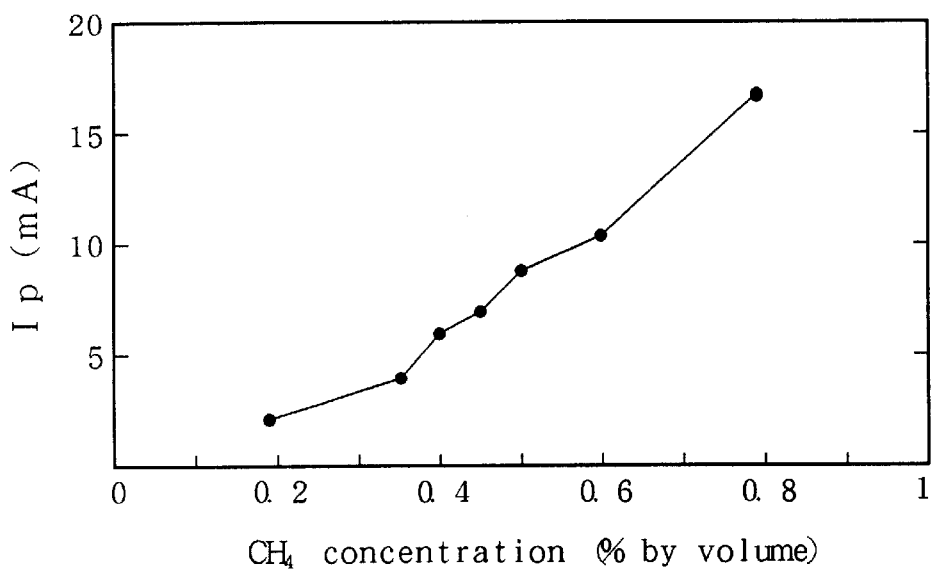

FIG. 66 illustrates the result of the same experiment which was performed with use of the test gases having various methane concentrations, in the state where the above position of the oxygen concentration cell element relative to the oxygen pump element was reversed, i.e., in the state where the arrangement was such that the second and third electrodes were the Au and Pd porous electrodes, respectively. In this case, as compared with the result in FIG. 64 in which the oxygen concentration cell element was unreversed, it is found that the rate of change (the gradient) of Ip relative to methane concentration increased and that the sensitivity of the sensor improved.

EXPERIMENT EXAMPLE 3

Figure 67:
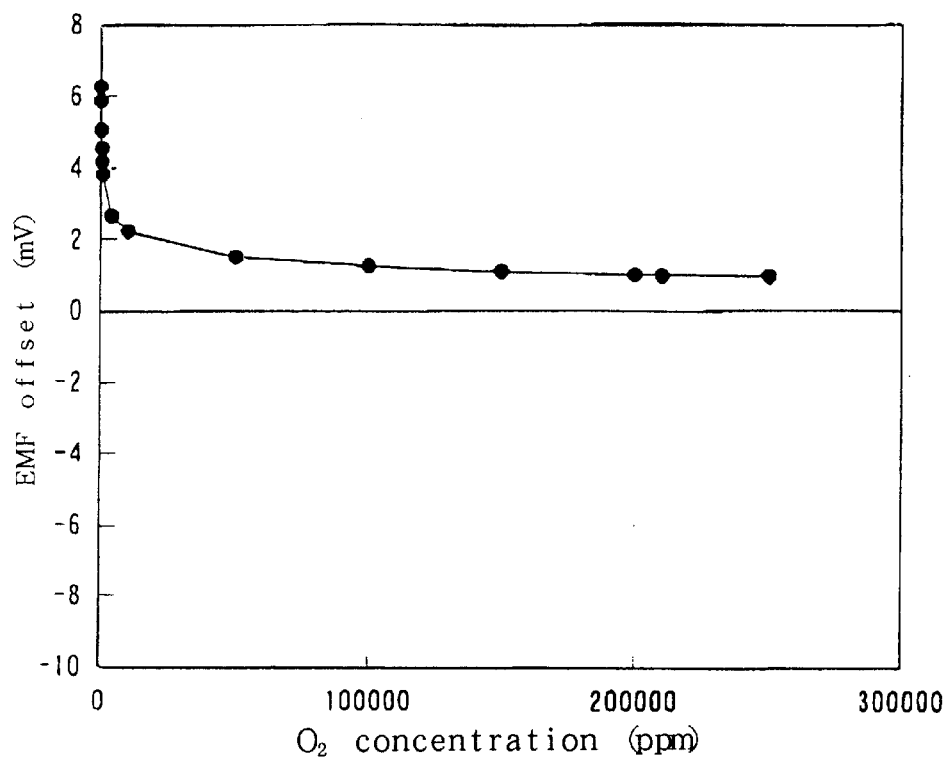

The exhaust gas sensor 500 shown in FIGS. 17 and 18 was produced in which the outside electrode 10, the first electrode 11 and the second electrode 12 were each formed of a Pt porous electrode and in which the third electrode 13 was formed of an Au porous electrode; however, the solid electrolyte used for the elements 2 to 5 was the same as in Experiment Examples 1 and 2, and the dimensions of the elements were 4 mm×45 mm×0.4 mm. The widths of the spaces 14, 15, and 16 were 0.06 mm, 0.15 mm, and 0.07 mm, respectively. The sensor 500 was held in test gases consisting of oxygen of 50 to 250000 ppm, 10% water vapor, 10% carbon dioxide and the residual parts of nitrogen, and heated by the heaters 2, 5 until the temperatures of the elements 3 and 4 reached 800° C. The temperatures of the heaters at this time were 900° C. In that state, the electromotive force EOS generated in the oxygen concentration cell element 4 in the case that the oxygen pump element 3 was not energized (i.e., the offset electromotive force) was measured for each oxygen concentration. FIG. 67 illustrates the result of the measurement. It is observed that the offset electromotive force EOS steeply increased as oxygen concentration went below 10000 ppm (1% by volume) and that, with respect to oxygen concentrations not less than 10000 ppm, especially not less than 100000 ppm, EOS was stable generally within the range from 1 to 1.5 mV, by contrast (it was 1.22 mV in the air).

Subsequently, the sensor 500 was mounted to an exhaust pipe and connected to the controlling section 40 shown in FIG. 8. The oxygen pump element 3 was operated with the set value of the operating temperature of the sensor of 800° C. and with various target values EC of the electromotive force between −5 mV and 8.3 mV. There were passed test gases (the temperature 300° C.) consisting of oxygen of 100 to 1000 ppm, 10% water vapor, 10% carbon dioxide, methane of 0 ppm or 300 ppm, and the residual parts of nitrogen, at a flow rate of 12 L/min, and the pump currents Ip (the sensor outputs) were measured. FIGS. 68 and 69 illustrate the result of the measurement for each methane concentration, in the form of the dependence of the sensor output upon oxygen concentration corresponding to each target value EC of the electromotive force. With EC of 1.22 mV (corresponding to EOS in the air), −1.8 mV, 0 mV, 3.7 mV and 4.2 mV (within the range of EOS±5 mV), the dependence of the sensor output upon oxygen concentration is found to be smaller, while, with EC of −5 mV, 5.1 mV and 8.3 mV, which fall outside the range not less than (EOS−5) mV and not more than (EOS+5 ) mV, the dependence of the sensor output upon oxygen concentration is found to be larger.

EXPERIMENT EXAMPLE 4

The same exhaust gas sensor 500 as in Experiment Example 3 was mounted to the exhaust pipe and there were passed test gases consisting of oxygen of 1000 ppm, 10% carbon dioxide, methane of 0 ppm to 500 ppm, and the residual parts of nitrogen at various flow rates of 4 to 20 L/min, and the pump currents Ip (the sensor outputs) were then measured. FIG. 70 illustrates the result of the measurement in the form of the dependence of the sensor output upon methane concentration corresponding to each flow rate. It is found that the sensor 500 in accordance with the invention exhibited the outputs which were linear with respect to methane concentrations and which were little influenced by the flow rate of the gas.

EXPERIMENT EXAMPLE 5

The same exhaust gas sensor 500 as in Experiment Example 3 was mounted to the exhaust pipe and there were passed test gases consisting of oxygen of 100 to 1000 ppm, 10% carbon dioxide, methane of 0 ppm to 500 ppm, and the residual parts of nitrogen at a flow rate of 12 L/min, and the pump currents Ip (the sensor outputs) were then measured. FIG. 71 illustrates the result of the measurement in the form of the dependence of the sensor output upon methane concentration corresponding to each oxygen concentration. It is found that the sensor 500 in accordance with the invention exhibited the outputs which were linear with respect to methane concentrations and which were little influenced by oxygen concentration.

EXPERIMENT EXAMPLE 6

The same exhaust gas sensor 500 as in Experiment Example 3 was mounted to the exhaust pipe and there were passed test gases consisting of oxygen of 1000 ppm, 10% carbon dioxide, methane of 0 ppm to 500 ppm, 0% to 10% water vapor and the residual parts of nitrogen at a flow rate of 12 L/min, and the pump currents Ip (the sensor outputs) were then measured. FIG. 72 illustrates the result of the measurement in the form of the dependence of the sensor output upon methane concentration corresponding to each amount of water vapor. It is found that the sensor 500 in accordance with the invention exhibited the outputs which were linear with respect to methane concentrations and which were little influenced by 10% humidification of the gas.

EXPERIMENT EXAMPLE 7

The same exhaust gas sensor 500 as in Experiment Example 3 was mounted to the exhaust pipe. There were passed at a flow rate of 12 L/min test gases which contained oxygen of 1000 ppm, 10% carbon dioxide, methane of 0 ppm to 500 ppm, 0% or 10% water vapor and nearly the residual parts of nitrogen and with which any one of nitrogen monoxide (270 ppm), carbon monoxide (270 ppm), and propylene (270 ppmC (ppmC represents carbon-equivalent concentration)) was mixed as interfering gas, and the pump currents Ip (the sensor outputs) were then measured. FIG. 73 illustrates the result of the measurement in the form of the dependence of the sensor output upon methane concentration for each composition of the interfering gas. It is found that the sensor 500 in accordance with the invention exhibited the outputs which were linear with respect to methane concentrations and which were little influenced by the interfering gases, and exhibited an excellent selectivity on methane.

EXPERIMENT EXAMPLE 8

As shown in FIG. 74, to an exhaust pipe of an in-line four-cylinder gasoline internal combustion engine having a displacement of 1500 cc were mounted a full-range oxygen sensor for controlling air-fuel ratio, a three way catalytic converter, a mass flow controller for introducing methane, an exhaust gas analyzer, the same exhaust gas sensor 500 as in Experiment Example 3, and a silencer, which were arranged in the listed order from the upstream side. In the three way catalytic converter were used two types of catalyst, individually, i.e., a commercially available unused product of a publicly-known three way catalyst, and the same catalyst heat-treated for 50 hours at 800° C. in the air, which assumed the condition deteriorated by a certain degree of use. With use of each catalyst, the engine was operated under each of the two sets of conditions shown in Table 1. While methane was added by the mass flow controller, the concentration of hydrocarbon in the exhaust gas containing the added methane was analyzed by the exhaust gas analyzer. Simultaneously, the pump current Ip (the sensor output) of the sensor 1 was measured.

In Table 2 is shown the result of measuring the purging ratios of each catalyst against all HC (THC), carbon monoxide (CO), and nitrogen monoxide (NO) under both the sets of operating conditions. It is found that the purging ability of the heat-treated catalyst against HC was degraded under the operating condition ② in Table 1. The degradation of the catalyst lowers the ability of ceria ($CeO_2$) or the like to reserve oxygen and thus increases the oxygen concentration in the exhaust gas; however, as is evident from the measurement result of the sensor outputs shown in FIG. 75, it is found that the dependence of the output upon HC concentration was not so much influenced by the degradation of the catalyst (nor by the operating condition) and exhibited a satisfactory linearity.

EXPERIMENT EXAMPLE 9

Figure 41:
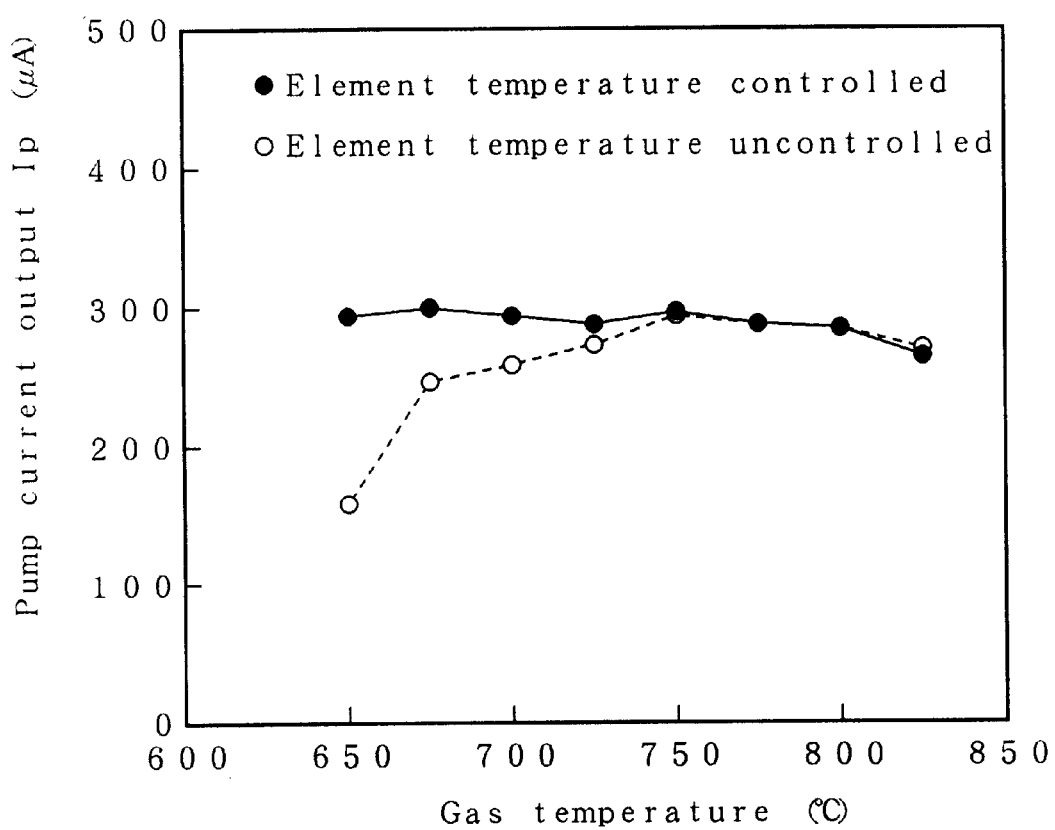
FIG. 41 is a graph illustrating the result of measurement in Experiment Example 9.

The same exhaust gas sensor as in Experiment Example 3 was incorporated into the sensor system 50 shown in FIG. 33. The offset electromotive force of the oxygen concentration cell element of the exhaust gas sensor was +1.2 mV, and the target value EC of the electromotive force was set at +1.2 mV. The temperature setting of the oxygen concentration cell element to be achieved by the heaters 2, 5 was of 750° C. In this state, the sensor was mounted to an exhaust pipe, and there was passed at a flow rate of 12 L/min test gas which consisted of oxygen of 100 ppm, 10% carbon dioxide, methane of 300 ppm, and the residual parts of nitrogen and which had been heated to various temperatures between 650° C. and 830° C. by a given heating apparatus. The outputs of the exhaust gas sensor were measured in the form of the pump currents Ip. In the case that the temperature of the oxygen concentration cell element was monitored from the value of the internal electromotive force, the element temperature was controlled within the range of 750±20° C., even though the temperature of the exhaust gas changed. In the case that the energizing voltage applied to the heaters 2, 5 was made constant and the control was not specially performed, for comparison, the temperature varied in the range of 750±50° C. FIG. 41 illustrates the output values of the pump current Ip. As can be seen from the drawing, in the case that the temperature was controlled (shown by "●" in the drawing), the output values Ip were generally uniform, irrespective of the exhaust gas temperature; in the case that the temperature was not controlled (shown by "○" in the drawing), Ip considerably varied depending on the exhaust gas temperature.

EXPERIMENT EXAMPLE 10

For the purpose of investigating the mechanical strength of the exhaust gas sensor in Experiment Example 3, three types of test pieces were prepared: i.e., a solid electrolyte plate having the same size as used for the elements 2 to 5 (4 mm×45 mm×0.4 mm) was used as a unit, and there were prepared a test piece in which three unit plates had been laminated and had been integrally sintered (corresponding to the sensor structure in which the first heater 2, the oxygen pump element 3, and the oxygen concentration cell element 4 are integrally sintered), a test piece in which two unit plates had been laminated and had been integrally sintered (corresponding to the sensor structure in which the oxygen pump element 3 and the oxygen concentration cell element 4 are integrally sintered), and a test piece in which the single solid electrolyte plate was used. Four-point bending load was applied to each test piece by a predetermined bending tester, with the direction of the thickness of the solid electrolyte plate used as the bending direction, on the conditions of an upper-side span of 10 mm, a lower-side span of 30 mm and a cross head speed of 0.5 mm/min. The bending load at the time when the destruction occurred was measured. FIG. 76 illustrates the result of the measurement in the form of the dependence of the four-point bending load (represented by the bending load at the time when the rupture occurred in the test piece) upon the thickness of the test piece. It is found that the bending load increased with increase in the thickness of the test piece, more specifically, in rough proportion to the square of the thickness of the test piece.

EXPERIMENT EXAMPLE 11

The exhaust gas sensor 400 shown in FIG. 51 was produced in which the outside electrode 10, the first electrode 11 and the second electrode 12 were each formed of a Pt porous electrode and in which the third electrode 13 was formed of an Au porous electrode; however, the solid electrolyte used for the elements 2 to 5 was the same as in Experiment Examples 1 and 2, and the dimensions of the elements were 4 mm×45 mm×0.4 mm. The height of the space 14 was 0.06 mm; the height h of the space 15 (i.e., the measuring chamber 403) was 0.4 mm; the width d of the slits 402 was 0.1 mm; and the height of the space 16 was 0.07 mm. For reference, there was also prepared a sensor in which the oxygen pump element 3 and the oxygen concentration cell element 4 were not integrated together, in which a space having a width of 0.4 mm was formed between the elements with use of a spacer, and in which the periphery of the space opened onto the atmosphere to be measured. These exhaust gas sensors were mounted to an exhaust pipe, and the following experiment was performed.

First, the oxygen pump element was not operated and there were passed at a flow rate of 12 L/min test gases consisting of oxygen of 100 ppm, 10% carbon dioxide, methane of 0 to 500 ppm, 0% or 10% water vapor and the residual parts of nitrogen. The electromotive forces of the oxygen concentration cell element 4 were then measured for each methane concentration. FIG. 77 illustrate the results of the measurement. In the sensor for reference (FIG. 77A), as can be seen from the drawing, the electromotive forces in the case that water vapor was not added were comparatively large while the addition of water vapor decreased the electromotive forces. In contrast to that, it is found that the sensor as the subject of the experiment (FIG. 77B) was little influenced by the humidification. Subsequently, the oxygen pump element was operated and there were passed at a flow rate of 12 L/min test gases consisting of oxygen of 100 ppm, 10% carbon dioxide, methane of 0 to 500 ppm, 0% or 10% water vapor and the residual parts of nitrogen. The sensor outputs were then measured for each methane concentration. FIG. 78 illustrate the results of the measurement. In the sensor for reference (FIG. 78A), as can be seen from the drawing, the sensor outputs in the case that water vapor was not added were comparatively large while the addition of water vapor decreased the outputs. In contrast to that, it is found that the sensor as the subject of the experiment (FIG. 78B) was little influenced by the humidification.

For the purpose of investigating the influence which oxygen concentration exerted upon the sensor output, the same experiment was performed under the same conditions except that water vapor concentration was fixed at 10% and that oxygen concentration was set at 100 or 1000 ppm. FIG. 79 illustrate the results of the experiment. As can be seen from the drawing, in the sensor for reference (FIG. 79A), the level of the sensor output varied in response to oxygen concentration; in contrast to that, the sensor as the subject of the experiment (FIG. 79B) was little influenced by the change in oxygen concentration.

EXPERIMENT EXAMPLE 12

The exhaust gas sensor 513 as shown in FIG. 80 and described below was produced. The exhaust gas sensor 513 has basically the same arrangement as shown in FIG. 52 and comprises a first heater 2 (a heater element), an oxygen pump element 3, an oxygen concentration cell element 4, and a second heater 5 (a heater element), which have been formed like elongated plates and have been laminated in the listed order. A first measuring chamber 15 is formed between the oxygen pump element 3 and the oxygen concentration cell element 4 which are arranged to face each other. The gas to be subjected to detection flows into the chamber 15 through first gas influx holes 203 (having a width of 100 $\mu$m) formed on both side surfaces of the exhaust gas sensor 1. The first gas influx holes 203 are formed between the solid electrolyte layer forming the oxygen pump element 3 and a spacer formed on the solid electrolyte layer forming the oxygen concentration cell element 4.

Between the oxygen concentration cell element 4 and a solid electrolyte layer 249 is formed a second measuring chamber 16, into which the gas to be subjected to detection flows through second gas influx holes 204 (having a width of 100 $\mu$m) formed on both side surfaces of the exhaust gas sensor 513. The second gas influx holes 204 are formed between the solid electrolyte layer forming the oxygen concentration cell element 4 and a spacer layer formed on the solid electrolyte layer 249. The first and second gas influx holes 203, 204 are formed with use of porous alumina having a diffusion resistance. Heaters 2 and 5 are fixed to the solid electrolyte layer forming the oxygen pump element 3 and to the solid electrolyte layer 249, respectively, with use of glass, adhesive or the like so that spaces 14 and 17 having a width of 100 $\mu$m are formed between the heater 2 and said solid electrolyte layer, and between the heater 5 and the solid electrolyte layer 249, respectively. The spaces 14 and 17 communicate with the atmosphere to be measured.

The $ZrO_2$ (or YSZ) solid electrolyte forming the oxygen pump element 3 and the oxygen concentration cell element 4 is the same as used in Experiment Example 3. With regard to the materials of electrodes 10 to 13, the outside electrode 10, the first electrode 11 and the second electrode 12 each comprises a Pt porous electrode having a certain oxygen permeability and having a relatively high oxidation catalyst activity on hydrocarbon, and the third electrode 13 comprises a Pd-added Pt porous electrode having a certain oxygen permeability and having an oxidation catalyst activity lower than that of the Pt porous electrode. To the electrodes 10 to 13 are electrically connected leads 10b to 13b, respectively, through which the outputs of the electrodes can be taken outside and through which voltages can be applied to the electrodes.

Processes of producing the exhaust gas sensor 1 will be described below. The processes of producing the pastes which are the raw materials of the solid electrolyte layers and of the electrodes will be illustrated in Tables 3 to 6, and then the processes of producing the elements will be described.

The oxygen pump element 3 was produced by the screen printing of the paste for oxygen pump outside electrode (see Table 4) on a surface of a $ZrO_2$ green sheet (see Table 3), the screen-printing of the first electrode paste (see Table 5) on the other surface, and the binder burn-out (degreasing) and sintering of the green sheet.

The oxygen concentration cell element 4 was produced by the following method: The second electrode paste (see Table 5) was screen-printed on a surface of a $ZrO_2$ green sheet (see Table 3), and the third electrode paste (see Table 6) was screen-printed on the other surface. The $ZrO_2$ paste shown in Table 3 was then screen-printed between the oxygen concentration cell element 4 and the solid electrolyte layer 249 so that, between the oxygen concentration cell element 4 and the solid electrolyte layer 249, the second measuring chamber 16 was formed in the center and the second gas influx holes 204 were formed in the upper areas on both sides. In this state, binder burn-out (degreasing) was performed at 400° C. for two hours, and sintering was carried out at 1500° C. for one hour. As a result, the oxygen concentration cell element 4 integrated with the solid electrolyte layer 249 was obtained. Pd content in the third electrode (Pd/(Pd+Pt+solid electrolyte)) was determined as 2.4 wt % (2.8 parts by weight of Pd/(2.8 parts of Pd+100 parts of Pt+14 parts of solid electrolyte) by inductively coupled plasma (ICP) emission spectrometry.

Subsequently, the $ZrO_2$ paste shown in Table 6 was screen-printed between the oxygen pump element 3 and the oxygen concentration cell element 4 so that, between the oxygen pump element 3 and the oxygen concentration cell element 4, the first measuring space 15 was formed in the center and the first gas influx holes 203 were formed in the lower areas on both sides. In this state, binder burn-out was performed at 400° C. for two hours, and sintering was carried out at 1500° C. for 1 hour so that both the elements were integrated together. With use of glass (or cement), the heater 2 was then bonded to the solid electrolyte layer of the oxygen pump element 3 so as to form the space 14, while the heater 5 was bonded to the solid electrolyte layer 249 so as to form the space 17.

An exhaust gas sensor in which the third electrode was a porous Au electrode was also produced as a referential example (which fell within the scope of the invention). The process of producing the sensor was the same as that of the exhaust gas sensor 513 of the embodiment except that, in the formation of the porous Au electrode, the paste in which a given amount of glass powder was mixed with Au powder was screen-printed on a sinter made of a sintered $ZrO_2$ green sheet and subjected to secondary baking at 800° C. for one hour.

The characteristics of the exhaust gas sensors were evaluated as follows: There was used test gas which contained $CH_4$ as the constituent to be detected, and contained $C_2H_6$, $C_3H_8$, and $C_3H_6$ as interfering gases. FIG. 81 is a block diagram illustrating the arrangement of the system for evaluating the characteristics of the gas sensors. The system comprises a gas mixer for mixing a plurality of gas constituents supplied from a plurality of gas cylinders and for supplying gas having a predetermined composition; a humidifier for humidifying the gas supplied from the gas mixer; and a measuring chamber, a flame ionized detector (FID), a magnetic pneumatic analyzer (MPA), a non dispersive infrared (NDIR), and a chemical luminescence detector (CLD), which are connected to the downstream side of the gas mixer in parallel and are supplied with the humidified gas (a model gas) having the predetermined composition.

The exhaust gas sensor was mounted into the measuring chamber through a metal fitting so that a specified part of the exhaust gas sensor was exposed to the test gas. The oxygen pump element and the oxygen concentration cell element were connected to the same circuit as shown in FIG. 7. In both the exhaust gas sensors of the embodiment and for reference, the offset electromotive force of the oxygen concentration cell element was 0.1 mV and the target value EC of the electromotive force was set at 0.1 mV. The oxygen pump element was operated so that the concentration cell electromotive force EMF of the oxygen concentration cell element equaled EC, and the pump current Ip was measured as the sensor output. Table 7 illustrates the conditions of the measurement. FIGS. 82 and 83 illustrate the evaluation results on the gas sensor of the embodiment and the gas sensor for reference, respectively.

As shown in FIG. 82, the gas sensor of the embodiment in which the third electrode was the Pd-added electrode was sensitive only to $CH_4$, and the output of the sensor hardly varied with changes in the concentrations of the other HC gases. On the other hand, as shown in FIG. 83, the gas sensor for comparison in which the third electrode was the Au electrode had a sensitivity to $CH_4$ slightly higher than that of the embodiment; however, it is found that the output of the sensor varied with changes in the concentrations of the other HC gases. Accordingly, the gas sensor of the embodiment has excellent characteristics as a sensor for selectively detecting the concentration of a particular HC gas ($CH_4$) in the presence of a plurality of types of HC gas, because the gas sensor of the embodiment has a high selective detectivity on $CH_4$ and has a sensitivity to $CH_4$ generally as high as that of the sensor for reference. Besides, the outputs of the gas sensor of the embodiment were stable in that the outputs had a satisfactory linearity with respect to $CH_4$ gas concentration.

What is claimed is:

1. An exhaust as sensor for detecting a constituent which is contained in exhaust gas, the exhaust gas sensor comprising:

a processing space;

an oxygen concentration cell element comprising a solid electrolyte which has an oxygen-ion conductivity, and which has surface electrodes which have an oxygen permeability, one of the electrodes facing said processing space;

an oxygen pump element for pumping oxygen into or out of the processing space in such a direction that the absolute value of a concentration cell electromotive force generated in the oxygen concentration cell element, decreases, the oxygen pump element comprising a solid electrolyte which has an oxygen-ion conductivity, and which has surface electrodes which have an oxygen permeability, one of the electrodes facing the processing space; and a heater element or heater elements for heating at least one of the oxygen pump element and the oxygen concentration cell element to a predetermined operating temperature of the sensor;

wherein exhaust gas containing the constituent and oxygen is introduced into the processing space and into a space (hereinafter referred to as an opposed space) that is across the oxygen concentration cell element from the processing space, wherein the exhaust gas contacts with both sides of the oxygen concentration cell element;

wherein the electrode facing the processing space on the oxygen pump element referred to as a first electrode, the electrode facing the processing space on the oxygen concentration cell element referred to as a second electrode, the electrode on the side of the opposed space on the oxygen concentration cell element referred to as a third electrode, oxidation catalyst activities of the first to third electrodes are adjusted so that the constituent in the exhaust gas introduced into the processing space and into the opposed space is consumed by the reaction thereof with oxygen in the exhaust gas with at least any one of the first to third electrodes acting as oxidation catalyst in at least one of the processing space and the opposed space and so that a difference in the consumption of the constituent which is caused by the reaction with oxygen occurs between the processing space and the opposed space;

wherein the value of a current flowing through the oxygen pump element at the time when the absolute value of the oxygen concentration cell element electromotive force reaches the absolute value of a target value EC which is set within the range not more than 10 mV is taken as information reflecting the concentration of the constituent in the exhaust gas.

2. An exhaust gas sensor as claimed in claim 1, wherein the second and third electrodes have different oxidation catalyst activities on the constituent.

3. An exhaust gas sensor as claimed in claim 2 wherein the second electrode has a higher oxidation catalyst activity than the third electrode, and wherein the oxygen pump element pumps oxygen into the processing space so that the absolute value of the concentration cell electromotive force generated in the oxygen concentration cell element decreases.

4. An exhaust gas sensor as claimed in claim 3 wherein the first and second electrodes have higher oxidation catalyst activities than the third electrode.

5. An exhaust gas sensor as claimed in claim 3 wherein at least one of the first electrode and the second electrode comprise any one of metal based on any one of Pt, Pd, and Rh, alloy based on Pt—Rh, alloy based on Rh—Pd, and alloy based on Pd—Ag, and wherein the third electrode comprises any one of metal based on any one of Au, Ni, and Ag, alloy based on Pt—Au, alloy based on Pt—Ni, alloy based on Pt—Ag, alloy based on Ag—Pd, alloy based on Pt—Pd, and alloy based on Au—Pd.

6. An exhaust gas sensor as claimed in claim 3 wherein at least one of the first electrode and the second electrode comprise alloy based on Pd—Ag, and wherein the third electrode comprises Au or alloy based on Au.

7. An exhaust gas sensor as claimed in claim 2 employing the second and third electrodes wherein; provided that a sample in which a disc-like porous electrode having a diameter of 8 mm is formed, with use of the same material and condition as the second or third electrode, on a disc of the oxygen-ion conductive solid electrolyte having a diameter of 12 mm and a thickness of 1 mm is placed in a cylindrical body having a gas inlet and a gas outlet and is heated to the operating temperature of the sensor and, in that state, test gas containing oxygen of 300 ppm, a constituent of 350 ppm, 3% water vapor and the residual parts of Ar is introduced into the cylindrical body through the gas inlet at a flow rate of 100 ml/min; the difference between the second and third electrodes in conversion ratio η (in %) of the constituent is not less than 20 percentage points, the conversion ratio η defined as:

$$\eta = \{350 - Cs/350\} \cdot 100$$

in which Cs is the concentration (in ppm) of the constituent in the test gas discharged through the gas outlet.

8. An exhaust gas sensor as claimed in claim 1, wherein the constituent is methane.

9. An exhaust gas sensor as claimed in claim 1 wherein a space-forming member for forming a space of a given width between itself and the oxygen concentration cell element is disposed on the side of the oxygen concentration cell element where the third electrode is formed.

10. An exhaust gas sensor as claimed in claim 9 wherein the space-forming member is a plate-like heater element for heating the oxygen concentration cell element to the operating temperature of the sensor.

11. An exhaust gas sensor as claimed in claim 1 wherein the oxygen pump element is disposed so as to face the oxygen concentration cell element so that a space of a given width as the processing space where the passage of exhaust gas is allowed is formed between the oxygen pump element and the oxygen concentration cell element.

12. An exhaust gas sensor as claimed in claim 11 wherein the width of the space formed between the oxygen concentration cell element and the oxygen pump element is not more than 1 mm.

13. An exhaust gas sensor as claimed in claim 11 wherein a gas holding member comprising metal meshes or porous metal is interposed into the space formed between the oxygen pump element and the oxygen concentration cell element so that the exhaust gas is held in interstices in the gas holding member.

14. An exhaust gas sensor as claimed in claim 1 further comprising:
  a measuring chamber or measuring chambers which are formed so as to contact at least one of a second electrode and a third electrode, wherein a first electrode is the electrode on the side of the space on the oxygen pump element, the second electrode being the electrode on the side of the space on the oxygen concentration cell element, the third electrode being the electrode on the side of the opposed space on the oxygen concentration cell element; and
  a gas communicating portion or gas communicating portions which are formed so as to penetrate a wall portion or wall portions of the measuring chamber or measuring chambers from the side of the atmosphere to be measured to the side of the measuring chamber or measuring chambers;
  wherein the gas communicating portion or gas communicating portions are diffusion flow regulator or diffusion flow regulators each comprising at least any one of small bores, a slit or slits, and a porous communicating portion which comprises porous ceramic or porous metal.

15. An exhaust gas sensor as claimed in claim 14 wherein a wall portion is formed between the oxygen concentration cell element and the oxygen pump element so as to surround the second electrode and so as to define as the measuring chamber a space surrounded by the inside surfaces of the wall portion and by the surfaces facing each other of the oxygen concentration cell element and of the oxygen pump element.

16. An exhaust gas sensor as claimed in claim 15 wherein the diffusion flow regulator is formed so as to penetrate at least one of the wall portion and the oxygen concentration cell element from the side of the atmosphere to be measured to the side of the measuring chamber and is formed as a slit or slits or small bores which provide a communication between the atmosphere to be measured and the measuring chamber.

17. An exhaust gas sensor as claimed in claim 16 wherein a wall-forming body constituting at least a part of the wall portion is disposed between the oxygen concentration cell element and the oxygen pump element, and wherein the slit or slits are formed between the wall-forming body and at least one of the oxygen concentration cell element and the oxygen pump element so as to extend along surfaces of the oxygen concentration cell element and/or the oxygen pump element.

18. An exhaust gas sensor as claimed in claim 17 wherein the wall-forming body is integrated by sintering with at least one of the oxygen pump element and the oxygen concentration cell element.

19. An exhaust gas sensor as claimed in claim 16 wherein the oxygen pump element and the oxygen concentration cell element are formed like elongated plates, and wherein the diffusion flow regulator comprises slits formed on both longitudinal sides of the oxygen pump element and the oxygen concentration cell element.

20. An exhaust gas sensor as claimed in claim 14 wherein a space-forming member is disposed facing a side of the oxygen concentration cell element opposite to the space and so as to form another space between the space-forming member and the oxygen concentration cell element, and
  wherein a wall portion is formed between the space-forming member and the oxygen concentration cell element so as to surround the third electrode so that a measuring chamber is formed of a space surrounded by the inside surfaces of the wall portion and by the surfaces facing each other of the space-forming member and the oxygen concentration cell element.

21. An exhaust gas sensor as claimed in claim 20 wherein the diffusion flow regulator is formed so as to penetrate at least one of the wall portion and the space-forming member from the side of the atmosphere to be measured to the side of the measuring chamber and is formed as a slit or slits or small bones which provide a communication between the atmosphere to be measured and the measuring chamber.

22. An exhaust gas sensor as claimed in claim 20 wherein a wall-forming body constituting at least a part of the wall portion is disposed between the space-forming member and the oxygen concentration cell element, and wherein the slit or slits are formed between the wall-forming body and at least one of the space-forming member and the oxygen concentration cell element so as to extend along a surface or surfaces of the space-forming member and/or the oxygen concentration cell element.

23. An exhaust gas sensor as claimed in claim 22 wherein the wall-forming body is integrated by sintering with at least one of the space-forming member and the oxygen concentration cell element.

24. An exhaust gas sensor as claimed in claim 22 wherein the space-forming member and the oxygen concentration cell element are formed like elongated plates, and wherein the diffusion flow regulator comprises slits formed on both longitudinal sides of the space-forming member and the oxygen concentration cell element.

25. An exhaust gas sensor for detecting a constituent which is contained in exhaust gas, the exhaust gas sensor comprising:

a processing space;

an oxygen concentration cell element comprising a solid electrolyte which has an oxygen-ion conductivity, and which has surface electrodes which have an oxygen permeability, one of the electrodes facing the processing space;

an oxygen pump element for pumping oxygen into or out of the processing space in such a direction that the absolute value of a concentration cell electromotive force generated in the oxygen concentration cell element decreases, the oxygen pump element comprising a solid electrolyte which has an oxygen-ion conductivity, and which has surface electrodes which have an oxygen permeability, one of the electrodes facing the processing space; and a heater element or heater elements for heating at least one of the oxygen pump element and the oxygen concentration cell element to a predetermined operating temperature of the sensor;

wherein exhaust gas containing the constituent and oxygen in introduced into the processing space and into a space (hereinafter referred to as an opposed space) that is across the oxygen concentration cell element from the processing space, wherein the exhaust gas contacts with both sides of the oxygen concentration cell element;

wherein the electrode facing the processing space on the oxygen pump element referred to as a first electrode, the electrode facing the processing space on the oxygen concentration cell element referred to as a second electrode, the electrode on the side of the opposed space on the oxygen concentration cell element referred to as a third electrode, oxidation catalyst activities of the first to third electrodes are adjusted so that the constituent in the exhaust gas introduced into the processing space and into the opposed space is consumed by the reaction thereof with oxygen in the exhaust gas with at least any one of the first to third electrodes acting as oxidation space and so that a different in the consumption of the constituent which is caused by the reaction with oxygen occurs between the processing space and the opposed space;

wherein the absolute value of an offset electromotive force which is generated in the oxygen concentration cell element when test gas containing not less than 1 percent oxygen by volume and containing substantially no constituent which may react with oxygen at the operating temperature of the sensor is introduced into the processing space and the opposed space, is provided as EOS (in mV) and, correspondingly, the absolute value of a target value EC of the electromotive force is set within the range not less than (EOS−5) mV and not more than (EOS+5) mV;

wherein the value of a current flowing through the oxygen pump element at the time when the absolute value of the concentration cell electromotive force of the oxygen concentration cell element reaches the target value EC of the electromotive force as taken as information reflecting the concentration of the constituent in the exhaust gas.

26. An exhaust gas sensor for detecting a constituent which is contained in exhaust gas, the exhaust gas sensor comprising:

a processing space;

an oxygen concentration cell element comprising a solid electrolyte which has an oxygen-ion conductivity, and which as surface electrodes which have an oxygen permeability, one of the electrodes facing the processing space;

an oxygen pump element for pumping oxygen into or out of the processing space in such a direction that the absolute value of concentration cell electromotive force generated in the oxygen concentration cell element decreases, the oxygen pump element comprising a solid electrolyte which has an oxygen-ion conductivity, and which has surface electrodes which have an oxygen permeability, one of the electrodes facing the processing space; and a heater element or heater elements for heating at least one of the oxygen pump element and the oxygen concentration cell element to a predetermined operating temperature of the sensor;

wherein exhaust gas containing the constituent and oxygen is introduced into the processing space and into a space (hereinafter referred to as an opposed space) that is across the oxygen concentration cell element from the processing space;

wherein the electrode facing the processing space on the oxygen pump element referred to as a first electrode, the electrode facing the processing space on the oxygen concentration cell element referred to as a second electrode, the electrode on the side of the opposed space on the oxygen concentration cell element referred to as a third electrode, oxidation catalyst activities of the first to third electrodes are adjusted so that the constituent in the exhaust gas introduced into the processing space and into the opposed space is consumed by the reaction thereof with oxygen in the exhaust gas with at least nay one of the first to third electrodes acting as oxidation catalyst in at least one of the processing space and the opposed space and so that a difference in consumption of the constituent which is caused by the reaction with oxygen occurs between the processing space and the opposed space;

wherein for the purpose of the selective detection of methane as the constituent the third electrode comprises Pd constituent which makes the oxidation catalyst activity on methane of the third electrode lower than at least that of the second electrode.

27. An exhaust gas sensor as claimed in claim 26 wherein the value of a current flowing through the oxygen pump element at the time when the absolute value of the concentration cell electromotive force of the oxygen concentration cell element reaches a target value EC which is set within the range not more than 10 mV is taken as information reflecting the concentration of the constituent in the exhaust gas.

28. An exhaust gas sensor as claimed in claim 26 wherein the absolute value of an offset electromotive force which is generated in the oxygen concentration cell element when test gas containing not less than 1 percent oxygen by volume and containing substantially no constituents which may reflect with oxygen at the operating temperature of the sensor is introduced into the space and the opposed space, is provided as EOS (in mV) and, correspondingly, a target value EC of the electromotive force is set within the range not less than (EOS−5) MV and not more than EOS+5) mV; and wherein the value of a current flowing through the oxygen pump element at the time when the absolute value of the concentration cell electromotive force of the oxygen concentration cell element reaches the target value EC of the electromotive force is taken as information reflecting the concentration of the constituent in the exhaust gas.

29. An exhaust gas senor as claimed in claim 26 wherein at least the first electrode and the second electrode are composed mainly of Pt.

30. An exhaust gas sensor as claimed in claim 26 wherein Pd content in the third electrode is preferably adjusted within the range not more than 90% by weight.

31. An exhaust gas sensor for detecting a constituent which is contained in exhaust gas, the exhaust gas sensor comprising:

an oxygen concentration cell element comprising a solid electrolyte which has an oxygen-ion conductivity, and which has surface electrodes;

an oxygen pump element comprising a solid electrolyte which has an oxygen-ion conductivity, having surface electrodes, facing the oxygen concentration cell element to form between the oxygen pump element and the oxygen concentration cell element a space of a given width where the flow of exhaust gas from atmosphere to be measured is allowed, and pumping oxygen into or out of the space in such a direction that the absolute value of a concentration cell electromotive force generated in the oxygen concentration cell element decreases; and a heater element or heater elements for heating at least one of the oxygen pump element and the oxygen concentration cell element to a predetermined operating temperature of the sensor;

wherein the oxygen concentration cell element and the oxygen pump element are formed as a unitary sintered body in which the elements are laminated with the space formed therebetween.

32. An exhaust gas sensor as claimed in claim 31 wherein exhaust gas containing the constituent and oxygen is introduced into the space and into a space (hereinafter referred to as an opposed space) that is across the oxygen concentration cell element therefrom; wherein, the electrode facing the space on the oxygen pump element referred to as a first electrode, the electrode facing the space on the oxygen concentration cell element referred to as a second electrode, the electrode on the side of the opposed space on the oxygen concentration cell element referred to as a third electrode, oxidation catalyst activities of the first to third electrodes are adjusted so that the constituent in the exhaust gas introduced into the space and into the opposed space is consumed by the reaction thereof with oxygen in the exhaust gas with at least any one of the first to third electrodes acting as oxidation catalyst in at least one of the space and the opposed space so that a different in the consumption of the constituent which is caused by the reaction with oxygen occurs between the space and the opposed space;

wherein the value of a current flowing through the oxygen pump element at the time when the absolute value of the concentration cell electromotive force of the oxygen concentration cell element reaches a predetermined target value EC of the electromotive force is taken as information reflecting the concentration of the constituent in the exhaust gas; and wherein the oxygen concentration cell element and the oxygen pump element are formed as a unitary sintered body in which the elements are laminated with the space formed between the first electrode and the second electrode.

33. An exhaust gas sensor as claimed in claim 32 wherein the value of a current flowing through the oxygen pump element at the time when the absolute value of the concentration cell electromotive force of the oxygen concentration cell element reaches a target value EC of the electromotive force which is set within the range not more than 10 mV is taken as information reflecting the concentration of the constituent in the exhaust gas.

34. An exhaust gas sensor as claimed in claim 32 wherein the absolute value of an offset electromotive force which is generated in the oxygen concentration cell element when test as containing not less than 1 percent oxygen by volume and containing substantially no constituents which may react with oxygen at the operating temperature of the sensor is introduced into the space and the opposed space, is provided as EOS (in mV) and, correspondingly, a target value EC of the electromotive force is set within the range not less than (EOS−5) mV and not more than (EOS+5) mV; and wherein the value of a current flowing through the oxygen pump element at the time when the absolute value of the concentration cell electromotive force of the oxygen concentration cell element reaches the target value eC of the electromotive force is taken as information reflecting the concentration of the constituent in the exhaust gas.

35. An exhaust gas sensor as claimed in claim 31 formed as a unitary sintered body in which the heater element or heater elements are laminated on the side opposite to the space of at least one of the oxygen concentration cell element and the oxygen pump element and in which the oxygen concentration cell element, the oxygen pump element, and the heater element or heater elements are laminated together.

36. An exhaust gas sensor as claimed in claim 31 wherein a prop or props which define the distance of the space without impeding gas from flowing into and out of the space are formed in the space between the oxygen concentration cell element and the oxygen pump element.

37. An exhaust gas sensor as claimed in claim 36 wherein the prop or props comprise ceramic material which can be integrated by sintering with the oxygen concentration cell element and with the oxygen pump element.

38. An exhaust gas sensor as claimed in claim 31 wherein the oxygen concentration cell element and the oxygen pump element are formed like elongated plates and are disposed so as to face each other, wherein the first to third electrodes are formed on one-end sides of the surfaces of the oxygen concentration cell element and of the oxygen pump element and a spacer having a thickness generally equal to the width of the space is interposed between the oxygen concentration cell element and the oxygen pump element on the other end sides of the surfaces, and wherein the spacer, the oxygen concentration cell element and the oxygen pump element are integrated together by firing.

39. An exhaust gas sensor as claimed in claim 31 wherein the oxygen concentration cell element and the oxygen pump element are formed like elongated plates and are disposed so as to face each other, wherein the electrodes are formed on one-end portions of the surfaces of the oxygen concentration cell element and the oxygen pump element;

wherein a prop or props which define the distance of the space without impeding gas from flowing into and out of the space are formed in the space between the oxygen concentration cell element and the oxygen pump element; and wherein, in the area except the space, the oxygen concentration cell element and the oxygen pump element are joined together through the medium of an insulating layer.

40. An exhaust gas sensor for detecting a constituent which is contained in exhaust gas, the exhaust gas sensor comprising:

an oxygen concentration cell element comprising a solid electrolyte which has an oxygen-ion conductivity, and which has surface electrodes;

an oxygen pump element comprising a solid electrolyte which has an oxygen-ion conductivity, having surface electrodes, facing the oxygen concentration cell element to form between the oxygen pump element and the oxygen concentration cell element a space of a given width where the flow of exhaust gas is allowed, and pumping oxygen into or out of the space in such a direction that the absolute value of a concentration cell electromotive force generated in the oxygen concentration cell element decreases;

a heater element or heater elements for heating at least one of the oxygen pump element and the oxygen concentration cell element to a predetermined operating temperature of the sensor;

a measuring chamber or measuring chambers which are formed so as to contact at least one of a second electrode and a third electrode, wherein a first electrode is the electrode on the side of the space on the oxygen pump element, the second electrode being the electrode on the side of the space on the oxygen concentration cell element, the third electrode being the electrode on the side of the space opposed to said space (hereinafter referred to as an opposed space) on the oxygen concentration cell element; and a gas communicating portion or gas communicating portions which are formed so as to penetrate a wall portion or wall portions of the measuring chamber or measuring chambers from the side of atmosphere to be measured to the side of the measuring chamber or measuring chambers;

wherein the gas communicating portion or gas communicating portions are diffusion flow regulator or diffusion flow regulators each comprising at least any one of small bores, a slit or slits and a porous communicating portion which comprises porous ceramic or porous metal.

41. An exhaust gas sensor system for detecting a constituent which is contained in exhaust gas, the exhaust gas sensor system comprising:

an exhaust gas sensor comprising:
a processing space;
an oxygen concentration cell element comprising a solid electrolyte which has an oxygen-ion conductivity, and which has surface electrodes which have an oxygen permeability, one of the electrode facing the processing space,
an oxygen pump element for pumping oxygen into or out of the processing space in such a direction that the absolute value of a concentration cell electromotive force generated in the oxygen concentration cell element decreases, the oxygen pump element comprising a solid electrolyte which has an oxygen-ion conductivity, and having surface electrodes which have an oxygen permeability, one of the electrodes facing the processing space, and
a heater element or heater elements for heating at least one of the oxygen pump element and the oxygen concentration cell element to a predetermined operating temperature of the sensor,
wherein exhaust has containing the constituent and oxygen is introduced into the processing space and into a space (hereinafter referred to as an opposed space) that is across an oxygen concentration cell element from the processing space, wherein the exhaust gas contacts with both sides of the oxygen concentration cell element;
wherein the electrode facing the processing space on the oxygen pump element referred to as a first electrode, the electrode facing the processing space on the oxygen concentration cell element referred to as a second electrode, the electrode on the side of the opposed space on the oxygen concentration cell element referred to as a third electrode, oxidation catalyst activities of the first to third electrode are adjusted to that the constituent in the exhaust gas introduced into the processing space and into the opposed space is consumed by the reaction thereof with oxygen in the exhaust gas with at least any one of the first to third electrodes acting as oxidation catalyst in at least one of the processing space and the opposed space and so that a difference in the consumption of the constituent which is caused by the reaction with oxygen occurs between the processing space and the opposed space;
electromotive-force detecting means for detecting a concentration cell electromotive force generated in the oxygen concentration cell element;
pump element voltage adjusting means for adjusting the voltage applied to the oxygen pump element so that oxygen is pumped into or out of the processing space in such a direction that the absolute value of the detected concentration cell electromotive force decreases; and
output means for outputting the value of, or information reflecting, a current which flows through the oxygen pump element at the time when the absolute value of the concentration cell electromotive force reaches the absolute value of a target value EC which is set within the range not more than 10 mV, as information reflecting the concentration of the constituent.

42. An exhaust gas sensor system as claimed in claim 41 further comprising:

a heater element or heater elements for heating the oxygen pump element and the oxygen concentration cell element to the predetermined operating temperature of the sensor, and heat generation control means for controlling heat generation in the heater element or heater elements so as to approach the temperature of the oxygen concentration cell element to a predetermined temperature target value.

43. An exhaust gas sensor system as claimed in claim 42 wherein the heat generation control means comprises:

temperature detecting means for detecting the temperature of the oxygen concentration cell element, and energization control means for controlling the energization for the heater element or heater elements so as to approach the temperature of the oxygen concentration cell element to the temperature target value on the basis of the temperature detected by the temperature detecting means.

44. An exhaust gas sensor system as claimed in claim 43 wherein the temperature detecting means comprises:

internal-resistance measuring means for measuring the internal resistance of the oxygen concentration cell element, temperature information producing means for producing information on the temperature of the oxygen concentration cell element on the basis of the measured internal resistance, and temperature information output means for outputting the produced information on the temperature.

45. An exhaust gas sensor system as claimed in claim 44 wherein the internal-resistance measuring means comprises:

detecting-current passing means for passing an internal-resistance detecting current of a constant value through the oxygen concentration cell element, and voltage information detecting means for detecting information (herein after referred to as voltage information) which reflects the voltage applied to the oxygen concentration cell element during the passage of the internal-resistance detecting current; and wherein the internal-resistance measuring means measures the internal resistance of the oxygen concentration cell element on the basis of the detected voltage information.

46. An exhaust gas sensor system as claimed in claim 45 wherein, in order to eliminate or decrease the influence of the concentration cell electromotive force of the oxygen concentration cell element, which influence is included in or superposed on the detected voltage information, the internal-resistance measuring means comprises:

concentration cell electromotive force measuring means for measuring the concentration cell electromotive force of the oxygen concentration cell element through which the internal-resistance detecting current is not passed, and voltage information correcting means for correcting the detected voltage information on the basis of the measured concentration cell electromotive force.

47. An exhaust gas sensor system as claimed in claim 46 further comprising correction current passing means for passing a correction current through the oxygen concentration cell element, opposite in direction to the internal-resistance detecting current, after the internal-resistance detecting current is passed through the oxygen concentration cell element and the internal resistance of the element is measured.

48. An exhaust gas sensor system as claimed in claim 45 further comprising pump current controlling means which compares the concentration cell electromotive force of the oxygen concentration cell element with a predetermined control reference value and outputs to the oxygen pump element a pump current according to the difference between the concentration cell electromotive force and the target value EC of the electromotive force, wherein the internal-resistance measuring means comprises pump current interrupting means for interrupting with predetermined timing the pump current output from the pump current controlling means to the oxygen pump element, and that the detecting current passing means passes the internal-resistance detecting current through the oxygen concentration cell element in the stat where the pump current output is interrupted.

49. An exhaust gas sensor system as claimed in claim 48 wherein the pump current interrupting means of the internal-resistance measuring means interrupts the pump current output from the pump current controlling means periodically at predetermined time intervals, so that the internal-resistance measuring means periodically measures the internal resistance of the oxygen concentration cell element, in accordance with the periodical interruption of the pump current output.

50. An exhaust gas sensor as claimed in claim 42 further comprising:

concentration information correcting means for producing information on the temperature-compensated concentration of the constituent on the basis of the temperature detected by the temperature detecting means and on the basis of the pump current information, and corrected measurement output means for outputting the produced information on the concentration of the constituent as a corrected measurement.

51. An exhaust gas sensor system as claimed in claim 50 wherein the concentration information correcting means comprises:

correction reference information storing means for storing, as correction reference information, information on relation between temperature deviation and pump current correction, which information provides the relation between temperature deviations from the temperature target value and corrections for the pump current information (hereinafter referred to as pump current correction);

pump current correction determining means for determining for a pump current correction which corresponds to the difference between the temperature detected by the temperature detecting means and the temperature target value, with reference to the correction reference information; and correction calculating means for calculating to correct the measured pump current, on the basis of the determined pump current correction.

52. An exhaust gas sensor system as claimed in claim 50 wherein the concentration information correcting means comprises:

correction reference information sorting means for storing, as correction reference information, pump current/concentration information which represents, for various temperatures, relationships between the pump currents and the concentrations of the constituent; and corrected concentration information producing means which refers to the correction reference information on the basis oaf the temperature detected by the temperature detecting means and the measured pump current, and thereby produces the value of the concentration of the constituent which corresponds to the temperature and the pump current, as the information on the temperature-compensated concentration of the constituent.

53. An exhaust gas sensor system for detecting a constituent which is contained in exhaust gas, the exhaust gas sensor system comprising:

an exhaust gas sensor comprising:

a processing space;

an oxygen concentration cell element comprising a solid electrolyte which has an oxygen-ion conductivity, and having surface electrode which have an oxygen permeability, one of the electrodes facing the processing space, an oxygen pump element for pumping oxygen into or out of the processing space in such a direction that the absolute value of a concentration cell electromotive force generated in the oxygen concentration cell element decreases, the oxygen pump element comprising a solid electrolyte which has an oxygen-ion conductivity, and having on both surfaces electrodes which have an oxygen permeability, one of the electrodes facing the processing space, and a heater element or heater elements for heating at least one of the oxygen pump element and the oxygen concentration cell element to a predetermined operating temperature of the sensor, wherein exhaust gas containing the constituent and oxygen in introduced into the processing space and into a space (hereinafter referred to as an opposed space) this is across the oxygen concentration cell element from the processing space, wherein the exhaust gas contacts with both sides of the oxygen concentration cell element;

wherein the electrode facing the processing space on the oxygen pump element referred to as a first electrode, the electrode facing the processing space on the oxygen concentration cell element referred to as a second electrode, the electrode on the side of the opposed space on the oxygen concentration cell element referred to as a third electrode, oxidation catalyst activities of the first to third electrodes are adjusted so that the constituent in the exhaust gas introduced into the processing space and into the opposed space is consumed by the reaction thereof with oxygen in the exhaust gas with at least any one of the first to third electrodes acting as oxidation catalyst in at least one of the processing space and the opposed space and so that a difference in the consumption of the constituent which is caused by the reaction with oxygen occurs between the processing space and the opposed space;

electromotive-force detecting means for detecting a concentration cell electromotive force generated in the oxygen concentration cell element;

pump element voltage adjusting means for adjusting the voltage applied to the oxygen pump element so that oxygen is pumped into or out of the processing space in such a direction that the absolute value of the detected concentration cell electromotive force decreases; and output means for outputting, as information reflecting the concentration of the constituent the value of, or information reflecting, a current which flows through the oxygen pump element at the time when the absolute value of the concentration cell electromotive force reaches the absolute value of a target value EC of the electromotive force which is set within the range not less than (EOS−5) mV and not more than (EOS+5) mV, wherein EOS (in mV) is the absolute value of an offset electromotive force which is generated in the oxygen concentration cell element when test gas containing not less than 1 percent oxygen by volume and containing substantially no constituents which may react with oxygen at the operating temperature of the sensor is introduced into the processing space and the opposed space.

54. An exhaust gas sensor for detecting a constituent which is contained in exhaust gas, the exhaust gas sensor comprising:

a processing space;

an oxygen concentration cell element comprising a solid electrolyte which has an oxygen-ion conductivity, and having surface electrodes which have an oxygen permeability, one of the electrodes facing the processing space;

an oxygen pump element for pumping oxygen into or out of the processing space in such a direction that the absolute value of a concentration cell electromotive force generated in the oxygen concentration cell element decreases, the oxygen pump element comprising a solid electrolyte which has an oxygen-ion conductivity, and having surface electrodes which have an oxygen permeability, one of the electrodes facing the processing space; and a heater element or heater elements for heating at least one of the oxygen pump element and the oxygen concentration cell element to a predetermined operating temperature of the sensor;

wherein exhaust gas containing the constituent and oxygen is introduced into the processing space and into a space (hereinafter referred to as an opposed space) this is across the oxygen concentration cell element from the processing space;

the electrode facing the processing space on the oxygen pump element referred to as a first electrode, the electrode facing the processing space on the oxygen concentration cell element referred to as a second electrode, the electrode on the side of the opposed space on the oxygen concentration cell element referred to as a third electrode, oxidation catalyst activities of the first to third electrodes are adjusted to that the constituent in the exhaust gas introduced into the processing space and into the opposed space is consumed by the reaction thereof with oxygen in the exhaust gas with at least any one of the first to third electrodes acting as oxidation catalyst in at least one of the processing space and the opposed space and so that a different in the consumption of the constituent which is caused by the reaction with oxygen occurs between the processing space and the opposed space;

wherein a gas holding member comprising metal meshes or porous metal is interposed into the space formed between the oxygen pump element and the oxygen concentration cell element so that the exhaust gas is held in interstices in the gas holding member.

* * * * *

UNITED STATES PATENT AND TRADEMARK OFFICE
CERTIFICATE OF CORRECTION

PATENT NO. : 6,136,170
DATED : December 24, 1997
INVENTOR(S) : Ryuji Inque et al.

It is certified that error appears in the above-identified patent and that said Letters Patent is hereby corrected as shown below:

Column 61,
Line 43, delete "as" and sustitute -- gas --;

Column 68,
Line 18, delete "eC" and substitute -- EC --;

Column 71,
Line 56, delete "stat" and substitute -- state --.

Signed and Sealed this

Twenty-fifth Day of September, 2001

Attest:

NICHOLAS P. GODICI
Attesting Officer  Acting Director of the United States Patent and Trademark Office